(12) United States Patent
Shaw et al.

(10) Patent No.: US 10,975,398 B2
(45) Date of Patent: *Apr. 13, 2021

(54) HETEROLOGOUS PRODUCTION OF 10-METHYLSTEARIC ACID

(71) Applicant: Ginkgo Bioworks, Inc., Boston, MA (US)

(72) Inventors: Arthur J. Shaw, Belmont, MA (US); Hannah Blitzblau, Arlington, MA (US); Donald V. Crabtree, Cambridge, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/664,378

(22) Filed: Oct. 25, 2019

(65) Prior Publication Data

US 2020/0123579 A1    Apr. 23, 2020

Related U.S. Application Data

(62) Division of application No. 15/710,734, filed on Sep. 20, 2017, now Pat. No. 10,457,963.

(60) Provisional application No. 62/396,870, filed on Sep. 20, 2016.

(51) Int. Cl.

| | |
|---|---|
| *C12P 7/64* | (2006.01) |
| *C11B 1/10* | (2006.01) |
| *A23D 9/02* | (2006.01) |
| *C11C 3/00* | (2006.01) |
| *C12N 9/02* | (2006.01) |
| *C12N 9/10* | (2006.01) |
| *C12Q 1/686* | (2018.01) |

(52) U.S. Cl.
CPC .............. *C12P 7/6409* (2013.01); *A23D 9/02* (2013.01); *C11B 1/10* (2013.01); *C11C 3/00* (2013.01); *C12N 9/001* (2013.01); *C12N 9/1007* (2013.01); *C12Q 1/686* (2013.01)

(58) Field of Classification Search
CPC ........ C12N 9/001; C12N 9/1007; C12N 9/10; C12N 9/02; C11C 3/00; C11B 1/10; C12P 7/6409; C12P 7/64; A23D 9/02; C12Q 1/686

See application file for complete search history.

(56) References Cited

U.S. PATENT DOCUMENTS

| 7,166,766 B1 | 1/2007 | Duhot et al. |
| 8,530,221 B2 | 9/2013 | Hu |
| 10,457,963 B2* | 10/2019 | Shaw, IV ............... C12N 9/001 |
| 2010/0115669 A1 | 5/2010 | Bao et al. |
| 2011/0195880 A1 | 8/2011 | Kawamura et al. |

FOREIGN PATENT DOCUMENTS

| EP | 1108790 A2 | 6/2001 |
| WO | WO/00/061740 A1 | 10/2000 |
| WO | WO/15/184277 A1 | 12/2015 |

OTHER PUBLICATIONS

Abghari, et al., "Yarrowia Lipolytica as an Oleaginous Cell Factory Platform for Production of Fatty Acid-Based Biofuel and Bioproducts," Frontiers in Energy Res., 2(Article 21): 1-21, 2014.
Actinobacteria/Wikipedia; 8 (eight) pages downloaded from http://en.wikipedia.org/wiki/Actinobacteria on Feb. 12, 2019. (Year: 2019).
Chertkov et al., Complete genome sequence of Thermomonospora curvata type starin (B9T). Stand. Genom. Sci., 2011, vol. 4:13-22. (Year: 2011).
International Search Report and Written Opinion in International Application No. PCT/US2017/052491 dated Dec. 21, 2017.
Korn-Wendisch et al., Thermocrispum gen. nov., a new genus of the order Actinomycetales and description of Thermocrispum agreste sp. nov. Int. J. System. Bacterial., 1995, vol. 45(1): 67-77. (Year: 1995).

\* cited by examiner

*Primary Examiner* — Ganapathirama Raghu
(74) *Attorney, Agent, or Firm* — Norton Rose Fulbright US LLP

(57) ABSTRACT

Nucleic acids and cells comprising a methyltransferase gene and/or a reductase gene are disclosed. These nucleic acids and cells may be used to produce branched (methyl)lipids, such as 10-methylstearate.

15 Claims, 32 Drawing Sheets

Specification includes a Sequence Listing.

A) *MYCOBACTERIUM SMEGMATIS*

B) *AGROMYCES SUBBETICUS*

C) *AMYCOLICICOCCUS SUBFLAVUS*

D) *CORYNEBACTERIUM GLUTAMICUM*

E) *CORYNEBACTERIUM GLYCINIPHILIUM*

F) *KNOELLA AEROLATA*

G) *MYCOBACTERIUM AUSTROAFRICANUM*

H) *MYCOBACTERIUM GILVUM*

I) *MYCOBACTERIUM INDICUS PRANII*

MYCOBACTERIUM INDICUS PRANII DSM 45239 tsm operon.gb FROM 1 TO 5148

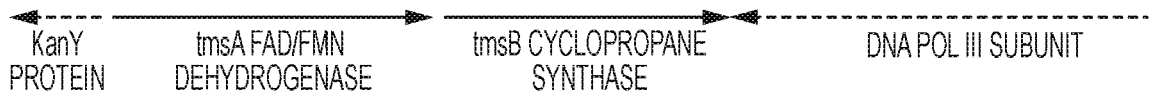

| KanY PROTEIN | tmsA FAD/FMN DEHYDROGENASE | tmsB CYCLOPROPANE SYNTHASE | DNA POL III SUBUNIT |

J) *MYCOBACTERIUM PHLEI*

MYCOBACTERIUM PHLEI tms operon.gb FROM 1 TO 3450

tmsA MPHLEI_RS13765 FAD OXIDASE    tmsB MPHLEI_RS13770 cfa SYNTHASE

K) *MYCOBACTERIUM TUBERCULOSIS*

MYCOBACTERIUM TUBERCULOSIS H37Rv tms operon.gb FROM 1 TO 4777

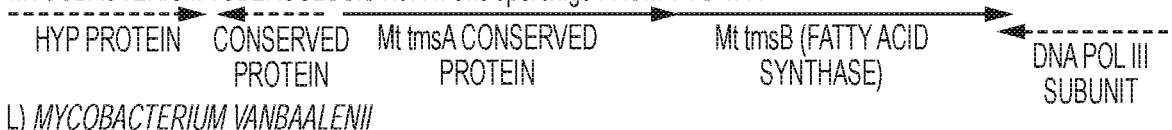

HYP PROTEIN   CONSERVED PROTEIN   Mt tmsA CONSERVED PROTEIN   Mt tmsB (FATTY ACID SYNTHASE)   DNA POL III SUBUNIT

L) *MYCOBACTERIUM VANBAALENII*

MYCOBACTERIUM VANBAALENII tms operon.gb FROM 1 TO 3825

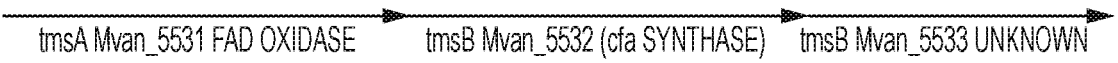

tmsA Mvan_5531 FAD OXIDASE    tmsB Mvan_5532 (cfa SYNTHASE)    tmsB Mvan_5533 UNKNOWN

M) *RHODOCOCCUS OPACUS*

RHODOCOCCUS OPACUS M213 tms operon.gb FROM 1 TO 5276

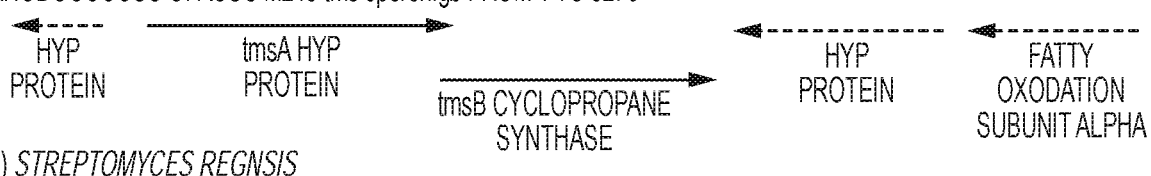

HYP PROTEIN   tmsA HYP PROTEIN   tmsB CYCLOPROPANE SYNTHASE   HYP PROTEIN   FATTY OXODATION SUBUNIT ALPHA

N) *STREPTOMYCES REGNSIS*

STREPTOMYCES REGNSIS tms operon.gb FROM 1 TO 4481

HYP PROTEIN   tmsA FAD-LINKED OXIDASE   tmsB CYCLOPROPANE SYNTHASE   tmsC HYP PROTEIN

O) *THERMOBIFIDE FUSCA*

THERMOBIFIDA FUSCA YX tms operon.gb FROM 1 TO 4401

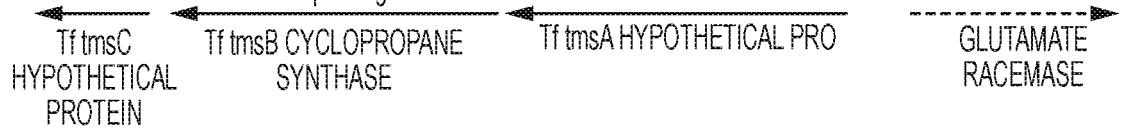

Tf tmsC HYPOTHETICAL PROTEIN   Tf tmsB CYCLOPROPANE SYNTHASE   Tf tmsA HYPOTHETICAL PRO   GLUTAMATE RACEMASE

P) *THERMOMONOSPORA CURVATA*

THERMOMONOSPORA CURVATA DSM 43183 tms operon.gb FROM 1 TO 5044

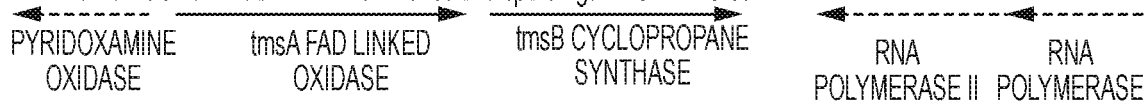

PYRIDOXAMINE OXIDASE   tmsA FAD LINKED OXIDASE   tmsB CYCLOPROPANE SYNTHASE   RNA POLYMERASE II   RNA POLYMERASE

FIG. 3B

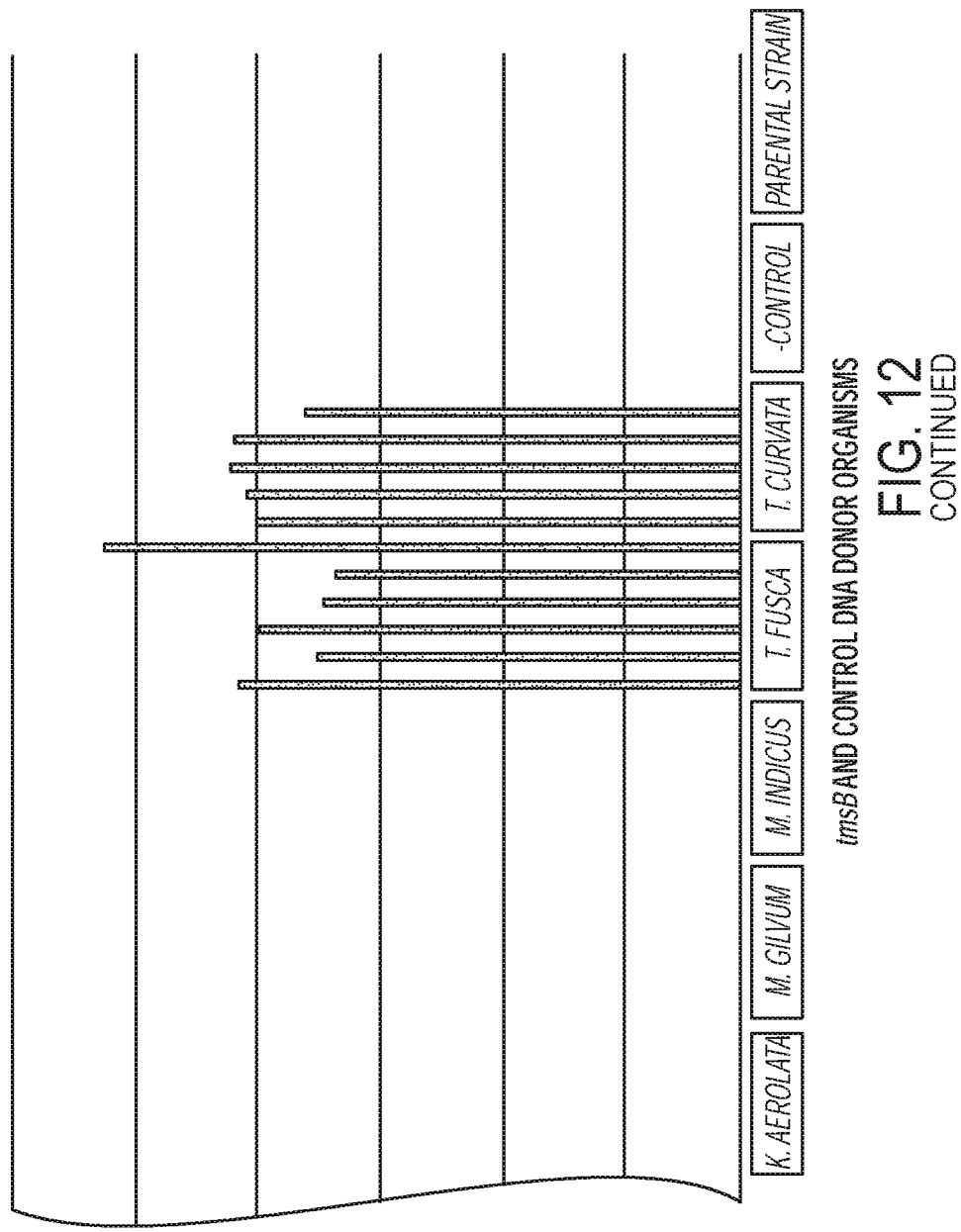

```
Ecoli_cfa       ---------------------MSSS-CIEEVSVPDDNWYRIANELLSRAGIAINGSAPADIRV    41
Cglycini_tmsB   ----------MS--RGFTPLTVGQIVDKVI-TPPAPFRVTAFDGS---TAGPADAELALEI    45
Cglut_tmsB      ----------MSNAVAQDLMTIADIVEATT-TAPIPFHITAFDGS---FTGPEDAPYQLFV    47
Tfus_tmsB       -------------------MRLAEVFERVV-GPDAPVHFRAYDGS---TAGDPRSEVAIVV    38
Tcurv_tmsB      -------------------MTLAKVFEELV-GADAPVELTAYDGS---RAGRLGSDLRVHV    38
Kaero_tmsB      -----------MSHTTDEIRTVADLVDEVV-VGPLPVRVTAYDGS---KTGPDSAPRTIHI    46
Asubflav_tmsB   ----MKAVLTAFTAPQLERMNVAEILSAVL-GRDFPIRFTAYDGS---ALGPETARYGLHL    53
Rop_tmsB        MTTLK------ASRSQDHKLTIAEILETLS-DGMLPLRFSAYDGS---AAGPEDAPYGLHL    51
Mind_tmsB       ---------------------MAEILEVFAATGRHPLKFTAYDGS---IAGNEDAELGLDL    37
Asubb_tmsB      -----------------------MLEIVV-AGRLPLRFTAYDGS---SAGPPDALFGLDL    33
Msmeg_tmsB      MTTFKERE---TSTADRKLTLAEILEIFA-AGKEPLKFTAYDGS---SAGPEDATMGLDL    53
Mvan_tmsB       MTTFRDGAADTGLHGDRKLTLAEVLEVFA-SGRLPLKFTAYDGS---SAGPDDATLGLDL    56
Mgliv_tmsB      MTTFREHTDSSASDPDRKLTLAEVLEIFA-AGRRPLKFTAYDGS---SCGPEDATLGLDL    56
                                    ..        ..    *         :  : :

Ecoli_cfa       KNPDFFK-RVLQEGSLGLGESYMDGWWECDRLDM------------FFSKVLRA------    82
Cglycini_tmsB   TSPDALAYIVTAPGDLGLARAYITGSLRVTGDEPGHPYLVFDHLQHLYDQIRRP--SAKD   103
Cglut_tmsB      ANTDAVSYIATAPGDLGLARAYLMGDLIVEGEHPGHPYGIFDALKEFYRCFKRP--DAST   105
Tfus_tmsB       RHPAAVNYIVQAPGALGLTRAYVAGYLDVE-----GDMYTALRAMADVVF-QDRPRLSPGE    93
Tcurv_tmsB      KSPYAVSYLVHSPSALGLARAYVAGHLDAY-----GDMYTLLREMTQLTE-AL----TPKA    89
Kaero_tmsB      ANQRAVAYLATAPGDLGMARAYTTGDLVVEGVHPGNPYEALVDL-ERVH-FRRP--DPRL   102
Asubflav_tmsB   TTPRGLTYLATAPGDLGLARAYVSGDLEVSGVHQGDPYEIMKILAHDVR-VRRP--SPAT   110
Rop_tmsB        KTTRGTTYLATAPGDLGMARAYVSGDLEARGVHPGDPYEILRVMGDELH-FRRP--SALT   108
Mind_tmsB       RSPRGATYLATAPGELGLARAYVSGDLQAYGVHPGDPYQLLKTLTDRVE-FKRP--PVRV    94
Asubb_tmsB      KTPRGTTYLATGRGDLGLARAYIAGDLEIQGVHPGDPYELLKALADSLV-FKLP--PPRV    90
Msmeg_tmsB      KTPRGTTYLATAPGDLGLARAYVSGDLEPHGVHPGDPYPLLRALAERME-FKRP--PARV   110
Mvan_tmsB       LTPRGTTYLATAPGDLGLARAYVSGDLQLQGVHPGDPYDLLNALVQKLD-FKRP--SARV   113
Mgliv_tmsB      LTPRGTTYLATAPGDLGLARAYIAGDLRLSGVHPGDPHDLLTALTERLE-YRRP--PVRV   113
                   .**:  .:*  *
```

HIGHLIGHTED = ACTIVE SITE BICARBONATE ION BINDING AMINO ACID, CONSERVED IN BOTH TmsB AND E. coli Cfa UNDERLINED = TmsB CONSERVED ONLY, NOT PRESENT IN E. coli Cfa
\* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 19A

```
Ecoli_cfa        ---------GLEN----------QLPH----HFKDTLRIAGARLFNLQSKKRAWIVGKEHYDL   122
Cglycini_tmsB    LLDIARSLKAMG-----AIKVQPAPEQETLPGWKRAILEGL-SRHSPERDKEVVSRHYDV   157
Cglut_tmsB       TLQIMWTLRKMN-----ALKFQEIPPMEQAPAWRKALINGLASRHSKSRDKKAISYHYDV   160
Tfus_tmsB        LLRIIRGIG-----WVKFVNRLPPPPQE-VRQSRLAAL---GWRHSKQRDAEAIQHHYDV   144
Tcurv_tmsB       RLRLLAGVLQDPLLRAAASRRLPPPPQE-VRTGRTS-----WFRHTKRRDAKAISHHYDV   143
Kaero_tmsB       LLDLARIVGPRN------LAPPPPPQEAVPRWRRVAE---GLRHSYGRDSEAIRHHYDV   153
Asubflav_tmsB    IASIMRSLGWER-----LRPVAPPPQENMPRWRRMAL---GLLHSKSRDAAAIHHHYDV   161
Rop_tmsB         LAAITRSLGWDL------LRPIAPPPQEHLPRWRRVAE---GLRHSKSRDAEVIHHHYDV   159
Mind_tmsB        LANVVRSLGFER------LLPVAPPPQEALPRWRRIAD---GLMHTRTRDAEAIHHHYDV   145
Asubb_tmsB       MTQIIRSIGVEH------LRPIAPPPQEVPPRWRRIAE---GLRHSKGRDAEAIHHHYDV   141
Msmeg_tmsB       LANIVRSIGIEH------LKPIAPPPQEALPRWRRIME---GLRHSKTRDAEAIHHHYDV   161
Mvan_tmsB        LAQVVRSIGIEH------LKPIAPPPQEALPRWRRIAE---GLRHSKTRDADAIHHHYDV   164
Mgliv_tmsB       LANVLRSIGIEH------LKPVAPPPQEHLPRWRRIAE---GLRHSKTRDAEAIQHHYDV   164
                                                                 ::  *   .   ***:

Ecoli_cfa        GNDLFSRMLDPFMQYSCAYWKDAD-------------------------NLESAQQAKLK   157
Cglycini_tmsB    GNDFYELFLGDSMAYTCAYYPEFDGENQVTGPTGGWRYDDWEKGPTAMGPLTQAQDNKHR   217
Cglut_tmsB       GNEFYSLFLDDSMTYTCAYYPTPE-------------------------SSLEEAQENKYR  196
Tfus_tmsB        SNAFYALVLGESMTYTCAVYPTEQ-------------------------ATLEQAQFFKHE  180
Tcurv_tmsB       SNTFYEWVLGPSMTYTCACFPTED-------------------------ATLEEAQFHKHD  179
Kaero_tmsB       SNHFYEQVLGPSMTYTCAVFPDHD-------------------------TGLDEAQEEKYR  189
Asubflav_tmsB    SNEFYEHILGPSMTYTCAAYPSAD-------------------------SSLEEAQDNKYR  197
Rop_tmsB         SNTFYEYVLGPSMTYTCACYENAE-------------------------QTLEEAQDNKYR  195
Mind_tmsB        SNTFYELVLGPSNTYTCAVYPDAD-------------------------ATLEQAQENKYR  181
Asubb_tmsB       SNTFYEWVLGPSMTYTCACYPGLD-------------------------ASLDEAQQNKYR  177
Msmeg_tmsB       SNTFYEWVLGPSMTYTCACYPTED-------------------------ATLEEAQDNKYR  197
Mvan_tmsB        SNTFYEWVLGPSMTYTCACYPHPD-------------------------ATLEEAQENKYR  200
Mgliv_tmsB       SNTFYSWVLGPSMTYTCACYPHPD-------------------------ATLEEAQENKYR  200
                   . *  ::  .*.  * *:**  :                              *  .**  *
```

HIGHLIGHTED = ACTIVE SITE BICARBONATE ION BINDING AMINO ACID, CONSERVED IN BOTH TmsB AND E. coli Cfa UNDERLINED = TmsB CONSERVED ONLY, NOT PRESENT IN E. coli Cfa
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 19B

```
Ecoli_cfa        MICEKLQLKPGMRVLDIGCWGGLAHYMASNYDVSVVGVTISAEQQKMAQERCEGLD---    214
Cglycini_tmsB    IVFDKLRLNPGDRLLDVGCWGGMVRYAAR-HGVKAIGVTLSREQYEWGKAKIEEEGLQD    276
Cglut_tmsB       LIFEKLRLKEGDRLLDVGCWGGMVRYAAK-HGVKAIGVTLSEQQYEWGQAEIKRQGLED    255
Tfus_tmsB        LIARKLGLAPGIRLLDVGCWGGMVIHAAREHGVKALGVTLSEEQAEWAQKRIAHEGLGD    240
Tcurv_tmsB       IVAKKLGLRPGMRLLDVGCWGGMVMHAAKHYGVRALGVTLSKQQAEWAQKAIAEAGLSD    239
Kaero_tmsB       IVFEKLALRPGDRLLDIGCWGGMVRYAAR-RGVRALGVTLSGEQAAWAQVAIAREGLGE    248
Asubflav_tmsB    IVFEKLGLKAGDRLLDVGCWGGMVRFAAK-RGVHVIGATLSRKQAEWAQKMIAHEGLGD    256
Rop_tmsB         IVFEKLGLQPGDRLLDIGCWGSMVRYAAR-RGVKVIGATLSREQAEWAQKAIAEEGLSD    254
Mind_tmsB        LIFEKLRLKAGDRLLDVGCWGGMVRYAAR-RGVRATGATLSAEQAKWAQKAIAEEGLAD    240
Asubb_tmsB       IVFEKLRLKPGDRLLDVGCWGGMVRYAAR-HGVQALGVTLSREQTAWAQQAIAVEGLAD    236
Msmeg_tmsB       IVFEKLRLKPGDRLLDVGCWGGMVRYAAR-HGVKALGVTLSREQATWAQKAIAQEGLTD    256
Mvan_tmsB        IVFEKLRLKPGDRLLDVGCWGGMVRYAAR-HGVKAIGVTLSREQAQWARAAIERDGLGD    259
Mgliv_tmsB       IVFEKLRLKPGDRLLDVGCWGGMVRYAAR-HGVKVLGVTLSKEQAQWAADAVERDGLGE    259
                  :  ** *   * *:****:*****.:   *    .*  .* .*.*:* .       .

Ecoli_cfa        -VTILLQDYRDLN-DQFDRIVSVGMFEHVGPKNYDTYFAVVDRNLKPEGIFLHTLGSKK    272
Cglycini_tmsB    LAEVRCMDYRDVPESDFDAVSAIGILEHIGVPNYEDYFTRLFAKLRPGGRMLNHCITRPH    336
Cglut_tmsB       LAEIRFMDYRDVPETGFDAISAIGIIEHIGVNNYPDYFELLSSKLKTGGLMLNHSITYPD    315
Tfus_tmsB        LAEVRHMDYRDLPDGEYDAISSIGLTEHVGKKNVPAYFASLYRKLVPGGRLLNHCITRPR    300
Tcurv_tmsB       LAEVRHQDYRDVTEGDFDAISSIGLTEHIGKANLPSYFGFLYGKLKPGGRLLNHCITRPD    299
Kaero_tmsB       LAAVRHEDYRHVAETGFDAISSIGITEHIGVRNYPTYFDWMLHHVKPGGLVLNHCITRPE    308
Asubflav_tmsB    LAEVRFCDYRDVTEAGFDAVSSIGLTEHIGLANYPSYFGFLKDKLRPGGRLLNHCITRPN    316
Rop_tmsB         LAEVRFSDYRDVPETGFDAISSIGLTEHIGVGNYPAYFGLLQSKLREGGRLLNHCITRPD    314
Mind_tmsB        LAEVRHTDYRDVGEAAFDAVSSIGLTEHIGVKNYPAYFGFLKSKLRTGGLLLNHCITRHD    300
Asubb_tmsB       LAEVRYGDYRDIAEDGFDAVSSIGLLEHIGVRNYASYFGFLQSRLRPGGLLLNHCITRPD    296
Msmeg_tmsB       LAEVRHGDYRDVIESGFDAVSSIGLTEHIGVHNYPAYFNFLKSKLRTGGLLLNHCITRPD    316
Mvan_tmsB        LAEVRHSDYRDVRESQFDAVSSLGLTEHIGVANYPSYFRFLKSKLRPGGLLLNHCITRHN    319
Mgliv_tmsB       LAEVRHGDYRDVRESHFDAVSSLGLTEHIGVANYPSYFRFLKSKLRPGGLLLNHCITRNN    319
                  :   ***.:    :*  :::*: ****  *    **  :  .:   *  * * * *
```

HIGHLIGHTED = ACTIVE SITE BICARBONATE ION BINDING AMINO ACID, CONSERVED IN BOTH TmsB AND *E. coli* Cfa UNDERLINED = TmsB CONSERVED ONLY, NOT PRESENT IN *E. coli* Cfa
\* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 19C

```
Ecoli_cfa       T---DLNVDPWINKYIFPNGCLPSVRQ-IAQSSEPHFVMEDWHNFGADYDTTLMAWYERF   328
Cglycini_tmsB   NRKT--KTGQFIDRYIFPDGELTGSGRIITIMQDTGFDVVHEENLRPHYQRTLHDWCELL   394
Cglut_tmsB      NRPR--HAGAFIDRYIFPDGELTGSGTLIKHMQDNGFEVLHEENLRFDYQRTLHAWCENL   373
Tfus_tmsB       NDLPPFKRGGVINRYVFPDGELEGPGWLQAAMNDAGFEIRHQENLREHYARTLRDWLANL   360
Tcurv_tmsB      NTQPAMKKDGFINRYVFPDGELEGPGYLQTQMNDAGFEIRHQENLREHYARTLAGWCRNL   359
Kaero_tmsB      NRAK--SVGRFIDRYIFPDGELTGSGRIITTMQDNGFEVVHSENLREHYALTLAAWGENL   366
Asubflav_tmsB   NLQSN-RAGDFIDRYVFPDGELAGPGFIISAVHDAGFEVRHEENLREHYALTLRDWNRNL   375
Rop_tmsB        NQSQA-RAGGFIDRYVFPDGELTGSGRIITEIQNVGLEVRHEENLREHYALTLAGWCQNL   373
Mind_tmsB       NTSTS-FAGGFTDRYVFPDGELTGSGRITCDVQDCGFEVLHAENFRHHYANTLRDWCRNL   359
Asubb_tmsB      NRSEP-SARGFIDRYVFPDGELTGSGRIITEAQDVGFEVLHEENLRQHYALTLRDWCANL   355
Msmeg_tmsB      NRSAP-SAGGFIDRYVFPDGELTGSGRIITEAQDVGLEVIHEENLRNHYAMTLRDWCRNL   375
Mvan_tmsB       NRTGP-AAGGFIDRYVFPDGELTGSGRIITEIQDVGLEVMHEENLRRHYALTLRDWCRNL   378
Mgliv_tmsB      NRSHA-TAGGFIDRYVFPDGELTGSGRIITEMQDVGLEVVHEENLRHHYALTLRDWSRNL   378
                     . ::*:**:* *    :  : ,.*: .*  ** *   :

Ecoli_cfa       LAAWPEIADNYSERFKRMFTYYLNACAGAFRARDIQLWQVVFSRGVENGLRVAR------   382
Cglycini_tmsB   ATNWDQAVHLVGEETARLFGLYMAGSEWGFEHNVIQLHQVLGVKPDAAGSSG-VPVRQWWRS---   455
Cglut_tmsB      KENWEEAVELAGEPTARLFGLYMAGSEWGFAHNIVQLHQVLGVKLDEQGSRGEVPERMWWTI---   435
Tfus_tmsB       DRNWDAAVREVGEGTARVWRLYMAGCVLGFERNVVQLHQILGVKLDG-TE-ARMPLRPDFEPPLP 423
Tcurv_tmsB      DEHWDEAVAEVGEGTARVWRLYMAGSRLGFELNWIQLHQILGVKLGERGE-SRMPLRPDWGV--- 420
Kaero_tmsB      VEHWASCVADVGEGTAKVWGLYLAGSRRGFERNVVQLHQVLAARPVPSRL-PQVPLRQWWTS--- 427
Asubflav_tmsB   ARDWDACVHASDEGTARVWGLYISGSRVAFETNSIQLHQVLAVKTARNGE-AQVPLGQWWTR--- 436
Rop_tmsB        VDNWDACVAEVGEGTARVWGLYMAGSRLGFERNVVQLHQVLAVKLGPKGE-AHVPLRPWWK---- 433
Mind_tmsB       VENWDAAVSEVGLPTAKVWGLYMAASRVAFEQNNLQLHHVLAAKTDARGD-DDLPLRPWWTA--- 420
Asubb_tmsB      VAHWEEAVAEVGLPTAKVWGLYMAGSRLAFESGGIQLHQVLAVRPDDRSDAAQLPLRPWWTP--- 417
Msmeg_tmsB      VEHWDEAVEEVGLPTAKVWGLYMAGSRLGFETNVVQLHQVLAVKLDDQGKDGGLPLRPWWSA--- 437
Mvan_tmsB       VQHWDEAVAEVGLPTAKVWGLYMAASRVGFEQNSIQLHQVLAVKLDERGGDGGLPLRPWWTA--- 440
Mgliv_tmsB      VAHWDDAVTEVGLPTAKVWGLYIAASRVGFEQNAIQLHQVLSVKLDERGSDGGLPLRPWWNA--- 440
                  *  .  . ::: *: .. .*  :** ::: :
```

HIGHLIGHTED = ACTIVE SITE BICARBONATE ION BINDING AMINO ACID, CONSERVED IN BOTH TmsB AND *E. coli* Cfa UNDERLINED = TmsB CONSERVED ONLY, NOT PRESENT IN *E. coli* Cfa
\* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 19D

```
Eco_GlcD        MSILYEE-----RLDGALPDV--------DRTSVLMALREHVPGLEILHTDEEIIPYECD  47
Cglycini_tmsA   --------------VTVAGRITDAVRIGNGLDQRDLAPVGWYAHEQAVARLKASFDAVPAGRR  49
Cglut_tmsA      MSGLVDPDSTFLKTIGKLSNSLSIGRGVDQKEVIPKGWNAHWEAITKLKRSFDAIPAGER  60
Kaero_tmsA      -----------------------------MSMDRTGPARVRTVGERRLLESFAAVPPGER  31
Asubflav_tmsA   -----------------------------MTPEASAAAHAAAVDRLIHSYRAIPDDAP  29
Rop_tmsA        MREGGRPFRAH------------------RTLPVTGIDAHRAGVERLLASYRAIPTDAT  41
Asubb_tmsA      -----------------------------VSAPATDARTAHADGVERLLESYRAVPAAAS  31
Mind_tmsA       MHGLLSKTRVY------------------VVPVLGSALSAHKSGVDRLLASYRSIPATSA  42
Msmeg_tmsA      -----------------------------VSVVTTDAQAAHAAGVSRLLASYRIPPSAT  31
Mvan_tmsA       -----------------------------VSVPSTDARSAHADGVQRLLASYRAIPQDAT  31
Mgilv_tmsA      -----------------------------VSVAVTDARSAYAHGVQRLVASYRAIPAGAT  31
Tcurv_tmsA      -----------------------------MSQLAVTDHHERAVEALRRSYAAIPPGTP  29
Tfus_tmsA       -----------V----------------NCQSSASNLANHINAVYELRRAYARLSADKP  32
                                                     .      *    :

Eco_GlcD        GLSAYRTRPLLVVLPKQMEQVTAILAVCHRLRVPVVTRGAGTGLSGGALPLEKGVLLVMA 107
Cglycini_tmsA   -------------VRLAKKT----------SNLFRGRSG-EAV---------------GLDVS  73
Cglut_tmsA      -------------VRLAKKT----------SNLFRGRSD-AGH---------------GLDVA  84
Kaero_tmsA      -------------VRLAKRT----------SNLFRAREGTSTR--------------GLDTS  56
Asubflav_tmsA   -------------VRLAKKT----------SNLFRHREKTSAP--------------GLDVS  54
Rop_tmsA        -------------VRLAKKT----------SNLFRARAQTSAP--------------GLDVS  66
Asubb_tmsA      -------------VRLAKRT----------SNLFRSRAATDAP--------------GLDTS  56
Mind_tmsA       -------------VRLAKPT----------SNLFRARTKRDAP--------------GLDTS  67
Msmeg_tmsA      -------------VRLAKPT----------SNLFRARARTNVK--------------GLDVS  56
Mvan_tmsA       -------------VRLAKPT----------SNLFRARAKTRTK--------------GLDTS  56
Mgilv_tmsA      -------------VRLAKPT----------SNLFRARAKSTAA--------------GLDTS  56
Tcurv_tmsA      -------------VRLAKQT----------SNLFRFREPTAAP--------------GLDVS  54
Tfus_tmsA       -------------VRLAKTT----------SNLFRFRSRDDAA--------------RLDVS  57
                             ^ ^               ^^^^ ^                    ^
                             * * *            .: :*                   *  :
```

^ = CONSERVED IN TmsA SEQUENCE BUT NOT *E. coli* GlcD SEQUENCE
\* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20A

```
Eco_GlcD         RFKEILDINPVGRRARVQPGVRNLAISQAVAPHNLYYAPDPSSQIACSIGGNVAENAGGV  167
Cglycini_tmsA    GLHGVIAVDPVEGTADVQGMCTYEDLVDVLLPYGLAPTVVPQ-LKTITLGGAVTGMGVES  132
Cglut_tmsA       ALGGVIAIDPVNATADVQGMCTYEDLVDATLSYGLMPLVVPQ-LKTITLGGAVTGMGVES  143
Kaero_tmsA       GLTGVRVVDAGTLTADVDGMCTYEDLVAATLPLGLAPLVVPQ-LRTITVGGAVTGLGIES  115
Asubflav_tmsA    GLARVIGIDSDTRTADVGGMCTYEDLVAATLEYDLVPLVVPQ-LKTITLGGAVTGLGIES  113
Rop_tmsA         GLGGVISVDEQDRTADVAGMCTYEDLVDATLPYGLAPLVVPQ-LKTITLGGAVTGLGIES  125
Asubb_tmsA       GLTHVIAVDPGARTADVAGMCTYDDLVAATLPHGLAPLVVPQ-LKTITLGGAVTGLGIES  115
Mind_tmsA        GLTGVLSVDPETRTADVAGMCTYADLVAATLPYGLSPLVVPQ-LKTITLGGAVSGLGIES  126
Msmeg_tmsA       GLTGVIGVDPDARTADVAGMCTYEDLVAATLPYGLAPLVVPQ-LKTITLGGAVTGLGIES  115
Mvan_tmsA        GLTNVIAVDAEARTADVAGMCTYEDLVAATLPHGLSPLVVPQ-LKTITLGGAVTGLGIES  115
Mgilv_tmsA       GLTHVIAVDPETRTAEVAGMCTYEDLVAATLPHGLSPLVVPQ-LKTITLGGAVTGLGIES  115
Tcurv_tmsA       GFNRVLAVDPDARTADVQGMTTYEDLVDATLPHGLMPLVVPQ-LKTITLGGAVTGLGIES  113
Tfus_tmsA        AFTSVISIDTEARVAEVGGMTTYEDLVAATLRHGLMPPVVPQ-LRTITLGGAVTGLGIES  116
                 ^  ^         ^^ ^^ ^^^   ^        ^ ^^ ^ ^ ^^^    ^   ^  ^^
                   :   ::     * *       :  . .*    *.    : ::** *:   .

Eco_GlcD         HCLKYGLTVHNLLKIEVQTLDGEALTLGSDALDSPGFDLLALFTGSEGMLGVTTEVTVKL  227
Cglycini_tmsA    TSFRNGLPHEAVLEMDVLTGTGDILTCSPT----QNTDLYRGFPNSYGSLGYSVRLKVRC  188
Cglut_tmsA       TSFRNGLPHESVLEMDIFTGTGEIVTCSPT----ENVDLYRGFPNSYGSLGYAVRLKIEL  199
Kaero_tmsA       TSFRNGLPHESVLEMDVLTGAGEIVTATAD---NEHADLFRGFPNSYGSLGYATCLRIEL  172
Asubflav_tmsA    TSFRNGLPHESVLEMDILTGAGEVVTAGPE---GPHSDLYWGFPNSYGTLGYATRLRIEL  170
Rop_tmsA         TSFRNGLPHESVLEIDVLTGSGDIVTARPE---GENSDLFWGFPNSYGTLGYSTRLRIQL  182
Asubb_tmsA       TSFRNGLPHESVLEIDVLTGAGEIITASPI----EHAELFRAFPNSYGTLGYAVRLRIEL  171
Mind_tmsA        ASFRNGLPHESVLEMDILTGAGDLLTASRT----QHPDLFRAFPNSYGTLGYSTRLRIEL  182
Msmeg_tmsA       TSFRNGLPHESVLEMDILTGSGEIVTASPD----QHSDLFHAFPNSYGTLGYSTRLRIEL  171
Mvan_tmsA        ASFRNGLPHESVLEMDVLTGTGDVVRASPD----ENPDLFRAFPNSYGTLGYSVRLKIEL  171
Mgilv_tmsA       ASFRNGLPHESVLEMDILTGTGDIVRAAPD----ENPDLFRTFPNSYGTLGYSVRLKIEL  171
Tcurv_tmsA       TSFRNGLPHESVLEMQIITGAGEVVTATPD---GEHSDLFWGFPNSYGTLGYALKLKIEL  170
Tfus_tmsA        SSFRNGLPHESVEEMEILTGSGQVVVARRD---NEHRDLFYGFPNSYGTLGYALRLRIQL  173
                 ^^^^ ^^^ ^ ^      ^                         ^^ ^    ^    ^
                 .::  **  , :  ::::: *  *:  :                :*    *.* ** ;  : :.
```

^ = CONSERVED IN TmsA SEQUENCE BUT NOT E. coli GlcD SEQUENCE
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20B

```
Eco_GlcD         LPKPPVARVLLASFDSVEKAGLAVGDIIANGIIPGG-LEMMDNLSIRAAEDFIHAGYPVD    286
Cglycini_tmsA    ERVEPYVDLRHVRFDDVQSLTDALDNIVVDKEYEGERVDYLDGVVFSLEESYLVLGRATS    248
Cglut_tmsA       EPVQDYVQLRHVRFNDLESLTKAIEEVASSLEFDNQPVDYLDGVVFSPTEAYLVLGTQTS    259
Kaero_tmsA       ERVGTCVEVRHVRFHDLDALCAAIAEVVATRSHEGEEVDHVDGVVFSRDEAYLTLGRHSD    232
Asubflav_tmsA    EPVEPYVELRHLRFTSLDELQETLDTVSYEHTYDGEPVHYVDGVMFSATESYLTLGRQTS    230
Rop_tmsA         EPVKRYVALRHLRFDSLDELQSAMDRIVTERVHDGIPVDYLDGVVFTASESYLTLGHQTD    242
Asubb_tmsA       EPVEPFVALTHLRFHALTDLIEAMERIIETGRLDGVAVDSLDGVVFSAEESYLCVGTQTA    231
Mind_tmsA        EPVAPFVALRHIRFRSLPALIAAAERIVDTGGQGGTPVDYLDGVVFSADESYLCVGRRTT    242
Msmeg_tmsA       EPVHPFVALRHLRFHSITDLVAAMDRIIETGGLDGEPVDYLDGVVFSATESYLCVGFKTK    231
Mvan_tmsA        EPVKPFVALRHLRFHSISALIEAMDRIVETGGLNGEPVDYLDGVVFSAEESYLCVGQRSA    231
Mgilv_tmsA       EPVKPFVALRHLRFHSLSTLIATMDRIVDTGSLDGEQVDYLDGVVFSAEESYLCVGTRSA    231
Tcurv_tmsA       EPVKPYVRLRHLRFDDAGECAAKLAELSESREHEGDEVHFLDGTFFGPREMYLTLGTFTD    230
Tfus_tmsA        EPVRPYVHLRHLRFTDAAAMAALEQICADRTHDGETVDFVDGVVFARNELYLTLGTFTD    233
                        ^ ^    ^  ^ ^                      ^   ^   ^    ^^
                       . :    *              :     . :. :*.  :   * ::   *

Eco_GlcD         AEAILLCELDGV---ESDVQEDCE----------RVNDILLKAGATDVRLAQDEAERVRF    333
Cglycini_tmsA    EAGPV-SDYTRERSYYRSLQHPSG----VLRDKLTIRDYLWR------------WDVDWF    291
Cglut_tmsA       QPGPT-SDYTRDLSYYRSLQHPEG----ITYDRLTIRDYIWR------------WDTDWF    302
Kaero_tmsA       RTGPT-SDYTGQQVYYRSIQHDGPS---PRRDLLTTHDYLWR------------WDTDWF    276
Asubflav_tmsA    EPGPV-SDYTGNQIYYRSIQHGGA--ETPVVDRMTIHDYLWR------------WDTDWF    275
Rop_tmsA         EGGPV-SDYTGQNIFYRSIQHSSV--NHPKTDKLTIRDYLWR------------WDTDWF    287
Asubb_tmsA       ASGPV-SDYTRQQIFYRSIQHD----DGAKHDRLTMHDYLWR------------WDADWF    274
Mind_tmsA        TPGPV-SDYTGKDIYYQSIRHDAPGLEATKDDRLTMHDYFWR------------WDTDWF    289
Msmeg_tmsA       TPGPV-SDYTGQQIFYRSIQHDGDT-GAEKHDRLTIHDYLWR------------WDTDWF    277
Mvan_tmsA        TPGPV-SDYTGKQIYYRSIQHDGPTDGAEKHDRLTIHDYLWR------------WDTDWF    278
Mgilv_tmsA       TPGPV-SDYTGEHIFYRSIQHDCPTEGGQKHDRLTAHDYFWR------------WDTDWF    278
Tcurv_tmsA       TAPYV-SDYTGQHIYYRSIQQ-------RSIDFLTIRDYLWR------------WDTDWF    270
Tfus_tmsA        RAPWT-SDYTGTDIYYRSIPRYAG---PGPGDYLTTHDYLWR------------WDTDWF    277
                      ^^^^   ^ ^             ^  ^  ^ ^^         ^^ ^^
                      . :       .: .             .* : :          : *
```

^ = CONSERVED IN TmsA SEQUENCE BUT NOT *E. coli* GlcD SEQUENCE  
\* = SINGLE, FULLY CONSERVED RESIDUE IN ALL SEQUENCES  
: = AMINO ACIDS WITH STRONGLY SIMILAR PROPERTIES  
. = AMINO ACIDS WITH WEAKLY SIMILAR PROPERTIES

FIG. 20C

```
Eco_GlcD        WAGRKNA--FPAVGRISP-------DYYCMDGTIPRRALPGVLEGI------ARLSQQYD 378
Cglycini_tmsA   WCNRAFGTQNPTIRTLWPRDLLRSSFYWKIIGWDRRFDIADRIEAHNGRPARERVVQDIE 351
Cglut_tmsA      WCSRAFGTQNPVVRKLWPRDLLRSSFYWKIIGWDRKYSIADRLEERKGRPARERVVQDVE 362
Kaero_tmsA      WCSRAFGAQDPRVRRWWPRRWRRSSVYWRLVAADRRVGFSDRLEARRGNPPRERVVQDVE 336
Asubflav_tmsA   WCSRAFGTQHPVVRRFWPRRYRRSSFYWKLIALDRQVGLADFIEQRKGNLPRERVVQDIE 335
Rop_tmsA        WCSRAFGAQNPTIRRLWPKNLLRSSFYWKLIALDHKYDIGDRLEKRKGNPPRERVVQDVE 347
Asubb_tmsA      WCSQAFGAQHPLIRRFWPRRYRRSRSYSTLMRLERRFDLGDRLEKLKGRPARERVIQDVE 334
Mind_tmsA       WCSRAFGVQDPRVRRFWPRRYRRSSFYWKLISLDRRFGISDRIEARNGRPPRERVVQDIE 349
Msmeg_tmsA      WCSRAFGAQHPVIRRFWPRRLRSSFYWKLVAYDQRYDIADRIEKRNGRPPRERVVQDVE 337
Mvan_tmsA       WCSRAFGAQNPRIRRWWPRRYRRSSVYWKLIGYDRRFGIADRIEKRNGRPPRERVVQDIE 338
Mgilv_tmsA      WCSRAFGAQNPKVRRWWPRRLRRSSFYWKLVGYDQRFGIADRIEKHHGRPPRERVVQDVE 338
Tcurv_tmsA      WCSRALGVQNPLIRRVWPKSAKRSDVYRKLVAYEKRYQFKARIDRWTGKPPREDVIQDIE 330
Tfus_tmsA       WCSRAFGLQHPVVRRLWPRSLKRSDVYRKLVAWDRRTDASRLLDYYRGRPPKEPVIQDIE 337
                 ^ ^ ^ ^   ^ ^  ^^                       ^    ^ ^ ^ ^
                *..:  .   *  :  *        *  :    :    ::      : *: :

Eco_GlcD        LRVANV-----FHAGDGNMHPLILF-----DANEPGEFA----RA--------EELGG-- 414
Cglycini_tmsA   VTPDNLPEFLTWFFTHCEIEPVWLCPIRLADDS-----------------GERTPWPL 392
Cglut_tmsA      VTIDKLPEFLKWFFESSDIEPLWLCPIKLREVPGSSVGAGEILSSAEAIDSGAAEHPWPL 422
Kaero_tmsA      IPLGQTAAFLHWFLDEVPIEPIWLCPLRLRDH---------------------QRWPL 373
Asubflav_tmsA   VPIENTASFLRWFLANVPIEPVWLCPLRLRKTRSPGLP----------SPTSPASRPWPL 385
Rop_tmsA        VPIERTADFVRWFLDEIPIEPLWLCPLRLREPAPAGA------------SSQRPWPL 392
Asubb_tmsA      VPIGRTVGFLEWFLANVPIEPIWLCPLRLRGD----------------------RGWPL 371
Mind_tmsA       IPIERTCDFLEWFLDNVPITPIWLCPLRLRDR----------------------DGWPL 386
Msmeg_tmsA      VPIERCADFVEWFLQNVPIEPIWLCPLRLRDSADGG------------------ASWPL 378
Mvan_tmsA       VPIERTVEFLQWFLDTVPIEPIWLCPLRLRDD----------------------RDWPL 375
Mgilv_tmsA      VPIERTVEFLQWFLDTIPIEPLWLCPLRLRDD----------------------NSWSL 375
Tcurv_tmsA      VPAERLPEFLEFFHDKIGMSPVWLCPLRAR------------------------HRWPL 365
Tfus_tmsA       VEVGRAAEFLDFFHTEIGMSPVWLCPLRLREDTAD----------------DTEPVWPL 380
                  ^  ^       ^ ^^                                    ^ ^
                :  .       :.    :*: *
```

^ = CONSERVED IN TmsA SEQUENCE BUT NOT E. coli GlcD SEQUENCE
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20D

```
Eco_GlcD        ---KILELCVEVG--GSIS-------GEHGIGREKINQMC------------AQFNSDE-     449
Cglycini_tmsA   YPLSPGDTWVNVGFWSSVPADLMGKDAPTGAFNREVERVVSDLGGHKSLYSEAFYSEEQF    452
Cglut_tmsA      YPLKKDVLWVNIGFWSSVPVDLMGSDAPEGAFNREIERVMAELGGHKSLYSEAFYTREDF    482
Kaero_tmsA      YPLEPGRTYVNVGFWSTVPGP--GPGEELGATNRAIERRVDEVGGHKSLYSDSYYSRSDF    431
Asubflav_tmsA   YPLEPQRTYVNVGFWSAVPV---VAGQPEGHTNRMIENEVDRLDGHKSLYSDAFYERKEF    442
Rop_tmsA        YPLEPKRTYVNIGFWSSVPI---VPGRPEGAANRLIEDKVSDFDGHKSLYSDSYYSREDF    449
Asubb_tmsA      YPIRPQQTYVNIGFWSTVPV---G--GSEGETNRSIERAVSEFDGHKSLYSDSYYSREEF    426
Mind_tmsA       YPMRPDHTYVNVGFWSSVPG---G--ATEGAANRMIEEKVSELDGHKSLYSDSFYSREDF    441
Msmeg_tmsA      YPLKAHHTYVNIGFWSSVPV---G--PEEGHTNRLIEKKVAELDGHKSLYSDAYYTRDEF    433
Mvan_tmsA       YPIRPHHTYVNVGFWSSVPV---G--PEEGYTNRMIERKVSDLDGHKSLYSDAYYSPEEF    430
Mgilv_tmsA      YPLRPHRTYVNVGFWSSVPV---G--PEEGHTNKLIERRISELEGHKSLYSDAFYSADEF    430
Tcurv_tmsA      YPLKPGVTYVNAGFWGTVPL---QPGQMPEYHNRLIERKVAQLDGHKSLYSTAFYSREEF    422
Tfus_tmsA       YPLKPRRLYVNFGFWGLVPI---RPGGGRTYHNRLIEKEVTRLGGHKSLYSDAFYDEDEF    437
                ^^         ^  ^^  ^^                ^  ^     ^^^^^^^  ^    ^
                *: *    . :                      .. ::        : :   .:

Eco_GlcD        ------ITTFHAVKAAFDPDGLLNPGKNIPTLHRCAEFGAMHVHHGHLPFPELERF       227
Cglycini_tmsA   AAL-YGGERPAQLKAVFDPDDRFPGLYEKTVGGV---------------------       188
Cglut_tmsA      EKL-YGGTIPALLKKQWDPHSRFPGLYEKTVKGA---------------------       199
Kaero_tmsA      DAL-YGGDAYAVLKATYDPDGRFPHLYDKAVRHA---------------------       172
Asubflav_tmsA   DAL-YGGDTYRELKETYDPNSRLLDLYAKAVQGR---------------------       170
Rop_tmsA        ERLYYGGDRYTELKKRYDPKSRLLDLFSKAVQRR---------------------       182
Asubb_tmsA      EEL-YGGEAYRAVKRRYDPDSRLLDLYAKAVQRR---------------------       171
Mind_tmsA       DEL-YGGETYNTVKKTYDPDSRLLDLYAKAVQRR---------------------       182
Msmeg_tmsA      DEL-YGGEVYNTVKKTYDPDSRLLDLYSKAVQRQ---------------------       171
Mvan_tmsA       DSL-YGGETYKTVKKTYDPDSRFLDLYGKAVGRQ---------------------       171
Mgilv_tmsA      DAL-YGGEIYRTVKKTYDPDSRFLDLYAKAVRRQ---------------------       171
Tcurv_tmsA      WRH-YDGETYRRLKDTYDPDARLLDLYDKCVRGR---------------------       170
Tfus_tmsA       WEL-YNGEIYRKLKAAYDPDGRLLDLYTKCVGGG---------------------       173
                    ^ ^         ^    ^   ^
                :*   :**. :            .
```

^ = CONSERVED IN TmsA SEQUENCE BUT NOT E. coli GlcD SEQUENCE
\* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20E

SEQUENCE LISTING

```
<160> NUMBER OF SEQ ID NOS: 98

<210> SEQ ID NO 1
<211> LENGTH: 1401
<212> TYPE: DNA
<213> ORGANISM: Mycobacterium smegmatis

<400> SEQUENCE: 1
gtgtctgtgg ttactactga cgcacaggct gcccatgccg ccggcgtctc gcgtcttctg      60
gccagctacc gggcgatccc gcccagcgcg acagtgcgcc ttgcgaaacc gacgtccaac     120
ctgttccgcg cccgcgcccg caccaatgtg aagggtctcg acgtctcggg cctgaccggt     180
gtgatcggtg tcgacccgga cgcgcgcacc gccgatgtgg cgggcatgtg cacctacgag     240
```

```
gacctggtgg cggccacgct tccgtacggc cttgccccac tggtggtgcc gcagctcaag    300
accatcacgc tcggtggcgc ggtcaccggt ctgggcatcg agtccacgtc gttccgcaac    360
ggtctgccgc acgaaagtgt cctggagatg gacatcttga ccggttcggg cgagatcgtc    420
acggcctcac cggatcagca ctcggatctg ttccatgcgt tccccaattc atatggaacc    480
cttggttatt ccacccggct gcgcatcgaa ctggagcccg tgcacccgtt tgtggcgttg    540
cgccacctgc gctttcactc gatcaccgat ctggtcgcgg cgatggaccg gatcatcgag    600
accggcgggc tggacggtga acccgtcgac tacctcgacg gcgtggtgtt cagcgcgact    660
gagagttacc tgtgtgttgg cttcaagacg aaaacgccgg ggccggtcag cgattacaca    720
ggtcagcaga tcttctaccg gtcgatccag catgacggcg acaccggcgc cgagaaacac    780
gaccggctga ccatccacga ctacctgtgg cgctgggaca ccgactggtt ctggtgctca    840
cgggcattcg gcgctcagca tccggtgatc cgcaggttct ggccgcggcg gctgcgccgc    900
agcagcttct actggaagct ggtggcctac gaccagcggt acgacatcgc cgaccgtatc    960
gagaagcgca acgggcgccc gccgcgcgag cgggtggtcc aggacgtcga ggtgcccatc   1020
gagcggtgcg cggacttcgt cgagtggttc ctgcagaatg tgccgatcga gccgatctgg   1080
ctgtgccccc tacggttgcg tgacagcgcc gacggcggtg cctcgtggcc cctgtatccg   1140
ctgaaggcgc accacaccta cgtcaacatc ggtttctggt catcagtgcc ggtgggcccc   1200
gaggagggcc acaccaaccg cctcatcgag aaaaaagtcg cggagctgga cgggcacaaa   1260
tctttgtact cggacgctta ttacacacgt gacgaattcg acgagctgta cggcggtgag   1320
gtctacaaca ccgtcaagaa gacgtacgac ccggattcac gtctgctaga cctgtattcg   1380
aaggcggtgc aaagacaatg a                                             1401
```

<210> SEQ ID NO 2
<211> LENGTH: 466
<212> TYPE: PRT
<213> ORGANISM: Mycobacterium smegmatis

<400> SEQUENCE: 2

```
Val Ser Val Val Thr Thr Asp Ala Gln Ala Ala His Ala Ala Gly Val
1               5                   10                  15

Ser Arg Leu Leu Ala Ser Tyr Arg Ala Ile Pro Pro Ser Ala Thr Val
                20                  25                  30

Arg Leu Ala Lys Pro Thr Ser Asn Leu Phe Arg Ala Arg Ala Arg Thr
            35                  40                  45

Asn Val Lys Gly Leu Asp Val Ser Gly Leu Thr Gly Val Ile Gly Val
        50                  55                  60

Asp Pro Asp Ala Arg Thr Ala Asp Val Ala Gly Met Cys Thr Tyr Glu
65                  70                  75                  80

Asp Leu Val Ala Ala Thr Leu Pro Tyr Gly Leu Ala Pro Leu Val Val
                85                  90                  95

Pro Gln Leu Lys Thr Ile Thr Leu Gly Gly Ala Val Thr Gly Leu Gly
                100                 105                 110

Ile Glu Ser Thr Ser Phe Arg Asn Gly Leu Pro His Glu Ser Val Leu
            115                 120                 125

Glu Met Asp Ile Leu Thr Gly Ser Gly Glu Ile Val Thr Ala Ser Pro
        130                 135                 140

Asp Gln His Ser Asp Leu Phe His Ala Phe Pro Asn Ser Tyr Gly Thr
145                 150                 155                 160

Leu Gly Tyr Ser Thr Arg Leu Arg Ile Glu Leu Glu Pro Val His Pro
```

```
                165                 170                 175
Phe Val Ala Leu Arg His Leu Arg Phe His Ser Ile Thr Asp Leu Val
            180                 185                 190

Ala Ala Met Asp Arg Ile Ile Glu Thr Gly Gly Leu Asp Gly Glu Pro
        195                 200                 205

Val Asp Tyr Leu Asp Gly Val Val Phe Ser Ala Thr Glu Ser Tyr Leu
    210                 215                 220

Cys Val Gly Phe Lys Thr Lys Thr Pro Gly Pro Val Ser Asp Tyr Thr
225                 230                 235                 240

Gly Gln Gln Ile Phe Tyr Arg Ser Ile Gln His Asp Gly Asp Thr Gly
                245                 250                 255

Ala Glu Lys His Asp Arg Leu Thr Ile His Asp Tyr Leu Trp Arg Trp
            260                 265                 270

Asp Thr Asp Trp Phe Trp Cys Ser Arg Ala Phe Gly Ala Gln His Pro
        275                 280                 285

Val Ile Arg Arg Phe Trp Pro Arg Arg Leu Arg Arg Ser Ser Phe Tyr
    290                 295                 300

Trp Lys Leu Val Ala Tyr Asp Gln Arg Tyr Asp Ile Ala Asp Arg Ile
305                 310                 315                 320

Glu Lys Arg Asn Gly Arg Pro Pro Arg Glu Arg Val Val Gln Asp Val
                325                 330                 335

Glu Val Pro Ile Glu Arg Cys Ala Asp Phe Val Glu Trp Phe Leu Gln
            340                 345                 350

Asn Val Pro Ile Glu Pro Ile Trp Leu Cys Pro Leu Arg Leu Arg Asp
        355                 360                 365

Ser Ala Asp Gly Gly Ala Ser Trp Pro Leu Tyr Pro Leu Lys Ala His
    370                 375                 380

His Thr Tyr Val Asn Ile Gly Phe Trp Ser Ser Val Pro Val Gly Pro
385                 390                 395                 400

Glu Glu Gly His Thr Asn Arg Leu Ile Glu Lys Val Ala Glu Leu
                405                 410                 415

Asp Gly His Lys Ser Leu Tyr Ser Asp Ala Tyr Tyr Thr Arg Asp Glu
            420                 425                 430

Phe Asp Glu Leu Tyr Gly Gly Glu Val Tyr Asn Thr Val Lys Lys Thr
        435                 440                 445

Tyr Asp Pro Asp Ser Arg Leu Leu Asp Leu Tyr Ser Lys Ala Val Gln
    450                 455                 460

Arg Gln
465

<210> SEQ ID NO 3
<211> LENGTH: 1314
<212> TYPE: DNA
<213> ORGANISM: Mycobacterium smegmatis

<400> SEQUENCE: 3
atgaccacat tcaaagaacg cgagacgtcc acagcggacc gcaagctcac cctggccgag    60
atcctcgaga tcttcgccgc gggtaaggag ccgctgaagt tcactgcgta cgacggcagc   120
tcggccggtc ccgaggacgc cacgatgggt ctggacctca agaccccgcg tgggaccacc   180
tatctggcca cggcacccgg cgatctgggc ctggcccgtg cgtatgtctc cggtgaccng   240
gagccgcacg cgtgcatcc cggcgatccc taccgctgc tgcgcgccct ggccgaacgc   300
atggagttca agcgcccgcc tgcgcgtgtg ctggcgaaca tcgtgcgctc catcggcatc   360
```

```
gagcacctca agccgatcgc accgccgccg caggaggcgc tgccccggtg gcgccgcatc    420
atggagggcc tgcggcacag caagacccgc gacgccgagg ccatccacca ccactacgac    480
gtgtcgaaca cgttctacga gtgggtgctg ggcccgtcga tgacctacac gtgcgcgtgc    540
taccccaccg aggacgcgac cctcgaagag gcccaggaca acaagtaccg cctggtgttc    600
gagaagctgc gcctgaagcc cggtgaccgg ttgctcgacg tgggctgcgg ctggggcggc    660
atggtccgct acgcggcccg ccacggcgtc aaggcgctcg tgtcacgct cagccgcgaa    720 caggcgacgt gggcgcagaa ggccatcgcc caggaaggtc tcaccgatct ggccgaggtg    780
cgtcacggtg attaccgcga cgtcatcgaa tccgggttcg acgcggtgtc ctcgatcggg    840
ctgaccgagc acatcggcgt gcacaactac ccggcgtact tcaacttcct caagtcgaag    900
ctgcgcaccg gtggcctgct gctcaaccac tgcatcaccc gcccggacaa ccggtcggcg    960
ccatcggccg gcgggttcat cgacaggtac gtgttccccg acggggagct caccggctcg   1020
ggccgcatca tcaccgaggc ccaggacgtg gccttgagg tgatccacga ggagaaccta   1080
cgcaatcact atgcgatgac gctgcgcgac tggtgccgca acctggtcga gcactgggac   1140
gaggcggtcg aagaggtcgg gctgcccacc gcgaaggtgt ggggcctgta catggccggc   1200
tcacgtctgg gcttcgagac caatgtggtt cagctgcacc aggttctggc ggtcaagctt   1260
gacgatcagg gcaaggacgg cggactgccg ttgcggccct ggtggtccgc ctag         1314
```

<210> SEQ ID NO 4
<211> LENGTH: 437
<212> TYPE: PRT
<213> ORGANISM: Mycobacterium smegmatis

<400> SEQUENCE: 4

```
Met Thr Thr Phe Lys Glu Arg Glu Thr Ser Thr Ala Asp Arg Lys Leu
1               5                   10                  15

Thr Leu Ala Glu Ile Leu Glu Ile Phe Ala Ala Gly Lys Glu Pro Leu
            20                  25                  30

Lys Phe Thr Ala Tyr Asp Gly Ser Ser Ala Gly Pro Glu Asp Ala Thr
        35                  40                  45

Met Gly Leu Asp Leu Lys Thr Pro Arg Gly Thr Thr Tyr Leu Ala Thr
    50                  55                  60

Ala Pro Gly Asp Leu Gly Leu Ala Arg Ala Tyr Val Ser Gly Asp Leu
65                  70                  75                  80

Glu Pro His Gly Val His Pro Gly Asp Pro Tyr Pro Leu Leu Arg Ala
                85                  90                  95

Leu Ala Glu Arg Met Glu Phe Lys Pro Pro Ala Arg Val Leu Ala
            100                 105                 110

Asn Ile Val Arg Ser Ile Gly Ile Glu His Leu Lys Pro Ile Ala Pro
        115                 120                 125

Pro Pro Gln Glu Ala Leu Pro Arg Trp Arg Arg Ile Met Glu Gly Leu
    130                 135                 140

Arg His Ser Lys Thr Arg Asp Ala Glu Ala Ile His His His Tyr Asp
145                 150                 155                 160

Val Ser Asn Thr Phe Tyr Glu Trp Val Leu Gly Pro Ser Met Thr Tyr
                165                 170                 175

Thr Cys Ala Cys Tyr Pro Thr Glu Asp Ala Thr Leu Glu Glu Ala Gln
            180                 185                 190

Asp Asn Lys Tyr Arg Leu Val Phe Glu Lys Leu Arg Leu Lys Pro Gly
        195                 200                 205
```

Asp Arg Leu Leu Asp Val Gly Cys Gly Trp Gly Gly Met Val Arg Tyr
    210                 215                 220

Ala Ala Arg His Gly Val Lys Ala Leu Gly Val Thr Leu Ser Arg Glu
225                 230                 235                 240

Gln Ala Thr Trp Ala Gln Lys Ala Ile Ala Gln Glu Gly Leu Thr Asp
                245                 250                 255

Leu Ala Glu Val Arg His Gly Asp Tyr Arg Asp Val Ile Glu Ser Gly
            260                 265                 270

Phe Asp Ala Val Ser Ser Ile Gly Leu Thr Glu His Ile Gly Val His
        275                 280                 285

Asn Tyr Pro Ala Tyr Phe Asn Phe Leu Lys Ser Lys Leu Arg Thr Gly
290                 295                 300

Gly Leu Leu Leu Asn His Cys Ile Thr Arg Pro Asp Asn Arg Ser Ala
305                 310                 315                 320

Pro Ser Ala Gly Gly Phe Ile Asp Arg Tyr Val Phe Pro Asp Gly Glu
                325                 330                 335

Leu Thr Gly Ser Gly Arg Ile Ile Thr Glu Ala Gln Asp Val Gly Leu
            340                 345                 350

Glu Val Ile His Glu Glu Asn Leu Arg Asn His Tyr Ala Met Thr Leu
        355                 360                 365

Arg Asp Trp Cys Arg Asn Leu Val Glu His Trp Asp Glu Ala Val Glu
370                 375                 380

Glu Val Gly Leu Pro Thr Ala Lys Val Trp Gly Leu Tyr Met Ala Gly
385                 390                 395                 400

Ser Arg Leu Gly Phe Glu Thr Asn Val Val Gln Leu His Gln Val Leu
                405                 410                 415

Ala Val Lys Leu Asp Asp Gln Gly Lys Asp Gly Gly Leu Pro Leu Arg
            420                 425                 430

Pro Trp Trp Ser Ala
            435

<210> SEQ ID NO 5
<211> LENGTH: 1380
<212> TYPE: DNA
<213> ORGANISM: Unknown
<220> FEATURE:
<223> OTHER INFORMATION: Agromyces subbeticus

<400> SEQUENCE: 5
gtgtccgctc ctgcgaccga tgcacgaacc gcccacgccg acggcgtgga gcgattgctc    60
gagagttatc gggcggtgcc ggcggccgca tcggtgcggc tcgccaagcg cacctcgaac   120
ctcttccggt cccgagcggc gacggatgcc cctggcctcg acacctccgg cctgacccac   180
gtcatcgcgg tcaccccgg ggcgcgcacg gccgacgtcg ccggcatgtg cacctacgac   240
gacctcgtcg ccgcgacact gccgcatggg ctcgcgccac tcgtggtgcc gcaactgaag   300
accatcaccc tcggggggcgc cgtaacggga ctcggcatcg agtcgacgtc gttccgcaac   360
ggtctgccgc acgagtcggt gctcgagatc gacgtgctca ccggcgcagg cgagatcatc   420
acggcgtcgc cgatcgagca cgcagagctg ttccgcgcct tccccaactc gtacggcacc   480
ctcggctacg ccgtgcgcct gcgcatcgag ctcgagccgg tcgagccgtt cgtcgcactc   540
acgcaccttc ggttccatgc gctcaccgac ctcatcgagg caatggagcg catcatcgag   600
accggtcgac tcgacggggt tgccgtcgat ccctcgacg gcgtggtgtt cagcgctgaa   660
gagagctacc tgtgcgtcgg cacgcagacc gcggcatccg gcccggtcag cgactacacc   720

```
cgccagcaga tcttctatcg ctccatccag catgacgacg gtgcgaagca cgaccggctc    780
accatgcacg actacctgtg cgctgggac gccgactggt tctggtgctc gcaggcgttc     840
ggcgcgcagc atccgctgat cgccggttc tggccgcggc gataccggcg cagccgctcg     900
tactcgacgc tcatgcgcct cgaacggcga ttcgacctcg cgatcgcct cgagaagctc     960 aagggccggc cggcgcgcga acgcgtgatc caagacgtcg aggtgccgat cgggcgcacc    1020
gtcggcttcc tcgaatggtt cctcgcgaac gtgccgatcg agccgatctg gttgtgcccg    1080
ctgcgcctgc ggggcgaccg cggctggcct ctctacccga tccggccgca gcagacctac    1140
gtcaacatcg gcttctggtc gacggttccg gtgggcggct ccgagggcga gacgaaccgc    1200
tcgatcgagc gcgccgtgag cgagttcgac ggacacaagt cgctgtactc cgactcgtac    1260
tactcgcgcg aggagttcga ggagctctac ggcggcgagg cgtaccgggc cgtgaagcgg    1320
cgatacgacc ccgactctcg actgctcgac ctctatgcga aggcggtgca acggcgatga   1380
```

<210> SEQ ID NO 6
<211> LENGTH: 459
<212> TYPE: PRT
<213> ORGANISM: Unknown
<220> FEATURE:
<223> OTHER INFORMATION: Agromyces subbeticus

<400> SEQUENCE: 6

```
Val Ser Ala Pro Ala Thr Asp Ala Arg Thr Ala His Ala Asp Gly Val
1               5                   10                  15

Glu Arg Leu Leu Glu Ser Tyr Arg Ala Val Pro Ala Ala Ala Ser Val
            20                  25                  30

Arg Leu Ala Lys Arg Thr Ser Asn Leu Phe Arg Ser Arg Ala Ala Thr
        35                  40                  45

Asp Ala Pro Gly Leu Asp Thr Ser Gly Leu Thr His Val Ile Ala Val
    50                  55                  60

Asp Pro Gly Ala Arg Thr Ala Asp Val Ala Gly Met Cys Thr Tyr Asp
65                  70                  75                  80

Asp Leu Val Ala Ala Thr Leu Pro His Gly Leu Ala Pro Leu Val Val
                85                  90                  95

Pro Gln Leu Lys Thr Ile Thr Leu Gly Gly Ala Val Thr Gly Leu Gly
            100                 105                 110

Ile Glu Ser Thr Ser Phe Arg Asn Gly Leu Pro His Glu Ser Val Leu
        115                 120                 125

Glu Ile Asp Val Leu Thr Gly Ala Gly Glu Ile Thr Ala Ser Pro
    130                 135                 140

Ile Glu His Ala Glu Leu Phe Arg Ala Phe Pro Asn Ser Tyr Gly Thr
145                 150                 155                 160

Leu Gly Tyr Ala Val Arg Leu Arg Ile Glu Leu Glu Pro Val Glu Pro
                165                 170                 175

Phe Val Ala Leu Thr His Leu Arg Phe His Ala Leu Thr Asp Leu Ile
            180                 185                 190

Glu Ala Met Glu Arg Ile Ile Glu Thr Gly Arg Leu Asp Gly Val Ala
        195                 200                 205

Val Asp Ser Leu Asp Gly Val Val Phe Ser Ala Glu Glu Ser Tyr Leu
    210                 215                 220

Cys Val Gly Thr Gln Thr Ala Ala Ser Gly Pro Val Ser Asp Tyr Thr
225                 230                 235                 240

Arg Gln Gln Ile Phe Tyr Arg Ser Ile Gln His Asp Asp Gly Ala Lys
                245                 250                 255
```

```
His Asp Arg Leu Thr Met His Asp Tyr Leu Trp Arg Trp Asp Ala Asp
                260                 265                 270

Trp Phe Trp Cys Ser Gln Ala Phe Gly Ala Gln His Pro Leu Ile Arg
            275                 280                 285

Arg Phe Trp Pro Arg Arg Tyr Arg Arg Ser Arg Ser Tyr Ser Thr Leu
        290                 295                 300

Met Arg Leu Glu Arg Arg Phe Asp Leu Gly Asp Arg Leu Glu Lys Leu
305                 310                 315                 320

Lys Gly Arg Pro Ala Arg Glu Arg Val Ile Gln Asp Val Glu Val Pro
                325                 330                 335

Ile Gly Arg Thr Val Gly Phe Leu Glu Trp Phe Leu Ala Asn Val Pro
                340                 345                 350

Ile Glu Pro Ile Trp Leu Cys Pro Leu Arg Leu Arg Gly Asp Arg Gly
            355                 360                 365

Trp Pro Leu Tyr Pro Ile Arg Pro Gln Gln Thr Tyr Val Asn Ile Gly
        370                 375                 380

Phe Trp Ser Thr Val Pro Val Gly Gly Ser Glu Gly Glu Thr Asn Arg
385                 390                 395                 400

Ser Ile Glu Arg Ala Val Ser Glu Phe Asp Gly His Lys Ser Leu Tyr
                405                 410                 415

Ser Asp Ser Tyr Tyr Ser Arg Glu Glu Phe Glu Glu Leu Tyr Gly Gly
            420                 425                 430

Glu Ala Tyr Arg Ala Val Lys Arg Arg Tyr Asp Pro Asp Ser Arg Leu
        435                 440                 445

Leu Asp Leu Tyr Ala Lys Ala Val Gln Arg Arg
    450                 455

<210> SEQ ID NO 7
<211> LENGTH: 1254
<212> TYPE: DNA
<213> ORGANISM: Unknown
<220> FEATURE:
<223> OTHER INFORMATION: Agromyces subbeticus

<400> SEQUENCE: 7
atcctcgaga tcgtcgtcgc cggtcggctg ccgctgaggt tcaccgccta cgacgggagc      60 tcggcgggc cgcctgacgc cctgttcggc ctcgacctga agactccgcg aggaacgacc     120
tatctcgcca ccggccgcgg cgatctcggc ctcgcccgcg cctacatcgc gggcgacctc     180
gagatacagg gggtgcaccc cggagacccc tacgagctgc tcaaggcact cgccgacagc     240
ctggtcttca agctgccacc gccgcgggtg atgacccaga tcatccgttc gatcggcgtc     300
gaacatctgc ggccgatcgc gccgccgccg caagaggtgc cgccccggtg cgccgcatc     360 gccgagggc tccgacacag caagggccgc gacgccgaag cgatccacca ccactacgac     420
gtgtcgaaca ccttctacga atgggtgctc gggccgtcga tgacctacac gtgcgcgtgc     480
tacccgggcc tcgacgcatc cctcgacgag gcgcagcaga acaagtaccg gctcgtgttc     540
gagaagctgc ggctgaagcc gggcgaccga ctgctcgacg tcggctgcgg gtggggcggc     600
atggtgcgct acgccgcgcg ccacggcgtg caggcgttgg gcgtgaccct gtcgcgagag     660
cagacggcgt gggcgcagca ggcgatcgcc gtcgagggcc tcgccgacct cgccgaggtg     720
cgctacggcg actaccgcga catcgccgaa gacggcttcg atgcggtgtc atcgatcggg     780
ctgctcgagc acatcggcgt gcgcaactac gcttcgtatt cggctttct gcagtcgcgc     840 ttgcggcccg ggggactctt gctcaaccac tgcatcaccc ggcccgacaa tcgctccgag     900
```

```
ccgtcggcgc gcggcttcat cgaccggtac gtgttccccg acggagagct caccggctcg   960
ggccgcatca tcaccgaggc gcaggatgtc ggcttcgaag tgctgcacga agagaacctg  1020
cgtcagcatt atgcactgac actgcgcgat tggtgcgcca acctcgtcgc gactgggaa   1080 gaggcggtcg ccgaggtcgg gctgccgacc gcgaaggtgt ggggcctcta catggccggg  1140
tcacggctcg cgttcgagag cggcggcatc cagttgcacc aggtgctggc ggtcagacca  1200
gacgatcgca gcgacgccgc ccagctgccg ctgcggccgt ggtggacgcc atag        1254
```

<210> SEQ ID NO 8
<211> LENGTH: 417
<212> TYPE: PRT
<213> ORGANISM: Unknown
<220> FEATURE:
<223> OTHER INFORMATION: Agromyces subbeticus

<400> SEQUENCE: 8

```
Ile Leu Glu Ile Val Val Ala Gly Arg Leu Pro Leu Arg Phe Thr Ala
1               5                   10                  15

Tyr Asp Gly Ser Ser Ala Gly Pro Pro Asp Ala Leu Phe Gly Leu Asp
                20                  25                  30

Leu Lys Thr Pro Arg Gly Thr Thr Tyr Leu Ala Thr Gly Arg Gly Asp
            35                  40                  45

Leu Gly Leu Ala Arg Ala Tyr Ile Ala Gly Asp Leu Glu Ile Gln Gly
        50                  55                  60

Val His Pro Gly Asp Pro Tyr Glu Leu Leu Lys Ala Leu Ala Asp Ser
65                  70                  75                  80

Leu Val Phe Lys Leu Pro Pro Arg Val Met Thr Gln Ile Ile Arg
                85                  90                  95

Ser Ile Gly Val Glu His Leu Arg Pro Ile Ala Pro Pro Gln Glu
                100                 105                 110

Val Pro Pro Arg Trp Arg Arg Ile Ala Glu Gly Leu Arg His Ser Lys
                115                 120                 125

Gly Arg Asp Ala Glu Ala Ile His His His Tyr Asp Val Ser Asn Thr
    130                 135                 140

Phe Tyr Glu Trp Val Leu Gly Pro Ser Met Thr Tyr Thr Cys Ala Cys
145                 150                 155                 160

Tyr Pro Gly Leu Asp Ala Ser Leu Asp Glu Ala Gln Gln Asn Lys Tyr
                165                 170                 175

Arg Leu Val Phe Glu Lys Leu Arg Leu Lys Pro Gly Asp Arg Leu Leu
                180                 185                 190

Asp Val Gly Cys Gly Trp Gly Gly Met Val Arg Tyr Ala Ala Arg His
            195                 200                 205

Gly Val Gln Ala Leu Gly Val Thr Leu Ser Arg Glu Gln Thr Ala Trp
        210                 215                 220

Ala Gln Gln Ala Ile Ala Val Glu Gly Leu Ala Asp Leu Ala Glu Val
225                 230                 235                 240

Arg Tyr Gly Asp Tyr Arg Asp Ile Ala Glu Asp Gly Phe Asp Ala Val
                245                 250                 255

Ser Ser Ile Gly Leu Leu Glu His Ile Gly Val Arg Asn Tyr Ala Ser
                260                 265                 270

Tyr Phe Gly Phe Leu Gln Ser Arg Leu Arg Pro Gly Gly Leu Leu Leu
            275                 280                 285

Asn His Cys Ile Thr Arg Pro Asp Asn Arg Ser Glu Pro Ser Ala Arg
        290                 295                 300
```

| | | | | | | | | | | | |
|---|---|---|---|---|---|---|---|---|---|---|---|
|Gly|Phe|Ile|Asp|Arg|Tyr|Val|Phe|Pro|Asp|Gly|Glu|Leu|Thr|Gly|Ser|
|305| | | | |310| | | | |315| | | | |320|

Gly Phe Ile Asp Arg Tyr Val Phe Pro Asp Gly Glu Leu Thr Gly Ser
305                 310                 315                 320

Gly Arg Ile Ile Thr Glu Ala Gln Asp Val Gly Phe Glu Val Leu His
            325                 330                 335

Glu Glu Asn Leu Arg Gln His Tyr Ala Leu Thr Leu Arg Asp Trp Cys
        340                 345                 350

Ala Asn Leu Val Ala His Trp Glu Glu Ala Val Ala Glu Val Gly Leu
        355                 360                 365

Pro Thr Ala Lys Val Trp Gly Leu Tyr Met Ala Gly Ser Arg Leu Ala
370                 375                 380

Phe Glu Ser Gly Gly Ile Gln Leu His Gln Val Leu Ala Val Arg Pro
385                 390                 395                 400

Asp Asp Arg Ser Asp Ala Ala Gln Leu Pro Leu Arg Pro Trp Trp Thr
                405                 410                 415

Pro

<210> SEQ ID NO 9
<211> LENGTH: 1428
<212> TYPE: DNA
<213> ORGANISM: Unknown
<220> FEATURE:
<223> OTHER INFORMATION: Amycolicicoccus subflavus

<400> SEQUENCE: 9

```
atgacgcctg aagctagtgc ggcggcgcac gccgctgcgg tggatcgcct catccatagc      60
tatcgggcga ttcctgatga cgcgccggtg cggctggcga agaagacgtc aaacctattc     120
cgccacaggg aaaagacttc tgctcctggg cttgacgtat ccggcctggc tcgcgtgatt     180
gggatcgact cagacactcg cactgccgac gttggcggca tgtgcacata cgaggacctt     240
gtcgcggcga cgctcgaata cgatctggtc ccctggtcg tcccgcaact caaaacgatc     300
actctcggcg gcgcgtgac gggcctggga attgagtcca cctcgttccg caatgggctt     360
ccccatgaat ctgttctcga atggatatc ctgacgggcg ccggggaggt cgtcacggcc     420
ggcccggaag cccccatag cgatttgtac tgggggtttc cgaattcgta cggcacgctc     480
ggctatgcga cgcgcctgcg catcgaacta gaaccggtcg agccgtacgt cgaactcagg     540
cacctgcggt tcactagcct cgatgagctt caggagacac ttgacaccgt ttcgtacgaa     600
cacacgtatg acggggaacc cgttcattac gtcgatggag tcatgttctc agccacggaa     660
agctacctca cgcttggccg tcagacgagc gaacccggcc cggtcagcga ctacaccgga     720
aaccagatct actaccgttc aatacagcac ggtggcgctg aaactcccgt cgtcgaccgg     780
atgaccattc atgactatct atggcgctgg gatactgact ggttctggtg ctcgcgtgcc     840
ttcggaacgc aacacccagt ggtccggaga ttctggccac gccgctatcg ccgcagcagc     900
ttctactgga agctgatcgc gcttgaccgc caggttgggc tcgcggactt catcgaacaa     960
cggaagggca acctcccccg ggaacgcgta gtccaggaca tcgaggtccc gatcgagaac    1020
actgcgagct tcttgcggtg gttcttggcg aacgtgccga tcgagccggt atggctatgc    1080
ccgctgcgcc tgcgaaaaac acgcagcccc ggcctgcctt cgccgacgtc cccggcttca    1140
cgcccatggc ccctctatcc gctcgagcct cagcgcacat acgtcaatgt tggcttctgg    1200
tcagcggtgc cggtcgtggc cggccagccc gaggggcaca ccaaccggat gatcgagaac    1260
gaagtcgatc gccttgacgg tcacaaatcg ctgtactcag atgcgtttta cgagcgaaaa    1320
gagtttgacg cgctgtacgg cggcgatacc tatagagaac tcaaagagac ctacgaccca    1380
```
aacagccggt tacttgatct ctatgcaaag gcggtgcaag gacgatga             1428

<210> SEQ ID NO 10
<211> LENGTH: 475
<212> TYPE: PRT
<213> ORGANISM: Unknown
<220> FEATURE:
<223> OTHER INFORMATION: Amycolicicoccus subflavus

<400> SEQUENCE: 10

Met Thr Pro Glu Ala Ser Ala Ala His Ala Ala Val Asp Arg
1               5                   10                  15

Leu Ile His Ser Tyr Arg Ala Ile Pro Asp Asp Ala Pro Val Arg Leu
            20                  25                  30

Ala Lys Lys Thr Ser Asn Leu Phe Arg His Arg Glu Lys Thr Ser Ala
        35                  40                  45

Pro Gly Leu Asp Val Ser Gly Leu Ala Arg Val Ile Gly Ile Asp Ser
    50                  55                  60

Asp Thr Arg Thr Ala Asp Val Gly Gly Met Cys Thr Tyr Glu Asp Leu
65                  70                  75                  80

Val Ala Ala Thr Leu Glu Tyr Asp Leu Val Pro Leu Val Val Pro Gln
                85                  90                  95

Leu Lys Thr Ile Thr Leu Gly Gly Ala Val Thr Gly Leu Gly Ile Glu
            100                 105                 110

Ser Thr Ser Phe Arg Asn Gly Leu Pro His Glu Ser Val Leu Glu Met
        115                 120                 125

Asp Ile Leu Thr Gly Ala Gly Glu Val Val Thr Ala Gly Pro Glu Gly
    130                 135                 140

Pro His Ser Asp Leu Tyr Trp Gly Phe Pro Asn Ser Tyr Gly Thr Leu
145                 150                 155                 160

Gly Tyr Ala Thr Arg Leu Arg Ile Glu Leu Glu Pro Val Glu Pro Tyr
                165                 170                 175

Val Glu Leu Arg His Leu Arg Phe Thr Ser Leu Asp Glu Leu Gln Glu
            180                 185                 190

Thr Leu Asp Thr Val Ser Tyr Glu His Thr Tyr Asp Gly Glu Pro Val
        195                 200                 205

His Tyr Val Asp Gly Val Met Phe Ser Ala Thr Glu Ser Tyr Leu Thr
    210                 215                 220

Leu Gly Arg Gln Thr Ser Glu Pro Gly Pro Val Ser Asp Tyr Thr Gly
225                 230                 235                 240

Asn Gln Ile Tyr Tyr Arg Ser Ile Gln His Gly Gly Ala Glu Thr Pro
                245                 250                 255

Val Val Asp Arg Met Thr Ile His Asp Tyr Leu Trp Arg Trp Asp Thr
            260                 265                 270

Asp Trp Phe Trp Cys Ser Arg Ala Phe Gly Thr Gln His Pro Val Val
        275                 280                 285

Arg Arg Phe Trp Pro Arg Tyr Arg Arg Ser Ser Phe Tyr Trp Lys
    290                 295                 300

Leu Ile Ala Leu Asp Arg Gln Val Gly Leu Ala Asp Phe Ile Glu Gln
305                 310                 315                 320

Arg Lys Gly Asn Leu Pro Arg Glu Arg Val Val Gln Asp Ile Glu Val
                325                 330                 335

Pro Ile Glu Asn Thr Ala Ser Phe Leu Arg Trp Phe Leu Ala Asn Val
            340                 345                 350

```
Pro Ile Glu Pro Val Trp Leu Cys Pro Leu Arg Leu Arg Lys Thr Arg
            355                 360                 365

Ser Pro Gly Leu Pro Ser Pro Thr Ser Pro Ala Ser Arg Pro Trp Pro
370                 375                 380

Leu Tyr Pro Leu Glu Pro Gln Arg Thr Tyr Val Asn Val Gly Phe Trp
385                 390                 395                 400

Ser Ala Val Pro Val Ala Gly Gln Pro Glu Gly His Thr Asn Arg
                405                 410                 415

Met Ile Glu Asn Glu Val Asp Arg Leu Asp Gly His Lys Ser Leu Tyr
            420                 425                 430

Ser Asp Ala Phe Tyr Glu Arg Lys Glu Phe Asp Ala Leu Tyr Gly Gly
        435                 440                 445

Asp Thr Tyr Arg Glu Leu Lys Glu Thr Tyr Asp Pro Asn Ser Arg Leu
    450                 455                 460

Leu Asp Leu Tyr Ala Lys Ala Val Gln Gly Arg
465                 470                 475

<210> SEQ ID NO 11
<211> LENGTH: 1311
<212> TYPE: DNA
<213> ORGANISM: Unknown
<220> FEATURE:
<223> OTHER INFORMATION: Amycolicicoccus subflavus

<400> SEQUENCE: 11
```

| | |
|---|---|
| atgaaggcag tgttgacggc gtttacggct ccccaactcg aaaggatgaa cgtcgctgag | 60 |
| atactcagcg cggtactcgg gcgagatttc ccgatccggt tcactgcgta cgacggcagc | 120 |
| gcgctcggcc ccgaaaccgc ccgctacggc ttgcacctca cgacgccgcg cgggctgacc | 180 |
| tacctcgcta ccgcgcccgg tgatctcggg ctcgcacgcg cgtacgtgtc cggcgacctc | 240 |
| gaggtcagtg gggttcatca gggtgacccg tacgagataa tgaagatcct cgcgcatgac | 300 |
| gtccgggtgc ggcggcccct gccagcaacg atcgcttcga tcatgcggtc cctcggctgg | 360 |
| gaacgcttgc gaccggtcgc gccgcccccg caagagaaca tgccccgttg cgccggatg | 420 |
| gcccttggcc tgctgcactc gaagagccgt gatgctgcgg caatccacca tcattacgac | 480 |
| gtgtcgaacg agttttacga gcacatcctc ggcccgtcga tgacgtacac atgcgcggcc | 540 |
| taccccagcg cagacagttc cctggaggaa gcacaggaca acaagtaccg actcgtcttc | 600 |
| gagaaacttg gcctgaaagc cggggatcgc ctgcttgacg tcgggtgcgg gtggggcggc | 660 |
| atggtgcggt tcgccgctaa gcgcggcgtt catgtcatcg gtgcgacatt gtcccgcaaa | 720 |
| caggcggaat gggctcagaa gatgattgcc catgaaggat tgggcgatct ggcggaagtc | 780 |
| cgtttctgcg actaccgcga tgtcacagag gcgggcttcg acgcagtgtc gtcgatcggc | 840 |
| ctcactgaac acatcggttt ggcgaactac ccgtcgtact tcggcttcct gaaggacaag | 900 |
| ttgcggccag gcggacgact gctgaaccat tgcatcactc gcccgaacaa ccttcaaagc | 960 |
| aaccgcgcag gtgacttcat tgaccggtac gtttttccctg acgagagct cgccggacct | 1020 |
| ggcttcatca tttcagctgt ccacgacgcc ggtttcgagg tgcggcacga agagaacctc | 1080 |
| cgcgagcact acgcactgac gctgcgggac tggaaccgca acctcgctcg cgactgggac | 1140 |
| gcgtgtgtgc acgcctccga cgagggcacc gcccgcgtct ggggactgta catttccggt | 1200 |
| tcacgagtcg cgtttgaaac gaactcgatt cagctgcacc aggtcctggc ggtcaaaacc | 1260 |
| gcgcggaatg gcgaagcgca ggtcccgttg ggtcagtggt ggaccccgctg a | 1311 |

<210> SEQ ID NO 12
<211> LENGTH: 436
<212> TYPE: PRT
<213> ORGANISM: Unknown
<220> FEATURE:
<223> OTHER INFORMATION: Amycolicicoccus subflavus

<400> SEQUENCE: 12

```
Met Lys Ala Val Leu Thr Ala Phe Thr Ala Pro Gln Leu Glu Arg Met
1               5                   10                  15

Asn Val Ala Glu Ile Leu Ser Ala Val Leu Gly Arg Asp Phe Pro Ile
            20                  25                  30

Arg Phe Thr Ala Tyr Asp Gly Ser Ala Leu Gly Pro Glu Thr Ala Arg
        35                  40                  45

Tyr Gly Leu His Leu Thr Thr Pro Arg Gly Leu Thr Tyr Leu Ala Thr
    50                  55                  60

Ala Pro Gly Asp Leu Gly Leu Ala Arg Ala Tyr Val Ser Gly Asp Leu
65                  70                  75                  80

Glu Val Ser Gly Val His Gln Gly Asp Pro Tyr Glu Ile Met Lys Ile
                85                  90                  95

Leu Ala His Asp Val Arg Val Arg Arg Pro Ser Pro Ala Thr Ile Ala
            100                 105                 110

Ser Ile Met Arg Ser Leu Gly Trp Glu Arg Leu Arg Pro Val Ala Pro
        115                 120                 125

Pro Pro Gln Glu Asn Met Pro Arg Trp Arg Arg Met Ala Leu Gly Leu
    130                 135                 140

Leu His Ser Lys Ser Arg Asp Ala Ala Ile His His His Tyr Asp
145                 150                 155                 160

Val Ser Asn Glu Phe Tyr Glu His Ile Leu Gly Pro Ser Met Thr Tyr
                165                 170                 175

Thr Cys Ala Ala Tyr Pro Ser Ala Asp Ser Ser Leu Glu Glu Ala Gln
            180                 185                 190

Asp Asn Lys Tyr Arg Leu Val Phe Glu Lys Leu Gly Leu Lys Ala Gly
        195                 200                 205

Asp Arg Leu Leu Asp Val Gly Cys Gly Trp Gly Gly Met Val Arg Phe
    210                 215                 220

Ala Ala Lys Arg Gly Val His Val Ile Gly Ala Thr Leu Ser Arg Lys
225                 230                 235                 240

Gln Ala Glu Trp Ala Gln Lys Met Ile Ala His Glu Gly Leu Gly Asp
                245                 250                 255

Leu Ala Glu Val Arg Phe Cys Asp Tyr Arg Asp Val Thr Glu Ala Gly
            260                 265                 270

Phe Asp Ala Val Ser Ser Ile Gly Leu Thr Glu His Ile Gly Leu Ala
        275                 280                 285

Asn Tyr Pro Ser Tyr Phe Gly Phe Leu Lys Asp Lys Leu Arg Pro Gly
    290                 295                 300

Gly Arg Leu Leu Asn His Cys Ile Thr Arg Pro Asn Asn Leu Gln Ser
305                 310                 315                 320

Asn Arg Ala Gly Asp Phe Ile Asp Arg Tyr Val Phe Pro Asp Gly Glu
                325                 330                 335

Leu Ala Gly Pro Gly Phe Ile Ile Ser Ala Val His Asp Ala Gly Phe
            340                 345                 350

Glu Val Arg His Glu Glu Asn Leu Arg Glu His Tyr Ala Leu Thr Leu
        355                 360                 365

Arg Asp Trp Asn Arg Asn Leu Ala Arg Asp Trp Asp Ala Cys Val His
```

```
                      370               375              380
Ala Ser Asp Glu Gly Thr Ala Arg Val Trp Gly Leu Tyr Ile Ser Gly
385                 390              395                  400

Ser Arg Val Ala Phe Glu Thr Asn Ser Ile Gln Leu His Gln Val Leu
                405                 410                 415

Ala Val Lys Thr Ala Arg Asn Gly Glu Ala Gln Val Pro Leu Gly Gln
            420                 425                 430

Trp Trp Thr Arg
        435

<210> SEQ ID NO 13
<211> LENGTH: 1548
<212> TYPE: DNA
<213> ORGANISM: Corynebacterium glutamicum

<400> SEQUENCE: 13
atgagcggat tagttgaccc ggatagtact ttttaaaga ccatcggaaa actgagcaac       60
agcttgtcca ttggtcgtgg agtagatcaa aaagaggtaa tccccaaagg ctggaacgcc      120
cattgggagg caattacaaa gcttaagaga gctttgacg cgattcctgc tggggagcgg      180
gtgcgtttag ctaagaaaac ctccaacctg ttccgtggac gctccgatgc aggtcacggc      240
ctagatgtgg cagcgcttgg gggagtgatt gccattgatc cggtcaatgc caccgccgat      300
gtacagggca tgtgcacgta tgaagacctg gtagatgcca cttttaagtta tggtctgatg      360 ccgttggttg tgcctcaact gaaaaccatc acgcttggtg gcgcagtgac cggaatgggc      420
gtggaatcca catccttccg caacggtttg ccacacgaat cagtgctgga gatggatatt      480
tttaccggca ctggtgagat cgtgacttgc tcgcccacag aaaatgtcga cctttacaga      540
ggttttccca actcttatgg ttcgctggga tacgcggtgc ggctaaaaat tgagctggaa      600
ccagtgcaag attacgtcca gctgcgccac gtgcgcttca cgatttaga gtctttgacc      660 aaagcgattg aggaagtcgc gtcttctctg gagtttgata ccaacccgt cgattacctt      720 gacggcgtgg tgttttcacc cacggaagcc tacttagttc ttggcacgca acctcacaa      780 cctggcccca ccagcgatta caccagggat ttaagctact accgctccct gcaacaccca      840
gagggcatca cctatgaccg cctgacaatc cgcgattaca tctggcgctg ggacaccgac      900
tggttctggt gttcacgcgc attcggcacc caaaacccg tggtgcgcaa actctggccc      960
agggatctgc tgcgctcgag tttctattgg aagatcatcg gctgggatcg aaaatactcc     1020
atcgctgatc gcctggaaga gcgcaaaggc cgcccggcta gggaacgggt ggtccaagac     1080
gtggaagtta cgattgataa actgccagaa ttttgaaat ggttctttga aagcagcgac     1140
atcgagccgc tgtggctgtg cccgatcaag cttcggagg taccaggtag ttcggttggt     1200
gctggagaaa ttttgagctc cgctgaagca atcgactccg tgctgctga acaccttgg     1260 ccgctgtatc ccttgaagaa ggacgtgctg tgggtcaaca tcggattctg gtcctcagtg     1320
ccggttgatc tgatgggctc cgatgcacca gagggagcat taacagaga atcgaacgc     1380 gtcatggcag agctaggcgg acataaatcg ctgtactccg aagcgttcta caccagggaa     1440
gactttgaaa aactttatgg cggaaccatc ccggcgctgc taaaaaagca gtgggatccc     1500
cacagccgat tccccggttt gtatgaaaag acagtaaaag gcgcctag               1548

<210> SEQ ID NO 14
<211> LENGTH: 515
<212> TYPE: PRT
<213> ORGANISM: Corynebacterium glutamicum
```

<400> SEQUENCE: 14

```
Met Ser Gly Leu Val Asp Pro Asp Ser Thr Phe Leu Lys Thr Ile Gly
1               5                   10                  15

Lys Leu Ser Asn Ser Leu Ser Ile Gly Arg Gly Val Asp Gln Lys Glu
            20                  25                  30

Val Ile Pro Lys Gly Trp Asn Ala His Trp Glu Ala Ile Thr Lys Leu
        35                  40                  45

Lys Arg Ser Phe Asp Ala Ile Pro Ala Gly Glu Arg Val Arg Leu Ala
    50                  55                  60

Lys Lys Thr Ser Asn Leu Phe Arg Gly Arg Ser Asp Ala Gly His Gly
65                  70                  75                  80

Leu Asp Val Ala Ala Leu Gly Gly Val Ile Ala Ile Asp Pro Val Asn
                85                  90                  95

Ala Thr Ala Asp Val Gln Gly Met Cys Thr Tyr Glu Asp Leu Val Asp
            100                 105                 110

Ala Thr Leu Ser Tyr Gly Leu Met Pro Leu Val Val Pro Gln Leu Lys
        115                 120                 125

Thr Ile Thr Leu Gly Gly Ala Val Thr Gly Met Gly Val Glu Ser Thr
    130                 135                 140

Ser Phe Arg Asn Gly Leu Pro His Glu Ser Val Leu Glu Met Asp Ile
145                 150                 155                 160

Phe Thr Gly Thr Gly Glu Ile Val Thr Cys Ser Pro Thr Glu Asn Val
                165                 170                 175

Asp Leu Tyr Arg Gly Phe Pro Asn Ser Tyr Gly Ser Leu Gly Tyr Ala
            180                 185                 190

Val Arg Leu Lys Ile Glu Leu Glu Pro Val Gln Asp Tyr Val Gln Leu
        195                 200                 205

Arg His Val Arg Phe Asn Asp Leu Glu Ser Leu Thr Lys Ala Ile Glu
    210                 215                 220

Glu Val Ala Ser Ser Leu Glu Phe Asp Asn Gln Pro Val Asp Tyr Leu
225                 230                 235                 240

Asp Gly Val Val Phe Ser Pro Thr Glu Ala Tyr Leu Val Leu Gly Thr
                245                 250                 255

Gln Thr Ser Gln Pro Gly Pro Thr Ser Asp Tyr Thr Arg Asp Leu Ser
            260                 265                 270

Tyr Tyr Arg Ser Leu Gln His Pro Glu Gly Ile Thr Tyr Asp Arg Leu
        275                 280                 285

Thr Ile Arg Asp Tyr Ile Trp Arg Trp Asp Thr Asp Trp Phe Trp Cys
    290                 295                 300

Ser Arg Ala Phe Gly Thr Gln Asn Pro Val Val Arg Lys Leu Trp Pro
305                 310                 315                 320

Arg Asp Leu Leu Arg Ser Ser Phe Tyr Trp Lys Ile Ile Gly Trp Asp
                325                 330                 335

Arg Lys Tyr Ser Ile Ala Asp Arg Leu Glu Arg Lys Gly Arg Pro
            340                 345                 350

Ala Arg Glu Arg Val Val Gln Asp Val Glu Val Thr Ile Asp Lys Leu
        355                 360                 365

Pro Glu Phe Leu Lys Trp Phe Phe Glu Ser Ser Asp Ile Glu Pro Leu
    370                 375                 380

Trp Leu Cys Pro Ile Lys Leu Arg Glu Val Pro Gly Ser Ser Val Gly
385                 390                 395                 400

Ala Gly Glu Ile Leu Ser Ser Ala Glu Ala Ile Asp Ser Gly Ala Ala
```

405                 410                 415
Glu His Pro Trp Pro Leu Tyr Pro Leu Lys Lys Asp Val Leu Trp Val
                420                 425                 430

Asn Ile Gly Phe Trp Ser Ser Val Pro Val Asp Leu Met Gly Ser Asp
            435                 440                 445

Ala Pro Glu Gly Ala Phe Asn Arg Glu Ile Glu Arg Val Met Ala Glu
    450                 455                 460

Leu Gly Gly His Lys Ser Leu Tyr Ser Glu Ala Phe Tyr Thr Arg Glu
465                 470                 475                 480

Asp Phe Glu Lys Leu Tyr Gly Gly Thr Ile Pro Ala Leu Leu Lys Lys
                485                 490                 495

Gln Trp Asp Pro His Ser Arg Phe Pro Gly Leu Tyr Glu Lys Thr Val
            500                 505                 510

Lys Gly Ala
        515

<210> SEQ ID NO 15
<211> LENGTH: 1308
<212> TYPE: DNA
<213> ORGANISM: Corynebacterium glutamicum

<400> SEQUENCE: 15
atgagtaacg ccgtagcgca ggacctcatg accatcgccg acatcgtcga ggccacgacc      60
actgcaccca tcccattcca catcactgcc ttcgatggaa gcttcactgg ccctgaagat     120
gctccctacc agctgtttgt tgccaacacg gatgcagtat cctacatcgc aacagcgcca     180
ggagatttgg gtttggcacg tgcctacctc atgggagacc tcatcgtgga aggtgagcat     240
cccggccatc cttatgggat ctttgatgcg ttgaaggagt tctaccgctg cttcaaacgc     300
ccagatgcat ccaccacctt gcagatcatg tggactctgc ggaaaatgaa tgccttaaaa     360
ttccaggaaa ttccaccaat ggaacaagcc cctgcatggc gtaaagcact gatcaacggg     420
ctagcatcca ggcactcgaa atcccgcgac aagaaagcca ttagctacca ctacgacgtg     480
ggcaatgagt tctactccct gttttagat gattccatga cctatacctg cgcgtattat     540
ccaacgccag aatcaagttt ggaagaagcc caagaaaaca ataccgcct catctttgaa     600 aaactgcgtc tgaaagaagg cgatcgcctc ctagacgtgg gatgcggttg gggaggcatg     660
gtccgctacg ccgccaaaca cggtgtgaaa gccatcggag ttacgctgtc tgaacagcaa     720
tatgagtggg gtcaagcaga gatcaaacgc caaggtttgg aagacctcgc ggaaattcgc     780
ttcatggatt accgcgatgt tccagaaact ggattcgatg cgatctcagc aatcggcatc     840
attgaacaca tcggtgtgaa caactatccc gactactttg aattgctcag cagcaaactc     900
aaaacaggcg gactgatgct caaccacagc atcacctacc agacaaccg cccccgccac     960 gcaggtgcat ttattgatcg ctacattttc cccgacggtg aactcactgg ctctggcacc    1020
ctgatcaagc acatgcagga caacggtttc gaagtgctgc acgaagaaaa cctccgcttt    1080
gattaccaac gcaccctgca cgcgtggtgc gaaaaacctca agaaaattg ggaggaagca    1140 gttgaactcg ccggtgaacc cactgcacga ctctttggcc tgtacatggc aggttcggaa    1200
tggggatttg cccacaacat cgtccagctg caccaagtac tgggtgtgaa actcgatgag    1260
cagggaagtc gcggagaagt tcctgaaaga atgtggtgga ctatctaa                 1308

<210> SEQ ID NO 16
<211> LENGTH: 435
<212> TYPE: PRT

<213> ORGANISM: Corynebacterium glutamicum

<400> SEQUENCE: 16

Met Ser Asn Ala Val Ala Gln Asp Leu Met Thr Ile Ala Asp Ile Val
1               5                   10                  15

Glu Ala Thr Thr Thr Ala Pro Ile Pro Phe His Ile Thr Ala Phe Asp
            20                  25                  30

Gly Ser Phe Thr Gly Pro Glu Asp Ala Pro Tyr Gln Leu Phe Val Ala
        35                  40                  45

Asn Thr Asp Ala Val Ser Tyr Ile Ala Thr Ala Pro Gly Asp Leu Gly
    50                  55                  60

Leu Ala Arg Ala Tyr Leu Met Gly Asp Leu Ile Val Glu Gly Glu His
65                  70                  75                  80

Pro Gly His Pro Tyr Gly Ile Phe Asp Ala Leu Lys Glu Phe Tyr Arg
                85                  90                  95

Cys Phe Lys Arg Pro Asp Ala Ser Thr Thr Leu Gln Ile Met Trp Thr
            100                 105                 110

Leu Arg Lys Met Asn Ala Leu Lys Phe Gln Glu Ile Pro Pro Met Glu
        115                 120                 125

Gln Ala Pro Ala Trp Arg Lys Ala Leu Ile Asn Gly Leu Ala Ser Arg
    130                 135                 140

His Ser Lys Ser Arg Asp Lys Lys Ala Ile Ser Tyr His Tyr Asp Val
145                 150                 155                 160

Gly Asn Glu Phe Tyr Ser Leu Phe Leu Asp Asp Ser Met Thr Tyr Thr
                165                 170                 175

Cys Ala Tyr Tyr Pro Thr Pro Glu Ser Ser Leu Glu Glu Ala Gln Glu
            180                 185                 190

Asn Lys Tyr Arg Leu Ile Phe Glu Lys Leu Arg Leu Lys Glu Gly Asp
        195                 200                 205

Arg Leu Leu Asp Val Gly Cys Gly Trp Gly Gly Met Val Arg Tyr Ala
    210                 215                 220

Ala Lys His Gly Val Lys Ala Ile Gly Val Thr Leu Ser Glu Gln Gln
225                 230                 235                 240

Tyr Glu Trp Gly Gln Ala Glu Ile Lys Arg Gln Gly Leu Glu Asp Leu
                245                 250                 255

Ala Glu Ile Arg Phe Met Asp Tyr Arg Asp Val Pro Glu Thr Gly Phe
            260                 265                 270

Asp Ala Ile Ser Ala Ile Gly Ile Ile Glu His Ile Gly Val Asn Asn
        275                 280                 285

Tyr Pro Asp Tyr Phe Glu Leu Leu Ser Ser Lys Leu Lys Thr Gly Gly
    290                 295                 300

Leu Met Leu Asn His Ser Ile Thr Tyr Pro Asp Asn Arg Pro Arg His
305                 310                 315                 320

Ala Gly Ala Phe Ile Asp Arg Tyr Ile Phe Pro Asp Gly Glu Leu Thr
                325                 330                 335

Gly Ser Gly Thr Leu Ile Lys His Met Gln Asp Asn Gly Phe Glu Val
            340                 345                 350

Leu His Glu Glu Asn Leu Arg Phe Asp Tyr Gln Arg Thr Leu His Ala
        355                 360                 365

Trp Cys Glu Asn Leu Lys Glu Asn Trp Glu Glu Ala Val Glu Leu Ala
    370                 375                 380

Gly Glu Pro Thr Ala Arg Leu Phe Gly Leu Tyr Met Ala Gly Ser Glu
385                 390                 395                 400

Trp Gly Phe Ala His Asn Ile Val Gln Leu His Gln Val Leu Gly Val
            405                 410                 415

Lys Leu Asp Glu Gln Gly Ser Arg Gly Glu Val Pro Glu Arg Met Trp
        420                 425                 430

Trp Thr Ile
        435

<210> SEQ ID NO 17
<211> LENGTH: 1458
<212> TYPE: DNA
<213> ORGANISM: Unknown
<220> FEATURE:
<223> OTHER INFORMATION: Corynebacterium glyciniphilium

<400> SEQUENCE: 17

| | | | | | |
|---|---|---|---|---|---|
| gtgaccgtcg | ccggcaggat | cactgacgcg | gtacgcatag | gaaatggact | tgaccagcga | 60 |
| gatctagccc | ccgtcgggtg | gtacgcacac | gaacaggccg | tggcgcgact | gaaggccagt | 120 |
| ttcgacgcgg | tccccgccgg | gcgtcgcgtg | cggctggcga | agaagacgtc | caacctttc | 180 |
| cgcgggcgtt | ccggcgaggc | agtcgggctc | gacgtgtcgg | ggctgcacgg | cgtcatcgcc | 240 |
| gtcgaccccg | ttgagggcac | cgctgacgtc | cagggcatgt | gcacgtacga | ggacctggtg | 300 |
| gacgtcctgc | tgccctacgg | tctggcgccc | accgtcgttc | cgcagctgaa | gaccatcact | 360 |
| ctcgccggtg | cggtgaccgg | catggggggtg | gaatccacct | ccttccgcaa | cggcctgccg | 420 |
| cacgaagccg | tcctggaaat | ggatgtgctc | accggtaccg | gagacatcct | cacctgttcg | 480 |
| ccgacccaga | acaccgacct | ctaccgcggc | ttccccaact | cctacggttc | cctgggatac | 540 |
| agcgtgcggc | tgaaggtgcg | gtgcgaacgg | gtggaaccct | acgtcgacct | gcggcatgta | 600 |
| cgcttcgatg | acgttcagtc | gctcaccgac | gccctcgaca | catcgtcgt | ggacaaggag | 660 |
| tacgagggtg | aacgggtcga | ctatctcgac | ggtgtggtct | tcagcctgga | ggagagctac | 720 |
| ctcgtcctgg | gacgggcgac | cagcgaggcc | ggccccgtta | gcgactacac | ccgcgagcgc | 780 |
| agttactacc | gttctctgca | gcatccgtcg | ggggtcctgc | gcgacaagtt | gaccatccgc | 840 |
| gactacctct | ggcggtggga | cgtcgactgg | ttctggtgca | accgggcctt | cggtacccag | 900 |
| aaccccacca | tccgtactct | gtggccgcgg | gatctcctgc | ggtcgagctt | ctactggaag | 960 |
| atcatcggct | gggaccgacg | cttcgacatc | gcggaccgga | tcgaggcaca | caacgggcgc | 1020 |
| cccgcacgcg | agcgcgtcgt | ccaggacatc | gaggtcaccc | ccgacaacct | gccggagttc | 1080 |
| ctcacgtggt | tcttcaccca | ctgcgagatc | gagccggtgt | ggctgtgccc | cattcgactg | 1140 |
| gccgacgact | cgggcgagcg | gacaccgtgg | ccctgtacc | cgctgtcacc | cggcgacacc | 1200 |
| tgggtcaacg | tgggattctg | gagctcggtg | cccgccgacc | tgatggggaa | ggacgccccg | 1260 |
| accggagcct | tcaaccggga | ggtggagaga | gtcgtctcgg | acctcggcgg | acacaagtcg | 1320 |
| ttgtactccg | aggcattcta | ttctgaggaa | cagttcgccg | ccctctacgg | cggtgaacgt | 1380 |
| cccgcacaac | tcaaggcggt | cttcgacccg | gatgaccggt | tccccgggtt | gtacgagaag | 1440 |
| accgtgggcg | gcgtctga | | | | | 1458 |

<210> SEQ ID NO 18
<211> LENGTH: 485
<212> TYPE: PRT
<213> ORGANISM: Unknown
<220> FEATURE:
<223> OTHER INFORMATION: Corynebacterium glyciniphilium

<400> SEQUENCE: 18

```
Val Thr Val Ala Gly Arg Ile Thr Asp Ala Val Arg Ile Gly Asn Gly
1               5                   10                  15

Leu Asp Gln Arg Asp Leu Ala Pro Val Gly Trp Tyr Ala His Glu Gln
            20                  25                  30

Ala Val Ala Arg Leu Lys Ala Ser Phe Asp Ala Val Pro Ala Gly Arg
            35                  40                  45

Arg Val Arg Leu Ala Lys Lys Thr Ser Asn Leu Phe Arg Gly Arg Ser
50                  55                  60

Gly Glu Ala Val Gly Leu Asp Val Ser Gly Leu His Gly Val Ile Ala
65                  70                  75                  80

Val Asp Pro Val Glu Gly Thr Ala Asp Val Gln Gly Met Cys Thr Tyr
                85                  90                  95

Glu Asp Leu Val Asp Val Leu Leu Pro Tyr Gly Leu Ala Pro Thr Val
            100                 105                 110

Val Pro Gln Leu Lys Thr Ile Thr Leu Gly Gly Ala Val Thr Gly Met
            115                 120                 125

Gly Val Glu Ser Thr Ser Phe Arg Asn Gly Leu Pro His Glu Ala Val
130                 135                 140

Leu Glu Met Asp Val Leu Thr Gly Thr Gly Asp Ile Leu Thr Cys Ser
145                 150                 155                 160

Pro Thr Gln Asn Thr Asp Leu Tyr Arg Gly Phe Pro Asn Ser Tyr Gly
                165                 170                 175

Ser Leu Gly Tyr Ser Val Arg Leu Lys Val Arg Cys Glu Arg Val Glu
            180                 185                 190

Pro Tyr Val Asp Leu Arg His Val Arg Phe Asp Asp Val Gln Ser Leu
            195                 200                 205

Thr Asp Ala Leu Asp Asn Ile Val Val Asp Lys Glu Tyr Glu Gly Glu
210                 215                 220

Arg Val Asp Tyr Leu Asp Gly Val Val Phe Ser Leu Glu Glu Ser Tyr
225                 230                 235                 240

Leu Val Leu Gly Arg Ala Thr Ser Glu Ala Gly Pro Val Ser Asp Tyr
                245                 250                 255

Thr Arg Glu Arg Ser Tyr Tyr Arg Ser Leu Gln His Pro Ser Gly Val
            260                 265                 270

Leu Arg Asp Lys Leu Thr Ile Arg Asp Tyr Leu Trp Arg Trp Asp Val
            275                 280                 285

Asp Trp Phe Trp Cys Asn Arg Ala Phe Gly Thr Gln Asn Pro Thr Ile
            290                 295                 300

Arg Thr Leu Trp Pro Arg Asp Leu Leu Arg Ser Ser Phe Tyr Trp Lys
305                 310                 315                 320

Ile Ile Gly Trp Asp Arg Arg Phe Asp Ile Ala Asp Arg Ile Glu Ala
                325                 330                 335

His Asn Gly Arg Pro Ala Arg Glu Arg Val Val Gln Asp Ile Glu Val
            340                 345                 350

Thr Pro Asp Asn Leu Pro Glu Phe Leu Thr Trp Phe Thr His Cys
            355                 360                 365

Glu Ile Glu Pro Val Trp Leu Cys Pro Ile Arg Leu Ala Asp Asp Ser
370                 375                 380

Gly Glu Arg Thr Pro Trp Pro Leu Tyr Pro Leu Ser Pro Gly Asp Thr
385                 390                 395                 400

Trp Val Asn Val Gly Phe Trp Ser Ser Val Pro Ala Asp Leu Met Gly
                405                 410                 415

Lys Asp Ala Pro Thr Gly Ala Phe Asn Arg Glu Val Glu Arg Val Val
```

```
                420             425             430
Ser Asp Leu Gly Gly His Lys Ser Leu Tyr Ser Glu Ala Phe Tyr Ser
            435                 440                 445

Glu Glu Gln Phe Ala Ala Leu Tyr Gly Gly Glu Arg Pro Ala Gln Leu
        450                 455                 460

Lys Ala Val Phe Asp Pro Asp Asp Arg Phe Pro Gly Leu Tyr Glu Lys
465                 470                 475                 480

Thr Val Gly Gly Val
            485

<210> SEQ ID NO 19
<211> LENGTH: 1368
<212> TYPE: DNA
<213> ORGANISM: Unknown
<220> FEATURE:
<223> OTHER INFORMATION: Corynebacterium glyciniphilium

<400> SEQUENCE: 19
atgagcaggg gattcacgcc gctgacggtg ggacagatcg tggacaaggt catcacaccg      60
ccggcaccgt tccgggtgac cgctttcgac ggatccaccg cggggccggc agacgcggaa    120
ctggcactga gatcacatc gccggacgcc ctggcctata tcgtgaccgc gccgggcgac     180
ctcggactgg cacgcgccta catcaccgga agcctccgcg tcaccggtga cgagcccggc    240
cacccgtacc tcgtctttga ccacctccag cacctttacg accagatccg acgccctcg    300 gcgaaggacc tgctggatat cgcccgctcg ctgaaggcca tggggcgat caaggtgcag    360 ccggcaccgg agcaggagac cctcccgggc tggaagaggg ccatactcga gggctgtcc    420 cggcactctc cggaacggga caaggaggtc gtgagccgcc actacgacgt gggcaatgac    480
ttctacgagc tcttcctcgg cgattccatg gcctacacct gtgcctacta tcccgagttt    540
gacggtgaga accaggtcac cggtcccacc ggcgggtggc ggtacgacga ctgggagaaa    600
gggccgaccg ccaacgggcc gttgaccccag gcgcaggaca caagcatcg cctggtcttc    660 gacaagctgc gactcaaccc gggtgaccgg ttgttggacg tcggctgcgg gtggggcggt    720
atggtgcggt acgccgcccg ccacggcgtg aaggccatcg tgtcacgct gtcccgagag    780 cagtacgagt ggggtaaggc gaagatcgag gaggagggtc tgcaggacct cgccgaggtc    840
cggtgtatgg actaccgtga cgtgccgagg tccgacttcg acgcggtcag tgccatcggc    900
atcctcgagc acatcggcgt gcccaactac gaggactact tcacccgcct gttcgccaag    960
ctgcgcccgg cggtcggat gctgaaccac tgcatcaccc gtccgcacaa ccggaagacg   1020
aagaccggcc agttcatcga ccgctacatc ttccccgacg tgagctgac cggctcgggc   1080 cggatcatca cgatcatgca ggacaccgga ttcgacgtcg tccacgagga gaatctgcga   1140
ccgcactacc agcgcacgtt gcatgactgg tgtgaactgt tggccaccaa ctgggaccag   1200
gccgtccatc tcgtgggcga ggagacggct cgtctgttcg cctgtacat ggcggggtcg    1260 gaatggggtt tcgaacacaa cgtgatccag ctccaccagg ttctcggcgt gaagccggac    1320
gcggcaggca gttccggggt gccggtccgc cagtggtgga ggtcctga                1368

<210> SEQ ID NO 20
<211> LENGTH: 455
<212> TYPE: PRT
<213> ORGANISM: Unknown
<220> FEATURE:
<223> OTHER INFORMATION: Corynebacterium glyciniphilium

<400> SEQUENCE: 20
```

```
Met Ser Arg Gly Phe Thr Pro Leu Thr Val Gly Gln Ile Val Asp Lys
1               5                   10                  15
Val Ile Thr Pro Pro Ala Pro Phe Arg Val Thr Ala Phe Asp Gly Ser
                20                  25                  30
Thr Ala Gly Pro Ala Asp Ala Glu Leu Ala Leu Glu Ile Thr Ser Pro
            35                  40                  45
Asp Ala Leu Ala Tyr Ile Val Thr Ala Pro Gly Asp Leu Gly Leu Ala
        50                  55                  60
Arg Ala Tyr Ile Thr Gly Ser Leu Arg Val Thr Gly Asp Glu Pro Gly
65                  70                  75                  80
His Pro Tyr Leu Val Phe Asp His Leu Gln His Leu Tyr Asp Gln Ile
                85                  90                  95
Arg Arg Pro Ser Ala Lys Asp Leu Leu Asp Ile Ala Arg Ser Leu Lys
                100                 105                 110
Ala Met Gly Ala Ile Lys Val Gln Pro Ala Pro Glu Gln Glu Thr Leu
            115                 120                 125
Pro Gly Trp Lys Arg Ala Ile Leu Glu Gly Leu Ser Arg His Ser Pro
        130                 135                 140
Glu Arg Asp Lys Glu Val Val Ser Arg His Tyr Asp Val Gly Asn Asp
145                 150                 155                 160
Phe Tyr Glu Leu Phe Leu Gly Asp Ser Met Ala Tyr Thr Cys Ala Tyr
                165                 170                 175
Tyr Pro Glu Phe Asp Gly Glu Asn Gln Val Thr Gly Pro Thr Gly Gly
                180                 185                 190
Trp Arg Tyr Asp Asp Trp Glu Lys Gly Pro Thr Ala Asn Gly Pro Leu
            195                 200                 205
Thr Gln Ala Gln Asp Asn Lys His Arg Leu Val Phe Asp Lys Leu Arg
        210                 215                 220
Leu Asn Pro Gly Asp Arg Leu Leu Asp Val Gly Cys Gly Trp Gly Gly
225                 230                 235                 240
Met Val Arg Tyr Ala Ala Arg His Gly Val Lys Ala Ile Gly Val Thr
                245                 250                 255
Leu Ser Arg Glu Gln Tyr Glu Trp Gly Lys Ala Lys Ile Glu Glu Glu
                260                 265                 270
Gly Leu Gln Asp Leu Ala Glu Val Arg Cys Met Asp Tyr Arg Asp Val
            275                 280                 285
Pro Glu Ser Asp Phe Asp Ala Val Ser Ala Ile Gly Ile Leu Glu His
        290                 295                 300
Ile Gly Val Pro Asn Tyr Glu Asp Tyr Phe Thr Arg Leu Phe Ala Lys
305                 310                 315                 320
Leu Arg Pro Gly Gly Arg Met Leu Asn His Cys Ile Thr Arg Pro His
                325                 330                 335
Asn Arg Lys Thr Lys Thr Gly Gln Phe Ile Asp Arg Tyr Ile Phe Pro
                340                 345                 350
Asp Gly Glu Leu Thr Gly Ser Gly Arg Ile Ile Thr Ile Met Gln Asp
            355                 360                 365
Thr Gly Phe Asp Val Val His Glu Glu Asn Leu Arg Pro His Tyr Gln
        370                 375                 380
Arg Thr Leu His Asp Trp Cys Glu Leu Leu Ala Thr Asn Trp Asp Gln
385                 390                 395                 400
Ala Val His Leu Val Gly Glu Glu Thr Ala Arg Leu Phe Gly Leu Tyr
                405                 410                 415
```

```
Met Ala Gly Ser Glu Trp Gly Phe Glu His Asn Val Ile Gln Leu His
            420                 425                 430
Gln Val Leu Gly Val Lys Pro Asp Ala Ala Gly Ser Ser Gly Val Pro
        435                 440                 445
Val Arg Gln Trp Trp Arg Ser
    450                 455

<210> SEQ ID NO 21
<211> LENGTH: 588
<212> TYPE: DNA
<213> ORGANISM: Unknown
<220> FEATURE:
<223> OTHER INFORMATION: Corynebacterium glyciniphilium

<400> SEQUENCE: 21
gtggcggtgc tgtgcacacc gttgctgctc ggagcctgca ccatcggcga cgcgggaccg      60
ggggacgaga ccacggaccc tgtcgtggac actgaagcac cgcccgataa accggtgccg     120
gactctgcgg cggaatccgg cgctgaagac ggacctgatt ctgaggtgcc ggacgacccc     180
gaccagcctg atgctgagcc ggtggagact gatcccgacg ccccggggc cggggactg      240 gcgatcggtg actgcgtcgc cgacatggac cagctcgacg gcaccggcga catcgacgtc     300
gtcgactgcg ccggccccca tgccggcgag gtgtacgcac aggcggatat cgcaggtaag     360
aacctgttcc ccggcaacga gccgttgggg caggaggcgg gagcgatctg cggggggtgac    420 tccttcaccg gctatgtcgg catcggattc cccgagtcct cgctggacgt cgtcacgatg     480
atgccgtcca aggagagctg ggcgcaggag accggacgg tgacctgtgt ggtcaccgac      540
ccgaacctcg agcagatcgc cggcacgctc gagcagagct ggcgttag                  588

<210> SEQ ID NO 22
<211> LENGTH: 195
<212> TYPE: PRT
<213> ORGANISM: Unknown
<220> FEATURE:
<223> OTHER INFORMATION: Corynebacterium glyciniphilium

<400> SEQUENCE: 22

Val Ala Val Leu Cys Thr Pro Leu Leu Leu Gly Ala Cys Thr Ile Gly
1               5                   10                  15
Asp Ala Gly Pro Gly Asp Glu Thr Thr Asp Pro Val Val Asp Thr Glu
            20                  25                  30
Ala Pro Pro Asp Lys Pro Val Pro Asp Ser Ala Ala Glu Ser Gly Ala
        35                  40                  45
Glu Asp Gly Pro Asp Ser Glu Val Pro Asp Pro Asp Gln Pro Asp
    50                  55                  60
Ala Glu Pro Val Glu Thr Asp Pro Asp Ala Pro Gly Ala Arg Gly Leu
65                  70                  75                  80
Ala Ile Gly Asp Cys Val Ala Asp Met Asp Gln Leu Asp Gly Thr Gly
                85                  90                  95
Asp Ile Asp Val Val Asp Cys Ala Gly Pro His Ala Gly Glu Val Tyr
            100                 105                 110
Ala Gln Ala Asp Ile Ala Gly Lys Asn Leu Phe Pro Gly Asn Glu Pro
        115                 120                 125
Leu Gly Gln Glu Ala Gly Ala Ile Cys Gly Gly Asp Ser Phe Thr Gly
    130                 135                 140
Tyr Val Gly Ile Gly Phe Pro Glu Ser Ser Leu Asp Val Val Thr Met
145                 150                 155                 160
```

Met Pro Ser Lys Glu Ser Trp Ala Gln Glu Asp Arg Thr Val Thr Cys
              165                 170                 175

Val Val Thr Asp Pro Asn Leu Glu Gln Ile Ala Gly Thr Leu Glu Gln
            180                 185                 190

Ser Trp Arg
        195

<210> SEQ ID NO 23
<211> LENGTH: 1395
<212> TYPE: DNA
<213> ORGANISM: Unknown
<220> FEATURE:
<223> OTHER INFORMATION: Knoella aerolata

<400> SEQUENCE: 23

```
atgagcatgg accggaccgg accgccagg gtgcggaccg tgggggagcg gcggctgctc        60
gagagcttcg ccgccgtccc cccgggcgaa cgcgtgcggc tggccaagcg cacgtccaac      120
ctcttccgcg cccgggaggg cacctcgaca cgcgggctcg acacgagcgg actgaccggc      180
gtgcgcgtgg tcgacgcagg caccctcacg gccgacgtcg acggaatgtg cacgtacgag      240
gacctcgtcg ccgcaacgct gccgctcggg ctcgcgccgc tcgtcgtgcc ccagctgcgg      300
accatcaccg tcggcggggc ggtcaccggt ctcgggatcg agtcgacgtc gttccgcaac      360
gggttgccgc acgagtccgt cctcgagatg gacgtcctca cggtgccgg cgagatcgtc       420
actgccacag cggacaacga gcacgccgac ctcttccgcg gcttccccaa ctcctacggg      480
tcgctgggct acgcgacgtg cctgcgcatc gagctcgagc gtgtgggtac ctgtgtggag      540
gtgaggcacg tccgcttcca cgacctcgac gccctgtgcg ccgccatcgc cgaggtcgtg      600
gcgacgagat cgcacgaggg cgaggaggtc gaccacgtgg acggggtggt cttctcccgc      660
gacgaggcgt acctcacgct gggtcgtcac tccgaccgga ccggaccgac cagcgactac      720
accgggcagc aggtctacta ccggtcgatc cagcacgacg gccccctctcc acggcgcgac    780
ctgctcacca ctcacgacta cctctggcgc tgggacaccg actggttctg gtgctcgcgc     840
gccttcgggg cccaggaccc gcgcgtccgg cggtggtggc cgcgccggtg cgcgggtcg      900
agcgtgtact ggaggctcgt ggcggcggac cggcgcgtcg ggttctcgga ccgctcgag      960
gcacgtcggg gcaacccgcc gcgggagcgg gtggtccagg acgtcgagat cccgctcggg    1020
cagaccgcgg ccttcctcca ctggttcctc gacgaggtgc cgatcgaacc gatctggctg    1080
tgcccgttgc gtcttcgcga ccatcagagg tggccgctct atccgctcga gcccggacgc    1140
acctacgtca acgtggggtt ctggtcgacc gtgccggggc ccggaccggg cgaggagctg    1200
ggcgccacca accgcgccat cgagcgccgt gtcgacgagg tcggcggcca caagtccctg    1260
tactccgact cctactactc ccggtccgac ttcgacgccc tctacggcgg ggacgcgtat    1320
gccgtgctga aggccaccta cgacccggac gggcggttcc ctcacctcta cgacaaggcg    1380
gtgcgacacg catga                                                     1395
```

<210> SEQ ID NO 24
<211> LENGTH: 464
<212> TYPE: PRT
<213> ORGANISM: Unknown
<220> FEATURE:
<223> OTHER INFORMATION: Knoella aerolata

<400> SEQUENCE: 24

Met Ser Met Asp Arg Thr Gly Pro Ala Arg Val Arg Thr Val Gly Glu
1               5                   10                  15

```
Arg Arg Leu Leu Glu Ser Phe Ala Ala Val Pro Pro Gly Glu Arg Val
            20                  25                  30

Arg Leu Ala Lys Arg Thr Ser Asn Leu Phe Arg Ala Arg Glu Gly Thr
        35                  40                  45

Ser Thr Arg Gly Leu Asp Thr Ser Gly Leu Thr Gly Val Arg Val Val
50                  55                  60

Asp Ala Gly Thr Leu Thr Ala Asp Val Asp Gly Met Cys Thr Tyr Glu
65                  70                  75                  80

Asp Leu Val Ala Ala Thr Leu Pro Leu Gly Leu Ala Pro Leu Val Val
                85                  90                  95

Pro Gln Leu Arg Thr Ile Thr Val Gly Gly Ala Val Thr Gly Leu Gly
            100                 105                 110

Ile Glu Ser Thr Ser Phe Arg Asn Gly Leu Pro His Glu Ser Val Leu
        115                 120                 125

Glu Met Asp Val Leu Thr Gly Ala Gly Glu Ile Val Thr Ala Thr Ala
    130                 135                 140

Asp Asn Glu His Ala Asp Leu Phe Arg Gly Phe Pro Asn Ser Tyr Gly
145                 150                 155                 160

Ser Leu Gly Tyr Ala Thr Cys Leu Arg Ile Glu Leu Gly Arg Val Gly
                165                 170                 175

Thr Cys Val Glu Val Arg His Val Arg Phe His Asp Leu Asp Ala Leu
            180                 185                 190

Cys Ala Ala Ile Ala Glu Val Val Ala Thr Arg Ser His Glu Gly Glu
        195                 200                 205

Glu Val Asp His Val Asp Gly Val Val Phe Ser Arg Asp Glu Ala Tyr
    210                 215                 220

Leu Thr Leu Gly Arg His Ser Asp Arg Thr Gly Pro Thr Ser Asp Tyr
225                 230                 235                 240

Thr Gly Gln Gln Val Tyr Tyr Arg Ser Ile Gln His Asp Gly Pro Ser
                245                 250                 255

Pro Arg Arg Asp Leu Leu Thr Thr His Asp Tyr Leu Trp Arg Trp Asp
            260                 265                 270

Thr Asp Trp Phe Trp Cys Ser Arg Ala Phe Gly Ala Gln Asp Pro Arg
        275                 280                 285

Val Arg Arg Trp Trp Pro Arg Arg Trp Arg Ser Ser Val Tyr Trp
    290                 295                 300

Arg Leu Val Ala Ala Asp Arg Arg Val Gly Phe Ser Asp Arg Leu Glu
305                 310                 315                 320

Ala Arg Arg Gly Asn Pro Pro Arg Glu Arg Val Val Gln Asp Val Glu
                325                 330                 335

Ile Pro Leu Gly Gln Thr Ala Ala Phe Leu His Trp Phe Leu Asp Glu
            340                 345                 350

Val Pro Ile Glu Pro Ile Trp Leu Cys Pro Leu Arg Leu Arg Asp His
        355                 360                 365

Gln Arg Trp Pro Leu Tyr Pro Leu Glu Pro Gly Arg Thr Tyr Val Asn
    370                 375                 380

Val Gly Phe Trp Ser Thr Val Pro Gly Pro Gly Glu Leu
385                 390                 395                 400

Gly Ala Thr Asn Arg Ala Ile Glu Arg Arg Val Asp Val Gly Gly
                405                 410                 415

His Lys Ser Leu Tyr Ser Asp Ser Tyr Tyr Ser Arg Ser Asp Phe Asp
            420                 425                 430
```

Ala Leu Tyr Gly Gly Asp Ala Tyr Ala Val Leu Lys Ala Thr Tyr Asp
        435                 440                 445

Pro Asp Gly Arg Phe Pro His Leu Tyr Asp Lys Ala Val Arg His Ala
    450                 455                 460

<210> SEQ ID NO 25
<211> LENGTH: 1284
<212> TYPE: DNA
<213> ORGANISM: Unknown
<220> FEATURE:
<223> OTHER INFORMATION: Knoella aerolata

<400> SEQUENCE: 25

| | | | | | |
|---|---|---|---|---|---|
| atgagccaca | cgaccgatga | gatccgcacg | gtcgccgacc | tcgtcgacga | ggtggtcgtc | 60 |
| ggcccgctgc | cggtgcgggt | cacggcctac | gacgggtcga | agacggggcc | ggacagcgcc | 120 |
| ccgcgaacca | tccacatcgc | caaccagcga | gcggtcgcct | acctcgccac | cgcgcccggg | 180 |
| gacctcggca | tggcccgcgc | ctacaccacc | ggtgacctcg | tcgtcgaggg | cgtgcacccg | 240 |
| ggcaacccct | acgaggccct | ggtcgacctc | gaacgtgtgc | acttccgccg | ccggaccccg | 300 |
| cggctgctcc | tcgacctcgc | gcgcatcgtc | gggccacgca | acctcgcgcc | ccgcccccg | 360 |
| ccgccgcagg | aggctgtgcc | gaggtggcgg | cgggtggccg | agggcctgcg | ccactcgtac | 420 |
| gggcgggaca | gcgaggcgat | ccgccaccac | tacgacgtct | ccaaccactt | ctacgagcag | 480 |
| gtgctcggcc | cgagcatgac | ctacacctgc | gcggtcttcc | ccgaccacga | caccgggctc | 540 |
| gacgaggcgc | aggaggagaa | gtaccgcctc | gtcttcgaga | agctcgcgct | cgtcccggt | 600 |
| gaccggttgc | tcgacatcgg | ctgcgggtgg | ggcgggatgg | tccggtacgc | cgcacggcgg | 660 |
| ggggtgcgag | cgctcggcgt | gacactgtcc | ggtgagcagg | cggcgtgggc | acaggtcgcc | 720 |
| atcgcccgcg | aggggctggg | ggagctcgcc | gccgtccggc | acgaggacta | ccgccacgtc | 780 |
| gccgagaccg | ggttcgacgc | catctcctcg | atcggcatca | ccgagcacat | cggggtgcgc | 840 |
| aactacccca | cgtacttcga | ctggatgctc | caccacgtca | agccgggagg | gctcgtgctc | 900 |
| aaccactgca | tcaccagacc | cgagaaccgg | gccaagagcg | tcggccggtt | catcgaccgc | 960 |
| tacatcttcc | ccgacggcga | gctcaccggg | tccggccgga | tcatcacgac | catgcaggac | 1020 |
| aacggtttcg | aggtcgtgca | ctccgagaac | ctgcgagagc | actacgccct | caccctggcg | 1080 |
| gcctggggcg | agaacctcgt | cgagcactgg | gcctcctgcg | tggccgacgt | ggggagggg | 1140 |
| acggcgaagg | tctggggcct | ctacctcgcg | ggctcgcgtc | gtggcttcga | gcgcaacgtc | 1200 |
| gtccagctgc | accaggtgct | ggccgcgagg | ccggtgccgt | cccgactccc | gcaggtgccg | 1260 |
| ctgcgccagt | ggtggaccct | cgtga | | | | 1284 |

<210> SEQ ID NO 26
<211> LENGTH: 427
<212> TYPE: PRT
<213> ORGANISM: Unknown
<220> FEATURE:
<223> OTHER INFORMATION: Knoella aerolata

<400> SEQUENCE: 26

Met Ser His Thr Thr Asp Glu Ile Arg Thr Val Ala Asp Leu Val Asp
1               5                   10                  15

Glu Val Val Val Gly Pro Leu Pro Val Arg Val Thr Ala Tyr Asp Gly
                20                  25                  30

Ser Lys Thr Gly Pro Asp Ser Ala Pro Arg Thr Ile His Ile Ala Asn
            35                  40                  45

Gln Arg Ala Val Ala Tyr Leu Ala Thr Ala Pro Gly Asp Leu Gly Met
            50                  55                  60

Ala Arg Ala Tyr Thr Thr Gly Asp Leu Val Val Glu Gly Val His Pro
 65                  70                  75                  80

Gly Asn Pro Tyr Glu Ala Leu Val Asp Leu Glu Arg Val His Phe Arg
                 85                  90                  95

Arg Pro Asp Pro Arg Leu Leu Asp Leu Ala Arg Ile Val Gly Pro
            100                 105                 110

Arg Asn Leu Ala Pro Pro Pro Pro Gln Glu Ala Val Pro Arg
            115                 120                 125

Trp Arg Arg Val Ala Glu Gly Leu Arg His Ser Tyr Gly Arg Asp Ser
130                 135                 140

Glu Ala Ile Arg His His Tyr Asp Val Ser Asn His Phe Tyr Glu Gln
145                 150                 155                 160

Val Leu Gly Pro Ser Met Thr Tyr Thr Cys Ala Val Phe Pro Asp His
                165                 170                 175

Asp Thr Gly Leu Asp Glu Ala Gln Glu Glu Lys Tyr Arg Leu Val Phe
            180                 185                 190

Glu Lys Leu Ala Leu Arg Pro Gly Asp Arg Leu Leu Asp Ile Gly Cys
            195                 200                 205

Gly Trp Gly Gly Met Val Arg Tyr Ala Ala Arg Arg Gly Val Arg Ala
210                 215                 220

Leu Gly Val Thr Leu Ser Gly Glu Gln Ala Ala Trp Ala Gln Val Ala
225                 230                 235                 240

Ile Ala Arg Glu Gly Leu Gly Glu Leu Ala Ala Val Arg His Glu Asp
                245                 250                 255

Tyr Arg His Val Ala Glu Thr Gly Phe Asp Ala Ile Ser Ser Ile Gly
            260                 265                 270

Ile Thr Glu His Ile Gly Val Arg Asn Tyr Pro Thr Tyr Phe Asp Trp
            275                 280                 285

Met Leu His His Val Lys Pro Gly Gly Leu Val Leu Asn His Cys Ile
            290                 295                 300

Thr Arg Pro Glu Asn Arg Ala Lys Ser Val Gly Arg Phe Ile Asp Arg
305                 310                 315                 320

Tyr Ile Phe Pro Asp Gly Glu Leu Thr Gly Ser Gly Arg Ile Ile Thr
                325                 330                 335

Thr Met Gln Asp Asn Gly Phe Glu Val Val His Ser Glu Asn Leu Arg
            340                 345                 350

Glu His Tyr Ala Leu Thr Leu Ala Ala Trp Gly Glu Asn Leu Val Glu
            355                 360                 365

His Trp Ala Ser Cys Val Ala Asp Val Gly Glu Gly Thr Ala Lys Val
370                 375                 380

Trp Gly Leu Tyr Leu Ala Gly Ser Arg Arg Gly Phe Glu Arg Asn Val
385                 390                 395                 400

Val Gln Leu His Gln Val Leu Ala Ala Arg Pro Val Pro Ser Arg Leu
                405                 410                 415

Pro Gln Val Pro Leu Arg Gln Trp Trp Thr Ser
            420                 425

<210> SEQ ID NO 27
<211> LENGTH: 1392
<212> TYPE: DNA
<213> ORGANISM: Mycobacterium austroafricanum

<400> SEQUENCE: 27
gtgtctgttc cttcgaccga cgcacgttct gctcacgccg acggcgtgca gcggcttctc         60
gccagctatc gggcgattcc ccaagacgcc acggtccggc tggccaaacc cacgtcgaac        120
ctcttccgtg cccgcgcgaa aaccaggacc aagggtctgg acacgtctgg gttgacgaac        180
gtgatcgcgg tcgacgcgga ggcacgcacc gccgatgtgg cagggatgtg cacctacgaa        240
gacctggtcg cggccacgct gccgcatgga ctttcgccgc tggtggtgcc gcagttgaag        300
acgatcaccc tcggcggggc ggtcaccgga ctcgggatcg agtccgcctc gttccgcaac        360
ggcctgccac acgaatcggt tctcgagatg gacgtcctca ccggcaccgg tgatgtcgtg        420
cgcgcctccc ccgacgagaa ccctgacctg tttcgggcgt ttccgaattc ctatggcacg        480
ttgggctatt cggttcggct caagatcgag ctggaaccgg tgaagccgtt cgtcgcgctg        540
cgccacctcc gtttccattc gctgtcggct ctcatcgagg cgatggaccg catcgtcgaa        600
accggcggcc tcaacggcga accggtggac tacctcgacg gcgtcgtgtt cagtgccgag        660
gagagttacc tgtgcgtggg gcagcgctcc gcgacaccgg gcccggtcag cgactacacg        720
ggcaagcaga tctactaccg ctcgattcag cacgacggcc cgaccgatgg cgccgagaag        780
cacgaccggt tgaccatcca cgactacctg tggcgctggg acaccgactg gttctggtgc        840
tcaagggcat tcggcgcgca gaacccgcgg atccggcgct ggtggccgcg ccggtaccgg        900
cgcagcagtg tgtactggaa gctgatcggc tacgaccggg gtttcggtat cgccgatcgc        960
atcgagaagc gcaacggccg accccgcgc gagcgggtgg tccaggacat cgaggtgccc       1020
atcgagcgga ccgtcgagtt tctgcagtgg tttctcgaca ccgtgcccat cgaaccgatc       1080
tggttgtgcc cgttgcggct ccgcgacgac cgcgattggc ccctgtatcc gatccgaccc       1140
caccacacct acgtcaacgt gggtttctgg tcgtcggtgc cggtgggccc ggaggagggc       1200
tacaccaaca ggatgatcga acggaaagtc agcgacctcg acggtcacaa atcgctgtat       1260
tccgatgcgt actactcgcc ggaagagttt gattcgctct atggcgggga gacgtacaag       1320
acggtgaaga agacatacga cccagactct cgtttcctgg acctgtacgg caaagcagtg       1380
gggcggcaat ga                                                          1392

<210> SEQ ID NO 28
<211> LENGTH: 463
<212> TYPE: PRT
<213> ORGANISM: Mycobacterium austroafricanum

<400> SEQUENCE: 28

Val Ser Val Pro Ser Thr Asp Ala Arg Ser Ala His Ala Asp Gly Val
1               5                   10                  15

Gln Arg Leu Leu Ala Ser Tyr Arg Ala Ile Pro Gln Asp Ala Thr Val
            20                  25                  30

Arg Leu Ala Lys Pro Thr Ser Asn Leu Phe Arg Ala Arg Ala Lys Thr
        35                  40                  45

Arg Thr Lys Gly Leu Asp Thr Ser Gly Leu Thr Asn Val Ile Ala Val
    50                  55                  60

Asp Ala Glu Ala Arg Thr Ala Asp Val Ala Gly Met Cys Thr Tyr Glu
65                  70                  75                  80

Asp Leu Val Ala Ala Thr Leu Pro His Gly Leu Ser Pro Leu Val Val
                85                  90                  95

Pro Gln Leu Lys Thr Ile Thr Leu Gly Gly Ala Val Thr Gly Leu Gly
            100                 105                 110

Ile Glu Ser Ala Ser Phe Arg Asn Gly Leu Pro His Glu Ser Val Leu

```
                    115                 120                 125
Glu Met Asp Val Leu Thr Gly Thr Gly Asp Val Val Arg Ala Ser Pro
            130                 135                 140

Asp Glu Asn Pro Asp Leu Phe Arg Ala Phe Pro Asn Ser Tyr Gly Thr
145                 150                 155                 160

Leu Gly Tyr Ser Val Arg Leu Lys Ile Glu Leu Glu Pro Val Lys Pro
                165                 170                 175

Phe Val Ala Leu Arg His Leu Arg Phe His Ser Leu Ser Ala Leu Ile
            180                 185                 190

Glu Ala Met Asp Arg Ile Val Glu Thr Gly Gly Leu Asn Gly Glu Pro
        195                 200                 205

Val Asp Tyr Leu Asp Gly Val Val Phe Ser Ala Glu Glu Ser Tyr Leu
    210                 215                 220

Cys Val Gly Gln Arg Ser Ala Thr Pro Gly Pro Val Ser Asp Tyr Thr
225                 230                 235                 240

Gly Lys Gln Ile Tyr Tyr Arg Ser Ile Gln His Asp Gly Pro Thr Asp
                245                 250                 255

Gly Ala Glu Lys His Asp Arg Leu Thr Ile His Asp Tyr Leu Trp Arg
            260                 265                 270

Trp Asp Thr Asp Trp Phe Trp Cys Ser Arg Ala Phe Gly Ala Gln Asn
        275                 280                 285

Pro Arg Ile Arg Arg Trp Trp Pro Arg Tyr Arg Arg Ser Ser Val
    290                 295                 300

Tyr Trp Lys Leu Ile Gly Tyr Asp Arg Arg Phe Gly Ile Ala Asp Arg
305                 310                 315                 320

Ile Glu Lys Arg Asn Gly Arg Pro Arg Glu Arg Val Val Gln Asp
                325                 330                 335

Ile Glu Val Pro Ile Glu Arg Thr Val Glu Phe Leu Gln Trp Phe Leu
            340                 345                 350

Asp Thr Val Pro Ile Glu Pro Ile Trp Leu Cys Pro Leu Arg Leu Arg
        355                 360                 365

Asp Asp Arg Asp Trp Pro Leu Tyr Pro Ile Arg Pro His His Thr Tyr
    370                 375                 380

Val Asn Val Gly Phe Trp Ser Ser Val Pro Val Gly Pro Glu Glu Gly
385                 390                 395                 400

Tyr Thr Asn Arg Met Ile Glu Arg Lys Val Ser Asp Leu Asp Gly His
                405                 410                 415

Lys Ser Leu Tyr Ser Asp Ala Tyr Tyr Ser Pro Glu Glu Phe Asp Ser
            420                 425                 430

Leu Tyr Gly Gly Glu Thr Tyr Lys Thr Val Lys Lys Thr Tyr Asp Pro
        435                 440                 445

Asp Ser Arg Phe Leu Asp Leu Tyr Gly Lys Ala Val Gly Arg Gln
    450                 455                 460
```

<210> SEQ ID NO 29
<211> LENGTH: 1323
<212> TYPE: DNA
<213> ORGANISM: Mycobacterium austroafricanum

<400> SEQUENCE: 29

```
ttgacgacat tcgggacgg cgcggccgac accggcctgc acggagaccg caagctcacc      60
ctggcggagg tcttggaggt cttcgcctcg ggccgactgc tctgaagtt cacgcgtac     120 gacggcagca gcgcgggccc ggacgacgcc acgctcgggc tggacctgct gaccccccgc   180
```

```
gggaccacgt acctcgcaac ggctcccggc gatctcggcc tggcccgggc ctacgtctcc    240
ggtgacctgc agttgcaggg ggtgcaccct ggcgacccgt acgacctgct caacgcactg    300
gtgcagaaac tggacttcaa gcgaccgtcc gcccgggtgc tggcgcaggt cgtccgatcg    360
atcgggatcg agcacctgaa accgatcgcg ccaccgccgc aggaggcgct gccgcggtgg    420
cggcgcatcg cagaaggact gcggcacagc aagacccgtg acgccgacgc gatccaccac    480
cattacgatg tctccaacac cttctacgag tgggtgctcg gccgtcgat gacctacacc    540 tgcgcctgct acccgcatcc cgacgccacc ctcgaggagg cgcaggagaa caaatatcgg    600
ctggtgttcg agaaactgcg cctcaagccg ggcgaccgcc ttctcgacgt ggggttgcggg   660 tggggcggaa tggtgcgcta cgcggcccgt cacggcgtca aggcgatcgg ggtgacgctg    720
tccagggagc aggcgcagtg ggcacgcgcc gccatcgaac gggacggcct gggtgacctc    780
gccgaggtcc gccacagcga ctaccgcgat gtgcgcgagt cccagttcga cgccgtgtct    840
tcgctggggc tcaccgagca catcggggtc gccaactatc cgtcgtactt ccggttcctc    900
aagtcgaagt tgcgcccggg cggcctactg ctcaaccact gcatcacccg gcacaacaat    960
cgcaccggcc ccgccgccgg gggattcatc gaccggtatg tgttcccgga cggggagctg   1020
accggatcgg gccggatcat caccgagatc caggacgtcg gtttggaggt gatgcacgaa   1080
gagaacctgc gccggcacta tgcgctgaca cttcgggact ggtgccggaa tctggtgcag   1140
cactgggacg aagcggtcgc agaggtcggc ctgcccaccg ccaaggtgtg gggtctgtac   1200
atggctgcct cgcgggtcgg cttcgagcag aacagcattc agctgcatca ggtactggcg   1260
gtgaagctcg acgaacgtgg cggggacggc ggtttgccgt tgcggccctg gtggaccgcg   1320
tag                                                                 1323
```

<210> SEQ ID NO 30
<211> LENGTH: 440
<212> TYPE: PRT
<213> ORGANISM: Mycobacterium austroafricanum

<400> SEQUENCE: 30

```
Leu Thr Thr Phe Arg Asp Gly Ala Ala Asp Thr Gly Leu His Gly Asp
1               5                   10                  15

Arg Lys Leu Thr Leu Ala Glu Val Leu Glu Val Phe Ala Ser Gly Arg
            20                  25                  30

Leu Pro Leu Lys Phe Thr Ala Tyr Asp Gly Ser Ser Ala Gly Pro Asp
        35                  40                  45

Asp Ala Thr Leu Gly Leu Asp Leu Leu Thr Pro Arg Gly Thr Thr Tyr
    50                  55                  60

Leu Ala Thr Ala Pro Gly Asp Leu Gly Leu Ala Arg Ala Tyr Val Ser
65                  70                  75                  80

Gly Asp Leu Gln Leu Gln Gly Val His Pro Gly Asp Pro Tyr Asp Leu
                85                  90                  95

Leu Asn Ala Leu Val Gln Lys Leu Asp Phe Lys Arg Pro Ser Ala Arg
            100                 105                 110

Val Leu Ala Gln Val Val Arg Ser Ile Gly Ile Glu His Leu Lys Pro
        115                 120                 125

Ile Ala Pro Pro Pro Gln Glu Ala Leu Pro Arg Trp Arg Arg Ile Ala
    130                 135                 140

Glu Gly Leu Arg His Ser Lys Thr Arg Asp Ala Asp Ala Ile His His
145                 150                 155                 160

His Tyr Asp Val Ser Asn Thr Phe Tyr Glu Trp Val Leu Gly Pro Ser
```

```
              165                 170                 175
Met Thr Tyr Thr Cys Ala Cys Tyr Pro His Pro Asp Ala Thr Leu Glu
              180                 185                 190

Glu Ala Gln Glu Asn Lys Tyr Arg Leu Val Phe Glu Lys Leu Arg Leu
              195                 200                 205

Lys Pro Gly Asp Arg Leu Leu Asp Val Gly Cys Gly Trp Gly Gly Met
210                 215                 220

Val Arg Tyr Ala Ala Arg His Gly Val Lys Ala Ile Gly Val Thr Leu
225                 230                 235                 240

Ser Arg Glu Gln Ala Gln Trp Ala Arg Ala Ile Glu Arg Asp Gly
              245                 250                 255

Leu Gly Asp Leu Ala Glu Val Arg His Ser Asp Tyr Arg Asp Val Arg
              260                 265                 270

Glu Ser Gln Phe Asp Ala Val Ser Ser Leu Gly Leu Thr Glu His Ile
              275                 280                 285

Gly Val Ala Asn Tyr Pro Ser Tyr Phe Arg Phe Leu Lys Ser Lys Leu
              290                 295                 300

Arg Pro Gly Gly Leu Leu Asn His Cys Ile Thr Arg His Asn Asn
305                 310                 315                 320

Arg Thr Gly Pro Ala Ala Gly Phe Ile Asp Arg Tyr Val Phe Pro
              325                 330                 335

Asp Gly Glu Leu Thr Gly Ser Gly Arg Ile Ile Thr Glu Ile Gln Asp
              340                 345                 350

Val Gly Leu Glu Val Met His Glu Glu Asn Leu Arg Arg His Tyr Ala
              355                 360                 365

Leu Thr Leu Arg Asp Trp Cys Arg Asn Leu Val Gln His Trp Asp Glu
370                 375                 380

Ala Val Ala Glu Val Gly Leu Pro Thr Ala Lys Val Trp Gly Leu Tyr
385                 390                 395                 400

Met Ala Ala Ser Arg Val Gly Phe Glu Gln Asn Ser Ile Gln Leu His
              405                 410                 415

Gln Val Leu Ala Val Lys Leu Asp Glu Arg Gly Gly Asp Gly Gly Leu
              420                 425                 430

Pro Leu Arg Pro Trp Trp Thr Ala
              435                 440

<210> SEQ ID NO 31
<211> LENGTH: 381
<212> TYPE: DNA
<213> ORGANISM: Mycobacterium austroafricanum

<400> SEQUENCE: 31
gtgatccgct ttctgctgcg cgtcgcggtc tttctcggat cgtcggcgat cgggctactg    60
gtggccggct ggctggtgcc gggggtgtcg ctgtcggtgc tgggcttcgt caccgcggtg   120
gtgatcttca cggtggcaca agggattctg tcgccgttct tcctgaagat ggccagccgc   180
tacgcgtcgg ccttcctcgg cggcatcggc ctggtgtcca cgttcgtggc gctgctgctc   240
gcgtcgctgc tgtccaacgg gctcagcatc cgcggcgtcg ggtcgtggat cgcggccacg   300
gtggtggtct ggctggtcac agccctggcg accgtcgtgc tgcccgttct ggtgctgcgg   360
gagaagaaga aagcagcctg a                                             381

<210> SEQ ID NO 32
<211> LENGTH: 126
<212> TYPE: PRT
```

<213> ORGANISM: Mycobacterium austroafricanum

<400> SEQUENCE: 32

```
Val Ile Arg Phe Leu Leu Arg Val Ala Val Phe Leu Gly Ser Ser Ala
1               5                   10                  15
Ile Gly Leu Leu Val Ala Gly Trp Leu Val Pro Gly Val Ser Leu Ser
            20                  25                  30
Val Leu Gly Phe Val Thr Ala Val Val Ile Phe Thr Val Ala Gln Gly
        35                  40                  45
Ile Leu Ser Pro Phe Phe Leu Lys Met Ala Ser Arg Tyr Ala Ser Ala
    50                  55                  60
Phe Leu Gly Gly Ile Gly Leu Val Ser Thr Phe Val Ala Leu Leu Leu
65                  70                  75                  80
Ala Ser Leu Leu Ser Asn Gly Leu Ser Ile Arg Gly Val Gly Ser Trp
                85                  90                  95
Ile Ala Ala Thr Val Val Val Trp Leu Val Thr Ala Leu Ala Thr Val
            100                 105                 110
Val Leu Pro Val Leu Val Leu Arg Glu Lys Lys Lys Ala Ala
        115                 120                 125
```

<210> SEQ ID NO 33
<211> LENGTH: 1392
<212> TYPE: DNA
<213> ORGANISM: Mycobacterium gilvum

<400> SEQUENCE: 33

```
gtgtctgttg ccgtaaccga cgcacgatcc gcctacgccc acggcgtgca gcggctggtc      60
gcgagttacc gcgccatccc cgccggcgcc accgtccgcc tggccaaacc cacgtccaac     120
ctgttccgcg ccagggcgaa gagcaccgcg gcgggcctcg acacctccgg cctgacacat     180
gtgatcgccg tggaccccga cgcgcaccc gccgaggtcg cggggatgtg cacctacgag     240
gacctggtgg cggcgacgct gccccacggg ctttcaccgc tggtggtccc gcaactcaag     300
acgatcaccc tcggcggcgc cgtcaccggg ctcggcatcg agtcggcgtc gttccgcaac     360
ggccttccgc acgaatcggt cctggagatg gacatcctca ccgggaccgg cgacatcgtg     420
cgcgccgcgc ccgacgagaa tcccgacctt ttccgcacct tcccgaattc ttatggaacg     480
ctgggttact cggttcggct gaagatcgag ctggagccgg tgaagccgtt cgtggcgtta     540
cgccatctcc gcttccactc actgtcgaca ctcatcgcga cgatggaccg catcgtcgac     600
accgggagtc tcgacggtga gcaggtcgac tatctcgacg gagtggtgtt cagcgccgag     660
gagagctacc tgtgcgtcgg aacacgttcc gcgacaccgg gtcctgtcag cgactacacc     720
ggcgagcaca tcttctaccg gtcgatccag cacgattgcc cgaccgaagg cggacagaag     780
cacgaccggc tgacggcgca cgactacttc tggcgctggg acaccgactg gttctggtgc     840
tcaagggcat tcggcgcgca gaacccgaag gtccgtcggt ggtggccccg acggctccgg     900
cgcagcagct tctactggaa gctcgtcggc tacgaccagc gtttcggcat cgccgaccgg     960
atcgagaaac accacggccg gccaccgcgc gaacgcgtcg tccaggacgt cgaggtcccc    1020
atcgagcgca ccgtcgaatt cctgcagtgg ttcctcgaca cgatcccgat agagccgctc    1080
tggttgtgcc cgttgcgact cgcgatgac aacagctggt cgctgtaccc gctccggccc    1140
catcgcacgt atgtcaacgt gggattctgg tcgtcggtgc ccgtcgggcc ggaggagggt    1200
cacaccaaca agctgatcga acgcaggatc agcgagctgg agggacacaa gtcgctgtac    1260
tccgacgcct tctattcggc cgacgagttc gacgcgctgt acggcggcga gatctaccgg    1320
```

```
accgtgaaga agacctacga cccagattct cgtttcctcg acctctatgc gaaggcggtg    1380
cgacggcaat ga                                                       1392
```

<210> SEQ ID NO 34
<211> LENGTH: 463
<212> TYPE: PRT
<213> ORGANISM: Mycobacterium gilvum

<400> SEQUENCE: 34

| | | | | | | | | | | | | | | |
|---|---|---|---|---|---|---|---|---|---|---|---|---|---|---|
| Val | Ser | Val | Ala | Val | Thr | Asp | Ala | Arg | Ser | Ala | Tyr | Ala | His | Gly | Val |
| 1 | | | | 5 | | | | | 10 | | | | | 15 | |

Gln Arg Leu Val Ala Ser Tyr Arg Ala Ile Pro Ala Gly Ala Thr Val
            20                  25                  30

Arg Leu Ala Lys Pro Thr Ser Asn Leu Phe Arg Ala Arg Ala Lys Ser
        35                  40                  45

Thr Ala Ala Gly Leu Asp Thr Ser Gly Leu Thr His Val Ile Ala Val
    50                  55                  60

Asp Pro Glu Thr Arg Thr Ala Glu Val Ala Gly Met Cys Thr Tyr Glu
65                  70                  75                  80

Asp Leu Val Ala Ala Thr Leu Pro His Gly Leu Ser Pro Leu Val Val
                85                  90                  95

Pro Gln Leu Lys Thr Ile Thr Leu Gly Gly Ala Val Thr Gly Leu Gly
            100                 105                 110

Ile Glu Ser Ala Ser Phe Arg Asn Gly Leu Pro His Glu Ser Val Leu
        115                 120                 125

Glu Met Asp Ile Leu Thr Gly Thr Gly Asp Ile Val Arg Ala Ala Pro
    130                 135                 140

Asp Glu Asn Pro Asp Leu Phe Arg Thr Phe Pro Asn Ser Tyr Gly Thr
145                 150                 155                 160

Leu Gly Tyr Ser Val Arg Leu Lys Ile Glu Leu Glu Pro Val Lys Pro
                165                 170                 175

Phe Val Ala Leu Arg His Leu Arg Phe His Ser Leu Ser Thr Leu Ile
            180                 185                 190

Ala Thr Met Asp Arg Ile Val Asp Thr Gly Ser Leu Asp Gly Glu Gln
        195                 200                 205

Val Asp Tyr Leu Asp Gly Val Val Phe Ser Ala Glu Glu Ser Tyr Leu
    210                 215                 220

Cys Val Gly Thr Arg Ser Ala Thr Pro Gly Pro Val Ser Asp Tyr Thr
225                 230                 235                 240

Gly Glu His Ile Phe Tyr Arg Ser Ile Gln His Asp Cys Pro Thr Glu
                245                 250                 255

Gly Gly Gln Lys His Asp Arg Leu Thr Ala His Asp Tyr Phe Trp Arg
            260                 265                 270

Trp Asp Thr Asp Trp Phe Trp Cys Ser Arg Ala Phe Gly Ala Gln Asn
        275                 280                 285

Pro Lys Val Arg Arg Trp Pro Arg Arg Leu Arg Ser Ser Phe
    290                 295                 300

Tyr Trp Lys Leu Val Gly Tyr Asp Gln Arg Phe Gly Ile Ala Asp Arg
305                 310                 315                 320

Ile Glu Lys His His Gly Arg Pro Arg Glu Arg Val Val Gln Asp
                325                 330                 335

Val Glu Val Pro Ile Glu Arg Thr Val Glu Phe Leu Gln Trp Phe Leu
            340                 345                 350

Asp Thr Ile Pro Ile Glu Pro Leu Trp Leu Cys Pro Leu Arg Leu Arg
            355                 360                 365

Asp Asp Asn Ser Trp Ser Leu Tyr Pro Leu Arg Pro His Arg Thr Tyr
            370                 375                 380

Val Asn Val Gly Phe Trp Ser Ser Val Pro Val Gly Pro Glu Glu Gly
385                 390                 395                 400

His Thr Asn Lys Leu Ile Glu Arg Arg Ile Ser Glu Leu Glu Gly His
            405                 410                 415

Lys Ser Leu Tyr Ser Asp Ala Phe Tyr Ser Ala Asp Glu Phe Asp Ala
            420                 425                 430

Leu Tyr Gly Gly Glu Ile Tyr Arg Thr Val Lys Lys Thr Tyr Asp Pro
            435                 440                 445

Asp Ser Arg Phe Leu Asp Leu Tyr Ala Lys Ala Val Arg Arg Gln
            450                 455                 460

<210> SEQ ID NO 35
<211> LENGTH: 1323
<212> TYPE: DNA
<213> ORGANISM: Mycobacterium gilvum

<400> SEQUENCE: 35
atgacgactt tcgggaaca taccgacagt tcggcgtccg acccggatcg gaaactcact      60
ttggcagagg tgttggagat cttcgccgcg ggtcgccgtc cgctgaagtt caccgcctat     120
gacggaagta gttgcgggcc tgaggatgcg acactgggcc tcgacctgct gaccccgcgg     180
ggcacgacct acctggccac ggcgccgggt gatctcggcc tggcgcgggc ctacatcgcc     240
ggcgatctgc gcctcagtgg tgtgcatccc ggcgatcccc atgacctgct cacggcgctg     300
acggaacgcc tggagtacag gcgtccgccg gtgcgagtgc tggccaatgt tctgcgctcc     360
atcgggatcg agcacctcaa gcccgtcgcg ccgccacccc aggagcacct gccgcggtgg     420
cggcggatcg cagaggggtt gcggcacagc aagacccgtg acgctgaggc catccagcac     480
cactacgacg tctcgaacac gttctactca tgggtcctgg gtccgtcgat gacctacacc     540
tgcgcctgct atccacaccc ggatgccacg ctggaggagg cgcaggagaa caagtaccgg     600
ctggtgttcg agaagcttcg actcaagccc ggtgaccggc tgctcgacgt cggttgcggc     660
tggggcggaa tggtccgcta cgccgcccgg cacgggtca aggtcctggg ggtgacgctg      720
tcgaaggagc aggcgcagtg gcggccgac gcagtcgagc gggacggcct gggtgagttg      780
gccgaggtcc gccacggcga ctaccgcgac gtgcgcgagt cgcacttcga cgcagtgtcc     840
tcgctcgggc tcaccgagca catcggcgtc gcgaactacc gtcgtacttc cgcttcctg      900
aagtcgaaac tgcggccggg tggcctgctg ctcaaccact gcatcacccg aaacaacaac     960
cggagtcacg ccaccgcagg cggattcatc gatcgctatg tctttcccga cggggagctg    1020
acggggtcgg ggcgaatcat caccgaaatg caggacgtcg gactcgaggt cgtgcacgag    1080
gagaatctgc gtcaccacta cgcgctgacg ctgcgcgact ggagccgcaa cctggtcgcg    1140
cactgggacg acgcggtgac cgaggtcggt ctgccgactg ccaaggtgtg gggcctctac    1200
atcgccgcgt cgcgagtcgg cttcgagcag aacgccattc agctgcacca ggtgctgtcg    1260
gtcaagctcg acgagcgtgg ctcggacggc ggactgccgt tacgaccctg gtggaacgcc    1320
tag                                                                    1323

<210> SEQ ID NO 36
<211> LENGTH: 440
<212> TYPE: PRT

<213> ORGANISM: Mycobacterium gilvum

<400> SEQUENCE: 36

```
Met Thr Thr Phe Arg Glu His Thr Asp Ser Ser Ala Ser Asp Pro Asp
1               5                   10                  15

Arg Lys Leu Thr Leu Ala Glu Val Leu Glu Ile Phe Ala Ala Gly Arg
            20                  25                  30

Arg Pro Leu Lys Phe Thr Ala Tyr Asp Gly Ser Ser Cys Gly Pro Glu
        35                  40                  45

Asp Ala Thr Leu Gly Leu Asp Leu Leu Thr Pro Arg Gly Thr Thr Tyr
    50                  55                  60

Leu Ala Thr Ala Pro Gly Asp Leu Gly Leu Ala Arg Ala Tyr Ile Ala
65                  70                  75                  80

Gly Asp Leu Arg Leu Ser Gly Val His Pro Gly Asp Pro His Asp Leu
                85                  90                  95

Leu Thr Ala Leu Thr Glu Arg Leu Glu Tyr Arg Arg Pro Pro Val Arg
            100                 105                 110

Val Leu Ala Asn Val Leu Arg Ser Ile Gly Ile Glu His Leu Lys Pro
        115                 120                 125

Val Ala Pro Pro Gln Glu His Leu Pro Arg Trp Arg Arg Ile Ala
    130                 135                 140

Glu Gly Leu Arg His Ser Lys Thr Arg Asp Ala Glu Ala Ile Gln His
145                 150                 155                 160

His Tyr Asp Val Ser Asn Thr Phe Tyr Ser Trp Val Leu Gly Pro Ser
                165                 170                 175

Met Thr Tyr Thr Cys Ala Cys Tyr Pro His Pro Asp Ala Thr Leu Glu
            180                 185                 190

Glu Ala Gln Glu Asn Lys Tyr Arg Leu Val Phe Glu Lys Leu Arg Leu
        195                 200                 205

Lys Pro Gly Asp Arg Leu Leu Asp Val Gly Cys Gly Trp Gly Gly Met
    210                 215                 220

Val Arg Tyr Ala Ala Arg His Gly Val Lys Val Leu Gly Val Thr Leu
225                 230                 235                 240

Ser Lys Glu Gln Ala Gln Trp Ala Ala Asp Ala Val Glu Arg Asp Gly
                245                 250                 255

Leu Gly Glu Leu Ala Glu Val Arg His Gly Asp Tyr Arg Asp Val Arg
            260                 265                 270

Glu Ser His Phe Asp Ala Val Ser Ser Leu Gly Leu Thr Glu His Ile
        275                 280                 285

Gly Val Ala Asn Tyr Pro Ser Tyr Phe Arg Phe Leu Lys Ser Lys Leu
    290                 295                 300

Arg Pro Gly Gly Leu Leu Leu Asn His Cys Ile Thr Arg Asn Asn
305                 310                 315                 320

Arg Ser His Ala Thr Ala Gly Gly Phe Ile Asp Arg Tyr Val Phe Pro
                325                 330                 335

Asp Gly Glu Leu Thr Gly Ser Gly Arg Ile Ile Thr Glu Met Gln Asp
            340                 345                 350

Val Gly Leu Glu Val Val His Glu Glu Asn Leu Arg His His Tyr Ala
        355                 360                 365

Leu Thr Leu Arg Asp Trp Ser Arg Asn Leu Val Ala His Trp Asp Asp
    370                 375                 380

Ala Val Thr Glu Val Gly Leu Pro Thr Ala Lys Val Trp Gly Leu Tyr
385                 390                 395                 400
```

```
Ile Ala Ala Ser Arg Val Gly Phe Glu Gln Asn Ala Ile Gln Leu His
                405                 410                 415

Gln Val Leu Ser Val Lys Leu Asp Glu Arg Gly Ser Asp Gly Gly Leu
            420                 425                 430

Pro Leu Arg Pro Trp Trp Asn Ala
        435                 440

<210> SEQ ID NO 37
<211> LENGTH: 387
<212> TYPE: DNA
<213> ORGANISM: Mycobacterium gilvum

<400> SEQUENCE: 37
atgatccggt tcctgctgcg catcgcggtc tttctgggct catcagcgat cgggctcctc    60
gtcgccggat ggctggtgcc cggggtgtcg ctgtcggtgt ggggcttcgt cacggcagtg   120
gtgatcttca ccgtggcgca ggcgatcctg tccccgttct tcctcaagat ggccagccgc   180
tacgcctcgg cgttcctcgg cgggatcggt ctggtgtcga cgtttgccgc gctgctgctc   240
gtctcgctgc tgtccaacgg tctgagcatc cgcggcatcg gatcctggat cgccgcaacc   300
gtggtggtct ggttggtgac cgccctggcg acgctggtgc tgccgatgtt ggtgctgcgc   360
gagaagaaaa ccgcgtcgcg cgtctga                                       387

<210> SEQ ID NO 38
<211> LENGTH: 128
<212> TYPE: PRT
<213> ORGANISM: Mycobacterium gilvum

<400> SEQUENCE: 38

Met Ile Arg Phe Leu Leu Arg Ile Ala Val Phe Leu Gly Ser Ser Ala
1               5                   10                  15

Ile Gly Leu Leu Val Ala Gly Trp Leu Val Pro Gly Val Ser Leu Ser
            20                  25                  30

Val Trp Gly Phe Val Thr Ala Val Val Ile Phe Thr Val Ala Gln Ala
        35                  40                  45

Ile Leu Ser Pro Phe Phe Leu Lys Met Ala Ser Arg Tyr Ala Ser Ala
    50                  55                  60

Phe Leu Gly Gly Ile Gly Leu Val Ser Thr Phe Ala Ala Leu Leu Leu
65                  70                  75                  80

Val Ser Leu Leu Ser Asn Gly Leu Ser Ile Arg Gly Ile Gly Ser Trp
                85                  90                  95

Ile Ala Ala Thr Val Val Val Trp Leu Val Thr Ala Leu Ala Thr Leu
            100                 105                 110

Val Leu Pro Met Leu Val Leu Arg Glu Lys Lys Thr Ala Ser Arg Val
        115                 120                 125

<210> SEQ ID NO 39
<211> LENGTH: 1425
<212> TYPE: DNA
<213> ORGANISM: Unknown
<220> FEATURE:
<223> OTHER INFORMATION: Mycobacterium indicus pranii

<400> SEQUENCE: 39
atgcacgggc tgttgtcgaa gactagggta tatgtggtgc ctgtccttgg atctgcactc    60
tcggcccaca gtcgggcgt tgaccggctg ctggcaagct atcgatccat tcccgcaacg   120
tccgcggtcc ggctggccaa accgacgtca aacctgttcc gcgcccgcac caaacgtgac   180
```

| | |
|---|---|
| gcgcccggct tggacacctc ggggctgacc ggcgtcctga gcgtggatcc cgaaacccgc | 240 |
| accgcggacg tcgccggcat gtgcacctac gcggacctgg tggccgcaac gctgccctac | 300 |
| ggcctgtcgc cgctggtcgt cccgcagctg aagaccatca ccctcggcgg ggcggtcagc | 360 |
| ggcctgggga tcgagtcggc gtcgtttcgc aacgggctgc cgcacgaatc ggtgctggag | 420 |
| atggatatcc tcaccggcgc tggcgatttg ctcaccgcat cacgtaccca gcacccggac | 480 |
| ctgttccgcg ccttcccgaa ttcctatggg acactggggt attcgacccg gcttcggatc | 540 |
| gagctggaac ccgtcgcacc gttcgtcgcg ctgcgccaca tccgcttccg ctcgctgccc | 600 |
| gcgctgatcg ccgcggccga acgcatcgtc gacaccggcg ggcagggcgg aacccccggtc | 660 |
| gactacctcg acggggtggt cttcagcgcc gacgaaagct acctgtgcgt gggccggcgg | 720 |
| accaccaccc ccggcccggt cagcgactac accggcaagg acatctacta ccagtccatc | 780 |
| cggcacgacg ccccgggcct ggaggcgacc aaggatgacc ggctgaccat gcacgactac | 840 |
| ttctggcgct gggacaccga ttggttctgg tgctcgcgcg cgttcggcgt gcaggacccg | 900 |
| cgggtgcgac gcttctggcc gcgccgttat cggcgcagca gcttctactg gaagctgatt | 960 |
| tccctggacc ggcgcttcgg gatctccgac cgcatcgagg cgcgcaacgg gcggcccca | 1020 |
| cgcgaacggg tggtgcaaga catcgagatt ccaatcgaac ggacctgcga cttcctggag | 1080 |
| tggttcctgg acaacgtgcc aatcacgccg atctggttgt gcccgttgcg ccttcgcgac | 1140 |
| cgcgacggct ggccgttgta cccgatgcgg ccggatcaca cgtacgtcaa cgtcggcttc | 1200 |
| tggtcgtcgg tgccgggggg cgcgaccgag ggcgccgcca accggatgat cgaagaaaag | 1260 |
| gtgagcgaac tcgacgggca caagtccctg tactccgatt ccttctactc ccgcgaggac | 1320 |
| ttcgacgagc tgtacggcgg cgagacctac aacaccgtca agaaaaccta cgaccccgat | 1380 |
| tctcgtttac tcgacctcta cgcaaaggcg gtgcaacggc gatga | 1425 |

<210> SEQ ID NO 40
<211> LENGTH: 474
<212> TYPE: PRT
<213> ORGANISM: Unknown
<220> FEATURE:
<223> OTHER INFORMATION: Mycobacterium indicus pranii

<400> SEQUENCE: 40

Met His Gly Leu Leu Ser Lys Thr Arg Val Tyr Val Val Pro Val Leu
1               5                   10                  15

Gly Ser Ala Leu Ser Ala His Lys Ser Gly Val Asp Arg Leu Leu Ala
                20                  25                  30

Ser Tyr Arg Ser Ile Pro Ala Thr Ser Ala Val Arg Leu Ala Lys Pro
            35                  40                  45

Thr Ser Asn Leu Phe Arg Ala Arg Thr Lys Arg Asp Ala Pro Gly Leu
        50                  55                  60

Asp Thr Ser Gly Leu Thr Gly Val Leu Ser Val Asp Pro Glu Thr Arg
65                  70                  75                  80

Thr Ala Asp Val Ala Gly Met Cys Thr Tyr Ala Asp Leu Val Ala Ala
                85                  90                  95

Thr Leu Pro Tyr Gly Leu Ser Pro Leu Val Val Pro Gln Leu Lys Thr
            100                 105                 110

Ile Thr Leu Gly Gly Ala Val Ser Gly Leu Gly Ile Glu Ser Ala Ser
        115                 120                 125

Phe Arg Asn Gly Leu Pro His Glu Ser Val Leu Glu Met Asp Ile Leu
    130                 135                 140

```
Thr Gly Ala Gly Asp Leu Leu Thr Ala Ser Arg Thr Gln His Pro Asp
145                 150                 155                 160

Leu Phe Arg Ala Phe Pro Asn Ser Tyr Gly Thr Leu Gly Tyr Ser Thr
                165                 170                 175

Arg Leu Arg Ile Glu Leu Glu Pro Val Ala Pro Phe Val Ala Leu Arg
            180                 185                 190

His Ile Arg Phe Arg Ser Leu Pro Ala Leu Ile Ala Ala Glu Arg
        195                 200                 205

Ile Val Asp Thr Gly Gly Gln Gly Gly Thr Pro Val Asp Tyr Leu Asp
    210                 215                 220

Gly Val Val Phe Ser Ala Asp Glu Ser Tyr Leu Cys Val Gly Arg Arg
225                 230                 235                 240

Thr Thr Thr Pro Gly Pro Val Ser Asp Tyr Thr Gly Lys Asp Ile Tyr
                245                 250                 255

Tyr Gln Ser Ile Arg His Asp Ala Pro Gly Leu Glu Ala Thr Lys Asp
            260                 265                 270

Asp Arg Leu Thr Met His Asp Tyr Phe Trp Arg Trp Asp Thr Asp Trp
        275                 280                 285

Phe Trp Cys Ser Arg Ala Phe Gly Val Gln Asp Pro Arg Val Arg Arg
290                 295                 300

Phe Trp Pro Arg Arg Tyr Arg Arg Ser Ser Phe Tyr Trp Lys Leu Ile
305                 310                 315                 320

Ser Leu Asp Arg Arg Phe Gly Ile Ser Asp Arg Ile Glu Ala Arg Asn
                325                 330                 335

Gly Arg Pro Pro Arg Glu Arg Val Val Gln Asp Ile Gly Ile Pro Ile
            340                 345                 350

Glu Arg Thr Cys Asp Phe Leu Glu Trp Phe Leu Asp Asn Val Pro Ile
        355                 360                 365

Thr Pro Ile Trp Leu Cys Pro Leu Arg Leu Arg Asp Arg Asp Gly Trp
370                 375                 380

Pro Leu Tyr Pro Met Arg Pro Asp His Thr Tyr Val Asn Val Gly Phe
385                 390                 395                 400

Trp Ser Ser Val Pro Gly Gly Ala Thr Glu Gly Ala Ala Asn Arg Met
                405                 410                 415

Ile Glu Glu Lys Val Ser Glu Leu Asp Gly His Lys Ser Leu Tyr Ser
            420                 425                 430

Asp Ser Phe Tyr Ser Arg Glu Asp Phe Asp Glu Leu Tyr Gly Gly Glu
        435                 440                 445

Thr Tyr Asn Thr Val Lys Lys Thr Tyr Asp Pro Asp Ser Arg Leu Leu
450                 455                 460

Asp Leu Tyr Ala Lys Ala Val Gln Arg Arg
465                 470

<210> SEQ ID NO 41
<211> LENGTH: 1263
<212> TYPE: DNA
<213> ORGANISM: Unknown
<220> FEATURE:
<223> OTHER INFORMATION: Mycobacterium indicus pranii

<400> SEQUENCE: 41
atggccgaga tcctggaggt cttcgccgcc accggccgac atccgctgaa gttcaccgcc      60
tacgacggca gcatcgccgg caacgaggac gccgaactgg gcctggacct tcgcagcccc     120
cgcggcgcca cctatctggc gaccgccccc ggcgaactcg gcctcgcccg cgcctacgtg     180
```

```
tcgggcgacc tgcaggccta cggcgtccat cccggcgacc cgtaccaact gctcaagacg      240
ctcaccgatc gggtggaatt caagcggccc ccggtgcggg tgctggccaa cgtcgtgcgg      300
tcgctggggt tcgagcggtt gctgccggtc gcgccgcccc cgcaggaggc gctgccccgg      360
tggcggcgca tcgccgacgg gctgatgcac acgaggaccc gcgacgccga ggccatccac      420
caccactacg acgtgtccaa caccttctac gaattggtgt tggggccgtc gatgacctac      480
acctgcgcgg tgtatcccga tgccgacgcg acactcgaac aggcgcagga gaacaagtac      540
cggctgatct tcgagaagct gcggctgaag gcgggcgacc ggctgctcga cgtcggctgc      600
ggctggggcg gcatggtgcg ctacgcggcc cggcgcggcg tccgggccac cggcgccacc      660
ctgtcggccg aacaggcgaa gtgggcgcag aaggcgatcg ccgaggaagg ccttgcggac      720
ctggccgagg tgcgccacac cgactatcgg gacgtgggcg aggcggcgtt cgacgccgtg      780
tcctcgatcg ggctgaccga gcacatcggc gtcaagaatt accccgccta cttcggcttc      840
ttgaagtcga agctgcgcac cggcggcctg ctgctcaatc actgcatcac ccgccacgac      900
aacacgtcga cgtcgttcgc gggcggattc accgatcgct atgtcttccc ggacggggag      960
ctgaccggct cgggccgcat cacctgcgac gtccaggact gcggcttcga ggtgctgcac     1020
gcggagaact tccgccacca ctacgcgatg acgctgcgcg actggtgccg caatctggtc     1080
gagaactggg acgccgcggt cagcgaggtc ggcctaccga ccgcgaaggt ctggggcctg     1140
tacatggcgg cgtcacgggt tgcgttcgag cagaacaacc ttcagctgca tcacgtgctg     1200
gcggccaaga ccgacgcgcg gggcgacgac gacctgccgc tgcggccgtg gtggacggcc     1260
tga                                                                  1263
```

<210> SEQ ID NO 42
<211> LENGTH: 420
<212> TYPE: PRT
<213> ORGANISM: Unknown
<220> FEATURE:
<223> OTHER INFORMATION: Mycobacterium indicus pranii

<400> SEQUENCE: 42

```
Met Ala Glu Ile Leu Glu Val Phe Ala Ala Thr Gly Arg His Pro Leu
1               5                   10                  15

Lys Phe Thr Ala Tyr Asp Gly Ser Ile Ala Gly Asn Glu Asp Ala Glu
            20                  25                  30

Leu Gly Leu Asp Leu Arg Ser Pro Arg Gly Ala Thr Tyr Leu Ala Thr
        35                  40                  45

Ala Pro Gly Glu Leu Gly Leu Ala Arg Ala Tyr Val Ser Gly Asp Leu
    50                  55                  60

Gln Ala Tyr Gly Val His Pro Gly Asp Pro Tyr Gln Leu Leu Lys Thr
65                  70                  75                  80

Leu Thr Asp Arg Val Glu Phe Lys Arg Pro Val Arg Val Leu Ala
                85                  90                  95

Asn Val Val Arg Ser Leu Gly Phe Glu Arg Leu Leu Pro Val Ala Pro
                100                 105                 110

Pro Pro Gln Glu Ala Leu Pro Arg Trp Arg Arg Ile Ala Asp Gly Leu
            115                 120                 125

Met His Thr Arg Thr Arg Asp Ala Glu Ala Ile His His Tyr Asp
        130                 135                 140

Val Ser Asn Thr Phe Tyr Glu Leu Val Leu Gly Pro Ser Met Thr Tyr
145                 150                 155                 160

Thr Cys Ala Val Tyr Pro Asp Ala Asp Ala Thr Leu Glu Gln Ala Gln
```

```
                    165                 170                 175
Glu Asn Lys Tyr Arg Leu Ile Phe Glu Lys Leu Arg Leu Lys Ala Gly
            180                 185                 190

Asp Arg Leu Leu Asp Val Gly Cys Gly Trp Gly Met Val Arg Tyr
        195                 200                 205

Ala Ala Arg Arg Gly Val Arg Ala Thr Gly Ala Thr Leu Ser Ala Glu
        210                 215                 220

Gln Ala Lys Trp Ala Gln Lys Ala Ile Ala Glu Glu Gly Leu Ala Asp
225                 230                 235                 240

Leu Ala Glu Val Arg His Thr Asp Tyr Arg Asp Val Gly Glu Ala Ala
            245                 250                 255

Phe Asp Ala Val Ser Ser Ile Gly Leu Thr Glu His Ile Gly Val Lys
            260                 265                 270

Asn Tyr Pro Ala Tyr Phe Gly Phe Leu Lys Ser Lys Leu Arg Thr Gly
            275                 280                 285

Gly Leu Leu Leu Asn His Cys Ile Thr Arg His Asp Asn Thr Ser Thr
290                 295                 300

Ser Phe Ala Gly Gly Phe Thr Asp Arg Tyr Val Phe Pro Asp Gly Glu
305                 310                 315                 320

Leu Thr Gly Ser Gly Arg Ile Thr Cys Asp Val Gln Asp Cys Gly Phe
                325                 330                 335

Glu Val Leu His Ala Glu Asn Phe Arg His His Tyr Ala Met Thr Leu
            340                 345                 350

Arg Asp Trp Cys Arg Asn Leu Val Glu Asn Trp Asp Ala Ala Val Ser
            355                 360                 365

Glu Val Gly Leu Pro Thr Ala Lys Val Trp Gly Leu Tyr Met Ala Ala
        370                 375                 380

Ser Arg Val Ala Phe Glu Gln Asn Asn Leu Gln Leu His His Val Leu
385                 390                 395                 400

Ala Ala Lys Thr Asp Ala Arg Gly Asp Asp Asp Leu Pro Leu Arg Pro
            405                 410                 415

Trp Trp Thr Ala
        420

<210> SEQ ID NO 43
<211> LENGTH: 1380
<212> TYPE: DNA
<213> ORGANISM: Mycobacterium phlei

<400> SEQUENCE: 43
gtgtctgaac cccgaaccga cgcacgtgtt gttcaggccg cgggcgtgca caagctgctg      60
gagagctacc gcgcgatccc gcccgaggcc accgtccggc tggccaaacc cacctcgaac     120
ctgttccggg cgcgcgccaa gacctcggtc aagggtctcg atgtctcggg cctgacccat     180
gtgatctccg tcgaccccga cgagcgcacc gctgaggtgg ccgggatgtg cacctacgag     240
gacctggtcg ccgcgacgct gccgtacggg ctgtcaccgc tggtggtgcc gcagctcaag     300
accatcaccc tcggcggcgc cgtgacgggt ctgggcatcg agtcggcgtc gttccgtaac     360
ggcctgccgc acgagtcggt gctggagatg gacatcctca ccggatcggg cgagatcctc     420
accgcctccc gcgaccagca ccccgacctg ttccgggcgt tcccgaactc ctatggcacg     480
ctgggctatt cggtgcggct gaagatcgag ttggagaccg tcaaaccgtt cgtcgcggtc     540
cgtcacctgc ggttccacga catcgaggac ctggtcgccg agatggaccg cattgtcgag     600
accggcggct acgacggcac cccggtcgac tatctcgacg gtgtggtgtt ctcggcccgc     660
```

```
gagagctacc tgacgctggg cttccagacc gccaccccgg gcccggtcag cgactacacc    720
ggccagcaga tctactaccg ctcgatccag cacgaggacg cgtcaagga cgaccggctg    780 acgatccacg actacttctg cgctgggac accgactggt tctggtgctc gcgggcgttc    840
ggcgtgcaga acccgacgat ccgccggttc tggccgcgcc ggctcaagcg cagcagcttc    900
tactggaagc tggtcgccta cgaccgcaag ttcaacatcg ccgatcgcat cgagatgcac    960
aacggccgcc cgccccgcga gcgcgtcgtg caggacatcg aggtgccgat cgagcgggtc   1020
gccgagtttt tgggctggtt cctcgacaac gtgccgatcg agccgatctg gctgtgcccg   1080
ttgcgtcttc gcgacgacgc cggctggccg ctgtacccga tccgggcgca gcacacctac   1140
gtcaacgtgg ggttctggtc ctcggtgccg gtggggccca ccgaggggca cacgaaccgg   1200
ctgatcgagc gcaaggtcag cgagctcgac gggcacaagt cgctgtactc ggacgcgtac   1260
tactcgcgcg acgagttcga ccagctctac ggcggcgaaa tctacaaaac cgttaaaaag   1320
gcctacgatc cagattcacg actgctcgac ctgtacgcga aggcggtgca gcgccagtga   1380
```

<210> SEQ ID NO 44
<211> LENGTH: 459
<212> TYPE: PRT
<213> ORGANISM: Mycobacterium phlei

<400> SEQUENCE: 44

```
Val Ser Glu Pro Arg Thr Asp Ala Arg Val Gln Ala Ala Gly Val
1               5                   10                  15

His Lys Leu Leu Glu Ser Tyr Arg Ala Ile Pro Pro Glu Ala Thr Val
                20                  25                  30

Arg Leu Ala Lys Pro Thr Ser Asn Leu Phe Arg Ala Arg Ala Lys Thr
            35                  40                  45

Ser Val Lys Gly Leu Asp Val Ser Gly Leu Thr His Val Ile Ser Val
        50                  55                  60

Asp Pro Asp Glu Arg Thr Ala Glu Val Ala Gly Met Cys Thr Tyr Glu
65                  70                  75                  80

Asp Leu Val Ala Ala Thr Leu Pro Tyr Gly Leu Ser Pro Leu Val Val
                85                  90                  95

Pro Gln Leu Lys Thr Ile Thr Leu Gly Gly Ala Val Thr Gly Leu Gly
                100                 105                 110

Ile Glu Ser Ala Ser Phe Arg Asn Gly Leu Pro His Glu Ser Val Leu
            115                 120                 125

Glu Met Asp Ile Leu Thr Gly Ser Gly Glu Ile Leu Thr Ala Ser Arg
        130                 135                 140

Asp Gln His Pro Asp Leu Phe Arg Ala Phe Pro Asn Ser Tyr Gly Thr
145                 150                 155                 160

Leu Gly Tyr Ser Val Arg Leu Lys Ile Glu Leu Glu Thr Val Lys Pro
                165                 170                 175

Phe Val Ala Val Arg His Leu Arg Phe His Asp Ile Glu Asp Leu Val
            180                 185                 190

Ala Glu Met Asp Arg Ile Val Glu Thr Gly Gly Tyr Asp Gly Thr Pro
        195                 200                 205

Val Asp Tyr Leu Asp Gly Val Val Phe Ser Ala Arg Glu Ser Tyr Leu
    210                 215                 220

Thr Leu Gly Phe Gln Thr Ala Thr Pro Gly Pro Val Ser Asp Tyr Thr
225                 230                 235                 240

Gly Gln Gln Ile Tyr Tyr Arg Ser Ile Gln His Glu Asp Gly Val Lys
```

```
                    245                 250                 255
Asp Asp Arg Leu Thr Ile His Asp Tyr Phe Trp Arg Trp Asp Thr Asp
                260                 265                 270

Trp Phe Trp Cys Ser Arg Ala Phe Gly Val Gln Asn Pro Thr Ile Arg
            275                 280                 285

Arg Phe Trp Pro Arg Arg Leu Lys Arg Ser Ser Phe Tyr Trp Lys Leu
        290                 295                 300

Val Ala Tyr Asp Arg Lys Phe Asn Ile Ala Asp Arg Ile Glu Met His
305                 310                 315                 320

Asn Gly Arg Pro Pro Arg Glu Arg Val Val Gln Asp Ile Glu Val Pro
                325                 330                 335

Ile Glu Arg Val Ala Glu Phe Leu Gly Trp Phe Leu Asp Asn Val Pro
            340                 345                 350

Ile Glu Pro Ile Trp Leu Cys Pro Leu Arg Leu Arg Asp Asp Ala Gly
        355                 360                 365

Trp Pro Leu Tyr Pro Ile Arg Ala Gln His Thr Tyr Val Asn Val Gly
    370                 375                 380

Phe Trp Ser Ser Val Pro Val Gly Pro Thr Glu Gly His Thr Asn Arg
385                 390                 395                 400

Leu Ile Glu Arg Lys Val Ser Glu Leu Asp Gly His Lys Ser Leu Tyr
                405                 410                 415

Ser Asp Ala Tyr Tyr Ser Arg Asp Glu Phe Asp Gln Leu Tyr Gly Gly
            420                 425                 430

Glu Ile Tyr Lys Thr Val Lys Lys Ala Tyr Asp Pro Asp Ser Arg Leu
        435                 440                 445

Leu Asp Leu Tyr Ala Lys Ala Val Gln Arg Gln
    450                 455

<210> SEQ ID NO 45
<211> LENGTH: 1314
<212> TYPE: DNA
<213> ORGANISM: Mycobacterium phlei

<400> SEQUENCE: 45
atgacggcga tcaaagagaa cccggtcctg acttcggcca ggaagctgtc cctggccgag      60
attctggaaa tccttgccgg gggcgaactc ccggtgcgtt tcacggccta cgacggcagc     120
tcggcgggcc cggcggactc cccgctcggc ctggagctgc tgaccccgcg cggcaccacc     180
tatctggcca ccgccccggg cgatctcggg ctggcacgcg cctacatcgc cggtgacctg     240
cagccgcacg gcgtgcatcc gggcgatccg tacgagctgc tcaaggccct gtcggagaag     300
atggagttca gcggccgcc cgcgaaggtg ctggccaaca tcgtgcgctc catcggtatc     360
gagcacctca gccgatcgc accgccgccg caggaggcgc agccgcgctg gcgccggatc     420
gcggaagggt gcggcacag caagactcgc gacgccgagg cgatccacca ccactacgac     480
gtgtccaaca cgttctacga gtgggtgctc ggcccgtcga tgacctacac ctgcgcgtgc     540
tacccggacg tcgacgcaac cctggagcag gcgcaggaga acaagtaccg cctggtgttc     600
gagaagctgc gcctgaagcc gggcgaccgg ctgctcgacg tgggctgcgg ctggggcggc     660
atggtgcgct acgccgccca gcacggggtc aaggccatcg cgtcacgct gtctcgggag     720 caggcgacgt gggcgcagaa ggcgatcgcc gagcaggggc tcagcgatct ggccgaggtc     780
cgccacggcg actaccgcga cattcgcgag tccgggttcg acgcggtgtc ctcgatcggg     840
ctgaccgagc acatcggcgt ggccaactac ccgtcgtact tccggttcct gcagtccaag     900
```

-continued

```
ctgcgtgtcg gcgggctgct gctcaaccac tgcatcaccc ggccggacaa caagtcgcag     960
gccagcgcgg gcgggttcat cgaccgctac gtgttccccg acggggagct caccgggtcc    1020
ggccgcatca tcgccgcggc ccaggacgtc ggcctcgagg tggtgcacga ggagaacctg    1080
cgccagcact acgcgatgac gctgcgcgac tggtgccgca acctcgtcga gcactgggac    1140
gaggcggtcg ccgaggtcgg cctggaacgc gccaagatct ggggcctgta catggccggc    1200
tcccggctcg gcttcgagac gaacatcgtg cagctgcacc aggtgctggc ggtcaagctg    1260
gaccgcaggg gcggcgacgg cgggctgccg ttgcgcccgt ggtggacgcc ctag          1314
```

<210> SEQ ID NO 46
<211> LENGTH: 437
<212> TYPE: PRT
<213> ORGANISM: Mycobacterium phlei

<400> SEQUENCE: 46

```
Met Thr Ala Ile Lys Glu Asn Pro Val Leu Thr Ser Ala Arg Lys Leu
1               5                   10                  15

Ser Leu Ala Glu Ile Leu Glu Ile Leu Ala Gly Gly Glu Leu Pro Val
            20                  25                  30

Arg Phe Thr Ala Tyr Asp Gly Ser Ala Gly Pro Ala Asp Ser Pro
        35                  40                  45

Leu Gly Leu Glu Leu Leu Thr Pro Arg Gly Thr Thr Tyr Leu Ala Thr
    50                  55                  60

Ala Pro Gly Asp Leu Gly Leu Ala Arg Ala Tyr Ile Ala Gly Asp Leu
65                  70                  75                  80

Gln Pro His Gly Val His Pro Gly Asp Pro Tyr Glu Leu Leu Lys Ala
                85                  90                  95

Leu Ser Glu Lys Met Glu Phe Lys Arg Pro Pro Ala Lys Val Leu Ala
            100                 105                 110

Asn Ile Val Arg Ser Ile Gly Ile Glu His Leu Lys Pro Ile Ala Pro
        115                 120                 125

Pro Pro Gln Glu Ala Gln Pro Arg Trp Arg Arg Ile Ala Glu Gly Leu
    130                 135                 140

Arg His Ser Lys Thr Arg Asp Ala Glu Ala Ile His His His Tyr Asp
145                 150                 155                 160

Val Ser Asn Thr Phe Tyr Glu Trp Val Leu Gly Pro Ser Met Thr Tyr
                165                 170                 175

Thr Cys Ala Cys Tyr Pro Asp Val Asp Ala Thr Leu Glu Gln Ala Gln
            180                 185                 190

Glu Asn Lys Tyr Arg Leu Val Phe Glu Lys Leu Arg Leu Lys Pro Gly
        195                 200                 205

Asp Arg Leu Leu Asp Val Gly Cys Gly Trp Gly Gly Met Val Arg Tyr
    210                 215                 220

Ala Ala Gln His Gly Val Lys Ala Ile Gly Val Thr Leu Ser Arg Glu
225                 230                 235                 240

Gln Ala Thr Trp Ala Gln Lys Ala Ile Ala Glu Gln Gly Leu Ser Asp
                245                 250                 255

Leu Ala Glu Val Arg His Gly Asp Tyr Arg Asp Ile Arg Glu Ser Gly
            260                 265                 270

Phe Asp Ala Val Ser Ser Ile Gly Leu Thr Glu His Ile Gly Val Ala
        275                 280                 285

Asn Tyr Pro Ser Tyr Phe Arg Phe Leu Gln Ser Lys Leu Arg Val Gly
    290                 295                 300
```

```
Gly Leu Leu Leu Asn His Cys Ile Thr Arg Pro Asp Asn Lys Ser Gln
305                 310                 315                 320

Ala Ser Ala Gly Gly Phe Ile Asp Arg Tyr Val Phe Pro Asp Gly Glu
            325                 330                 335

Leu Thr Gly Ser Gly Arg Ile Ile Ala Ala Ala Gln Asp Val Gly Leu
            340                 345                 350

Glu Val Val His Glu Glu Asn Leu Arg Gln His Tyr Ala Met Thr Leu
        355                 360                 365

Arg Asp Trp Cys Arg Asn Leu Val Glu His Trp Asp Glu Ala Val Ala
370                 375                 380

Glu Val Gly Leu Glu Arg Ala Lys Ile Trp Gly Leu Tyr Met Ala Gly
385                 390                 395                 400

Ser Arg Leu Gly Phe Glu Thr Asn Ile Val Gln Leu His Gln Val Leu
            405                 410                 415

Ala Val Lys Leu Asp Arg Arg Gly Gly Asp Gly Gly Leu Pro Leu Arg
            420                 425                 430

Pro Trp Trp Thr Pro
        435
```

<210> SEQ ID NO 47
<211> LENGTH: 1413
<212> TYPE: DNA
<213> ORGANISM: Mycobacterium tuberculosis

<400> SEQUENCE: 47

```
atgcagggc agttgtcgag gactagggta tatacggtgc ctgtccctgg atctgcacag    60
tcggcttacg cctgcggcgt cgagcggttg ctggcgagct atcgatccat ccccgcgact  120
gcatccatcc ggcttgccaa gcccacctca aatctgttcc gcgcccgcgt caaaacgat   180
gcacgcggcc tggacgcatc gggactgacc ggtgtcatcg gtatcgatcc cgaggcccgc  240
accgccgacg tggccggcat gtgcacatac gaggacctaa tcgccgcgac actgcactac  300
ggtctgtcac cattggtggt tccgcagctg aggacgatca cattgggcgg agcggtcacc  360
ggcttgggta tcgagtcggc gtcgttccgc aacggcctgc ccacgagtc ggtgctggag   420
atggatatcc tcaccggcgc aggagaactt ctcaccgtct cgcccggaca gcactccgac  480
ttgtaccgtg cattccctaa ctcgtatggg acactgggct attcaacccg gcttcgaatc  540
cagctggagc cggtccggcc gtttgtcgcg ctgcggcaca tccgatttag ctcgttgacg  600
gcgatggtgg ccgcaatgga gcgcatcatc gacaccggcg gactggacgg cgaatcggtg  660
gactatctcg acggggtggt tttcagcgct gacgaaagct acctgtgcat cggcatgcag  720
acgagcgtac cgggcccggt cagcgactac accggacaag acatctacta ccggtcgatc  780
caacacgagg cggggatcaa ggaagaccgg ttgaccatcc acgattactt ctggcgctgg  840
gacaccgatt ggttctggtg ctcacgatcg tttggtgccc aaaaccccgcg gctgcgccgc  900
tggtggccgc ggcgctaccg gcgtagcagt gtctactgga ggttgatggc gctcgatcag  960
cgcttcggga tcgccgaccg gttcgagaac agcagggtc gtcccgcgcg tgaacgggtg  1020
gtgcaggata tcgaagtgcc gatcgaacgg acctgcgagt ttctggagtg gttcggggaa  1080
aacgtgccca tttcgccaat ctggttgtgc ccgttgcggc tacgcgatca cgccggctgg  1140
ccgctgtacc cgatccggcc tgaccgtagc tatgtcaaca tcgggttctg gtcgtcggtg  1200
ccggttggcg ccaccgaggg cgccaccaac cgcaagatcg agaacaaggt gagtgcgctc  1260
gacgggcaca gtcgctccta ctccgactcc ttctataccc gcgaggagtt cgacgagctc  1320
```

```
tacggcggcg agacttacaa cactgtgaag aaagcctacg atcccgattc gcgtctcctc    1380
gatctttacg caaaggcggt gcaacgacga tga                                 1413
```

<210> SEQ ID NO 48
<211> LENGTH: 470
<212> TYPE: PRT
<213> ORGANISM: Mycobacterium tuberculosis

<400> SEQUENCE: 48

```
Met Gln Gly Gln Leu Ser Arg Thr Arg Val Tyr Thr Val Pro Val Pro
1               5                   10                  15

Gly Ser Ala Gln Ser Ala Tyr Ala Cys Gly Val Glu Arg Leu Leu Ala
            20                  25                  30

Ser Tyr Arg Ser Ile Pro Ala Thr Ala Ser Ile Arg Leu Ala Lys Pro
        35                  40                  45

Thr Ser Asn Leu Phe Arg Ala Arg Val Lys His Asp Ala Arg Gly Leu
    50                  55                  60

Asp Ala Ser Gly Leu Thr Gly Val Ile Gly Ile Asp Pro Glu Ala Arg
65                  70                  75                  80

Thr Ala Asp Val Ala Gly Met Cys Thr Tyr Glu Asp Leu Ile Ala Ala
                85                  90                  95

Thr Leu His Tyr Gly Leu Ser Pro Leu Val Pro Gln Leu Arg Thr
            100                 105                 110

Ile Thr Leu Gly Gly Ala Val Thr Gly Leu Gly Ile Glu Ser Ala Ser
        115                 120                 125

Phe Arg Asn Gly Leu Pro His Glu Ser Val Leu Glu Met Asp Ile Leu
    130                 135                 140

Thr Gly Ala Gly Glu Leu Leu Thr Val Ser Pro Gly Gln His Ser Asp
145                 150                 155                 160

Leu Tyr Arg Ala Phe Pro Asn Ser Tyr Gly Thr Leu Gly Tyr Ser Thr
                165                 170                 175

Arg Leu Arg Ile Gln Leu Glu Pro Val Arg Pro Phe Val Ala Leu Arg
            180                 185                 190

His Ile Arg Phe Ser Ser Leu Thr Ala Met Val Ala Ala Met Glu Arg
        195                 200                 205

Ile Ile Asp Thr Gly Gly Leu Asp Gly Glu Ser Val Asp Tyr Leu Asp
    210                 215                 220

Gly Val Val Phe Ser Ala Asp Glu Ser Tyr Leu Cys Ile Gly Met Gln
225                 230                 235                 240

Thr Ser Val Pro Gly Pro Val Ser Asp Tyr Thr Gly Gln Asp Ile Tyr
                245                 250                 255

Tyr Arg Ser Ile Gln His Glu Ala Gly Ile Lys Glu Asp Arg Leu Thr
            260                 265                 270

Ile His Asp Tyr Phe Trp Arg Trp Asp Thr Asp Trp Phe Trp Cys Ser
        275                 280                 285

Arg Ser Phe Gly Ala Gln Asn Pro Arg Leu Arg Arg Trp Trp Pro Arg
    290                 295                 300

Arg Tyr Arg Arg Ser Ser Val Tyr Trp Arg Leu Met Ala Leu Asp Gln
305                 310                 315                 320

Arg Phe Gly Ile Ala Asp Arg Phe Glu Asn Ser Arg Gly Arg Pro Ala
                325                 330                 335

Arg Glu Arg Val Val Gln Asp Ile Glu Val Pro Ile Glu Arg Thr Cys
            340                 345                 350

Glu Phe Leu Glu Trp Phe Gly Glu Asn Val Pro Ile Ser Pro Ile Trp
```

```
                355                 360                 365
Leu Cys Pro Leu Arg Leu Arg Asp His Ala Gly Trp Pro Leu Tyr Pro
    370                 375                 380

Ile Arg Pro Asp Arg Ser Tyr Val Asn Ile Gly Phe Trp Ser Ser Val
385                 390                 395                 400

Pro Val Gly Ala Thr Glu Gly Ala Thr Asn Arg Lys Ile Glu Asn Lys
                405                 410                 415

Val Ser Ala Leu Asp Gly His Lys Ser Leu Tyr Ser Asp Ser Phe Tyr
            420                 425                 430

Thr Arg Glu Glu Phe Asp Glu Leu Tyr Gly Gly Glu Thr Tyr Asn Thr
        435                 440                 445

Val Lys Lys Ala Tyr Asp Pro Asp Ser Arg Leu Leu Asp Leu Tyr Ala
    450                 455                 460

Lys Ala Val Gln Arg Arg
465                 470

<210> SEQ ID NO 49
<211> LENGTH: 1263
<212> TYPE: DNA
<213> ORGANISM: Mycobacterium tuberculosis

<400> SEQUENCE: 49
```

| | | | | |
|---|---|---|---|---|
| atggccgaga | tcctggagat | cttcaccgcg | accgggcaac | acccgctgaa gttcaccgcg | 60 |
| tatgacggca | gcaccgcggg | acaagacgac | gccacactgg | gcctggatct tcggacgccc | 120 |
| cgcggcgcca | cctacttagc | taccgctccc | ggcgaactcg | gcctggcccg cgcttatgtg | 180 |
| tcgggtgacc | tacaggcaca | cggagtacat | cccggcgatc | cgtacgaact gctcaaaacg | 240 |
| ctgaccgaaa | gggtcgactt | caaacggccg | tcggcgcggg | tgctggctaa tgtggtgcgc | 300 |
| tcgatcggcg | ttgagcacat | actgcccatc | gcgccgccac | cccaggaggc gcgaccccgg | 360 |
| tggcgtcgaa | tggctaatgg | cttgctgcac | agcaagaccc | gtgacgccga ggctatccat | 420 |
| caccactacg | acgtctccaa | caacttctac | gagtgggtgc | tcgggccatc gatgacctac | 480 |
| acgtgcgcgg | tgtttccgaa | cgctgaggct | tcgctggagc | aggcccaaga gaacaaatac | 540 |
| cgactcattt | tcgaaaagct | acggctagag | ccgggtgacc | ggctactcga cgtcggctgc | 600 |
| ggctggggcg | gcatggtgcg | ctacgccgcc | cgacgcggtg | tccgggtgat cggcgccacg | 660 |
| ctctcggccg | agcaggccaa | gtgggccag | aaagcagtcg | aggacgaggg attgagcgac | 720 |
| ctcgcgcagg | tgcggcattc | cgactaccgc | gacgtagccg | agaccggttt cgacgccgtt | 780 |
| tcttcgatcg | ggctaaccga | gcacatcggc | gtcaagaatt | acccgttcta cttcgggttt | 840 |
| ctcaagtcga | agttgcgcac | cggcggcttg | ctgctcaatc | actgcatcac ccgccacgac | 900 |
| aacaggtcga | cgtcctttgc | cggcgggttc | accaccgtt | acgttttccc cgacggggag | 960 |
| ctgacgggct | cggacgtat | accaccgag | atccagcagg | tcggcttgga agtgctgcac | 1020 |
| gaggagaact | tccgccatca | ctacgcgatg | acgctgcgcg | actggtgcgg caacctcgtc | 1080 |
| gaacactggg | acgacgcggt | cgccgaggtc | ggtctgccga | ccgccaaggt gtggggcctg | 1140 |
| tacatggcgg | cttcgcgggt | ggccttcgaa | cgaaacaacc | tgcagctaca tcacgtattg | 1200 |
| gcgaccaagg | tggacccccg | gggcgacgac | agcttgccac | tgcggccctg gtggcagccc | 1260 |
| tag | | | | | 1263 |

```
<210> SEQ ID NO 50
<211> LENGTH: 420
<212> TYPE: PRT
```

<213> ORGANISM: Mycobacterium tuberculosis

<400> SEQUENCE: 50

```
Met Ala Glu Ile Leu Glu Ile Phe Thr Ala Thr Gly Gln His Pro Leu
1               5                   10                  15

Lys Phe Thr Ala Tyr Asp Gly Ser Thr Ala Gly Gln Asp Asp Ala Thr
            20                  25                  30

Leu Gly Leu Asp Leu Arg Thr Pro Arg Gly Ala Thr Tyr Leu Ala Thr
        35                  40                  45

Ala Pro Gly Glu Leu Gly Leu Ala Arg Ala Tyr Val Ser Gly Asp Leu
    50                  55                  60

Gln Ala His Gly Val His Pro Gly Asp Pro Tyr Glu Leu Leu Lys Thr
65                  70                  75                  80

Leu Thr Glu Arg Val Asp Phe Lys Arg Pro Ser Ala Arg Val Leu Ala
                85                  90                  95

Asn Val Val Arg Ser Ile Gly Val Glu His Ile Leu Pro Ile Ala Pro
            100                 105                 110

Pro Pro Gln Glu Ala Arg Pro Arg Trp Arg Arg Met Ala Asn Gly Leu
        115                 120                 125

Leu His Ser Lys Thr Arg Asp Ala Glu Ala Ile His His His Tyr Asp
    130                 135                 140

Val Ser Asn Asn Phe Tyr Glu Trp Val Leu Gly Pro Ser Met Thr Tyr
145                 150                 155                 160

Thr Cys Ala Val Phe Pro Asn Ala Glu Ala Ser Leu Glu Gln Ala Gln
                165                 170                 175

Glu Asn Lys Tyr Arg Leu Ile Phe Glu Lys Leu Arg Leu Glu Pro Gly
            180                 185                 190

Asp Arg Leu Leu Asp Val Gly Cys Gly Trp Gly Gly Met Val Arg Tyr
        195                 200                 205

Ala Ala Arg Arg Gly Val Arg Val Ile Gly Ala Thr Leu Ser Ala Glu
    210                 215                 220

Gln Ala Lys Trp Gly Gln Lys Ala Val Glu Asp Glu Gly Leu Ser Asp
225                 230                 235                 240

Leu Ala Gln Val Arg His Ser Asp Tyr Arg Asp Val Ala Glu Thr Gly
                245                 250                 255

Phe Asp Ala Val Ser Ser Ile Gly Leu Thr Glu His Ile Gly Val Lys
            260                 265                 270

Asn Tyr Pro Phe Tyr Phe Gly Phe Leu Lys Ser Lys Leu Arg Thr Gly
        275                 280                 285

Gly Leu Leu Leu Asn His Cys Ile Thr Arg His Asp Asn Arg Ser Thr
    290                 295                 300

Ser Phe Ala Gly Gly Phe Thr Asp Arg Tyr Val Phe Pro Asp Gly Glu
305                 310                 315                 320

Leu Thr Gly Ser Gly Arg Ile Thr Thr Glu Ile Gln Gln Val Gly Leu
                325                 330                 335

Glu Val Leu His Glu Glu Asn Phe Arg His His Tyr Ala Met Thr Leu
            340                 345                 350

Arg Asp Trp Cys Gly Asn Leu Val Glu His Trp Asp Asp Ala Val Ala
        355                 360                 365

Glu Val Gly Leu Pro Thr Ala Lys Val Trp Gly Leu Tyr Met Ala Ala
    370                 375                 380

Ser Arg Val Ala Phe Glu Arg Asn Asn Leu Gln Leu His His Val Leu
385                 390                 395                 400
```

Ala Thr Lys Val Asp Pro Arg Gly Asp Asp Ser Leu Pro Leu Arg Pro
            405                 410                 415

Trp Trp Gln Pro
        420

<210> SEQ ID NO 51
<211> LENGTH: 1392
<212> TYPE: DNA
<213> ORGANISM: Unknown
<220> FEATURE:
<223> OTHER INFORMATION: Mycobacterium vanbaalenii

<400> SEQUENCE: 51

| | | |
|---|---|---|
| gtgtctgttc cttcgaccga cgcacgttct gctcacgccg acggcgtgca gcggcttctc | 60 |
| gccagctatc gggcgattcc ccaagacgcc acggtccggc tggccaaacc cacgtcgaac | 120 |
| ctcttccgtg cccgcgcgaa accaggacc aagggtctgg acacgtctgg gttgacgaac | 180 |
| gtgatcgcgg tcgacgcgga ggcacgcacc gccgatgtgg cagggatgtg cacctacgaa | 240 |
| gacctggtcg cggccacgct gccgcatgga ctttcgccgc tggtggtgcc gcagttgaag | 300 |
| acgatcaccc tcggcggggc ggtcaccgga ctcgggatcg agtccgcctc gttccgcaac | 360 |
| ggcctgccac acgaatcggt tctcgagatg gacgtcctca ccggcaccgg tgatgtcgtg | 420 |
| cgcgcctccc ccgacgagaa ccctgacctg tttcgggcgt ttccgaattc ctatggcacg | 480 |
| ttgggctatt cggttcggct caagatcgag ctggaaccgg tgaagccgtt cgtcgcgctg | 540 |
| cgccacctcc gtttccattc gctgtcggct ctcatcgagg cgatggaccg catcgtcgaa | 600 |
| accggcggcc tcaacggcga accggtggac tacctcgacg gcgtcgtgtt cagtgccgag | 660 |
| gagagttacc tgtgcgtggg gcagcgctcc gcgacaccgg gcccggtcag cgactacacg | 720 |
| ggcaagcaga tctactaccg ctcgattcag cacgacggcc cgaccgatgg cgccgagaag | 780 |
| cacgaccggc tgaccatcca cgactacctg tggcgctggg acaccgactg gttctggtgc | 840 |
| tcaagggcat cggcgcgca gaacccgcgg atccggcgct ggtggccgcg ccggtaccgg | 900 |
| cgcagcagtg tgtactggaa gctgatcggc tacgaccggc gtttcggtat cgccgatcgc | 960 |
| atcgagaagc gcaacggccg accccgcgc gagcgggtgg tccaggacat cgaggtgccc | 1020 |
| atcgagcgga ccgtcgagtt tctgcagtgg tttctcgaca ccgtgcccat cgaaccgatc | 1080 |
| tggttgtgcc cgttgcggct ccgcgacgac cgcgattggc ccctgtatcc gatccgaccc | 1140 |
| caccacacct acgtcaacgt gggtttctgg tcgtcggtgc cggtgggccc ggaggagggc | 1200 |
| tacaccaaca ggatgatcga acggaaagtc agcgacctcg acggtcacaa atcgctgtat | 1260 |
| tccgatgcgt actactcgcc ggaagagttt gattcgctct atggcgggga gacgtacaag | 1320 |
| acggtgaaga agacatacga cccagactct cgtttcctgg acctgtacgg caaagcagtg | 1380 |
| gggcggcaat ga | 1392 |

<210> SEQ ID NO 52
<211> LENGTH: 463
<212> TYPE: PRT
<213> ORGANISM: Unknown
<220> FEATURE:
<223> OTHER INFORMATION: Mycobacterium vanbaalenii

<400> SEQUENCE: 52

Val Ser Val Pro Ser Thr Asp Ala Arg Ser Ala His Ala Asp Gly Val
1               5                   10                  15

Gln Arg Leu Leu Ala Ser Tyr Arg Ala Ile Pro Gln Asp Ala Thr Val
            20                  25                  30

-continued

```
Arg Leu Ala Lys Pro Thr Ser Asn Leu Phe Arg Ala Arg Ala Lys Thr
             35                  40                  45

Arg Thr Lys Gly Leu Asp Thr Ser Gly Leu Thr Asn Val Ile Ala Val
 50                  55                  60

Asp Ala Glu Ala Arg Thr Ala Asp Val Ala Gly Met Cys Thr Tyr Glu
 65                  70                  75                  80

Asp Leu Val Ala Ala Thr Leu Pro His Gly Leu Ser Pro Leu Val Val
                 85                  90                  95

Pro Gln Leu Lys Thr Ile Thr Leu Gly Gly Ala Val Thr Gly Leu Gly
            100                 105                 110

Ile Glu Ser Ala Ser Phe Arg Asn Gly Leu Pro His Glu Ser Val Leu
            115                 120                 125

Glu Met Asp Val Leu Thr Gly Thr Gly Asp Val Val Arg Ala Ser Pro
        130                 135                 140

Asp Glu Asn Pro Asp Leu Phe Arg Ala Phe Pro Asn Ser Tyr Gly Thr
145                 150                 155                 160

Leu Gly Tyr Ser Val Arg Leu Lys Ile Glu Leu Pro Val Lys Pro
                165                 170                 175

Phe Val Ala Leu Arg His Leu Arg Phe His Ser Leu Ser Ala Leu Ile
                180                 185                 190

Glu Ala Met Asp Arg Ile Val Glu Thr Gly Gly Leu Asn Gly Glu Pro
        195                 200                 205

Val Asp Tyr Leu Asp Gly Val Val Phe Ser Ala Glu Glu Ser Tyr Leu
    210                 215                 220

Cys Val Gly Gln Arg Ser Ala Thr Pro Gly Pro Val Ser Asp Tyr Thr
225                 230                 235                 240

Gly Lys Gln Ile Tyr Tyr Arg Ser Ile Gln His Asp Gly Pro Thr Asp
                245                 250                 255

Gly Ala Glu Lys His Asp Arg Leu Thr Ile His Asp Tyr Leu Trp Arg
            260                 265                 270

Trp Asp Thr Asp Trp Phe Trp Cys Ser Arg Ala Phe Gly Ala Gln Asn
        275                 280                 285

Pro Arg Ile Arg Arg Trp Trp Pro Arg Arg Tyr Arg Arg Ser Ser Val
    290                 295                 300

Tyr Trp Lys Leu Ile Gly Tyr Asp Arg Arg Phe Gly Ile Ala Asp Arg
305                 310                 315                 320

Ile Glu Lys Arg Asn Gly Arg Pro Arg Glu Arg Val Val Gln Asp
                325                 330                 335

Ile Glu Val Pro Ile Glu Arg Thr Val Glu Phe Leu Gln Trp Phe Leu
            340                 345                 350

Asp Thr Val Pro Ile Glu Pro Ile Trp Leu Cys Pro Leu Arg Leu Arg
        355                 360                 365

Asp Asp Arg Asp Trp Pro Leu Tyr Pro Ile Arg Pro His His Thr Tyr
    370                 375                 380

Val Asn Val Gly Phe Trp Ser Ser Val Pro Val Gly Pro Glu Glu Gly
385                 390                 395                 400

Tyr Thr Asn Arg Met Ile Glu Arg Lys Val Ser Asp Leu Asp Gly His
                405                 410                 415

Lys Ser Leu Tyr Ser Asp Ala Tyr Tyr Ser Pro Glu Glu Phe Asp Ser
            420                 425                 430

Leu Tyr Gly Gly Glu Thr Tyr Lys Thr Val Lys Lys Thr Tyr Asp Pro
        435                 440                 445
```

```
Asp Ser Arg Phe Leu Asp Leu Tyr Gly Lys Ala Val Gly Arg Gln
        450                 455                 460
```

<210> SEQ ID NO 53
<211> LENGTH: 1323
<212> TYPE: DNA
<213> ORGANISM: Unknown
<220> FEATURE:
<223> OTHER INFORMATION: Mycobacterium vanbaalenii

<400> SEQUENCE: 53

```
ttgacgacat tcgggacgg cgcggccgac accggcctgc acggagaccg caagctcacc      60
ctggcgagg tcttggaggt cttcgcctcg ggccgactgc ctctgaagtt cacggcgtac     120
gacggcagca gcgcgggccc ggacgacgcc acgctcgggc tggacctgct gacccccgc     180
gggaccacgt acctcgcaac ggctcccggc gatctcggcc tggcccgggc ctacgtctcc     240
ggtgacctgc agttgcaggg ggtgcaccct ggcgacccgt acgacctgct caacgcactg     300
gtgcagaaac tggacttcaa gcgaccgtcc gcccgggtgc tggcgcaggt cgtccgatcg     360
atcgggatcg agcacctgaa accgatcgcg ccaccgccgc aggaggcgct gccgcggtgg     420
cggcgcatcg cagaaggact gcggcacagc aagacccgtg acgccgacgc gatccaccac     480
cattacgatg tctccaacac cttctacgag tgggtgctcg ggccgtcgat gacctacacc     540
tgcgcctgct acccgcatcc cgacgccacc ctcgaggagg cgcaggagaa caaatatcgg     600
ctggtgttcg agaaactgcg cctcaagccg gcgaccgcc ttctcgacgt ggggttgcggg     660
tggggcggaa tggtgcgcta cgcggcccgt cacggcgtca aggcgatcgg ggtgacgctg     720
tccagggagc aggcgcagtg ggcacgcgcc gccatcgaac gggacggcct gggtgacctc     780
gccgaggtcc gccacagcga ctaccgcgat gtgcgcgagt cccagttcga cgccgtgtct     840
tcgctggggc tcaccgagca catcggggtc gccaactatc cgtcgtactt ccggttcctc     900
aagtcgaagt tgcgcccggg cggcctactg ctcaaccact gcatcacccg gcacaacaat     960
cgcaccggcc ccgccgccgg gggattcatc gaccggtatg tgttcccgga cggggagctg    1020
accggatcgg gccggatcat caccgagatc caggacgtcg gtttggaggt gatgcacgaa    1080
gagaacctgc gccggcacta tgcgctgaca cttcgggact ggtgccggaa tctggtgcag    1140
cactgggacg aagcggtcgc agaggtcggc ctgcccaccg ccaaggtgtg gggtctgtac    1200
atggctgcct cgcgggtcgg cttcgagcag aacagcattc agctgcatca ggtactggcg    1260
gtgaagctcg acgaacgtgg cggggacggc ggtttgccgt tgcggccctg gtggaccgcg    1320
tag                                                                  1323
```

<210> SEQ ID NO 54
<211> LENGTH: 440
<212> TYPE: PRT
<213> ORGANISM: Unknown
<220> FEATURE:
<223> OTHER INFORMATION: Mycobacterium vanbaalenii

<400> SEQUENCE: 54

```
Leu Thr Thr Phe Arg Asp Gly Ala Ala Asp Thr Gly Leu His Gly Asp
1               5                   10                  15

Arg Lys Leu Thr Leu Ala Glu Val Leu Glu Val Phe Ala Ser Gly Arg
            20                  25                  30

Leu Pro Leu Lys Phe Thr Ala Tyr Asp Gly Ser Ser Ala Gly Pro Asp
        35                  40                  45

Asp Ala Thr Leu Gly Leu Asp Leu Leu Thr Pro Arg Gly Thr Thr Tyr
```

```
              50                  55                  60
Leu Ala Thr Ala Pro Gly Asp Leu Gly Leu Ala Arg Ala Tyr Val Ser
 65                  70                  75                  80

Gly Asp Leu Gln Leu Gln Gly Val His Pro Gly Asp Pro Tyr Asp Leu
                 85                  90                  95

Leu Asn Ala Leu Val Gln Lys Leu Asp Phe Lys Arg Pro Ser Ala Arg
            100                 105                 110

Val Leu Ala Gln Val Val Arg Ser Ile Gly Ile Glu His Leu Lys Pro
        115                 120                 125

Ile Ala Pro Pro Pro Gln Glu Ala Leu Pro Arg Trp Arg Arg Ile Ala
130                 135                 140

Glu Gly Leu Arg His Ser Lys Thr Arg Asp Ala Asp Ala Ile His His
145                 150                 155                 160

His Tyr Asp Val Ser Asn Thr Phe Tyr Glu Trp Val Leu Gly Pro Ser
                165                 170                 175

Met Thr Tyr Thr Cys Ala Cys Tyr Pro His Pro Asp Ala Thr Leu Glu
            180                 185                 190

Glu Ala Gln Glu Asn Lys Tyr Arg Leu Val Phe Glu Lys Leu Arg Leu
        195                 200                 205

Lys Pro Gly Asp Arg Leu Leu Asp Val Gly Cys Gly Trp Gly Gly Met
210                 215                 220

Val Arg Tyr Ala Ala Arg His Gly Val Lys Ala Ile Gly Val Thr Leu
225                 230                 235                 240

Ser Arg Glu Gln Ala Gln Trp Ala Arg Ala Ile Glu Arg Asp Gly
                245                 250                 255

Leu Gly Asp Leu Ala Glu Val Arg His Ser Asp Tyr Arg Asp Val Arg
            260                 265                 270

Glu Ser Gln Phe Asp Ala Val Ser Ser Leu Gly Leu Thr Glu His Ile
        275                 280                 285

Gly Val Ala Asn Tyr Pro Ser Tyr Phe Arg Phe Leu Lys Ser Lys Leu
290                 295                 300

Arg Pro Gly Gly Leu Leu Asn His Cys Ile Thr Arg His Asn Asn
305                 310                 315                 320

Arg Thr Gly Pro Ala Ala Gly Phe Ile Asp Arg Tyr Val Phe Pro
                325                 330                 335

Asp Gly Glu Leu Thr Gly Ser Gly Arg Ile Ile Thr Glu Ile Gln Asp
            340                 345                 350

Val Gly Leu Glu Val Met His Glu Glu Asn Leu Arg Arg His Tyr Ala
        355                 360                 365

Leu Thr Leu Arg Asp Trp Cys Arg Asn Leu Val Gln His Trp Asp Glu
370                 375                 380

Ala Val Ala Glu Val Gly Leu Pro Thr Ala Lys Val Trp Gly Leu Tyr
385                 390                 395                 400

Met Ala Ala Ser Arg Val Gly Phe Glu Gln Asn Ser Ile Gln Leu His
                405                 410                 415

Gln Val Leu Ala Val Lys Leu Asp Glu Arg Gly Gly Asp Gly Gly Leu
            420                 425                 430

Pro Leu Arg Pro Trp Trp Thr Ala
        435                 440

<210> SEQ ID NO 55
<211> LENGTH: 381
<212> TYPE: DNA
<213> ORGANISM: Unknown
```

```
<220> FEATURE:
<223> OTHER INFORMATION: Mycobacterium vanbaalenii

<400> SEQUENCE: 55
gtgatccgct ttctgctgcg cgtcgcggtc tttctcggat cgtcggcgat cgggctactg      60
gtggccggct ggctggtgcc gggggtgtcg ctgtcggtgc tgggcttcgt caccgcggtg     120
gtgatcttca cggtggcaca agggattctg tcgccgttct tcctgaagat ggccagccgc     180
tacgcgtcgg ccttcctcgg cggcatcggc ctggtgtcca cgttcgtggc gctgctgctc     240
gcgtcgctgc tgtccaacgg gctcagcatc cgcggcgtcg gtcgtggat cgcggccacg      300 gtggtggtct ggctggtcac agccctggcg accgtcgtgc tgcccgttct ggtgctgcgg     360
gagaagaaga aagcagcctg a                                               381

<210> SEQ ID NO 56
<211> LENGTH: 126
<212> TYPE: PRT
<213> ORGANISM: Unknown
<220> FEATURE:
<223> OTHER INFORMATION: Mycobacterium vanbaalenii

<400> SEQUENCE: 56

Val Ile Arg Phe Leu Leu Arg Val Ala Val Phe Leu Gly Ser Ser Ala
1               5                   10                  15

Ile Gly Leu Leu Val Ala Gly Trp Leu Val Pro Gly Val Ser Leu Ser
            20                  25                  30

Val Leu Gly Phe Val Thr Ala Val Val Ile Phe Thr Val Ala Gln Gly
        35                  40                  45

Ile Leu Ser Pro Phe Phe Leu Lys Met Ala Ser Arg Tyr Ala Ser Ala
    50                  55                  60

Phe Leu Gly Gly Ile Gly Leu Val Ser Thr Phe Val Ala Leu Leu Leu
65                  70                  75                  80

Ala Ser Leu Leu Ser Asn Gly Leu Ser Ile Arg Gly Val Gly Ser Trp
                85                  90                  95

Ile Ala Ala Thr Val Val Val Trp Leu Val Thr Ala Leu Ala Thr Val
            100                 105                 110

Val Leu Pro Val Leu Val Leu Arg Glu Lys Lys Lys Ala Ala
        115                 120                 125

<210> SEQ ID NO 57
<211> LENGTH: 1452
<212> TYPE: DNA
<213> ORGANISM: Rhodococcus opacus

<400> SEQUENCE: 57
atgcgggagg gtggacgccc cttccgtgcg catcgcactc tgcccgtcac cgggatcgac      60
gctcaccgcg ccggcgtcga acggcttctc gcgtcctacc gcgcgattcc cacggacgcc     120
accgtgcgac tcgcgaagaa gacgtccaac ctgttccggg gcgcggccca gaccagcgca     180
cccggcctcg acgtctccgg gctcggcgga gtcatctcgg tcgacgagca ggaccggacc     240
gcggatgtcg ccggaatgtg cacgtacgaa gacctggtgg acgccaccct cccgtacggg     300
ctggcgccgc tggtggttcc gcaactcaag accatcacac tcgcggcgc ggtcaccggc      360 ctcggcatcg agtcgacgtc gttccgcaac gggctccccc acgaatcggt cctcgagatc     420
gacgtcctga ccggaagcgg cgacatcgtc accgcgagac cggaaggcga gaactccgac     480
ctgttctggg ggttccccaa ctcctacgga accctcggct actccacccg actgcgcatc     540
```

```
cagctcgaac cgtcaaacg gtatgtggca ctgcgccatc tgcgtttcga ctccctggac    600
gagctgcagt cggcaatgga tcgcatcgtc accgagcgcg tccacgacgg catccccgtc    660
gactatctgg acggcgtcgt gttcaccgcg tccgagagtt acctgacact gggccatcag    720
accgacgagg gcggcccgt cagcgactac accgggcaga acatcttcta ccggtccatc    780
cagcacagtt ccgtgaacca ccccaaaacg gacaaactca ccatccgaga ctacctgtgg    840
cgctgggaca ccgactggtt ctggtgctcg cgcgccttcg gcgcccagaa ccccaccatc    900
cgccggctgt ggccgaagaa cctcctccgc agcagcttct actggaagct catcgccctc    960
gaccacaagt acgacatcgg cgaccgactc gagaagcgca agggcaaccc gccacgcgaa   1020
cgcgtcgtgc aggacgtcga agtgcccatc gagcgcaccg cggacttcgt ccgctggttc   1080
ctcgacgaaa tcccgatcga accgctgtgg ctgtgcccgt tgcggttgcg ggaacctgcc   1140
cccgccggcg cgtcctcgca acgcccctgg cccctgtacc ccctcgaacc gaaacgcacg   1200
tacgtgaaca tcggattctg gtcatcggtg cccatcgttc cgggccgacc cgaggggggcc   1260 gcgaatcggc tgatcgaaga caaggtcagt gacttcgacg gacacaagtc cctctactcc   1320
gattcgtact attcacgcga agatttcgaa cgcctctact acggcggcga tcgatacacg   1380
gaactgaaaa aacgctacga cccgaaatca cgattactgg accttttctc caaggcggtg   1440
caacgtcgat ga                                                      1452
```

<210> SEQ ID NO 58
<211> LENGTH: 483
<212> TYPE: PRT
<213> ORGANISM: Rhodococcus opacus

<400> SEQUENCE: 58

Met Arg Glu Gly Gly Arg Pro Phe Arg Ala His Arg Thr Leu Pro Val
1               5                   10                  15

Thr Gly Ile Asp Ala His Arg Ala Gly Val Glu Arg Leu Leu Ala Ser
            20                  25                  30

Tyr Arg Ala Ile Pro Thr Asp Ala Thr Val Arg Leu Ala Lys Lys Thr
        35                  40                  45

Ser Asn Leu Phe Arg Ala Arg Ala Gln Thr Ser Ala Pro Gly Leu Asp
    50                  55                  60

Val Ser Gly Leu Gly Gly Val Ile Ser Val Asp Glu Gln Asp Arg Thr
65                  70                  75                  80

Ala Asp Val Ala Gly Met Cys Thr Tyr Glu Asp Leu Val Asp Ala Thr
                85                  90                  95

Leu Pro Tyr Gly Leu Ala Pro Leu Val Val Pro Gln Leu Lys Thr Ile
            100                 105                 110

Thr Leu Gly Gly Ala Val Thr Gly Leu Gly Ile Glu Ser Thr Ser Phe
        115                 120                 125

Arg Asn Gly Leu Pro His Glu Ser Val Leu Glu Ile Asp Val Leu Thr
    130                 135                 140

Gly Ser Gly Asp Ile Val Thr Ala Arg Pro Glu Gly Glu Asn Ser Asp
145                 150                 155                 160

Leu Phe Trp Gly Phe Pro Asn Ser Tyr Gly Thr Leu Gly Tyr Ser Thr
                165                 170                 175

Arg Leu Arg Ile Gln Leu Glu Pro Val Lys Arg Tyr Val Ala Leu Arg
            180                 185                 190

His Leu Arg Phe Asp Ser Leu Asp Glu Leu Gln Ser Ala Met Asp Arg
        195                 200                 205

Ile Val Thr Glu Arg Val His Asp Gly Ile Pro Val Asp Tyr Leu Asp
210                 215                 220

Gly Val Val Phe Thr Ala Ser Glu Ser Tyr Leu Thr Leu Gly His Gln
225                 230                 235                 240

Thr Asp Glu Gly Gly Pro Val Ser Asp Tyr Thr Gly Gln Asn Ile Phe
            245                 250                 255

Tyr Arg Ser Ile Gln His Ser Ser Val Asn His Pro Lys Thr Asp Lys
                260                 265                 270

Leu Thr Ile Arg Asp Tyr Leu Trp Arg Trp Asp Thr Asp Trp Phe Trp
            275                 280                 285

Cys Ser Arg Ala Phe Gly Ala Gln Asn Pro Thr Ile Arg Arg Leu Trp
290                 295                 300

Pro Lys Asn Leu Leu Arg Ser Ser Phe Tyr Trp Lys Leu Ile Ala Leu
305                 310                 315                 320

Asp His Lys Tyr Asp Ile Gly Asp Arg Leu Glu Lys Arg Lys Gly Asn
                325                 330                 335

Pro Pro Arg Glu Arg Val Val Gln Asp Val Glu Val Pro Ile Glu Arg
            340                 345                 350

Thr Ala Asp Phe Val Arg Trp Phe Leu Asp Glu Ile Pro Ile Glu Pro
            355                 360                 365

Leu Trp Leu Cys Pro Leu Arg Leu Arg Glu Pro Ala Pro Ala Gly Ala
            370                 375                 380

Ser Ser Gln Arg Pro Trp Pro Leu Tyr Pro Leu Glu Pro Lys Arg Thr
385                 390                 395                 400

Tyr Val Asn Ile Gly Phe Trp Ser Ser Val Pro Ile Val Pro Gly Arg
                405                 410                 415

Pro Glu Gly Ala Ala Asn Arg Leu Ile Glu Asp Lys Val Ser Asp Phe
            420                 425                 430

Asp Gly His Lys Ser Leu Tyr Ser Asp Ser Tyr Tyr Ser Arg Glu Asp
            435                 440                 445

Phe Glu Arg Leu Tyr Tyr Gly Gly Asp Arg Tyr Thr Glu Leu Lys Lys
            450                 455                 460

Arg Tyr Asp Pro Lys Ser Arg Leu Leu Asp Leu Phe Ser Lys Ala Val
465                 470                 475                 480

Gln Arg Arg

<210> SEQ ID NO 59
<211> LENGTH: 1302
<212> TYPE: DNA
<213> ORGANISM: Rhodococcus opacus

<400> SEQUENCE: 59
atgacaactc tgaaagcttc acgctcccag gaccacaagc tgaccatcgc agagattctc     60
gaaactctgt ccgacggcat gctcccctg cggttctccg cctacgacgg cagcgccgcc    120
ggcccggagg acgccccta cggtctccac ctcaagacga cccgaggcac acctacctg     180 gcgaccgccc ccggcgacct cggcatggcc cgggcctacg tgtccggcga cctcgaggcc    240
cgcggcgtcc accccggcga cccgtacgag atcctccgcg tgatgggcga cgaactgcac    300
ttccgccgtc cgtccgcgct cacgctcgcc gccatcacgc gctcgctcgg ctgggatctg    360
ctgcgcccca tgcccctcc cccgcaggag catctcccgc ggtggcgtcg agtcgcggaa    420
gggttgcggc actccaagtc ccgcgacgcc gaggtcatcc accaccacta cgacgtctcg    480
aacaccttct acgagtatgt cctcggcccg tccatgacgt acacgtgcgc ctgctacgag    540

-continued

```
aacgccgagc agaccctcga agaggcacag gacaacaagt accgcctcgt cttcgagaag    600
ctcggcctcc agcccggcga ccgactgctc gacatcggtt gcggctgggg atcgatggtc    660
cggtacgccg ccgccgcgg cgtcaaggtc atcggcgcca ccctgtcccg agagcaggcc     720
gaatgggcac agaaggccat cgccgaagaa ggactgtccg acctcgccga ggtccggttc    780
tccgactacc gtgacgtccc cgagaccgga ttcgacgcca tctcctcgat cggcctgacc    840
gagcacatcg cgtcggcaa ctaccccgcc tacttcggac tgctgcagag caagctccgc     900
gagggcggcc ggctgctgaa ccactgcatc acccggcccg acaaccagag tcaggcacgc    960
gcgggcggct tcatcgaccg gtacgtcttc cccgacggcg aactcaccgg ctccggacgc    1020
atcatcaccg agatccagaa cgtcggactc gaggtgcggc acgaggagaa tctgcgcgag   1080
cactacgcac tcaccctcgc cggctggtgc cagaacctcg tcgacaactg ggacgcctgc   1140
gtcgccgagg tcggcgaagg caccgcacgt gtgtggggtc tctacatggc cgggtcgcga   1200
ctgggcttcg aacgcaacgt cgttcagctg caccaggtcc tcgccgtcaa gctcggaccc   1260
aagggcgagg cgcatgtgcc gctgcgtccg tggtggaagt ag                       1302
```

<210> SEQ ID NO 60
<211> LENGTH: 433
<212> TYPE: PRT
<213> ORGANISM: Rhodococcus opacus

<400> SEQUENCE: 60

```
Met Thr Thr Leu Lys Ala Ser Arg Ser Gln Asp His Lys Leu Thr Ile
1               5                   10                  15

Ala Glu Ile Leu Glu Thr Leu Ser Asp Gly Met Leu Pro Leu Arg Phe
            20                  25                  30

Ser Ala Tyr Asp Gly Ser Ala Ala Gly Pro Glu Asp Ala Pro Tyr Gly
        35                  40                  45

Leu His Leu Lys Thr Thr Arg Gly Thr Thr Tyr Leu Ala Thr Ala Pro
    50                  55                  60

Gly Asp Leu Gly Met Ala Arg Ala Tyr Val Ser Gly Asp Leu Glu Ala
65                  70                  75                  80

Arg Gly Val His Pro Gly Asp Pro Tyr Glu Ile Leu Arg Val Met Gly
                85                  90                  95

Asp Glu Leu His Phe Arg Arg Pro Ser Ala Leu Thr Leu Ala Ala Ile
            100                 105                 110

Thr Arg Ser Leu Gly Trp Asp Leu Leu Arg Pro Ile Ala Pro Pro Pro
        115                 120                 125

Gln Glu His Leu Pro Arg Trp Arg Arg Val Ala Glu Gly Leu Arg His
    130                 135                 140

Ser Lys Ser Arg Asp Ala Glu Val Ile His His Tyr Asp Val Ser
145                 150                 155                 160

Asn Thr Phe Tyr Glu Tyr Val Leu Gly Pro Ser Met Thr Tyr Thr Cys
                165                 170                 175

Ala Cys Tyr Glu Asn Ala Glu Gln Thr Leu Glu Glu Ala Gln Asp Asn
            180                 185                 190

Lys Tyr Arg Leu Val Phe Glu Lys Leu Gly Leu Gln Pro Gly Asp Arg
        195                 200                 205

Leu Leu Asp Ile Gly Cys Gly Trp Gly Ser Met Val Arg Tyr Ala Ala
    210                 215                 220

Arg Arg Gly Val Lys Val Ile Gly Ala Thr Leu Ser Arg Glu Gln Ala
225                 230                 235                 240
```

```
Glu Trp Ala Gln Lys Ala Ile Ala Glu Glu Gly Leu Ser Asp Leu Ala
                245                 250                 255
Glu Val Arg Phe Ser Asp Tyr Arg Asp Val Pro Glu Thr Gly Phe Asp
            260                 265                 270
Ala Ile Ser Ser Ile Gly Leu Thr Glu His Ile Gly Val Gly Asn Tyr
        275                 280                 285
Pro Ala Tyr Phe Gly Leu Leu Gln Ser Lys Leu Arg Glu Gly Gly Arg
    290                 295                 300
Leu Leu Asn His Cys Ile Thr Arg Pro Asp Asn Gln Ser Gln Ala Arg
305                 310                 315                 320
Ala Gly Gly Phe Ile Asp Arg Tyr Val Phe Pro Asp Gly Glu Leu Thr
                325                 330                 335
Gly Ser Gly Arg Ile Ile Thr Glu Ile Gln Asn Val Gly Leu Glu Val
            340                 345                 350
Arg His Glu Glu Asn Leu Arg Glu His Tyr Ala Leu Thr Leu Ala Gly
        355                 360                 365
Trp Cys Gln Asn Leu Val Asp Asn Trp Asp Ala Cys Val Ala Glu Val
    370                 375                 380
Gly Glu Gly Thr Ala Arg Val Trp Gly Leu Tyr Met Ala Gly Ser Arg
385                 390                 395                 400
Leu Gly Phe Glu Arg Asn Val Val Gln Leu His Gln Val Leu Ala Val
                405                 410                 415
Lys Leu Gly Pro Lys Gly Glu Ala His Val Pro Leu Arg Pro Trp Trp
            420                 425                 430
Lys
```

<210> SEQ ID NO 61
<211> LENGTH: 1428
<212> TYPE: DNA
<213> ORGANISM: Unknown
<220> FEATURE:
<223> OTHER INFORMATION: Streptomyces regnsis

<400> SEQUENCE: 61

```
atgatcacac tggcaggccg ggccggtgcg cgcgatcatg ggtgtatggc cttcggtgcc     60
gccatcccca cggggtcggg acacgccggg tacgccgagc gcgtcgcaac ccttcgcgcc    120
cacctggccg acctcccgga ggggacgccg gtccggctgg cgaagggcac ctcgaacctg    180
ttccggccgc ggtcccgcgc acggcgggg ctcgacgtgt cggccttcga ccacgtgctg    240
tcgatcgatc cgcagaaccg gaccgccgac gtcgagggca tggtcaccta cgagcggctc    300
gtcgacgcga cgttgccgca cggcctgatg ccgctcgtcg ttccgcagct caagacgatc    360
acgctgggcg gggcggtcac gggactgggc atcgagtcgt cgtcgttccg cgagggcatg    420
ccccacgaat ccgtggtgga gatggacatc ctcacgggtg cgggagacgt ggtgaccgcg    480
accccggacg gcgagcacag cgacctgttc ttcgggttcc ccaactccta cggaacgctg    540
ggatacgcgc tgcgcctgcg gatcgaactc gcgccggtgc gcccgtacgt acgactcgaa    600
cacctgcgtt tctccgatcc ggcacgctac ttcgagcgcc tggcgcgtgc gtgccgcgac    660
cgggaggccg acttcgtcga cggcaccgtc ttcgctcccg acgagctgta cctgacgttg    720
gccacgttca gcggcgagcc cgacgaggtc agcgactaca cgtggatgga cgtctactac    780
cgctcgatca gggagaagac ggtcgaccat ctgccgatcc gcgactacct gtggcggtgg    840
gacaccgact ggtctggtg ttcgcgcgcg ctcgagcgc agaacggct cgtgcggctg    900
ctcgcgggtc cacgtctgct gcgttccgat gtgtactgga agatcgtcgg tttcgaacgc    960
```

```
aggcaccggc tgtgggagcg tgcgagccgg ctgctgggca ggcccgagcg cgaagcggtg    1020
atgcaggaca tcgaggtgcc ggtgcaccgc gccgaggagt tcctgacgtt cctgcaccgg    1080
gagatcccca tcagtccggt gtggatctgc ccgctgagtg ggcgggacgc gcgccggtgg    1140
ccgctgtacg agctcgaccc ggacgagctg tacgtcaact tcggtttctg gggcaccggtg    1200 ccgctcgagc caggcgaacc gcagggttcg cacaaccggc gggtggagaa cgtggttacc    1260
gaactcgacg gacggaaatc cctgtactcg gagagtttct acgaccgcga cacgttctgg    1320
cggttgtacg gagggaatca aggacagacg taccaggccc tgaagcatcg ctacgacccg    1380
aacgggagat tgctggacct gtacgccaag tgcgttcaag cgaggtga                 1428
```

<210> SEQ ID NO 62
<211> LENGTH: 475
<212> TYPE: PRT
<213> ORGANISM: Unknown
<220> FEATURE:
<223> OTHER INFORMATION: Streptomyces regnsis

<400> SEQUENCE: 62

```
Met Ile Thr Leu Ala Gly Arg Ala Gly Ala Arg Asp His Gly Cys Met
1               5                   10                  15

Ala Phe Gly Ala Ala Ile Pro Thr Gly Ser Gly His Ala Gly Tyr Ala
                20                  25                  30

Glu Arg Val Ala Thr Leu Arg Ala His Leu Ala Asp Leu Pro Glu Gly
            35                  40                  45

Thr Pro Val Arg Leu Ala Lys Gly Thr Ser Asn Leu Phe Arg Pro Arg
        50                  55                  60

Ser Arg Ala Thr Ala Gly Leu Asp Val Ser Ala Phe Asp His Val Leu
65                  70                  75                  80

Ser Ile Asp Pro Gln Asn Arg Thr Ala Asp Val Glu Gly Met Val Thr
                85                  90                  95

Tyr Glu Arg Leu Val Asp Ala Thr Leu Pro His Gly Leu Met Pro Leu
            100                 105                 110

Val Val Pro Gln Leu Lys Thr Ile Thr Leu Gly Gly Ala Val Thr Gly
        115                 120                 125

Leu Gly Ile Glu Ser Ser Phe Arg Glu Gly Met Pro His Glu Ser
    130                 135                 140

Val Val Glu Met Asp Ile Leu Thr Gly Ala Gly Asp Val Val Thr Ala
145                 150                 155                 160

Thr Pro Asp Gly Glu His Ser Asp Leu Phe Phe Gly Phe Pro Asn Ser
                165                 170                 175

Tyr Gly Thr Leu Gly Tyr Ala Leu Arg Leu Arg Ile Glu Leu Ala Pro
            180                 185                 190

Val Arg Pro Tyr Val Arg Leu Glu His Leu Arg Phe Ser Asp Pro Ala
        195                 200                 205

Arg Tyr Phe Glu Arg Leu Ala Arg Ala Cys Arg Asp Arg Glu Ala Asp
    210                 215                 220

Phe Val Asp Gly Thr Val Phe Ala Pro Asp Glu Leu Tyr Leu Thr Leu
225                 230                 235                 240

Ala Thr Phe Ser Gly Glu Pro Asp Glu Val Ser Asp Tyr Thr Trp Met
                245                 250                 255

Asp Val Tyr Tyr Arg Ser Ile Arg Glu Lys Thr Val Asp His Leu Pro
            260                 265                 270

Ile Arg Asp Tyr Leu Trp Arg Trp Asp Thr Asp Trp Phe Trp Cys Ser
```

```
                275                 280                 285
Arg Ala Leu Gly Ala Gln Asn Arg Leu Val Arg Leu Ala Gly Pro
    290                 295                 300
Arg Leu Leu Arg Ser Asp Val Tyr Trp Lys Ile Val Gly Phe Glu Arg
305                 310                 315                 320
Arg His Arg Leu Trp Glu Arg Ala Ser Arg Leu Leu Gly Arg Pro Glu
                325                 330                 335
Arg Glu Ala Val Met Gln Asp Ile Glu Val Pro Val His Arg Ala Glu
            340                 345                 350
Glu Phe Leu Thr Phe Leu His Arg Glu Ile Pro Ile Ser Pro Val Trp
        355                 360                 365
Ile Cys Pro Leu Ser Gly Arg Asp Ala Arg Arg Trp Pro Leu Tyr Glu
    370                 375                 380
Leu Asp Pro Asp Glu Leu Tyr Val Asn Phe Gly Phe Trp Gly Thr Val
385                 390                 395                 400
Pro Leu Glu Pro Gly Glu Pro Gln Gly Ser His Asn Arg Arg Val Glu
                405                 410                 415
Asn Val Val Thr Glu Leu Asp Gly Arg Lys Ser Leu Tyr Ser Glu Ser
            420                 425                 430
Phe Tyr Asp Arg Asp Thr Phe Trp Arg Leu Tyr Gly Gly Asn Gln Gly
        435                 440                 445
Gln Thr Tyr Gln Ala Leu Lys His Arg Tyr Asp Pro Asn Gly Arg Leu
    450                 455                 460
Leu Asp Leu Tyr Ala Lys Cys Val Gln Ala Arg
465                 470                 475

<210> SEQ ID NO 63
<211> LENGTH: 1317
<212> TYPE: DNA
<213> ORGANISM: Unknown
<220> FEATURE:
<223> OTHER INFORMATION: Streptomyces regnsis

<400> SEQUENCE: 63
ttggcgtcgt cggggccacc gctgcccgcc agggcggggt cccgatcggc tgactcgacg      60
gcgttggacg cgatcctgcg ccgcgtgctc ggggacgacc cgcccgtggc cgtgaccgcg     120
ttcgacggca cggtggtcgg tgacccggac tcggcgctgc agctgcacat ccgcacgccg     180
acggccctga gctacgtgct caccgcgccc aacgaactcg ggttggcgcg ggcctacgtc     240
acgggacatc tcgacgtgac cggcgacgtc taccaggtgc tgcgcgcact gacgagcgtg     300
gccgagaacc tcacgacggc cgatcggatg tggctggccg gccgtctcgc acgggacttc     360
accgaccggc tgcggccggt gccgatcccc gtcgaggagg cgccgtcgcg gctccgcagg     420
accgcacgtg gcctccggca ttccaaggcg cgcgacagcg acgcgatctc ccggcactac     480
gacgtctcga accgcttcta cgagctggtg ctcggcccgt cgatggccta cacgtgcgcc     540
tgctacccgg aggatgcggc cacgctggag caggcacagt tccacaagtt cgacctcgtg     600
tgccgaaagc tcggtctgaa gccggggatg cgcctgctcg acgtgggctg cggttggggc     660
ggcatggtcg cccacgccgt ggagcactac ggggtgcggg cgatcggcgt caccctctcg     720
cgccagcagg cggagtgggg acagcgggac ctcgaggcca ggggcctggc cgatcgcggc     780
gagatccgcc atctggacta ccgcgacgtg cccgagaccg ggttcgacgc ggtgtcgtcc     840
atcgggctca ccgaacacat cggcgcgcgg aacctgccgt cgtacttccg cttcctgcac     900
tcgaagttgc gtcccggcgg acggttgctc aaccactgca tcgtgcgccc gcacacctac     960
```

```
gactcccatc ggacgggccc gttcatcgac cgctacgtct tcccggacgg cgaactcgag    1020
ggcgtcggga cgatcgtgtc ggcgatgcag gaccacgggt tcgaggtacg gcacgcggag    1080
aacctgcggg aacactacgg gcgcaccctc gcggcgtggt gcgccaatct cgacgcgcac    1140
tgggaggcgg cggtggccga ggcgggcgtg cagcgggcca gggtgtgggc gctgtacatg    1200
gcggcctccc ggctgtcgtt cgaacgtcat gagctcgagc tgcagcaggt gctcggcgtg    1260
aaacccgacg ccgcgggcgg gtcgtcgatg ccgcttcgcc cggactgggg ggtgtga      1317
```

<210> SEQ ID NO 64
<211> LENGTH: 438
<212> TYPE: PRT
<213> ORGANISM: Unknown
<220> FEATURE:
<223> OTHER INFORMATION: Streptomyces regnsis

<400> SEQUENCE: 64

```
Leu Ala Ser Ser Gly Pro Pro Leu Pro Ala Arg Ala Gly Ser Arg Ser
1               5                   10                  15

Ala Asp Ser Thr Ala Leu Asp Ala Ile Leu Arg Arg Val Leu Gly Asp
            20                  25                  30

Asp Pro Pro Val Ala Val Thr Ala Phe Asp Gly Thr Val Val Gly Asp
        35                  40                  45

Pro Asp Ser Ala Leu Gln Leu His Ile Arg Thr Pro Thr Ala Leu Ser
    50                  55                  60

Tyr Val Leu Thr Ala Pro Asn Glu Leu Gly Leu Ala Arg Ala Tyr Val
65                  70                  75                  80

Thr Gly His Leu Asp Val Thr Gly Asp Val Tyr Gln Val Leu Arg Ala
                85                  90                  95

Leu Thr Ser Val Ala Glu Asn Leu Thr Thr Ala Asp Arg Met Trp Leu
            100                 105                 110

Ala Gly Arg Leu Ala Arg Asp Phe Thr Asp Arg Leu Arg Pro Val Pro
        115                 120                 125

Ile Pro Val Glu Glu Ala Pro Ser Arg Leu Arg Arg Thr Ala Arg Gly
    130                 135                 140

Leu Arg His Ser Lys Ala Arg Asp Ser Asp Ala Ile Ser Arg His Tyr
145                 150                 155                 160

Asp Val Ser Asn Arg Phe Tyr Glu Leu Val Leu Gly Pro Ser Met Ala
                165                 170                 175

Tyr Thr Cys Ala Cys Tyr Pro Glu Asp Ala Ala Thr Leu Glu Gln Ala
            180                 185                 190

Gln Phe His Lys Phe Asp Leu Val Cys Arg Lys Leu Gly Leu Lys Pro
        195                 200                 205

Gly Met Arg Leu Leu Asp Val Gly Cys Gly Trp Gly Gly Met Val Ala
    210                 215                 220

His Ala Val Glu His Tyr Gly Val Arg Ala Ile Gly Val Thr Leu Ser
225                 230                 235                 240

Arg Gln Gln Ala Glu Trp Gly Gln Arg Asp Leu Glu Ala Arg Gly Leu
                245                 250                 255

Ala Asp Arg Gly Glu Ile Arg His Leu Asp Tyr Arg Asp Val Pro Glu
            260                 265                 270

Thr Gly Phe Asp Ala Val Ser Ser Ile Gly Leu Thr Glu His Ile Gly
        275                 280                 285

Ala Arg Asn Leu Pro Ser Tyr Phe Arg Phe Leu His Ser Lys Leu Arg
    290                 295                 300
```

Pro Gly Gly Arg Leu Leu Asn His Cys Ile Val Arg Pro His Thr Tyr
305                 310                 315                 320

Asp Ser His Arg Thr Gly Pro Phe Ile Asp Arg Tyr Val Phe Pro Asp
                325                 330                 335

Gly Glu Leu Glu Gly Val Gly Thr Ile Val Ser Ala Met Gln Asp His
            340                 345                 350

Gly Phe Glu Val Arg His Ala Glu Asn Leu Arg Glu His Tyr Gly Arg
        355                 360                 365

Thr Leu Ala Ala Trp Cys Ala Asn Leu Asp Ala His Trp Glu Ala Ala
    370                 375                 380

Val Ala Glu Ala Gly Val Gln Arg Ala Arg Val Trp Ala Leu Tyr Met
385                 390                 395                 400

Ala Ala Ser Arg Leu Ser Phe Glu Arg His Glu Leu Glu Leu Gln Gln
                405                 410                 415

Val Leu Gly Val Lys Pro Asp Ala Ala Gly Ser Ser Met Pro Leu
            420                 425                 430

Arg Pro Asp Trp Gly Val
            435

<210> SEQ ID NO 65
<211> LENGTH: 501
<212> TYPE: DNA
<213> ORGANISM: Unknown
<220> FEATURE:
<223> OTHER INFORMATION: Streptomyces regnsis

<400> SEQUENCE: 65
gtgcgcgtgg caccgccccg catcggtgcc acaccggcg cggtgggcgc accggactac      60
gcctccgcct tccgcgtgcc gacggcggcg gcccgcaggc gttcgccgcg ggaatggacg     120
cgtgcggtgt tcgagggcgc gcccgcgccg ttggcgctgt tcgtgcgttg gggatggctg    180
gccgtgctcc ggttgcgcct cagtgaggac cccgaggcgg tggcgggctg agacccacg     240 acgctcgacc ccggcacctc cgacgccccc gacacctctg agacagccgg aaactccgac    300
gctgccgcac tggaggccga atcgccgctg ctggaggcgt gcaacgtggc gttcgtcgac    360
gacgacggtg tcacgtgggc gacctacgtc cggttccgtg gtggcctcgg ccgcgcggtg    420
tgggcggtgg cggcgcggat ccaccacgtc gtcatcccct acctgctgcg gcgggcggtg    480
cggcgcacgg aacgggagtg a                                              501

<210> SEQ ID NO 66
<211> LENGTH: 166
<212> TYPE: PRT
<213> ORGANISM: Unknown
<220> FEATURE:
<223> OTHER INFORMATION: Streptomyces regnsis

<400> SEQUENCE: 66

Val Arg Val Ala Pro Pro Arg Ile Gly Ala Thr Pro Gly Ala Val Gly
1               5                   10                  15

Ala Pro Asp Tyr Ala Ser Ala Phe Arg Val Pro Thr Ala Ala Ala Arg
            20                  25                  30

Arg Arg Ser Pro Arg Glu Trp Thr Arg Ala Val Phe Glu Gly Ala Pro
        35                  40                  45

Ala Pro Leu Ala Leu Phe Val Arg Trp Gly Trp Leu Ala Val Leu Arg
    50                  55                  60

Leu Arg Leu Ser Glu Asp Pro Glu Ala Val Ala Gly Trp Arg Pro Thr

```
            65                  70                  75                  80
Thr Leu Asp Pro Gly Thr Ser Asp Ala Pro Asp Thr Ser Glu Thr Ala
                85                  90                  95
Gly Asn Ser Asp Ala Ala Ala Leu Glu Ala Glu Ser Pro Leu Leu Glu
            100                 105                 110
Ala Cys Asn Val Ala Phe Val Asp Asp Asp Gly Val Thr Trp Ala Thr
            115                 120                 125
Tyr Val Arg Phe Arg Gly Gly Leu Gly Arg Ala Val Trp Ala Val Ala
            130                 135                 140
Ala Arg Ile His His Val Val Ile Pro Tyr Leu Leu Arg Arg Ala Val
145                 150                 155                 160
Arg Arg Thr Glu Arg Glu
            165

<210> SEQ ID NO 67
<211> LENGTH: 1413
<212> TYPE: DNA
<213> ORGANISM: Unknown
<220> FEATURE:
<223> OTHER INFORMATION: Thermobifida fusca

<400> SEQUENCE: 67
gtgaactgtc agtcttccgc gtccaacctc gccaaccaca tcaacgcggt gtacgagctg      60
cgccgcgcct atgcgcggct gtccgccgac aagccggtgc cctggcgaa gaccaccctcc    120
aacctcttcc gcttccgcag ccgggacgat gccgcgcgtc tcgacgtcag cgctttcacc    180
tcggtgatca gcatcgacac ggaggcgcgg gtcgcgagg tgggcggcat gaccacctac     240
gaggacctgg tcgccgccac cctgcggcat ggcctgatgc cgccggtggt ccgcaactg    300
cgcacgatca ccctgggcgg tgcggtcacc gggctgggga tcgaatcctc gtccttccgc    360
aacgggctcc cgcacgagtc agtggaagag atggagatcc tcaccggcag cggccaggtg    420
gtggtggccc ggcgcgacaa cgagcaccgc gacctgttct acggtttccc caactcgtac    480
ggcacccctcg gttacgcgct gcggctccgc atccagctcg aacggtccg ccctacgtc    540
cacctgcggc acctgcggtt caccgatgcc gcagcggcca tggccgcgct ggagcagatc    600
tgcgcggacc gcacccacga cggggagacc gtcgacttcg tcgacggcgt cgtgttcgcc    660
cgcaacgagc tgtacctgac cttggggacg ttcaccgacc gggctccgtg gaccagcgac    720
tacaccggaa ccgacatcta ctaccggtcg atccccgct acgcgggccc cggccccggc    780
gactacctca ccacgcacga ctacctgtgg cggtgggaca ccgactggtt ctggtgctcc    840
cgcgccttcg gactgcagca tcccgtggtg cgccgcctgt ggccgcgttc cttgaaacgc    900
tccgacgtct accgcaagct cgtcgcctgg gaccggcgca ctgacgcgag ccgcctgctc    960
gactactacc gcgggcgccc gcccaaggaa ccggtgatcc aggacatcga ggttgaggtg   1020
gggcgggctg ccgagttcct cgacttcttc cacaccgaga tcggcatgtc cccggtgtgg   1080
ctgtgcccgc tgcggctgcg agaagacaca gccgacgata cggaaccggt ctggccgctc   1140
taccccctca aaccccgccg cctctacgtc aacttcgggt tttggggcct cgttccgatc   1200
cgtcccggtg gaggcaggac ataccacaac cggctgatcg aaaaagaagt gacccggttg   1260
ggcgggcaca agtcgctcta ctcggacgcc ttctacgacg aggacgagtt ctgggagctc   1320
tacaacgggg agatctaccg caagctcaaa gctgcctacg accccgacgg tcgactgctc   1380
gacctgtaca ccaagtgcgt cggcggcggg tga                                1413
```

-continued

```
<210> SEQ ID NO 68
<211> LENGTH: 470
<212> TYPE: PRT
<213> ORGANISM: Unknown
<220> FEATURE:
<223> OTHER INFORMATION: Thermobifida fusca

<400> SEQUENCE: 68
```

| | | | | | | | | | | | | | | |
|---|---|---|---|---|---|---|---|---|---|---|---|---|---|---|
| Val | Asn | Cys | Gln | Ser | Ser | Ala | Ser | Asn | Leu | Ala | Asn | His | Ile | Asn | Ala |
| 1 | | | | 5 | | | | | 10 | | | | | 15 | |
| Val | Tyr | Glu | Leu | Arg | Arg | Ala | Tyr | Ala | Arg | Leu | Ser | Ala | Asp | Lys | Pro |
| | | | 20 | | | | | 25 | | | | | 30 | | |
| Val | Arg | Leu | Ala | Lys | Thr | Thr | Ser | Asn | Leu | Phe | Arg | Phe | Arg | Ser | Arg |
| | | 35 | | | | | 40 | | | | | 45 | | | |
| Asp | Asp | Ala | Ala | Arg | Leu | Asp | Val | Ser | Ala | Phe | Thr | Ser | Val | Ile | Ser |
| | 50 | | | | | 55 | | | | | 60 | | | | |
| Ile | Asp | Thr | Glu | Ala | Arg | Val | Ala | Glu | Val | Gly | Gly | Met | Thr | Thr | Tyr |
| 65 | | | | | 70 | | | | | 75 | | | | | 80 |
| Glu | Asp | Leu | Val | Ala | Ala | Thr | Leu | Arg | His | Gly | Leu | Met | Pro | Pro | Val |
| | | | | 85 | | | | | 90 | | | | | 95 | |
| Val | Pro | Gln | Leu | Arg | Thr | Ile | Thr | Leu | Gly | Gly | Ala | Val | Thr | Gly | Leu |
| | | | 100 | | | | | 105 | | | | | 110 | | |
| Gly | Ile | Glu | Ser | Ser | Ser | Phe | Arg | Asn | Gly | Leu | Pro | His | Glu | Ser | Val |
| | | 115 | | | | | 120 | | | | | 125 | | | |
| Glu | Glu | Met | Glu | Ile | Leu | Thr | Gly | Ser | Gly | Gln | Val | Val | Ala | Arg |
| | 130 | | | | | 135 | | | | | 140 | | | | |
| Arg | Asp | Asn | Glu | His | Arg | Asp | Leu | Phe | Tyr | Gly | Phe | Pro | Asn | Ser | Tyr |
| 145 | | | | | 150 | | | | | 155 | | | | | 160 |
| Gly | Thr | Leu | Gly | Tyr | Ala | Leu | Arg | Leu | Arg | Ile | Gln | Leu | Glu | Pro | Val |
| | | | | 165 | | | | | 170 | | | | | 175 | |
| Arg | Pro | Tyr | Val | His | Leu | Arg | His | Leu | Arg | Phe | Thr | Asp | Ala | Ala | Ala |
| | | | 180 | | | | | 185 | | | | | 190 | | |
| Ala | Met | Ala | Ala | Leu | Glu | Gln | Ile | Cys | Ala | Asp | Arg | Thr | His | Asp | Gly |
| | | 195 | | | | | 200 | | | | | 205 | | | |
| Glu | Thr | Val | Asp | Phe | Val | Asp | Gly | Val | Val | Phe | Ala | Arg | Asn | Glu | Leu |
| | 210 | | | | | 215 | | | | | 220 | | | | |
| Tyr | Leu | Thr | Leu | Gly | Thr | Phe | Thr | Asp | Arg | Ala | Pro | Trp | Thr | Ser | Asp |
| 225 | | | | | 230 | | | | | 235 | | | | | 240 |
| Tyr | Thr | Gly | Thr | Asp | Ile | Tyr | Tyr | Arg | Ser | Ile | Pro | Arg | Tyr | Ala | Gly |
| | | | | 245 | | | | | 250 | | | | | 255 | |
| Pro | Gly | Pro | Gly | Asp | Tyr | Leu | Thr | Thr | His | Asp | Tyr | Leu | Trp | Arg | Trp |
| | | | 260 | | | | | 265 | | | | | 270 | | |
| Asp | Thr | Asp | Trp | Phe | Trp | Cys | Ser | Arg | Ala | Phe | Gly | Leu | Gln | His | Pro |
| | | 275 | | | | | 280 | | | | | 285 | | | |
| Val | Val | Arg | Arg | Leu | Trp | Pro | Arg | Ser | Leu | Lys | Arg | Ser | Asp | Val | Tyr |
| | 290 | | | | | 295 | | | | | 300 | | | | |
| Arg | Lys | Leu | Val | Ala | Trp | Asp | Arg | Thr | Asp | Ala | Ser | Arg | Leu | Leu |
| 305 | | | | | 310 | | | | | 315 | | | | | 320 |
| Asp | Tyr | Tyr | Arg | Gly | Arg | Pro | Lys | Glu | Pro | Val | Ile | Gln | Asp | Ile |
| | | | | 325 | | | | | 330 | | | | | 335 | |
| Glu | Val | Glu | Val | Gly | Arg | Ala | Ala | Glu | Phe | Leu | Asp | Phe | Phe | His | Thr |
| | | | 340 | | | | | 345 | | | | | 350 | | |
| Glu | Ile | Gly | Met | Ser | Pro | Val | Trp | Leu | Cys | Pro | Leu | Arg | Leu | Arg | Glu |
| | | 355 | | | | | 360 | | | | | 365 | | | |
| Asp | Thr | Ala | Asp | Asp | Thr | Glu | Pro | Val | Trp | Pro | Leu | Tyr | Pro | Leu | Lys |

```
                370             375             380
Pro Arg Arg Leu Tyr Val Asn Phe Gly Phe Trp Gly Leu Val Pro Ile
385                 390                 395                 400

Arg Pro Gly Gly Gly Arg Thr Tyr His Asn Arg Leu Ile Glu Lys Glu
            405                 410                 415

Val Thr Arg Leu Gly Gly His Lys Ser Leu Tyr Ser Asp Ala Phe Tyr
                420                 425                 430

Asp Glu Asp Glu Phe Trp Glu Leu Tyr Asn Gly Glu Ile Tyr Arg Lys
            435                 440                 445

Leu Lys Ala Ala Tyr Asp Pro Asp Gly Arg Leu Leu Asp Leu Tyr Thr
            450                 455                 460

Lys Cys Val Gly Gly Gly
465                 470
```

<210> SEQ ID NO 69
<211> LENGTH: 1272
<212> TYPE: DNA
<213> ORGANISM: Unknown
<220> FEATURE:
<223> OTHER INFORMATION: Thermobifida fusca

<400> SEQUENCE: 69

| | | | | | |
|---|---|---|---|---|---|
| atgcgactgg | cggaggtatt | cgaacgtgtc | gtcggacccg | atgcgcccgt | ccacttccgg | 60 |
| gcctacgacg | gcagcactgc | gggagatcca | cgcagtgaag | tcgctatcgt | ggttcgccac | 120 |
| ccggcagccg | tcaactacat | cgtccaagcg | ccgggagcac | tcggtttgac | ccgcgcctac | 180 |
| gtggcgggat | acctcgacgt | cgaaggggac | atgtacaccg | cgctgcgggc | aatggccgac | 240 |
| gtggtgttcc | aggaccggcc | gcggctgtcc | ccggggaac | tgctgcggat | catccgcggg | 300 |
| atcgggtggg | tgaagttcgt | caaccggctt | ccaccgccgc | cgcaggaggt | gcgccagtcc | 360 |
| cgcctcgccg | ccctgggctg | gcgccactcc | aagcagcgcg | acgccgaagc | catccagcac | 420 |
| cactacgacg | tctccaacgc | cttctacgcc | ctggtcttgg | gcgagtcgat | gacctacacc | 480 |
| tgcgcggtct | acccgaccga | gcaggccacg | ctggagcagg | cacagttctt | caagcacgag | 540 |
| ctgatcgccc | gcaagctcgg | tcttgcccct | gggatacgac | tgctggatgt | ggggtgcggc | 600 |
| tggggcggca | tggtcatcca | cgcggcccgg | gagcacgggg | tcaaagccct | ggggtgacc | 660 |
| ctgtccaaag | agcaggctga | gtgggcgcag | aagcggatcg | cccacgaggg | cctgggcgac | 720 |
| ctggcagaag | tccggcacat | ggactaccgg | gacctgcccg | acggcgagta | cgacgcgatc | 780 |
| agctcgatcg | ggttgaccga | gcacgtcggc | aaaaagaacg | tgcccgccta | cttcgcgtcg | 840 |
| ctgtaccgca | agctcgtccc | gggaggccgc | ctgctcaacc | actgcatcac | ccggccccgc | 900 |
| aacgacctgc | cgcccttcaa | cgcggcgggg | gtgatcaacc | gctacgtctt | ccccgatggg | 960 |
| gagctggaag | ggcccggctg | gctgcaggcg | gcgatgaacg | acgccgggtt | cgaaatccgc | 1020 |
| caccaggaga | acctgcggga | gcactacgca | cggaccctgc | gggactggct | ggccaacctg | 1080 |
| gaccgcaact | gggatgccgc | ggtgcgggaa | gtggggagg | cacgccccg | agtgtggcgg | 1140 |
| ctctacatgg | ccgggtgcgt | gctcggcttc | gaacgcaacg | tggtgcaact | gcaccagatc | 1200 |
| ctcggggtga | agctcgacgg | gaccgaggcg | cggatgccgc | tgcgccccga | cttcgaaccg | 1260 |
| ccgctgcctt | aa | | | | | 1272 |

<210> SEQ ID NO 70
<211> LENGTH: 423
<212> TYPE: PRT
<213> ORGANISM: Unknown

<220> FEATURE:
<223> OTHER INFORMATION: Thermobifida fusca

<400> SEQUENCE: 70

```
Met Arg Leu Ala Glu Val Phe Glu Arg Val Gly Pro Asp Ala Pro
1               5                   10                  15

Val His Phe Arg Ala Tyr Asp Gly Ser Thr Ala Gly Asp Pro Arg Ser
            20                  25                  30

Glu Val Ala Ile Val Val Arg His Pro Ala Ala Val Asn Tyr Ile Val
            35                  40                      45

Gln Ala Pro Gly Ala Leu Gly Leu Thr Arg Ala Tyr Val Ala Gly Tyr
50                      55                      60

Leu Asp Val Glu Gly Asp Met Tyr Thr Ala Leu Arg Ala Met Ala Asp
65                  70                  75                  80

Val Val Phe Gln Asp Arg Pro Arg Leu Ser Pro Gly Glu Leu Leu Arg
                85                  90                  95

Ile Ile Arg Gly Ile Gly Trp Val Lys Phe Val Asn Arg Leu Pro Pro
            100                 105                 110

Pro Pro Gln Glu Val Arg Gln Ser Arg Leu Ala Ala Leu Gly Trp Arg
        115                 120                 125

His Ser Lys Gln Arg Asp Ala Glu Ala Ile Gln His His Tyr Asp Val
    130                 135                 140

Ser Asn Ala Phe Tyr Ala Leu Val Leu Gly Glu Ser Met Thr Tyr Thr
145                 150                 155                 160

Cys Ala Val Tyr Pro Thr Glu Gln Ala Thr Leu Glu Gln Ala Gln Phe
                165                 170                 175

Phe Lys His Glu Leu Ile Ala Arg Lys Leu Gly Leu Ala Pro Gly Ile
            180                 185                 190

Arg Leu Leu Asp Val Gly Cys Gly Trp Gly Gly Met Val Ile His Ala
        195                 200                 205

Ala Arg Glu His Gly Val Lys Ala Leu Gly Val Thr Leu Ser Lys Glu
    210                 215                 220

Gln Ala Glu Trp Ala Gln Lys Arg Ile Ala His Glu Gly Leu Gly Asp
225                 230                 235                 240

Leu Ala Glu Val Arg His Met Asp Tyr Arg Asp Leu Pro Asp Gly Glu
                245                 250                 255

Tyr Asp Ala Ile Ser Ser Ile Gly Leu Thr Glu His Val Gly Lys Lys
            260                 265                 270

Asn Val Pro Ala Tyr Phe Ala Ser Leu Tyr Arg Lys Leu Val Pro Gly
        275                 280                 285

Gly Arg Leu Leu Asn His Cys Ile Thr Arg Pro Arg Asn Asp Leu Pro
    290                 295                 300

Pro Phe Lys Arg Gly Gly Val Ile Asn Arg Tyr Val Phe Pro Asp Gly
305                 310                 315                 320

Glu Leu Glu Gly Pro Gly Trp Leu Gln Ala Ala Met Asn Asp Ala Gly
                325                 330                 335

Phe Glu Ile Arg His Gln Glu Asn Leu Arg Glu His Tyr Ala Arg Thr
            340                 345                 350

Leu Arg Asp Trp Leu Ala Asn Leu Asp Arg Asn Trp Asp Ala Ala Val
        355                 360                 365

Arg Glu Val Gly Glu Gly Thr Ala Arg Val Trp Arg Leu Tyr Met Ala
    370                 375                 380

Gly Cys Val Leu Gly Phe Glu Arg Asn Val Val Gln Leu His Gln Ile
385                 390                 395                 400
```

Leu Gly Val Lys Leu Asp Gly Thr Glu Ala Arg Met Pro Leu Arg Pro
            405                 410                 415

Asp Phe Glu Pro Pro Leu Pro
            420

<210> SEQ ID NO 71
<211> LENGTH: 447
<212> TYPE: DNA
<213> ORGANISM: Unknown
<220> FEATURE:
<223> OTHER INFORMATION: Thermobifida fusca

<400> SEQUENCE: 71
atggctgcga ccgatgacga ccggcaccac accaccgtcg ccctcgacct catcgacgcg    60
tatgtgcgcg ccgaccgcag aatgatcggt gaacgttccg cggggatcag cgcggaggcg   120
ggggagcgga tcgtctccac cctgaaagtg tgcgcggcct tccttgcccg ccgggtccag   180
gagaccgggg tgccgtggcg cgccgcggac tcccgggaag cggtcgcccg caccgtcgcc   240
gacctgctgg aacccgaggt ggaattcgcg gtcgtctccg cctgggaggc gtacgcgatc   300
ggggagcacg aggccgcctg gtccggggcg cacggcgatc cgctggtctt cgtccacatg   360
ctggccgcgt tctccgctgc tatcggcaca gcggtctacg gccgtgagga gctgctgccc   420
acgctgcgca gggtgacagc acgataa                                       447

<210> SEQ ID NO 72
<211> LENGTH: 148
<212> TYPE: PRT
<213> ORGANISM: Unknown
<220> FEATURE:
<223> OTHER INFORMATION: Thermobifida fusca

<400> SEQUENCE: 72

Met Ala Ala Thr Asp Asp Arg His His Thr Thr Val Ala Leu Asp
1               5                   10                  15

Leu Ile Asp Ala Tyr Val Arg Ala Asp Arg Arg Met Ile Gly Glu Arg
            20                  25                  30

Ser Ala Gly Ile Ser Ala Glu Ala Gly Glu Arg Ile Val Ser Thr Leu
        35                  40                  45

Lys Val Cys Ala Ala Phe Leu Ala Arg Arg Val Gln Glu Thr Gly Val
    50                  55                  60

Pro Trp Arg Ala Ala Asp Ser Arg Glu Ala Val Ala Arg Thr Val Ala
65                  70                  75                  80

Asp Leu Leu Glu Pro Glu Val Glu Phe Ala Val Val Ser Ala Trp Glu
                85                  90                  95

Ala Tyr Ala Ile Gly Glu His Glu Ala Ala Trp Val Arg Ala His Gly
            100                 105                 110

Asp Pro Leu Val Phe Val His Met Leu Ala Ala Phe Ser Ala Ala Ile
        115                 120                 125

Gly Thr Ala Val Tyr Gly Arg Glu Glu Leu Leu Pro Thr Leu Arg Arg
    130                 135                 140

Val Thr Ala Arg
145

<210> SEQ ID NO 73
<211> LENGTH: 1368
<212> TYPE: DNA
<213> ORGANISM: Thermomonospora curvata

<400> SEQUENCE: 73

```
atgtcacagc tggcggtcac agaccaccac gagcgagcgg tcgaggcgct gcgcaggtcg      60
tatgcggcga tcccgccggg cacaccggtc cgcttggcca agcagacctc caacctgttc     120
cgcttccgcg agccgacggc cgcgcccggc ctggacgtgt ccggcttcaa ccgggtgctg     180
gcggtggacc cggatgcgcg caccgccgac gtgcagggca tgaccaccta cgaggacctg     240
gtcgacgcca ccctgccgca cgggctgatg ccgctggtgg tgccccagct caagacgatc     300
acgctgggcg gggcggtgac cggcctgggc atcgagtcca cctccttccg caacggcctg     360
ccgcacgagt cggtgctgga gatgcagatc atcaccggcg ccggcgaagt ggtcaccgcc     420
accccggacg gggagcactc cgacctgttc tggggcttcc ccaactccta cgggacgctg     480
gggtacgccc tgaagctgaa gatcgaactg gagccggtca agccgtacgt ccggctgcgg     540
cacctgcgct tcgacgacgc cggcgagtgc gccgccaagc tcgccgagct gagcgaaagc     600
cgcgagcacg agggcgatga ggtgcacttt ttggacggca ccttcttcgg gccgcgcgag     660
atgtacctga cgctcggcac gttcaccgac accgcccctt atgtgtcgga ctacaccggg     720
cagcacatct actaccggtc gatccagcag cggtcgatcg acttttttga catccgcgac     780
tacctgtggc gctgggacac cgactggttc tggtgctcgc gcgccctggg cgtgcagaac     840
ccgctgatcc ggcgggtgtg gccgaagagc gccaagcggt cggatgtgta ccgcaagctg     900
gtggcctacg aaaagcgcta ccagttcaag gcgcgcatcg accggtggac gggcaagccg     960
ccgcgcgagg acgtcatcca ggacatcgag gtgccggcag aacgcctgcc ggagttcctg    1020
gagttcttcc acgacaagat cgggatgagc ccggtgtggc tgtgcccgct gcgggcgcgc    1080
caccgctggc cgctgtaccc gctcaagccc ggcgtcacct acgtcaacgc cggcttctgg    1140
gggacggtgc cgctgcagcc ggggcagatg cccgagtacc acaaccggct gatcgaacgg    1200
aaggtcgccc aactggacgg ccacaagtct ctgtactcga cggcgttcta ctcgcgtgag    1260
gagttctggc ggcactacga cggggaaacc taccggcgtc tgaaggacac ctacgacccc    1320
gacgcgcgcc tgctcgacct ctacgacaag tgcgtgcggg gacgctga                 1368
```

<210> SEQ ID NO 74
<211> LENGTH: 455
<212> TYPE: PRT
<213> ORGANISM: Thermomonospora curvata

<400> SEQUENCE: 74

```
Met Ser Gln Leu Ala Val Thr Asp His His Glu Arg Ala Val Glu Ala
1               5                   10                  15

Leu Arg Arg Ser Tyr Ala Ala Ile Pro Pro Gly Thr Pro Val Arg Leu
            20                  25                  30

Ala Lys Gln Thr Ser Asn Leu Phe Arg Phe Arg Glu Pro Thr Ala Ala
        35                  40                  45

Pro Gly Leu Asp Val Ser Gly Phe Asn Arg Val Leu Ala Val Asp Pro
    50                  55                  60

Asp Ala Arg Thr Ala Asp Val Gln Gly Met Thr Thr Tyr Glu Asp Leu
65                  70                  75                  80

Val Asp Ala Thr Leu Pro His Gly Leu Met Pro Leu Val Val Pro Gln
                85                  90                  95

Leu Lys Thr Ile Thr Leu Gly Gly Ala Val Thr Gly Leu Gly Ile Glu
            100                 105                 110

Ser Thr Ser Phe Arg Asn Gly Leu Pro His Glu Ser Val Leu Glu Met
        115                 120                 125
```

Gln Ile Ile Thr Gly Ala Gly Glu Val Val Thr Ala Thr Pro Asp Gly
            130                 135                 140

Glu His Ser Asp Leu Phe Trp Gly Phe Pro Asn Ser Tyr Gly Thr Leu
145                 150                 155                 160

Gly Tyr Ala Leu Lys Leu Lys Ile Glu Leu Glu Pro Val Lys Pro Tyr
                165                 170                 175

Val Arg Leu Arg His Leu Arg Phe Asp Asp Ala Gly Glu Cys Ala Ala
            180                 185                 190

Lys Leu Ala Glu Leu Ser Glu Ser Arg Glu His Glu Gly Asp Glu Val
            195                 200                 205

His Phe Leu Asp Gly Thr Phe Phe Gly Pro Arg Glu Met Tyr Leu Thr
            210                 215                 220

Leu Gly Thr Phe Thr Asp Thr Ala Pro Tyr Val Ser Asp Tyr Thr Gly
225                 230                 235                 240

Gln His Ile Tyr Tyr Arg Ser Ile Gln Gln Arg Ser Ile Asp Phe Leu
                245                 250                 255

Thr Ile Arg Asp Tyr Leu Trp Arg Trp Asp Thr Asp Trp Phe Trp Cys
            260                 265                 270

Ser Arg Ala Leu Gly Val Gln Asn Pro Leu Ile Arg Arg Val Trp Pro
            275                 280                 285

Lys Ser Ala Lys Arg Ser Asp Val Tyr Arg Lys Leu Val Ala Tyr Glu
290                 295                 300

Lys Arg Tyr Gln Phe Lys Ala Arg Ile Asp Arg Trp Thr Gly Lys Pro
305                 310                 315                 320

Pro Arg Glu Asp Val Ile Gln Asp Ile Glu Val Pro Ala Glu Arg Leu
                325                 330                 335

Pro Glu Phe Leu Glu Phe Phe His Asp Lys Ile Gly Met Ser Pro Val
            340                 345                 350

Trp Leu Cys Pro Leu Arg Ala Arg His Arg Trp Pro Leu Tyr Pro Leu
            355                 360                 365

Lys Pro Gly Val Thr Tyr Val Asn Ala Gly Phe Trp Gly Thr Val Pro
370                 375                 380

Leu Gln Pro Gly Gln Met Pro Glu Tyr His Asn Arg Leu Ile Glu Arg
385                 390                 395                 400

Lys Val Ala Gln Leu Asp Gly His Lys Ser Leu Tyr Ser Thr Ala Phe
                405                 410                 415

Tyr Ser Arg Glu Glu Phe Trp Arg His Tyr Asp Gly Glu Thr Tyr Arg
            420                 425                 430

Arg Leu Lys Asp Thr Tyr Asp Pro Asp Ala Arg Leu Leu Asp Leu Tyr
            435                 440                 445

Asp Lys Cys Val Arg Gly Arg
450                 455

<210> SEQ ID NO 75
<211> LENGTH: 1263
<212> TYPE: DNA
<213> ORGANISM: Thermomonospora curvata

<400> SEQUENCE: 75
atgacgctgg ccaaggtctt cgaggagctg gtcggggcgg acgcccctgt ggagctcacc    60
gcctacgacg gatcgagagc cggacgcctg ggcagtgatc tgcgggtcca cgtgaagtcg   120
ccgtacgcgg tgtcctacct ggtgcactcg ccgagcgcgc tcgggctggc ccgcgcgtac   180
gtggccgggc acctggacgc ctacggcgac atgtacacgc tgctgcggga gatgacgcag   240

```
ctgaccgagg cgctgacgcc caaggcccgg ctgcggctgc tggccggtgt cctgcaggat      300
ccgctgctgc gcgcggcggc cagccgccgt ctgccgcccc cgccgcagga ggtgcggacc      360
ggccgcacct cctggttccg gcacaccaag cggcgggacg ccaaggccat ctcccaccac      420
tacgacgtgt ccaacacctt ctatgagtgg gtgctgggcc cgtcgatgac ctacacctgc      480
gcctgtttcc ccaccgagga cgccaccttg gaggaggcgc agttccacaa gcacgacctg      540
gtcgccaaga agctcgggct gcggccgggc atgcggctgc tggacgtggg ctgcggctgg      600
ggcggcatgg tgatgcacgc cgccaagcac tacggggtgc gggcgctggg cgtcacgctg      660
tccaagcagc aggccgagtg ggcgcagaag gccatcgccg aggcgggcct gagcgacctg      720
gccgaggtcc gccaccagga ctaccgggac gtcaccgagg gcgacttcga cgccatcagc      780
tcgatcggcc tcaccgagca catcggcaag gccaacctgc cgtcctactt cggcttcctg      840
tacggcaagc tcaagccggg cgggcggctg ctcaaccact gcatcacccg gcccgacaac      900
acccagccgg ccatgaagaa ggacgggttc atcaaccggt acgtcttccc cgacggggag      960
ctggaggggc ccggctacct gcagacccag atgaacgacg ccggttttga gatccgccac     1020
caggagaacc tgcgcgagca ctacgcccgc accctggccg gatggtgccg caacctcgat     1080
gagcactggg acgaggcggt ggccgaggtc ggcgagggca ccgcgcgggt gtggcggctg     1140
tacatggccg gcagccggct cggtttcgag ctcaactgga tccagctgca ccagatcctg     1200
ggcgtcaagc tcggcgagcg cggcgagtcc cgcatgccgt tgcggcccga ctggggcgtg     1260
tga                                                                  1263
```

<210> SEQ ID NO 76
<211> LENGTH: 420
<212> TYPE: PRT
<213> ORGANISM: Thermomonospora curvata

<400> SEQUENCE: 76

```
Met Thr Leu Ala Lys Val Phe Glu Glu Leu Val Gly Ala Asp Ala Pro
1               5                   10                  15

Val Glu Leu Thr Ala Tyr Asp Gly Ser Arg Ala Gly Arg Leu Gly Ser
            20                  25                  30

Asp Leu Arg Val His Val Lys Ser Pro Tyr Ala Val Ser Tyr Leu Val
        35                  40                  45

His Ser Pro Ser Ala Leu Gly Leu Ala Arg Ala Tyr Val Ala Gly His
    50                  55                  60

Leu Asp Ala Tyr Gly Asp Met Tyr Thr Leu Leu Arg Glu Met Thr Gln
65                  70                  75                  80

Leu Thr Glu Ala Leu Thr Pro Lys Ala Arg Leu Arg Leu Leu Ala Gly
                85                  90                  95

Val Leu Gln Asp Pro Leu Leu Arg Ala Ala Ser Arg Arg Leu Pro
            100                 105                 110

Pro Pro Pro Gln Glu Val Arg Thr Gly Arg Thr Ser Trp Phe Arg His
        115                 120                 125

Thr Lys Arg Arg Asp Ala Lys Ala Ile Ser His His Tyr Asp Val Ser
    130                 135                 140

Asn Thr Phe Tyr Glu Trp Val Leu Gly Pro Ser Met Thr Tyr Thr Cys
145                 150                 155                 160

Ala Cys Phe Pro Thr Glu Asp Ala Thr Leu Glu Glu Ala Gln Phe His
                165                 170                 175

Lys His Asp Leu Val Ala Lys Lys Leu Gly Leu Arg Pro Gly Met Arg
```

```
                    180                 185                 190
Leu Leu Asp Val Gly Cys Gly Trp Gly Gly Met Val Met His Ala Ala
            195                 200                 205
Lys His Tyr Gly Val Arg Ala Leu Gly Val Thr Leu Ser Lys Gln Gln
            210                 215                 220
Ala Glu Trp Ala Gln Lys Ala Ile Ala Glu Ala Gly Leu Ser Asp Leu
225                 230                 235                 240
Ala Glu Val Arg His Gln Asp Tyr Arg Asp Val Thr Glu Gly Asp Phe
                245                 250                 255
Asp Ala Ile Ser Ser Ile Gly Leu Thr Glu His Ile Gly Lys Ala Asn
            260                 265                 270
Leu Pro Ser Tyr Phe Gly Phe Leu Tyr Gly Lys Leu Lys Pro Gly Gly
        275                 280                 285
Arg Leu Leu Asn His Cys Ile Thr Arg Pro Asp Asn Thr Gln Pro Ala
        290                 295                 300
Met Lys Lys Asp Gly Phe Ile Asn Arg Tyr Val Phe Pro Asp Gly Glu
305                 310                 315                 320
Leu Glu Gly Pro Gly Tyr Leu Gln Thr Gln Met Asn Asp Ala Gly Phe
                325                 330                 335
Glu Ile Arg His Gln Glu Asn Leu Arg Glu His Tyr Ala Arg Thr Leu
            340                 345                 350
Ala Gly Trp Cys Arg Asn Leu Asp Glu His Trp Asp Glu Ala Val Ala
        355                 360                 365
Glu Val Gly Glu Gly Thr Ala Arg Val Trp Arg Leu Tyr Met Ala Gly
        370                 375                 380
Ser Arg Leu Gly Phe Glu Leu Asn Trp Ile Gln Leu His Gln Ile Leu
385                 390                 395                 400
Gly Val Lys Leu Gly Glu Arg Gly Glu Ser Arg Met Pro Leu Arg Pro
                405                 410                 415
Asp Trp Gly Val
        420
```

<210> SEQ ID NO 77
<211> LENGTH: 7102
<212> TYPE: DNA
<213> ORGANISM: Artificial Sequence
<220> FEATURE:
<223> OTHER INFORMATION: Synthetic Nucleic Acid

<400> SEQUENCE: 77

```
gtttgtggaa gcggtattcg caatttaatt aaagctggtg acaattaatc atcggctcgt      60
ataatgtgtg gaattgaatc gatataagga ggttaatcat gtgtctgtgg ttactactga     120
cgcacaggct gccatgccg ccggcgtctc gcgtcttctg gccagctacc gggcgatccc      180
gcccagcgcg acagtgcgcc ttgcgaaacc gacgtccaac ctgttccgcg cccgcgcccg     240
caccaatgtg aagggtctcg acgtctcggg cctgaccggt gtgatcggtg tcgacccgga     300
cgcgcgcacc gccgatgtgg cgggcatgtg cacctacgag gacctggtgg cggccacgct     360
tccgtacggc cttgcccac tggtggtgcc gcagctcaag accatcacgc tcggtggcgc      420
ggtcaccggt ctgggcatcg agtccacgtc gttccgcaac ggtctgccgc acgaaagtgt     480
cctggagatg gacatcttga ccggttcggg cgagatcgtc acggcctcac cggatcagca     540
ctcggatctg ttccatgcgt tccccaattc atatggaacc cttggttatt ccacccggct     600
gcgcatcgaa ctggagcccg tgcacccgtt tgtggcgttg cgccacctgc gctttcactc     660
```

```
gatcaccgat ctggtcgcgg cgatggaccg gatcatcgag accggcgggc tggacggtga    720
acccgtcgac tacctcgacg gcgtggtgtt cagcgcgact gagagttacc tgtgtgttgg    780
cttcaagacg aaaacgccgg ggccggtcag cgattacaca ggtcagcaga tcttctaccg    840
gtcgatccag catgacggcg acaccggcgc cgagaaacac gaccggctga ccatccacga    900
ctacctgtgg cgctgggaca ccgactggtt ctggtgctca cgggcattcg gcgctcagca    960
tccggtgatc cgcaggttct ggccgcggcg gctgcgccgc agcagcttct actggaagct   1020
ggtggcctac gaccagcggt acgacatcgc cgaccgtatc gagaagcgca acgggcgccc   1080
gccgcgcgag cgggtggtcc aggacgtcga ggtgcccatc gagcggtgcg cggacttcgt   1140
cgagtggttc ctgcagaatg tgccgatcga gccgatctgg ctgtgccccc tacggttgcg   1200
tgacagcgcc gacggcggtg cctcgtggcc cctgtatccg ctgaaggcgc accacaccta   1260
cgtcaacatc ggtttctggt catcagtgcc ggtgggcccc gaggagggcc acaccaaccg   1320
cctcatcgag aaaaagtcg cggagctgga cgggcacaaa tctttgtact cggacgctta   1380
ttacacacgt gacgaattcg acgagctgta cggcggtgag gtctacaaca ccgtcaagaa   1440
gacgtacgac ccggattcac gtctgctaga cctgtattcg aaggcggtgc aaagacaatg   1500
accacattca agaacgcga gacgtccaca gcggaccgca agctcaccct ggccgagatc   1560
ctcgagatct tcgccgcggg taaggagccg ctgaagttca ctgcgtacga cggcagctcg   1620
gccggtcccg aggacgccac gatgggtctg gacctcaaga ccccgcgtgg gaccacctat   1680
ctggccacgg cacccggcga tctgggcctg gcccgtgcgt atgtctccgg tgacctggag   1740
ccgcacggcg tgcatcccgg cgatccctac ccgctgctgc gcgccctggc cgaacgcatg   1800
gagttcaagc gcccgcctgc gcgtgtgctg gcgaacatcg tgcgctccat cggcatcgag   1860
cacctcaagc cgatcgcacc gccgccgcag gaggcgctgc cccggtggcg ccgcatcatg   1920
gagggcctgc ggcacagcaa gacccgcgac gccgaggcca tccaccacca ctacgacgtg   1980
tcgaacacgt tctacgagtg ggtgctgggc cgtcgatga cctacacgtg cgcgtgctac   2040
cccaccgagg acgcgaccct cgaagaggcc caggacaaca agtaccgcct ggtgttcgag   2100
aagctgcgcc tgaagcccgg tgaccggttg ctcgacgtgg gctgcggctg gggcggcatg   2160
gtccgctacg cggcccgcca cggcgtcaag gcgctcggtg tcacgctcag ccgcgaacag   2220
gcgacgtggg cgcagaaggc catcgcccag gaaggtctca ccgatctggc cgaggtgcgt   2280
cacggtgatt accgcgacgt catcgaatcc gggttcgacg cggtgtcctc gatcgggctg   2340
accgagcaca tcggcgtgca caactacccg gcgtacttca acttcctcaa gtcgaagctg   2400
cgcaccggtg gcctgctgct caaccactgc atcacccgcc cggacaaccg gtcggcgcca   2460
tcggccggcg ggttcatcga caggtacgtg ttccccgacg gggagctcac cggctcgggc   2520
cgcatcatca ccgaggccca ggacgtgggc cttgaggtga tccacgagga gaacctacgc   2580
aatcactatg cgatgacgct gcgcgactgg tgccgcaacc tggtcgagca ctggacgag    2640 gcggtcgaag aggtcgggct gcccaccgcg aaggtgtggg gcctgtacat ggccggctca   2700
cgtctgggct tcgagaccaa tgtggttcag ctgcaccagg ttctggcggt caagcttgac   2760
gatcagggca aggacggcgg actgccgttg cggccctggt ggtccgccta gcctcaaaat   2820
atattttccc tctatcttct cgttgcgctt aatttgacta attctcatta gcgaggcgcg   2880
cctttccata ggctccgccc ccctgacgag catcacaaaa atcgacgctc aagtcagagg   2940
tggcgaaacc cgacaggact ataaagatac caggcgtttc cccctggaag ctccctcgtg   3000
cgctctcctg ttccgaccct gccgcttacc ggatacctgt ccgcctttct cccttcggga   3060
```

-continued

```
agcgtggcgc tttctcatag ctcacgctgt aggtatctca gttcggtgta ggtcgttcgc   3120
tccaagctgg gctgtgtgca cgaacccccc gttcagcccg accgctgcgc cttatccggt   3180
aactatcgtc ttgagtccaa cccggtaaga cacgacttat cgccactggc agcagccact   3240
ggtaacagga ttagcagagc gaggtatgta ggcggtgcta cagagttctt gaagtggtgg   3300
cctaactacg gctacactag aagaacagta tttggtatct gcgctctgct gaagccagtt   3360
accttcggaa aaagagttgg tagctcttga tccggcaaac aaaccaccgc tggtagcggt   3420
ggtttttttg tttgcaagca gcagattacg cgcagaaaaa aaggatctca agaagatcct   3480
ttgatctttt ctacggggtc tgacgctcag tggaacgaaa actcacgtta agggattttg   3540
gtcatgagat tatcaaaaag gatcttcacc tagatccttt taaattaaaa atgaagtttt   3600
aaatcaatct aaagtatata tgagtaaact tggtctgaca gttaccaatg cttaatcagt   3660
gaggcaccta tctcagcgat ctgtctattt cgttcatcca tagttgcctg actccccgtc   3720
gtgtagataa ctacgatacg ggagggctta ccatctggcc ccagtgctgc aatgataccg   3780
cgagacccac gctcaccggc tccagattta tcagcaataa accagccagc cggaagggcc   3840
gagcgcagaa gtggtcctgc aactttatcc gcctccatcc agtctattaa ttgttgccgg   3900
gaagctagag taagtagttc gccagttaat agtttgcgca acgttgttgc cattgctaca   3960
ggcatcgtgg tgtcacgctc gtcgtttggt atggcttcat tcagctccgg ttcccaacga   4020
tcaaggcgag ttacatgatc ccccatgttg tgcaaaaaag cggttagctc cttcggtcct   4080
ccgatcgttg tcagaagtaa gttggccgca gtgttatcac tcatggttat ggcagcactg   4140
cataattctc ttactgtcat gccatccgta agatgctttt ctgtgactgg tgagtactca   4200
accaagtcat tctgagaata gtgtatgcgg cgaccgagtt gctcttgccc ggcgtcaata   4260
cgggataata ccgcgccaca tagcagaact ttaaaagtgc tcatcattgg aaaacgttct   4320
tcggggcgaa aactctcaag gatcttaccg ctgttgagat ccagttcgat gtaacccact   4380
cgtgcaccca actgatcttc agcatctttt actttcacca gcgtttctgg gtgagcaaaa   4440
acaggaaggc aaaatgccgc aaaaaaggga ataagggcga cacggaaatg ttgaatactc   4500
atactcttcc ttttttcaata ttattgaagc atttatcagg gttattgtct catgagcgga   4560
tacatatttg aatgtattta gaaaaataaa cagcgatcgc gcggccgcgg gtaataactg   4620
atataattaa attgaagctc taatttgtga gtttagtata catgcattta cttataatac   4680
agttttttag ttttgctggc cgcatcttct caaatatgct tcccagcctg cttttctgta   4740
acgttcaccc tctaccttag catcccttcc ctttgcaaat agtcctcttc caacaataat   4800
aatgtcagat cctgtagaga ccacatcatc cacggttcta tactgttgac ccaatgcgtc   4860
tcccttgtca tctaaaccca caccgggtgt cataatcaac caatcgtaac cttcatctct   4920
tccacccatg tctctttgag caataaagcc gataacaaaa tctttgtcgc tcttcgcaat   4980
gtcaacagta cccttagtat attctccagt agctagggag cccttgcatg acaattctgc   5040
taacatcaaa aggcctctag gttcctttgt tacttcttcc gccgcctgct tcaaaccgct   5100
aacaatacct gggcccacca caccgtgtgc attcgtaatg tctgcccatt ctgctattct   5160
gtatacaccc gcagagtact gcaatttgac tgtattacca atgtcagcaa attttctgtc   5220
ttcgaagagt aaaaaattgt acttggcgga taatgccttt agcggcttaa ctgtgccctc   5280
catgaaaaaa tcagtcaaga tatccacatg tgttttagt aaacaaattt tgggacctaa   5340
tgcttcaact aactccagta attccttggt ggtacgaaca tccaatgaag cacacaagtt   5400
```

```
tgtttgcttt tcgtgcatga tattaaatag cttggcagca acaggactag gatgagtagc    5460
agcacgttcc ttatatgtag ctttcgacat gatttatctt cgtttcctgc aggtttttgt    5520
tctgtgcagt tgggttaaga atactgggca atttcatgtt tcttcaacac cacatatgcg    5580
tatatatacc aatctaagtc tgtgctcctt ccttcgttct tccttctgct cggagattac    5640
cgaatcaaag ctagcttatc gatgataagc tgtcaaagat gagaattaat tccacggact    5700
atagactata ctagatactc cgtctactgt acgatacact tccgctcagg tccttgtcct    5760
ttaacgaggc cttaccactc ttttgttact ctattgatcc agctcagcaa aggcagtgtg    5820
atctaagatt ctatcttcgc gatgtagtaa aactagctag accgagaaag agactagaaa    5880
tgcaaaaggc acttctacaa tggctgccat cattattatc cgatgtgacg ctgcagcttc    5940
tcaatgatat tcgaatacgc tttgaggaga tacagcctaa tatccgacaa actgttttac    6000
agatttacga tcgtacttgt tacccatcat tgaattttga acatccgaac ctgggagttt    6060
tccctgaaac agatagtata tttgaacctg tataataata tatagtctag cgctttacgg    6120
aagacaatgt atgtatttcg gttcctggag aaactattgc atctattgca taggtaatct    6180
tgcacgtcgc atccccggtt cattttctgc gtttccatct tgcacttcaa tagcatatct    6240
ttgttaacga agcatctgtg cttcattttg tagaacaaaa atgcaacgcg agagcgctaa    6300
tttttcaaac aaagaatctg agctgcattt ttacagaaca gaaatgcaac gcgaaagcgc    6360
tattttacca acgaagaatc tgtgcttcat ttttgtaaaa caaaaatgca acgcgacgag    6420
agcgctaatt tttcaaacaa agaatctgag ctgcatttttt acagaacaga atgcaacgc    6480 gagagcgcta ttttaccaac aaagaatcta acttcttttt tgttctaca aaaatgcatc    6540 ccgagagcgc tattttttcta caaagcatc ttagattact ttttttctcc tttgtgcgct    6600
ctataatgca gtctcttgat aacttttgc actgtaggtc cgttaaggtt agaagaaggc    6660
tactttggtg tctatttttct cttccataaa aaagcctga ctccacttcc cgcgtttact    6720
gattactagc gaagctgcgg gtgcatttt tcaagataaa ggcatccccg attatattct    6780
ataccgatgt ggattgcgca actttgtga acagaaagtg atagcgttga tgattcttca    6840
ttggtcagaa aattatgaac ggtttcttct attttgtctc tatatactac gtataggaaa    6900
tgtttacatt ttcgtattgt tttcgattca ctctatgaat agttcttact acaattttttt    6960 tgtctaaaga gtaatactag agataaacat aaaaaatgta gaggtcgagt ttagatgcaa    7020
gttcaaggag cgaaaggtgg atgggtaggt tatatagga tatagcacag agatatatag    7080
caaagagata cttttgagca at                                            7102
```

<210> SEQ ID NO 78
<211> LENGTH: 10766
<212> TYPE: DNA
<213> ORGANISM: Artificial Sequence
<220> FEATURE:
<223> OTHER INFORMATION: Synthetic Nucleic Acid

<400> SEQUENCE: 78

```
ttatcgatga taagctgtca aagatgagaa ttaattccac ggactataga ctatactaga     60
tactccgtct actgtacgat acacttccgc tcaggtcctt gtcctttaac gaggccttac    120
cactcttttg ttactctatt gatccagctc agcaaaggca gtgtgatcta agattctatc    180
ttcgcgatgt agtaaaacta gctagaccga gaaagagact agaaatgcaa aaggcacttc    240
tacaatggct gccatcatta ttatccgatg tgacgctgca gcttctcaat gatattcgaa    300
tacgctttga ggagatacag cctaatatcc gacaaactgt tttacagatt tacgatcgta    360
```

```
cttgttaccc atcattgaat tttgaacatc cgaacctggg agttttccct gaaacagata       420
gtatatttga acctgtataa taatatatag tctagcgctt tacggaagac aatgtatgta       480
tttcggttcc tggagaaact attgcatcta ttgcataggt aatcttgcac gtcgcatccc       540
cggttcattt tctgcgtttc catcttgcac ttcaatagca tatctttgtt aacgaagcat       600
ctgtgcttca ttttgtagaa caaaaatgca acgcgagagc gctaattttt caaacaaaga       660
atctgagctg cattttttaca gaacagaaat gcaacgcgaa agcgctattt taccaacgaa       720
gaatctgtgc ttcattttttg taaaacaaaa atgcaacgcg acgagagcgc taattttttca      780 aacaaagaat ctgagctgca tttttacaga acagaaatgc aacgcgagag cgctatttta       840
ccaacaaaga atctatactt ctttttttgtt ctacaaaaat gcatcccgag agcgctattt       900
ttctaacaaa gcatcttaga ttactttttt tctcctttgt gcgctctata atgcagtctc       960
ttgataactt tttgcactgt aggtccgtta aggttagaag aaggctactt ggtgtctat       1020 tttctcttcc ataaaaaaag cctgactcca cttcccgcgt ttactgatta ctagcgaagc      1080
tgcgggtgca tttttttcaag ataaaggcat ccccgattat attctatacc gatgtggatt      1140
gcgcatactt tgtgaacaga aagtgatagc gttgatgatt cttcattggt cagaaaatta      1200
tgaacggttt cttctatttt gtctctatat actacgtata ggaaatgttt acattttcgt      1260
attgttttcg attcactcta tgaatagttc ttactacaat ttttttgtct aaagagtaat      1320
actagagata aacataaaaa atgtagaggt cgagtttaga tgcaagttca aggagcgaaa      1380
ggtggatggg taggttatat agggatatag cacagagata tatagcaaag agatacttt       1440 gagcaatgtt tgtggaagcg gtattcgcaa tgtttaaact gcgtcggaac gggatatgca      1500
ttcccctagt ttcgccgcag tgcagaatca ggcggtttct ttgcaccaca ccacatacgg      1560
aggatgacgg gcattattga tgttgaatag taacctgatc gtgactagta tgacggaacc      1620
caacagcaac agccgaccgt ttgtgagcgt ttttgcggcc ggtcaggcga gttttttccgg      1680 cctgccaatg gtccttccgt acccttttacc ctgtacgctg tacctgccac ggataggccg      1740
tgctccacct gctcactatg gtgggtgcgg ggaaaacaac aggcaggctc aattgctctg      1800
caaatgggtt gagggggtga ttgatgtcac tggtacacca acaggggaat gctcggcgtt      1860 gattttggggc cacctctttt gtttgccaga gcttgtctct attgtcaaat ttaacggtct      1920
gcaactgttg cccaaaatgg gacaatgatc cgatgcctgc atagacaccc tgcttgaggg      1980
tgcgatcgcc ctaatacgag gcaaaccaag ttttccaatt gaccttcaat gacgagcgg       2040 ttgttgcgac aggggactgg agtgctacct gtttagagtt caaatccgtc acccagcatt      2100
gaaagttttt ccccgcattg gatgattgca atgccgctaa cccgctcatc cgccaaagtt      2160
catagtccca ccctgcctcg acttatcgga ccacatgggg ctcccttatg cgcgcgcata      2220
tggcgcttga ttgctttttg gtcaacgttt gggacaaatt tcctttgtta aggcggaccc      2280
gccagcagat acgaaggtat aaatagggct cactttcacc atcttgtcca ttcaattgca      2340
agactcaaaa gtaataatga ccactctgga tgacaccgct taccgatacc gaacttccgt      2400
tcctggcgat gccgaggcta ttgaggctct ggatggatct ttcaccactg acaccgtttt      2460
ccgagtgacc gctactggcg acggcttcac cctgcgagag gtgcctgtcg accctcctct      2520
caccaaggtt ttccctgacg atgagtcgga cgatgagtct gacgctggag aggacggcga      2580
ccctgactct cgaactttcg tggcttacgg cgacgatgga gacctggccg gctttgtggt      2640
cgtttcttac tccggatgga accgacgact gaccgtggag gacatcgagg tcgctcctga      2700
```

```
gcaccgaggt catggtgtcg gacgagctct gatgggtctc gctactgagt tcgctcgaga    2760
gcgaggtgct ggccacctgt ggctcgaggt caccaacgtt aacgcccctg ctattcatgc    2820
ctaccgacga atgggtttta ccctgtgtgg cctcgatact gccctgtacg acggaaccgc    2880
ttccgatgga gagcaggccc tctacatgtc gatgccctgc ccttaaacag gccccttttc    2940
ctttgtcgat atcatgtaat tagttatgtc acgcttacat tcacgccctc ctcccacatc    3000
cgctctaacc gaaaggaag gagttagaca acctgaagtc taggtcccta tttattttt    3060 ttaatagtta tgttagtatt aagaacgtta tttatatttc aaattttct ttttttctg    3120 tacaaacgcg tgtacgcatg taacattata ctgaaaacct tgcttgagaa ggttttggga    3180
cgctcgaagg ctttaatttg cagagaccgg gttggcggcg catttgtgtc ccaaaaaaca    3240
gccccaattg ccccaattga ccccaaattg acccagtagc gggcccaacc ccggcgagag    3300
cccccttctc cccacatatc aaacctcccc cggttcccac acttgccgtt aagggcgtag    3360
ggtactgcag tctggaatct acgcttgttc agactttgta ctagtttctt tgtctggcca    3420
tccgggtaac ccatgccgga cgcaaaatag actactgaaa attttttttgc tttgtggttg    3480 ggactttagc caagggtata aaagaccacc gtccccgaat tacctttcct cttcttttct    3540
ctctctcctt gtcaactcac acccgaaatc gttaagcatt tccttctgag tataagaatc    3600
attcaaaatg tccgttgtta ccaccgatgc tcaagctgct catgctgctg gtgtttctag    3660
attattggct tcttatagag ccattccacc atctgctact gttagattgg ctaagccaac    3720
ttctaatttg ttcagagcta gagctagaac taacgttaag ggtttggatg tttctggttt    3780
gactggtgtt attggtgttg atccagatgc tagaactgct gatgttgctg gtatgtgtac    3840
ttacgaagat ttggttgctg ctactttgcc atatggtttg gctccattgg ttgttccaca    3900
attgaaaact attactttgg gtggtgctgt taccggtttg ggtattgaat ctacttcttt    3960
cagaaacggt ttgccacacg aatctgtttt ggaaatggat attttgaccg gttccggtga    4020
aatagttact gcttctccag atcaacactc cgatttgttt catgcttttc caaactctta    4080
cggtacattg ggttactcta ccagattgag aattgaattg gaaccagttc atccattcgt    4140
tgccttgaga catttgagat tccattccat tactgatttg tcgcagcca tggatagaat    4200 tattgaaact ggtggtttag acggtgaacc agttgattat ttggatggtg ttgttttctc    4260
tgccaccgaa tcatatttgt gtgttggttt caaaactaag accccaggtc cagtttctga    4320
ttatactggt caacaaatct tctacagatc catccaacat gatggtgata ctggtgctga    4380
aaaacatgat agattgacca tccatgacta cttgtggaga tgggatactg attggttttg    4440
gtgttctaga gcttttggtg ctcaacatcc agttattaga agattctggc caagaagatt    4500
aagaagatcc tccttctact ggaaattggt tgcttacgat caaagatacg atatcgccga    4560
tagaatcgaa aagagaaatg gtagaccacc aagagaaaga gttgttcaag acgttgaagt    4620
tccaattgaa agatgcgctg atttcgttga atggttcttg caaaatgttc caatcgaacc    4680
tatttggttg tgcccattga gattgagaga ttctgctgat ggtggtgctt catggccatt    4740
atatccattg aaagctcatc acacctacgt caatattggt ttctggtcat ctgttccagt    4800
tggtccagaa gaaggtcata ccaatagatt gattgaaaaa aaggtcgccg aattggacgg    4860
tcacaaatca ttatattctg atgcctacta caccagagat gaattcgatg aattatacgg    4920
tggtgaagtt tacaacaccg tcaaaaaaac ttacgaccca gactcaagat tattagactt    4980
gtactctaag gccgtccaaa gacaatgagc tgcttgtacc tagtgcaacc ccagtttgtt    5040
aaaaattagt agtcaaaaac ttctgagtta gaaatttgtg agtgtagtga gattgtagag    5100
```

```
tatcatgtgt gtccgtaagt gaagtgttat tgactcttag ttagtttatc tagtactcgt   5160
ttagttgaca ctgatctagt attttacgag gcgtatgact ttagccaagt gttgtactta   5220
gtcttctctc caaacatgag agggctctgt cactcagtcg gcctatgggt gagatggctt   5280
ggtgagatct ttcgatagtc tcgtcaagat ggtaggatga tggggggaata cattactgct   5340 ctcgtcaagg aaaccacaat cagatcacac catcctccat ggtatccgat gactctcttc   5400
tccacagtcg cagtaggatg tcctgcacgg gtctttttgt ggggtgtgga gaaaggggtg   5460
cttggagatg gaagccggta gaaccgggct gcttgggggg atttggggcc gctgggctcc   5520
aaagaggggt aggcatttcg ttggggttac gtaattgcgg catttgggtc ctgcgcgcat   5580
gtcccattgg tcagaattag tccggatagg agacttatca gccaatcaca gcgccggatc   5640
cacctgtagg ttgggttggg tgggagcacc cctccacaga gtagagtcaa acagcagcag   5700
caacgtgata gttgggggtg tgcgtgttaa aggaaaaaaa aagaagcttg ggttatattc   5760
ccgctctatt tagaggttgc gggatagacg ccgacggagg gcaatggcgc catggaacct   5820
tgcggatatc gatacgccgc ggcggactgc gtccgaacca gctccagcag cgttttttcc   5880
gggccattga gccgactgcg accccgccaa cgtgtcttgg cccacgcact catgtcatgt   5940
tggtgttggg aggccacttt ttaagtagca caaggcacct agctcgcggc agggtgtccg   6000
aaccaaagaa gcggctgcag tggtgcaaac ggggcggaaa cggcgggaaa aagccacggg   6060
ggcacgaatt gaggcacgcc ctcgaatttg agacgagtca cggcccatt cgcccgcgca    6120 atggctcgcc aacgcccggt cttttgcacc acatcaggtt accccaagcc aaacctttgt   6180
gttaaaaagc ttaacatatt ataccgaacg taggtttggg cgggcttgct ccgtctgtcc   6240
aaggcaacat ttatataagg gtctgcatcg ccggctcaat tgaatctttt ttcttcttct   6300
cttctctata ttcattcttg aattaaacac acatcaacaa tgaccacctt caaagaaaga   6360
gaaacttcta ccgctgatag aaagttgacc ttggctgaaa ttttggaaat tttcgctgct   6420
ggtaaagaac cattgaagtt cactgcttat gatggttctt ctgctggtcc tgaagatgct   6480
actatgggtt tggatttgaa aactccaaga ggtactactt acttggctac tgctccaggt   6540
gatttgggtt tggctagagc ttatgttcct ggtgacttgg aaccacatgg tgttcatcct   6600
ggtgatccat atccattatt gagagcttta gccgaaagaa tggaattcaa aagaccacca   6660
gctagagttt tggctaacat cgttagatcc attggtatcg aacatttgaa gccaattgct   6720
ccaccaccac aagaagcttt gccaagatgg agaagaatta tggaaggttt gagacactct   6780
aagaccagag atgctgaagc tattcatcat cactacgatg tttctaacac cttctacgaa   6840
tgggttttgg gtccatctat gacttatact tgtgcttgtt acccaacaga agatgccact   6900
ttggaagaag ctcaagataa caagtacaga ttggtctttg aaaagttgag attgaagcca   6960
ggtgacagat tattggatgt tggttgtggt tggggtggta tggttagata tgctgctaga   7020
catggtgtaa aagctttggg tgttactttg tctagagaac aagctacttg ggctcaaaaa   7080
gctattgctc aagaaggttt aaccgatttg gctgaagtta gacacggtga ttacagagat   7140
gttatcgaat ctggtttcga tgccgttttct tctattggtt tgactgaaca tatcggtgtt   7200
cataactatc cagcctactt caacttcttg aagtctaagt tgagaaccgg tggtttgttg   7260
ttgaaccatt gcattactag accagataac agatctgctc catctgctgg tggttttatt   7320
gatagatacg ttttcccaga tggtgaattg actggttccg gtagaattat tactgaagca   7380
caagatgtcg gtttggaagt tatccatgaa gaaaacttga gaaaccatta cgccatgact   7440
```

```
ttgagagatt ggtgtagaaa cttggttgaa cattgggatg aagccgttga agaagttggt    7500
ttgccaactg ctaaagtttg gggtttgtat atggctggtt ctagattagg ttttgaaact    7560
aacgttgtcc aattgcacca agttttggca gttaagttgg atgatcaagg taaagatggt    7620
ggtttgcctt taagaccatg gtggtctgct tgagcattag cgactactaa tatatatttg    7680
aatccatgga attataacaa acaagcatca aaacaagaat tagcgacatt atacttgaaa    7740
tcagcattag cgatactact aatatagttt attctatgta atgatccatg gaagttcgat    7800
tgatttgcca agttaatttg atagattatg catgccattt agtcgacgca ggtacgatct    7860
acagcgataa agaagaggtt gtgggtcatt caattttgca ccaattttgc accatcatag    7920
atcataatac atttacaagg cctacaattc ttacagggtc ttctcgagag caattcctta    7980
attaaggcgc gccttttccat aggctccgcc cccctgacga gcatcacaaa aatcgacgct    8040
caagtcagag gtggcgaaac ccgacaggac tataaagata ccaggcgttt ccccctggaa    8100
gctccctcgt gcgctctcct gttccgaccc tgccgcttac cggatacctg tccgcctttc    8160
tcccttcggg aagcgtggcg ctttctcata gctcacgctg taggtatctc agttcggtgt    8220
aggtcgttcg ctccaagctg ggctgtgtgc acgaaccccc cgttcagccc gaccgctgcg    8280
ccttatccgg taactatcgt cttgagtcca acccggtaag acacgactta tcgccactgg    8340
cagcagccac tggtaacagg attagcagag cgaggtatgt aggcggtgct acagagttct    8400
tgaagtggtg gcctaactac ggctacacta gaagaacagt atttggtatc tgcgctctgc    8460
tgaagccagt taccttcgga aaaagagttg gtagctcttg atccggcaaa caaaccaccg    8520
ctggtagcgg tggttttttt gtttgcaagc agcagattac gcgcagaaaa aaaggatctc    8580
aagaagatcc tttgatcttt tctacggggt ctgacgctca gtggaacgaa aactcacgtt    8640
aagggatttt ggtcatgaga ttatcaaaaa ggatcttcac ctagatcctt ttaaattaaa    8700
aatgaagttt taaatcaatc taaagtatat atgagtaaac ttggtctgac agttaccaat    8760
gcttaatcag tgaggcacct atctcagcga tctgtctatt tcgttcatcc atagttgcct    8820
gactccccgt cgtgtagata actacgatac gggagggctt accatctggc cccagtgctg    8880
caatgatacc gcgagaccca cgctcaccgg ctccagattt atcagcaata aaccagccag    8940
ccggaagggc cgagcgcaga agtggtcctg caactttatc cgcctccatc cagtctatta    9000
attgttgccg ggaagctaga gtaagtagtt cgccagttaa tagtttgcgc aacgttgttg    9060
ccattgctac aggcatcgtg gtgtcacgct cgtcgtttgg tatggcttca ttcagctccg    9120
gttcccaacg atcaaggcga gttacatgat cccccatgtt gtgcaaaaaa gcggttagct    9180
ccttcggtcc tccgatcgtt gtcagaagta agttggccgc agtgttatca ctcatggtta    9240
tggcagcact gcataattct cttactgtca tgccatccgt aagatgcttt tctgtgactg    9300
gtgagtactc aaccaagtca ttctgagaat agtgtatgcg gcgaccgagt tgctcttgcc    9360
cggcgtcaat acgggataat accgcgccac atagcagaac tttaaaagtg ctcatcattg    9420
gaaaacgttc ttcggggcga aaactctcaa ggatcttacc gctgttgaga tccagttcga    9480
tgtaacccac tcgtgcaccc aactgatctt cagcatcttt tactttcacc agcgtttctg    9540
ggtgagcaaa aacaggaagg caaaatgccg caaaaaaggg aataagggcg acacggaaat    9600
gttgaatact catactcttc cttttcaat attattgaag catttatcag ggttattgtc    9660
tcatgagcgg atacatattt gaatgtattt agaaaaataa acagcgatcg cgcggccgcg    9720
ggtaataact gatataatta aattgaagct ctaatttgtg agtttagtat acatgcattt    9780
acttataata cagttttttta gttttgctgg ccgcatcttc tcaaatatgc ttcccagcct    9840
```

```
gcttttctgt aacgttcacc ctctacctta gcatcccttc cctttgcaaa tagtcctctt    9900
ccaacaataa taatgtcaga tcctgtagag accacatcat ccacggttct atactgttga    9960
cccaatgcgt ctcccttgtc atctaaaccc acaccgggtg tcataatcaa ccaatcgtaa   10020
ccttcatctc ttccacccat gtctctttga gcaataaagc cgataacaaa atctttgtcg   10080
ctcttcgcaa tgtcaacagt acccttagta tattctccag tagctaggga gcccttgcat   10140
gacaattctg ctaacatcaa aaggcctcta ggttcctttg ttacttcttc cgccgcctgc   10200
ttcaaaccgc taacaatacc tgggcccacc acaccgtgtg cattcgtaat gtctgcccat   10260
tctgctattc tgtatacacc cgcagagtac tgcaatttga ctgtattacc aatgtcagca   10320 aatttctgt cttcgaagag taaaaaattg tacttggcgg ataatgcctt tagcggctta   10380
actgtgccct ccatggaaaa atcagtcaag atatccacat gtgtttttag taaacaaatt   10440
ttgggaccta atgcttcaac taactccagt aattccttgg tggtacgaac atccaatgaa   10500
gcacacaagt ttgtttgctt ttcgtgcatg atattaaata gcttggcagc aacaggacta   10560
ggatgagtag cagcacgttc cttatatgta gctttcgaca tgatttatct tcgtttcctg   10620 caggttttg ttctgtgcag ttgggttaag aatactgggc aatttcatgt ttcttcaaca   10680
ccacatatgc gtatatatac caatctaagt ctgtgctcct tccttcgttc ttccttctgc   10740
tcggagatta ccgaatcaaa gctagc                                        10766
```

<210> SEQ ID NO 79
<211> LENGTH: 10970
<212> TYPE: DNA
<213> ORGANISM: Artificial Sequence
<220> FEATURE:
<223> OTHER INFORMATION: Synthetic Nucleic Acid

<400> SEQUENCE: 79

```
ttatcgatga taagctgtca aagatgagaa ttaattccac ggactataga ctatactaga     60
tactccgtct actgtacgat acacttccgc tcaggtcctt gtcctttaac gaggccttac    120 cactctttg ttactctatt gatccagctc agcaaaggca gtgtgatcta agattctatc    180
ttcgcgatgt agtaaaacta gctagaccga gaaagagact agaaatgcaa aaggcacttc    240
tacaatggct gccatcatta ttatccgatg tgacgctgca gcttctcaat gatattcgaa    300
tacgctttga ggagatacag cctaatatcc gacaaactgt tttacagatt tacgatcgta    360
cttgttaccc atcattgaat tttgaacatc cgaacctggg agttttccct gaaacagata    420
gtatatttga acctgtataa taatatatag tctagcgctt tacggaagac aatgtatgta    480
tttcggttcc tggagaaact attgcatcta ttgcataggt aatcttgcac gtcgcatccc    540
cggttcattt tctgcgtttc catcttgcac ttcaatagca tatctttgtt aacgaagcat    600
ctgtgcttca ttttgtagaa caaaatgca acgcgagagc gctaattttt caaacaaaga    660
atctgagctg cattttttaca gaacagaaat gcaacgcgaa agcgctattt taccaacgaa    720
gaatctgtgc ttcattttg taaaacaaaa atgcaacgcg acgagagcgc taattttttca    780 aacaaagaat ctgagctgca tttttacaga acagaaatgc aacgcgagag cgctatttta    840
ccaacaaaga atctatactt ctttttttgtt ctacaaaaat gcatcccgag agcgctattt    900
ttctaacaaa gcatcttaga ttacttttttt tctcctttgt gcgctctata atgcagtctc    960
ttgataactt tttgcactgt aggtccgtta aggttagaag aaggctactt tggtgtctat   1020
tttctcttcc ataaaaaaag cctgactcca cttcccgcgt ttactgatta ctagcgaagc   1080
```

-continued

```
tgcgggtgca ttttttcaag ataaaggcat ccccgattat attctatacc gatgtggatt    1140
gcgcatactt tgtgaacaga aagtgatagc gttgatgatt cttcattggt cagaaaatta    1200
tgaacggttt cttctatttt gtctctatat actacgtata ggaaatgttt acattttcgt    1260
attgttttcg attcactcta tgaatagttc ttactacaat ttttttgtct aaagagtaat    1320
actagagata aacataaaaa atgtagaggt cgagtttaga tgcaagttca aggagcgaaa    1380
ggtggatggg taggttatat agggatatag cacagagata tatagcaaag agatactttt    1440
gagcaatgtt tgtggaagcg gtattcgcaa tgtttaaact gcgtcggaac gggatatgca    1500
ttcccctagt ttcgccgcag tgcagaatca ggcggtttct ttgcaccaca ccacatacgg    1560
aggatgacgg gcattattga tgttgaatag taacctgatc gtgactagta tgacggaacc    1620
caacagcaac agccgaccgt ttgtgagcgt ttttgcggcc ggtcaggcga gttttccgg     1680
cctgccaatg gtccttccgt acccttaccc ctgtacgctg tacctgccac ggataggccg    1740
tgctccacct gctcactatg gtgggtgcgg ggaaaacaac aggcaggctc aattgctctg    1800
caaatgggtt gaggggtgtga ttgatgtcac tggtacacca acaggggaat gctcggcgtt    1860
gattttgggc cacctctttt gtttgccaga gcttgtctct attgtcaaat ttaacggtct    1920
gcaactgttg cccaaaatgg gacaatgatc cgatgcctgc atagacaccc tgcttgaggg    1980
tgcgatcgcc ctaatacgag gcaaaccaag ttttccaatt gaccttcaat tgacgagcgg    2040
ttgttgcgac aggggactgg agtgctacct gtttagagtt caaatccgtc acccagcatt    2100
gaaagttttt ccccgcattg gatgattgca atgccgctaa cccgctcatc cgccaaagtt    2160
catagtccca ccctgcctcg acttatcgga ccacatgggg ctcccttatg cgcgcgcata    2220
tggcgcttga ttgcttttg gtcaacgttt gggacaaatt cctttgtta aggcggaccc     2280
gccagcagat acgaaggtat aaatagggct cactttcacc atcttgtcca ttcaattgca    2340
agactcaaaa gtaataatga ccactctgga tgacaccgct taccgatacc gaacttccgt    2400
tcctggcgat gccgaggcta ttgaggctct ggatggatct ttcaccactg acaccgtttt    2460
ccgagtgacc gctactggcg acggcttcac cctgcgagag gtgcctgtcg accctcctct    2520
caccaaggtt ttccctgacg atgagtcgga cgatgagtct gacgctggag aggacggcga    2580
ccctgactct cgaactttcg tggcttacgg cgacgatgga gacctggccg gctttgtggt    2640
cgtttcttac tccggatgga accgacgact gaccgtggag gacatcgagg tcgctcctga    2700
gcaccgaggt catggtgtcg gacgagctct gatgggtctc gctactgagt tcgctcgaga    2760
gcgaggtgct ggccacctgt ggctcgaggt caccaacgtt aacgcccctg ctattcatgc    2820
ctaccgacga atgggtttta ccctgtgtgg cctcgatact gccctgtacg acggaaccgc    2880
ttccgatgga gagcaggccc tctacatgtc gatgccctgc ccttaaacag gcccctttc    2940
ctttgtcgat atcatgtaat tagttatgtc acgcttacat tcacgccctc ctcccacatc    3000
cgctctaacc gaaaggaag gagttagaca acctgaagtc taggtcccta ttatttttt     3060
ttaatagtta tgttagtatt aagaacgtta tttatatttc aaattttct ttttttctg     3120
tacaaacgcg tgtacgcatg taacattata ctgaaaacct tgcttgagaa ggttttggga    3180
cgctcgaagg ctttaatttg cagagaccgg gttggcggcg catttgtgtc ccaaaaaaca    3240
gccccaattg ccccaattga ccccaaattg acccagtagc gggcccaacc ccggcgagag    3300
ccccccttctc cccacatatc aaacctcccc cggttcccac acttgccgtt aagggcgtag    3360
ggtactgcag tctggaatct acgcttgttc agactttgta ctagtttctt tgtctggcca    3420
tccgggtaac ccatgccgga cgcaaaatag actactgaaa attttttgc tttgtggttg     3480
```

```
ggactttagc caagggtata aaagaccacc gtccccgaat tacctttcct cttcttttct    3540
ctctctcctt gtcaactcac acccgaaatc gttaagcatt tccttctgag tataagaatc    3600
attcaaaatg aagttctcta tgccatcttg gggtgttgtt ttttacgctt tgttggtttg    3660
tttgttgcca ttcttgtcta aggctggtgt tcaagctatg tccgttgtta ccaccgatgc    3720
tcaagctgct catgctgctg tgtttctag  attattggct tcttatagag ccattccacc    3780
atctgctact gttagattgg ctaagccaac ttctaatttg ttcagagcta gagctagaac    3840
taacgttaag ggtttggatg tttctggttt gactggtgtt attggtgttg atccagatgc    3900
tagaactgct gatgttgctg gtatgtgtac ttacgaagat ttggttgctg ctactttgcc    3960
atatggtttg gctccattgg ttgttccaca attgaaaact attactttgg gtggtgctgt    4020
taccggtttg ggtattgaat ctacttcttt cagaaacggt ttgccacacg aatctgtttt    4080
ggaaatggat attttgaccg gttccggtga atagttact  gcttctccag atcaacactc    4140
cgatttgttt catgctttc  caaactctta cggtacattg ggttactcta ccagattgag    4200
aattgaattg gaaccagttc atccattcgt tgccttgaga catttgagat tccattccat    4260
tactgatttg gtcgcagcca tggatagaat tattgaaact ggtggtttag acggtgaacc    4320
agttgattat ttggatggtg ttgttttctc tgccaccgaa tcatatttgt gtgttggttt    4380
caaaactaag accccaggtc cagtttctga ttatactggt caacaaatct tctacagatc    4440
catccaacat gatggtgata ctggtgctga aaaacatgat agattgacca tccatgacta    4500
cttgtggaga tgggatactg attggttttg gtgttctaga gcttttggtg ctcaacatcc    4560
agttattaga agattctggc caagaagatt aagaagatcc tccttctact ggaaattggt    4620
tgcttacgat caaagatacg atatcgccga tagaatcgaa aagagaaatg gtagaccacc    4680
aagagaaaga gttgttcaag acgttgaagt tccaattgaa agatgcgctg atttcgttga    4740
atggttcttg caaaatgttc caatcgaacc tatttggttg tgcccattga gattgagaga    4800
ttctgctgat ggtggtgctt catggccatt atatccattg aaagctcatc acacctacgt    4860
caatattggt ttctggtcat ctgttccagt tggtccagaa gaaggtcata ccaatagatt    4920
gattgaaaaa aaggtcgccg aattggacgg tcacaaatca ttatattctg atgcctacta    4980
caccagagat gaattcgatg aattatacgg tggtgaagtt tacaacaccg tcaaaaaaac    5040
ttacgaccca gactcaagat tattagactt gtactctaag gccgtccaaa gacaacatga    5100
tgaattgtga gctgcttgta cctagtgcaa ccccagtttg ttaaaaatta gtagtcaaaa    5160
acttctgagt tagaaatttg tgagtgtagt gagattgtag agtatcatgt gtgtccgtaa    5220
gtgaagtgtt attgactctt agttagttta tctagtactc gtttagttga cactgatcta    5280
gtattttacg aggcgtatga ctttagccaa gtgttgtact tagtcttctc tccaaacatg    5340
agagggctct gtcactcagt cggcctatgg gtgagatggc ttggtgagat ctttcgatag    5400
tctcgtcaag atggtaggat gatgggggaa tacattactg ctctcgtcaa ggaaaccaca    5460
atcagatcac accatcctcc atggtatccg atgactctct tctccacagt cgcagtagga    5520
tgtcctgcac gggtcttttt gtggggtgtg gagaaagggg tgcttggaga tggaagccgg    5580
tagaaccggg ctgcttgggg ggatttgggg ccgctgggct ccaaagaggg gtaggcattt    5640
cgttggggtt acgtaattgc ggcatttggg tcctgcgcgc atgtcccatt ggtcagaatt    5700
agtccggata ggagacttat cagccaatca cagcgccgga tccacctgta ggttgggttg    5760
ggtgggagca cccctccaca gagtagagtc aaacagcagc agcaacgtga tagttggggg    5820
```

```
tgtgcgtgtt aaaggaaaaa aaaagaagct tgggttatat tcccgctcta tttagaggtt    5880
gcgggataga cgccgacgga gggcaatggc gccatggaac cttgcggata tcgatacgcc    5940
gcggcggact gcgtccgaac cagctccagc agcgtttttt ccgggccatt gagccgactg    6000
cgaccccgcc aacgtgtctt ggcccacgca ctcatgtcat gttggtgttg ggaggccact    6060
ttttaagtag cacaaggcac ctagctcgcg gcagggtgtc cgaaccaaag aagcggctgc    6120
agtggtgcaa acggggcgga aacggcggga aaaagccacg ggggcacgaa ttgaggcacg    6180
ccctcgaatt tgagacgagt cacggcccca ttcgcccgcg caatggctcg ccaacgcccg    6240
gtcttttgca ccacatcagg ttaccccaag ccaaacctttt gtgttaaaaa gcttaacata    6300
ttataccgaa cgtaggtttg ggcgggcttg ctccgtctgt ccaaggcaac atttatataa    6360
gggtctgcat cgccggctca attgaatctt ttttcttctt ctcttctcta tattcattct    6420
tgaattaaac acacatcaac aatgaagttc tctatgccat cttggggtgt tgttttttac    6480
gctttgttgg tttgtttgtt gccattcttg tctaaggctg gtgttcaagc tatgaccacc    6540
ttcaaagaaa gagaaacttc taccgctgat agaaagttga ccttggctga aattttggaa    6600 atttttcgctg ctggtaaaga accattgaag ttcactgctt atgatggttc ttctgctggt    6660
cctgaagatg ctactatggg tttggatttg aaaactccaa gaggtactac ttacttggct    6720
actgctccag gtgatttggg tttggctaga gcttatgttt ctggtgactt ggaaccacat    6780
ggtgttcatc ctggtgatcc atatccatta ttgagagctt tagccgaaag aatggaattc    6840
aaaagaccac cagctagagt tttggctaac atcgttagat ccattggtat cgaacatttg    6900
aagccaattg ctccaccacc acaagaagct tgccaagat ggagaagaat tatggaaggt    6960
ttgagacact ctaagaccag agatgctgaa gctattcatc atcactacga tgtttctaac    7020
accttctacg aatgggtttt gggtccatct atgacttata cttgtgcttg ttacccaaca    7080
gaagatgcca cttttggaaga agctcaagat aacaagtaca gattggtctt tgaaaagttg    7140
agattgaagc caggtgacag attattggat gttggttgtg gttggggtgg tatggttaga    7200
tatgctgcta gacatggtgt aaaagctttg ggtgttactt tgtctagaga caagctact    7260 tgggctcaaa aagctattgc tcaagaaggt ttaaccgatt tggctgaagt tagacacggt    7320
gattacagag atgttatcga atctggttttc gatgccgttt cttctattgg tttgactgaa    7380
catatcggtg ttcataacta ccagcctac ttcaacttct tgaagtctaa gttgagaacc    7440
ggtggtttgt tgttgaacca ttgcattact agaccagata acagatctgc tccatctgct    7500
ggtggtttta ttgatagata cgttttccca gatggtgaat tgactggttc cggtagaatt    7560
attactgaag cacaagatgt cggtttggaa gttatccatg aagaaaactt gagaaaccat    7620
tacgccatga ctttgagaga ttggtgtaga aacttggttg aacattggga tgaagccgtt    7680
gaagaagttg gtttgccaac tgctaaagtt tgggggtttgt atatggctgg ttctagatta    7740
ggttttgaaa ctaacgttgt ccaattgcac caagttttgg cagttaagtt ggatgatcaa    7800
ggtaaagatg gtggtttgcc tttaagacca tggtggtctg ctcatgatga attgtgagca    7860
ttagcgacta ctaatatata tttgaatcca tggaattata caaacaagc atcaaaacaa    7920 gaattagcga cattatactt gaaatcagca ttagcgatac tactaatata gtttattcta    7980
tgtaatgatc catggaagtt cgattgattt gccaagttaa tttgatagat tatgcatgcc    8040
atttagtcga cgcaggtacg atctacagcg ataagaaga ggttgtgggt cattcaattt    8100
tgcaccaatt ttgcaccatc atagatcata atacatttac aaggcctaca attcttacag    8160
ggtcttctcg agagcaattc cttaattaag gcgcgccttt ccataggctc cgcccccctg    8220
```

```
acgagcatca caaaaatcga cgctcaagtc agaggtggcg aaacccgaca ggactataaa    8280
gataccaggc gtttccccct ggaagctccc tcgtgcgctc tcctgttccg accctgccgc    8340
ttaccggata cctgtccgcc tttctcccct cgggaagcgt ggcgctttct catagctcac    8400
gctgtaggta tctcagttcg gtgtaggtcg ttcgctccaa gctgggctgt gtgcacgaac    8460
cccccgttca gcccgaccgc tgcgccttat ccggtaacta tcgtcttgag tccaacccgg    8520
taagacacga cttatcgcca ctggcagcag ccactggtaa caggattagc agagcgaggt    8580
atgtaggcgg tgctacagag ttcttgaagt ggtggcctaa ctacggctac actagaagaa    8640
cagtatttgg tatctgcgct ctgctgaagc cagttacctt cggaaaaaga gttggtagct    8700
cttgatccgg caaacaaacc accgctggta gcggtggttt ttttgtttgc aagcagcaga    8760
ttacgcgcag aaaaaaagga tctcaagaag atcctttgat cttttctacg ggtctgacg    8820
ctcagtggaa cgaaaactca cgttaaggga ttttggtcat gagattatca aaaggatct    8880
tcacctagat ccttttaaat taaaatgaa gttttaaatc aatctaaagt atatatgagt    8940
aaacttggtc tgacagttac caatgcttaa tcagtgaggc acctatctca gcgatctgtc    9000
tatttcgttc atccatagtt gcctgactcc ccgtcgtgta gataactacg atacgggagg    9060
gcttaccatc tggccccagt gctgcaatga taccgcgaga cccacgctca ccggctccag    9120
atttatcagc aataaaccag ccagccggaa gggccgagcg cagaagtggt cctgcaactt    9180
tatccgcctc catccagtct attaattgtt gccgggaagc tagagtaagt agttcgccag    9240
ttaatagttt gcgcaacgtt gttgccattg ctacaggcat cgtggtgtca cgctcgtcgt    9300
ttggtatggc ttcattcagc tccggttccc aacgatcaag gcgagttaca tgatccccca    9360
tgttgtgcaa aaaagcggtt agctccttcg gtcctccgat cgttgtcaga agtaagttgg    9420
ccgcagtgtt atcactcatg gttatggcag cactgcataa ttctcttact gtcatgccat    9480
ccgtaagatg cttttctgtg actggtgagt actcaaccaa gtcattctga ataagtgta    9540
tgcggcgacc gagttgctct tgcccggcgt caatacggga taataccgcg ccacatagca    9600
gaactttaaa agtgctcatc attggaaaac gttcttcggg gcgaaaactc tcaaggatct    9660
taccgctgtt gagatccagt tcgatgtaac ccactcgtgc acccaactga tcttcagcat    9720
cttttacttt caccagcgtt tctgggtgag caaaaacagg aaggcaaaat gccgcaaaaa    9780
agggaataag ggcgacacgg aaatgttgaa tactcatact cttccttttt caatattatt    9840
gaagcattta tcagggttat tgtctcatga gcggatacat atttgaatgt atttagaaaa    9900
ataaacagcg atcgcgcggc cgcgggtaat aactgatata attaaattga agctctaatt    9960
tgtgagttta gtatacatgc atttacttat aatacagttt tttagttttg ctggccgcat    10020
cttctcaaat atgcttccca gcctgctttt ctgtaacgtt cacctctac cttagcatcc    10080
cttccctttg caaatagtcc tcttccaaca ataataatgt cagatcctgt agagaccaca    10140
tcatccacgg ttctatactg ttgacccaat gcgtctccct tgtcatctaa acccacaccg    10200
ggtgtcataa tcaaccaatc gtaaccttca tctcttccac ccatgtctct tgagcaata    10260
aagccgataa caaaatcttt gtcgctcttc gcaatgtcaa cagtacccct agtatattct    10320
ccagtagcta gggagccctt gcatgacaat tctgctaaca tcaaaaggcc tctaggttcc    10380
tttgttactt cttccgccgc ctgcttcaaa ccgctaacaa tacctgggcc caccacaccg    10440
tgtgcattcg taatgtctgc ccattctgct attctgtata cacccgcaga gtactgcaat    10500
ttgactgtat taccaatgtc agcaaatttt ctgtcttcga agagtaaaaa attgtacttg    10560
```

```
gcggataatg cctttagcgg cttaactgtg ccctccatgg aaaaatcagt caagatatcc   10620
acatgtgttt ttagtaaaca aattttggga cctaatgctt caactaactc cagtaattcc   10680
ttggtggtac gaacatccaa tgaagcacac aagtttgttt gcttttcgtg catgatatta   10740
aatagcttgg cagcaacagg actaggatga gtagcagcac gttccttata tgtagctttc   10800
gacatgattt atcttcgttt cctgcaggtt tttgttctgt gcagttgggt taagaatact   10860
gggcaatttc atgtttcttc aacaccacat atgcgtatat ataccaatct aagtctgtgc   10920
tccttccttc gttcttcctt ctgctcggag attaccgaat caaagctagc              10970
```

<210> SEQ ID NO 80
<211> LENGTH: 1410
<212> TYPE: DNA
<213> ORGANISM: Artificial Sequence
<220> FEATURE:
<223> OTHER INFORMATION: Synthetic Nucleic Acid

<400> SEQUENCE: 80

```
atgtccgttg ttaccaccga tgctcaagct gctcatgctg ctggtgtttc tagattattg     60
gcttcttata gagccattcc accatctgct actgttagat tggctaagcc aacttctaat    120
ttgttcagag ctagagctag aactaacgtt aagggtttgg atgtttctgg tttgactggt    180
gttattggtg ttgatccaga tgctagaact gctgatgttg ctggtatgtg tacttacgaa    240
gatttggttc tgctactttt gccatatggt ttggctccat tggttgttcc acaattgaaa    300
actattactt tgggtggtgc tgttaccggt ttgggtattg aatctacttc tttcagaaac    360
ggtttgccac acgaatctgt tttggaaatg gatattttga ccggttccgg tgaaatagtt    420
actgcttctc cagatcaaca ctccgatttg tttcatgctt ttccaaactc ttacggtaca    480
ttgggttact ctaccagatt gagaattgaa ttggaaccag ttcatccatt cgttgccttg    540
agacatttga gattccattc cattactgat ttggtcgcag ccatggatag aattattgaa    600
actggtggtt tagacggtga accagttgat tatttggatg gtgttgtttt ctctgccacc    660
gaatcatatt tgtgtgttgg tttcaaaact aagaccccag gtccagtttc tgattatact    720
ggtcaacaaa tcttctacag atccatccaa catgatggtg atactggtgc tgaaaaacat    780
gatagattga ccatccatga ctacttgtgg agatgggata ctgattggtt ttggtgttct    840
agagcttttg gtgctcaaca tccagttatt agaagattct ggccaagaag attaagaaga    900
tcctccttct actggaaatt ggttgcttac gatcaaagat acgatatcgc cgatagaatc    960
gaaaagagaa atggtagacc accaagagaa agagttgttc aagacgttga agttccaatt   1020
gaaagatgcg ctgatttcgt tgaatggttc ttgcaaaatg ttccaatcga acctatttgg   1080
ttgtgcccat tgagattgag agattctgct gatggtggtg cttcatggcc attatatcca   1140
ttgaaagctc atcacaccta cgtcaatatt ggtttctggt catctgttcc agttggtcca   1200
gaagaaggtc ataccaatag attgattgaa aaaaaggtcg ccgaattgga cggtcacaaa   1260
tcattatatt ctgatgccta ctacaccaga gatgaattcg atgaattata cggtggtgaa   1320
gtttacaaca ccgtcaaaaa aacttacgac ccagactcaa gattattaga cttgtactct   1380
aaggccgtcc aaagacaaca tgatgaattg                                      1410
```

<210> SEQ ID NO 81
<211> LENGTH: 1311
<212> TYPE: DNA
<213> ORGANISM: Artificial Sequence
<220> FEATURE:
<223> OTHER INFORMATION: Synthetic Nucleic Acid

<400> SEQUENCE: 81

```
atgaccacct tcaaagaaag agaaacttct accgctgata gaaagttgac cttggctgaa      60
attttggaaa ttttcgctgc tggtaaagaa ccattgaagt tcactgctta tgatggttct     120
tctgctggtc ctgaagatgc tactatgggt ttggatttga aaactccaag aggtactact     180
tacttggcta ctgctccagg tgatttgggt ttggctagag cttatgtttc tggtgacttg     240
gaaccacatg tgttcatcc tggtgatcca tatccattat tgagagcttt agccgaaaga      300
atggaattca aaagaccacc agctagagtt ttggctaaca tcgttagatc cattggtatc     360
gaacatttga agccaattgc tccaccacca caagaagctt tgccaagatg gagaagaatt     420
atggaaggtt tgagacactc taagaccaga gatgctgaag ctattcatca tcactacgat     480
gtttctaaca ccttctacga atgggttttg ggtccatcta tgacttatac ttgtgcttgt     540
tacccaacag aagatgccac tttggaagaa gctcaagata caagtacag attggtctt      600
gaaaagttga gattgaagcc aggtgacaga ttattggatg ttggttgtgg ttggggtggt     660
atggttagat atgctgctag acatggtgta aaagctttgg gtgttacttt gtctagagaa     720
caagctactt gggctcaaaa agctattgct caagaaggtt taaccgattt ggctgaagtt     780
agacacggtg attacagaga tgttatcgaa tctggtttcg atgccgtttc ttctattggt     840
ttgactgaac atatcggtgt tcataactat ccagcctact tcaacttctt gaagtctaag     900
ttgagaaccg gtggtttgtt gttgaaccat tgcattacta gaccagataa cagatctgct     960
ccatctgctg gtggttttat tgatagatac gttttcccag atggtgaatt gactggttcc    1020
ggtagaatta ttactgaagc acaagatgtc ggtttggaag ttatccatga agaaaacttg    1080
agaaaccatt acgccatgac tttgagagat tggtgtagaa acttggttga acattgggat    1140
gaagccgttg aagaagttgg tttgccaact gctaaagttt ggggtttgta tatggctggt    1200
tctagattag ttttgaaaac taacgttgtc caattgcacc aagttttggc agttaagttg    1260
gatgatcaag gtaaagatgg tggttttgcct ttaagaccat ggtggtctgc t            1311
```

<210> SEQ ID NO 82
<211> LENGTH: 4399
<212> TYPE: DNA
<213> ORGANISM: Artificial Sequence
<220> FEATURE:
<223> OTHER INFORMATION: Synthetic Nucleic Acid

<400> SEQUENCE: 82

```
tgggtaggtt atagggat atagcacaga gatatatagc aaagagatac ttttgagcaa       60
tgtttgtgga agcggtattc gcaatttaat taaagctggt gacaattaat catcggctcg    120
tataatgtgt ggaattgaat cgatataagg aggttaatca tgtttaaacc ctcaaaatat    180
atttcctc tatcttctcg ttgcgcttaa tttgactaat tctcattagc gaggcgcgcc      240
tttccatagg ctccgccccc ctgacgagca tcacaaaaat cgacgctcaa gtcagaggtg    300
gcgaaacccg acaggactat aaagatacca ggcgtttccc cctggaagct ccctcgtgcg    360
ctctcctgtt ccgaccctgc cgcttaccgg atacctgtcc gcctttctcc cttcgggaag    420
cgtggcgctt tctcatagct cacgctgtag gtatctcagt tcggtgtagg tcgttcgctc    480
caagctgggc tgtgtgcacg aaccccccgt tcagcccgac cgctgcgcct tatccggtaa    540
ctatcgtctt gagtccaacc cggtaagaca cgacttatcg ccactggcag cagccactgg    600
taacaggatt agcagagcga ggtatgtagg cggtgctaca gagttcttga agtggtggcc    660
```

```
taactacggc tacactagaa gaacagtatt tggtatctgc gctctgctga agccagttac    720
cttcggaaaa agagttggta gctcttgatc cggcaaacaa accaccgctg gtagcggtgg    780
tttttttgtt tgcaagcagc agattacgcg cagaaaaaaa ggatctcaag aagatccttt    840
gatcttttct acggggtctg acgctcagtg gaacgaaaac tcacgttaag gattttggt    900
catgagatta tcaaaaagga tcttcaccta gatcctttta aattaaaaat gaagttttaa    960
atcaatctaa agtatatatg agtaaacttg gtctgacagt taccaatgct taatcagtga   1020
ggcacctatc tcagcgatct gtctatttcg ttcatccata gttgcctgac tccccgtcgt   1080
gtagataact acgatacggg agggcttacc atctggcccc agtgctgcaa tgataccgcg   1140
agacccacgc tcaccggctc cagatttatc agcaataaac cagccagccg aagggccga    1200
gcgcagaagt ggtcctgcaa ctttatccgc ctccatccag tctattaatt gttgccggga   1260
agctagagta agtagttcgc cagttaatag tttgcgcaac gttgttgcca ttgctacagg   1320
catcgtggtg tcacgctcgt cgtttggtat ggcttcattc agctccggtt cccaacgatc   1380
aaggcgagtt acatgatccc ccatgttgtg caaaaaagcg gttagctcct tcggtcctcc   1440
gatcgttgtc agaagtaagt tggccgcagt gttatcactc atggttatgg cagcactgca   1500
taattctctt actgtcatgc catccgtaag atgcttttct gtgactggtg agtactcaac   1560
caagtcattc tgagaatagt gtatgcggcg accgagttgc tcttgcccgg cgtcaatacg   1620
ggataatacc gcgccacata gcagaacttt aaaagtgctc atcattggaa acgttcttc    1680
ggggcgaaaa ctctcaagga tcttaccgct gttgagatcc agttcgatgt aacccactcg   1740
tgcacccaac tgatcttcag catcttttac tttcaccagc gtttctgggt gagcaaaaac   1800
aggaaggcaa aatgccgcaa aaaagggaat aagggcgaca cggaaatgtt gaatactcat   1860
actcttcctt tttcaatatt attgaagcat ttatcagggt tattgtctca tgagcggata   1920
catatttgaa tgtatttaga aaaataaaca gcgatcgcgc ggccgcgggt aataactgat   1980
ataattaaat tgaagctcta atttgtgagt ttagtataca tgcatttact tataatacag   2040
ttttttagtt ttgctggccg catcttctca aatatgcttc ccagcctgct tttctgtaac   2100
gttcaccctc tacctttagca tcccttccct ttgcaaatag tcctcttcca acaataataa   2160
tgtcagatcc tgtagagacc acatcatcca cggttctata ctgttgaccc aatgcgtctc   2220
ccttgtcatc taaacccaca ccgggtgtca atcaaccca atcgtaacct tcatctcttc    2280
cacccatgtc tctttgagca ataaagccga taacaaaatc tttgtcgctc ttcgcaatgt   2340
caacagtacc cttagtatat tctccagtag ctagggagcc cttgcatgac aattctgcta   2400
acatcaaaag gcctctaggt tcctttgtta cttcttccgc cgcctgcttc aaaccgctaa   2460
caatacctgg gcccaccaca ccgtgtgcat tcgtaatgtc tgcccattct gctattctgt   2520
atacacccgc agagtactgc aatttgactg tattaccaat gtcagcaaat tttctgtctt   2580
cgaagagtaa aaaattgtac ttggcggata atgcctttag cggcttaact gtgcccttca   2640
tggaaaaatc agtcaagata tccacatgtg tttttagtaa acaaattttg ggacctaatg   2700
cttcaactaa ctccagtaat tccttggtgg tacgaacatc caatgaagca cacaagtttg   2760
tttgcttttc gtgcatgata ttaaatagct tggcagcaac aggactagga tgagtagcag   2820
cacgttcctt atatgtagct ttcgacatga tttatcttcg tttcctgcag gtttttgttc   2880
tgtgcagttg ggttaagaat actgggcaat tcatgtttc ttcaacacca catatgcgta    2940
tatataccaa tctaagtctg tgctccttcc ttcgttcttc cttctgctcg agattaccg    3000
aatcaaagct agcttatcga tgataagctg tcaaagatga gaattaattc cacggactat   3060
```

```
agactatact agatactccg tctactgtac gatacacttc cgctcaggtc cttgtccttt    3120
aacgaggcct taccactctt ttgttactct attgatccag ctcagcaaag gcagtgtgat    3180
ctaagattct atcttcgcga tgtagtaaaa ctagctagac cgagaaagag actagaaatg    3240
caaaaggcac ttctacaatg gctgccatca ttattatccg atgtgacgct gcagcttctc    3300
aatgatattc gaatacgctt tgaggagata cagcctaata tccgacaaac tgttttacag    3360
atttacgatc gtacttgtta cccatcattg aattttgaac atccgaacct gggagttttc    3420
cctgaaacag atagtatatt tgaacctgta taataatata tagtctagcg ctttacggaa    3480
gacaatgtat gtatttcggt tcctggagaa actattgcat ctattgcata ggtaatcttg    3540
cacgtcgcat ccccggttca ttttctgcgt ttccatcttg cacttcaata gcatatcttt    3600
gttaacgaag catctgtgct tcattttgta gaacaaaaat gcaacgcgag agcgctaatt    3660
tttcaaacaa agaatctgag ctgcattttt acagaacaga aatgcaacgc gaaagcgcta    3720
ttttaccaac gaagaatctg tgcttcattt ttgtaaaaca aaaatgcaac gcgacgagag    3780
cgctaatttt tcaaacaaag aatctgagct gcattttta cagaacagaaa tgcaacgcga    3840 gagcgctatt ttaccaacaa agaatctata cttcttttt gttctacaaa atgcatccc    3900 gagagcgcta ttttctaac aaagcatctt agattacttt ttttctcctt tgtgcgctct    3960
ataatgcagt ctcttgataa cttttttgcac tgtaggtccg ttaaggttag aagaaggcta    4020
ctttggtgtc tatttctct tccataaaaa aagcctgact ccacttcccg cgtttactga    4080
ttactagcga agctgcgggt gcattttttc aagataaagg catccccgat tatattctat    4140
accgatgtgg attgcgcata ctttgtgaac agaaagtgat agcgttgatg attcttcatt    4200
ggtcagaaaa ttatgaacgg tttcttctat tttgtctcta tatactacgt ataggaaatg    4260
tttacatttt cgtattgttt tcgattcact ctatgaatag ttcttactac aattttttg    4320 tctaaagagt aatactagag ataaacataa aaaatgtaga ggtcgagttt agatgcaagt    4380
tcaaggagcg aaaggtgga                                                 4399
```

<210> SEQ ID NO 83  
<211> LENGTH: 7531  
<212> TYPE: DNA  
<213> ORGANISM: Artificial Sequence  
<220> FEATURE:  
<223> OTHER INFORMATION: Synthetic Nucleic Acid

<400> SEQUENCE: 83

```
gtttgtggaa gcggtattcg caatttaatt aaagctggtg acaattaatc atcggctcgt      60
ataatgtgtg gaattgaatc gatataagga ggttaatcat gtgtctgttc cttcgaccga     120
cgcacgttct gctcacgccg acggcgtgca gcggcttctc gccagctatc gggcgattcc     180
ccaagacgcc acggtccggc tggccaaacc cacgtcgaac ctcttccgtg cccgcgcgaa     240
aaccaggacc aagggtctgg acacgtctgg gttgacgaac gtgatcgcgg tcgacgcgga     300
ggcacgcacc gccgatgtgg cagggatgtg cacctacgaa gacctggtcg cggccacgct     360
gccgcatgga ctttcgccgc tggtggtgcc gcagttgaag acgatcaccc tcggcggggc     420
ggtcaccgga ctcgggatcg agtccgcctc gttccgcaac ggcctgccac acgaatcggt     480
tctcgagatg gacgtcctca ccggcaccgg tgatgtcgtg cgcgcctccc ccgacgagaa     540
ccctgacctg tttcgggcgt ttccgaattc ctatggcacg ttgggctatt cggttcggct     600
caagatcgag ctggaaccgg tgaagccgtt cgtcgcgctg cgccacctcc gtttccattc     660
```

```
gctgtcggct ctcatcgagg cgatggaccg catcgtcgaa accggcggcc tcaacggcga    720
accggtggac tacctcgacg gcgtcgtgtt cagtgccgag gagagttacc tgtgcgtggg    780
gcagcgctcc gcgacaccgg gcccggtcag cgactacacg ggcaagcaga tctactaccg    840
ctcgattcag cacgacggcc cgaccgatgg cgccgagaag cacgaccggc tgaccatcca    900
cgactacctg tggcgctggg acaccgactg gttctggtgc tcaagggcat tcggcgcgca    960
gaacccgcgg atccggcgct ggtggccgcg ccggtaccgg cgcagcagtg tgtactggaa   1020
gctgatcggc tacgaccggc gtttcggtat cgccgatcgc atcgagaagc gcaacggccg   1080
acccccgcgc gagcgggtgg tccaggacat cgaggtgccc atcgagcgga ccgtcgagtt   1140
tctgcagtgg tttctcgaca ccgtgcccat cgaaccgatc tggttgtgcc cgttgcggct   1200
ccgcgacgac cgcgattggc ccctgtatcc gatccgaccc caccacacct acgtcaacgt   1260
gggtttctgg tcgtcggtgc cggtgggccc ggaggagggc tacaccaaca ggatgatcga   1320
acggaaagtc agcgacctcg acggtcacaa atcgctgtat tccgatgcgt actactcgcc   1380
ggaagagttt gattcgctct atggcgggga gacgtacaag acggtgaaga agacatacga   1440
cccagactct cgtttcctgg acctgtacgg caaagcagtg gggcggcaat gagcgttgac   1500
gcgaagaacg gaggccacag ttgacgacat ttcgggacgg cgcggccgac accggcctgc   1560
acggagaccg caagctcacc ctggcggagg tcttggaggt cttcgcctcg ggccgactgc   1620
ctctgaagtt cacggcgtac gacgcagca gcgcgggccc ggacgacgcc acgctcgggc   1680
tggacctgct gaccccccgc gggaccacgt acctcgcaac ggctcccggc gatctcggcc   1740
tggcccgggc ctacgtctcc ggtgacctgc agttgcaggg ggtgcaccct ggcgacccgt   1800
acgacctgct caacgcactg gtgcagaaac tggacttcaa gcgaccgtcc gcccgggtgc   1860
tggcgcaggt cgtccgatcg atcgggatcg agcacctgaa accgatcgcg ccaccgccgc   1920
aggaggcgct gccgcggtgg cggcgcatcg cagaaggact gcggcacagc aagacccgtg   1980
acgccgacgc gatccaccac cattacgatg tctccaacac cttctacgag tgggtgctcg   2040
ggccgtcgat gacctacacc tgcgcctgct accgcatcc cgacgccacc ctcgaggagg   2100
cgcaggagaa caaatatcgg ctggtgttcg agaaactgcg cctcaagccg gcgaccgcc   2160
ttctcgacgt gggttgcggg tggggcggaa tggtgcgcta cgcggcccgt cacggcgtca   2220
aggcgatcgg ggtgacgctg tccagggagc aggcgcagtg ggcacgcgcc gccatcgaac   2280
gggacggcct gggtgacctc gccgaggtcc gccacagcga ctaccgcgat gtgcgcgagt   2340
cccagttcga cgccgtgtct tcgctggggc tcaccgagca catcggggtc gccaactatc   2400
cgtcgtactt ccggttcctc aagtcgaagt tgcgcccggg cggcctactg ctcaaccact   2460
gcatcacccg gcacaacaat cgcaccggcc ccgccgccgg gggattcatc gaccggtatg   2520
tgttcccgga cggggagctg accggatcgg gccggatcat caccgagatc caggacgtcg   2580
gtttggaggt gatgcacgaa gagaacctgc gccggcacta tgcgctgaca cttcgggact   2640
ggtgccggaa tctggtgcag cactgggacg aagcggtcgc agaggtcggc ctgcccaccg   2700
ccaaggtgtg gggtctgtac atggctgcct cgcgggtcgg cttcgagcag aacagcattc   2760
agctgcatca ggtactggcg gtgaagctcg acgaacgtgg cggggacggc ggtttgccgt   2820
tgcggcccctg gtggaccgcg tagcaactat gctcaccgtg tgatccgctt tctgctgcgc   2880
gtcgcggtct ttctcggatc gtcggcgatc gggctactgg tggccggctg gctggtgccg   2940
ggggtgtcgc tgtcggtgct gggcttcgtc accgcggtgt tgatcttcac ggtggcacaa   3000
gggattctgt cgccgttctt cctgaagatg gccagccgct acgcgtcggc cttcctcggc   3060
```

```
ggcatcggcc tggtgtccac gttcgtggcg ctgctgctcg cgtcgctgct gtccaacggg    3120
ctcagcatcc gcggcgtcgg gtcgtggatc gcggccacgg tggtggtctg gctggtcaca    3180
gccctggcga ccgtcgtgct gcccgttctg gtgctgcggg agaagaagaa agcagcctga    3240
cctcaaaata tattttccct ctatcttctc gttgcgctta atttgactaa ttctcattag    3300
cgaggcgcgc ctttccatag gctccgcccc cctgacgagc atcacaaaaa tcgacgctca    3360
agtcagaggt ggcgaaaccc gacaggacta aaagatacc aggcgtttcc ccctggaagc     3420
tccctcgtgc gctctcctgt tccgaccctg ccgcttaccg gatacctgtc cgcctttctc    3480
ccttcgggaa gcgtggcgct ttctcatagc tcacgctgta ggtatctcag ttcggtgtag    3540
gtcgttcgct ccaagctggg ctgtgtgcac gaaccccccg ttcagcccga ccgctgcgcc    3600
ttatccggta actatcgtct tgagtccaac ccggtaagac acgacttatc gccactggca    3660
gcagccactg gtaacaggat tagcagagcg aggtatgtag gcggtgctac agagttcttg    3720
aagtggtggc ctaactacgg ctacactaga agaacagtat ttggtatctg cgctctgctg    3780
aagccagtta ccttcggaaa aagagttggt agctcttgat ccggcaaaca aaccaccgct    3840
ggtagcggtg gttttttttgt ttgcaagcag cagattacgc gcagaaaaaa aggatctcaa   3900
gaagatcctt tgatcttttc tacggggtct gacgctcagt ggaacgaaaa ctcacgttaa    3960
gggattttgg tcatgagatt atcaaaaagg atcttcacct agatcctttt aaattaaaaa    4020
tgaagtttta aatcaatcta agtatatat gagtaaactt ggtctgacag ttaccaatgc     4080
ttaatcagtg aggcacctat ctcagcgatc tgtctatttc gttcatccat agttgcctga    4140
ctccccgtcg tgtagataac tacgatacgg gagggcttac catctggccc cagtgctgca    4200
atgataccgc gagacccacg ctcaccggct ccagatttat cagcaataaa ccagccagcc    4260
ggaagggccg agcgcagaag tggtcctgca actttatccg cctccatcca gtctattaat    4320
tgttgccggg aagctagagt aagtagttcg ccagttaata gtttgcgcaa cgttgttgcc    4380
attgctacag gcatcgtggt gtcacgctcg tcgtttggta tggcttcatt cagctccggt    4440
tcccaacgat caaggcgagt tacatgatcc cccatgttgt gcaaaaaagc ggttagctcc    4500
ttcggtcctc cgatcgttgt cagaagtaag ttggccgcag tgttatcact catggttatg    4560
gcagcactgc ataattctct tactgtcatg ccatccgtaa gatgcttttc tgtgactggt    4620
gagtactcaa ccaagtcatt ctgagaatag tgtatgcggc gaccgagttg ctcttgcccg    4680
gcgtcaatac gggataatac cgcgccacat agcagaactt taaaagtgct catcattgga    4740
aaacgttctt cggggcgaaa actctcaagg atcttaccgc tgttgagatc cagttcgatg    4800
taacccactc gtgcacccaa ctgatcttca gcatctttta ctttcaccag cgtttctggg    4860
tgagcaaaaa caggaaggca aaatgccgca aaaaagggaa taaggcgac acggaaatgt     4920
tgaatactca tactcttcct ttttcaatat tattgaagca tttatcaggg ttattgtctc    4980
atgagcggat acatatttga atgtatttag aaaaataaac agcgatcgcg cggccgcggg    5040
taataactga tataattaaa ttgaagctct aatttgtgag tttagtatac atgcatttac    5100
ttataataca gttttttagt tttgctggcc gcatcttctc aaatatgctt cccagcctgc    5160
ttttctgtaa cgttcaccct ctaccttagc atcccttccc tttgcaaata gtcctcttcc    5220
aacaataata atgtcagatc ctgtagagac cacatcatcc acggttctat actgttgacc    5280
caatgcgtct cccttgtcat ctaaacccac accgggtgtc ataatcaacc aatcgtaacc    5340
ttcatctctt ccacccatgt ctctttgagc aataaagccg ataacaaaat ctttgtcgct    5400
```

```
cttcgcaatg tcaacagtac ccttagtata ttctccagta gctagggagc ccttgcatga    5460
caattctgct aacatcaaaa ggcctctagg ttcctttgtt acttcttccg ccgcctgctt    5520
caaaccgcta acaatacctg gcccaccac accgtgtgca ttcgtaatgt ctgcccattc     5580
tgctattctg tatacacccg cagagtactg caatttgact gtattaccaa tgtcagcaaa    5640
ttttctgtct tcgaagagta aaaaattgta cttggcggat aatgccttta gcggcttaac    5700
tgtgccctcc atggaaaaat cagtcaagat atccacatgt gttttagta aacaaatttt     5760 gggacctaat gcttcaacta actccagtaa ttccttggtg gtacgaacat ccaatgaagc    5820
acacaagttt gtttgctttt cgtgcatgat attaaatagc ttggcagcaa caggactagg    5880
atgagtagca gcacgttcct tatatgtagc tttcgacatg atttatcttc gtttcctgca    5940 ggttttttgtt ctgtgcagtt gggttaagaa tactgggcaa tttcatgttt cttcaacacc   6000
acatatgcgt atatatacca atctaagtct gtgctccttc cttcgttctt ccttctgctc    6060
ggagattacc gaatcaaagc tagcttatcg atgataagct gtcaaagatg agaattaatt    6120
ccacggacta tagactatac tagatactcc gtctactgta cgatacactt ccgctcaggt    6180
ccttgtcctt taacgaggcc ttaccactct tttgttactc tattgatcca gctcagcaaa    6240
ggcagtgtga tctaagattc tatcttcgcg atgtagtaaa actagctaga ccgagaaaga    6300
gactagaaat gcaaaaggca cttctacaat ggctgccatc attattatcc gatgtgacgc    6360
tgcagcttct caatgatatt cgaatacgct ttgaggagat acagcctaat atccgacaaa    6420
ctgttttaca gatttacgat cgtacttgtt acccatcatt gaattttgaa catccgaacc    6480
tgggagtttt ccctgaaaca gatagtatat ttgaacctgt ataataatat atagtctagc    6540
gctttacgga agacaatgta tgtatttcgg ttcctggaga aactattgca tctattgcat    6600
aggtaatctt gcacgtcgca tccccggttc attttctgcg tttccatctt gcacttcaat    6660
agcatatctt tgttaacgaa gcatctgtgc ttcattttgt agaacaaaaa tgcaacgcga    6720
gagcgctaat ttttcaaaca aagaatctga gctgcatttt tacagaacag aaatgcaacg    6780
cgaaagcgct attttaccaa cgaagaatct gtgcttcatt tttgtaaaac aaaaatgcaa    6840
cgcgacgaga gcgctaattt ttcaaacaaa gaatctgagc tgcattttta cagaacagaa    6900
atgcaacgcg agagcgctat tttaccaaca agaatctat acttcttttt tgttctacaa    6960
aaatgcatcc cgagagcgct atttttctaa caaagcatct tagattactt ttttttctcct   7020 ttgtgcgctc tataatgcag tctcttgata acttttttgca ctgtaggtcc gttaaggtta   7080
gaagaaggct actttggtgt ctattttctc ttccataaaa aaagcctgac tccacttccc    7140
gcgtttactg attactagcg aagctgcggg tgcatttttt caagataaag gcatcccga    7200 ttatattcta taccgatgtg gattgcgcat actttgtgaa cagaaagtga tagcgttgat    7260
gattcttcat tggtcagaaa attatgaacg gtttcttcta ttttgtctct atatactacg    7320
tataggaaat gtttacattt tcgtattgtt ttcgattcac tctatgaata gttcttacta    7380
caattttttt gtctaaagag taatactaga gataaacata aaaaatgtag aggtcgagtt    7440
tagatgcaag ttcaaggagc gaaaggtgga tgggtaggtt atatagggat atagcacaga    7500
gatatatagc aaagagatac ttttgagcaa t                                    7531

<210> SEQ ID NO 84
<211> LENGTH: 7126
<212> TYPE: DNA
<213> ORGANISM: Artificial Sequence
<220> FEATURE:
<223> OTHER INFORMATION: Synthetic Nucleic Acid
```

<400> SEQUENCE: 84

```
gtttgtggaa gcggtattcg caatttaatt aaagctggtg acaattaatc atcggctcgt      60
ataatgtgtg gaattgaatc gatataagga ggttaatcat atgacgcctg aagctagtgc     120
ggcggcgcac gccgctgcgg tggatcgcct catccatagc tatcgggcga ttcctgatga     180
cgcgccggtg cggctggcga agaagacgtc aaacctattc cgccacaggg aaaagacttc     240
tgctcctggg cttgacgtat ccggcctggc tcgcgtgatt gggatcgact cagacactcg     300
cactgccgac gttggcggca tgtgcacata cgaggacctt gtcgcggcga cgctcgaata     360
cgatctggtc ccctggtcg tcccgcaact caaaacgatc actctcggcg gcgcggtgac     420
gggcctggga attgagtcca cctcgttccg caatgggctt ccccatgaat ctgttctcga     480
aatggatatc ctgacgggcg ccggggaggt cgtcacggcc ggcccggaag cccccatag     540
cgatttgtac tgggggtttc gaattcgta cggcacgctc ggctatgcga cgcgcctgcg     600
catcgaacta gaaccggtcg agccgtacgt cgaactcagg cacctgcggt tcactagcct     660
cgatgagctt caggagacac ttgacaccgt ttcgtacgaa cacacgtatg acggggaacc     720
cgttcattac gtcgatggag tcatgttctc agccacggaa agctacctca cgcttggccg     780
tcagacgagc gaacccggcc cggtcagcga ctacaccgga accagatctc actaccgttc     840
aatacagcac ggtggcgctg aaactcccgt cgtcgaccgg atgaccattc atgactatct     900
atggcgctgg gatactgact ggttctggtg ctcgcgtgcc ttcggaacgc aacacccagt     960
ggtccggaga ttctggccac gccgctatcg ccgcagcagc ttctactgga agctgatcgc    1020
gcttgaccgc caggttgggc tcgcggactt catcgaacaa cggaagggca acctcccccg    1080
ggaacgcgta gtccaggaca tcgaggtccc gatcgagaac actgcgagct tcttgcggtg    1140
gttcttggcg aacgtgccga tcgagccggt atggctatgc ccgctgcgcc tgcgaaaaac    1200
acgcagcccc ggcctgcctt cgccgacgtc cccggcttca cgcccatggc ccctctatcc    1260
gctcgagcct cagcgcacat acgtcaatgt tggcttctgg tcagcggtgc cggtcgtggc    1320
cggccagccc gaggggcaca ccaaccggat gatcgagaac gaagtcgatc gccttgacgg    1380
tcacaaatcg ctgtactcag atgcgtttta cgagcgaaaa gagtttgacg cgctgtacgg    1440
cggcgatacc tatagagaac tcaaagagac ctacgaccca aacagccggt tacttgatct    1500
ctatgcaaag gcggtgcaag gacgatgaag gcagtgttga cggcgtttac ggctccccaa    1560
ctcgaaagga tgaacgtcgc tgagatactc agcgcggtac tcgggcgaga tttcccgatc    1620
cggttcactg cgtacgacgg cagcgcgctc ggccccgaaa ccgcccgcta cggcttgcac    1680
ctcacgacgc cgcgcgggct gacctacctc gctaccgcgc ccggtgatct cgggctcgca    1740
cgcgcgtacg tgtccggcga cctcgaggtc agtggggttc atcagggtga cccgtacgag    1800
ataatgaaga tcctcgcgca tgacgtccgg gtgcggcggc cctcgccagc aacgatcgct    1860
tcgatcatgc ggtccctcgg ctgggaacgc ttgcgaccgg tcgcgccgcc cccgcaagag    1920
aacatgcccc gttggcgccg gatggccctt ggcctgctgc actcgaagag ccgtgatgct    1980
gcggcaatcc accatcatta cgacgtgtcg aacgagtttt acgagcacat cctcggcccg    2040
tcgatgacgt acacatgcgc ggcctacccc agcgcagaca gttccctgga ggaagcacag    2100
gacaacaagt accgactcgt cttcgagaaa cttggcctga agccggggga tcgcctgctt    2160
gacgtcgggt gcgggtgggg cggcatggtg cggttcgccg ctaagcgcgg cgttcatgtc    2220
atcggtgcga cattgtcccg caaacaggcg gaatgggctc agaagatgat tgcccatgaa    2280
```

-continued

```
ggattgggcg atctggcgga agtccgtttc tgcgactacc gcgatgtcac agaggcgggc    2340
ttcgacgcag tgtcgtcgat cggcctcact gaacacatcg gtttggcgaa ctacccgtcg    2400
tacttcggct tcctgaagga caagttgcgg ccaggcggac gactgctgaa ccattgcatc    2460
actcgcccga caaccttca aagcaaccgc gcaggtgact tcattgaccg gtacgttttc    2520
cctgacggag agctcgccgg acctggcttc atcatttcag ctgtccacga cgccggtttc    2580
gaggtgcggc acgaagagaa cctccgcgag cactacgcac tgacgctgcg ggactggaac    2640
cgcaacctcg ctcgcgactg ggacgcgtgt gtgcacgcct ccgacgaggg caccgcccgc    2700
gtctggggac tgtacatttc cggttcacga gtcgcgtttg aaacgaactc gattcagctg    2760
caccaggtcc tggcggtcaa accgcgcgg aatggcgaag cgcaggtccc gttgggtcag    2820
tggtggaccc gctgacctca aaatatattt tccctctatc ttctcgttgc gcttaatttg    2880
actaattctc attagcgagg cgcgcctttc cataggctcc gcccccctga cgagcatcac    2940
aaaaatcgac gctcaagtca gaggtggcga aacccgacag gactataaag ataccaggcg    3000
tttccccctg gaagctccct cgtgcgctct cctgttccga ccctgccgct taccggatac    3060
ctgtccgcct ttctcccttc gggaagcgtg gcgctttctc atagctcacg ctgtaggtat    3120
ctcagttcgg tgtaggtcgt tcgctccaag ctgggctgtg tgcacgaacc cccgttcag     3180
cccgaccgct gcgccttatc cggtaactat cgtcttgagt ccaacccggt aagacacgac    3240
ttatcgccac tggcagcagc cactggtaac aggattagca gagcgaggta tgtaggcggt    3300
gctacagagt tcttgaagtg gtggcctaac tacggctaca ctagaagaac agtatttggt    3360
atctgcgctc tgctgaagcc agttaccttc ggaaaaagag ttggtagctc ttgatccggc    3420
aaacaaacca ccgctggtag cggtggtttt tttgtttgca agcagcagat tacgcgcaga    3480
aaaaaaggat ctcaagaaga tcctttgatc ttttctacgg ggtctgacgc tcagtggaac    3540
gaaaactcac gttaagggat tttggtcatg agattatcaa aaggatcttc acctagatc     3600
cttttaaatt aaaaatgaag ttttaaatca atctaaagta tatatgagta aacttggtct    3660
gacagttacc aatgcttaat cagtgaggca cctatctcag cgatctgtct atttcgttca    3720
tccatagttg cctgactccc cgtcgtgtag ataactacga tacgggaggg cttaccatct    3780
ggccccagtg ctgcaatgat accgcgagac ccacgctcac cggctccaga tttatcagca    3840
ataaccagc cagccggaag ggccgagcgc agaagtggtc ctgcaacttt atccgcctcc     3900
atccagtcta ttaattgttg ccgggaagct agagtaagta gttcgccagt taatagtttg    3960
cgcaacgttg ttgccattgc tacaggcatc gtggtgtcac gctcgtcgtt tggtatggct    4020
tcattcagct ccggttccca acgatcaagg cgagttacat gatccccat gttgtgcaaa     4080
aaagcggtta gctccttcgg tcctccgatc gttgtcagaa gtaagttggc cgcagtgtta    4140
tcactcatgg ttatggcagc actgcataat tctcttactg tcatgccatc cgtaagatgc    4200
ttttctgtga ctggtgagta ctcaaccaag tcattctgag aatagtgtat gcggcgaccg    4260
agttgctctt gcccggcgtc aatacgggat aataccgcgc cacatagcag aactttaaaa    4320
gtgctcatca ttggaaaacg ttcttcgggg cgaaaactct caaggatctt accgctgttg    4380
agatccagtt cgatgtaacc cactcgtgca cccaactgat cttcagcatc ttttactttc    4440
accagcgttt ctgggtgagc aaaaacagga aggcaaaatg ccgcaaaaaa gggaataagg    4500
gcgacacgga aatgttgaat actcatactc ttcctttttc aatattattg aagcatttat    4560
cagggttatt gtctcatgag cggatacata tttgaatgta tttagaaaaa taaacagcga    4620
tcgcgcggcc gcgggtaata actgatataa ttaaattgaa gctctaattt gtgagtttag    4680
```

```
tatacatgca tttacttata atacagtttt ttagttttgc tggccgcatc ttctcaaata   4740
tgcttcccag cctgctttc tgtaacgttc accctctacc ttagcatccc ttcccttgc    4800 aaatagtcct cttccaacaa taataatgtc agatcctgta gagaccacat catccacggt   4860
tctatactgt tgacccaatg cgtctccctt gtcatctaaa cccacaccgg gtgtcataat   4920
caaccaatcg taaccttcat ctcttccacc catgtctctt tgagcaataa agccgataac   4980
aaaatctttg tcgctcttcg caatgtcaac agtaccctta gtatattctc cagtagctag   5040
ggagcccttg catgacaatt ctgctaacat caaaaggcct ctaggttcct tgttacttc    5100 ttccgccgcc tgcttcaaac cgctaacaat acctgggccc accacaccgt gtgcattcgt   5160
aatgtctgcc cattctgcta ttctgtatac acccgcagag tactgcaatt tgactgtatt   5220
accaatgtca gcaaattttc tgtcttcgaa gagtaaaaaa ttgtacttgg cggataatgc   5280
ctttagcggc ttaactgtgc cctccatgga aaaatcagtc aagatatcca catgtgtttt   5340
tagtaaacaa attttgggac ctaatgcttc aactaactcc agtaattcct tggtggtacg   5400
aacatccaat gaagcacaca agtttgtttg ctttttcgtgc atgatattaa atagcttggc   5460
agcaacagga ctaggatgag tagcagcacg ttccttatat gtagctttcg acatgattta   5520
tcttcgtttc ctgcaggttt ttgttctgtg cagttgggtt aagaatactg ggcaatttca   5580 tgttcttca acaccacata tgcgtatata taccaatcta agtctgtgct ccttccttcg    5640
ttcttccttc tgctcggaga ttaccgaatc aaagctagct tatcgatgat aagctgtcaa   5700
agatgagaat taattccacg gactatagac tatactagat actccgtcta ctgtacgata   5760
cacttccgct caggtccttg tcctttaacg aggccttacc actcttttgt tactctattg   5820
atccagctca gcaaaggcag tgtgatctaa gattctatct tcgcgatgta gtaaaactag   5880
ctagaccgag aaagagacta gaaatgcaaa aggcacttct acaatggctg ccatcattat   5940
tatccgatgt gacgctgcag cttctcaatg atattcgaat acgctttgag gagatacagc   6000
ctaatatccg acaaactgtt ttacagattt acgatcgtac ttgttaccca tcattgaatt   6060
ttgaacatcc gaacctggga gttttccctg aaacagatag tatatttgaa cctgtataat   6120
aatatatagt ctagcgcttt acggaagaca atgtatgtat ttcggttcct ggagaaacta   6180
ttgcatctat tgcataggta atcttgcacg tcgcatcccc ggttcatttt ctgcgtttcc   6240
atcttgcact tcaatagcat atctttgtta acgaagcatc tgtgcttcat tttgtagaac   6300
aaaaatgcaa cgcgagagcg ctaattttc aaacaaagaa tctgagctgc atttttacag    6360
aacagaaatg caacgcgaaa gcgctatttt accaacgaag aatctgtgct tcattttgt    6420 aaaacaaaaa tgcaacgcga cgagagcgct aattttcaa acaaagaatc tgagctgcat    6480
ttttacagaa cagaaatgca acgcgagagc gctattttac caacaaagaa tctatacttc   6540 tttttgttc tacaaaaatg catcccgaga gcgctatttt tctaacaaag catcttagat    6600 tactttttt ctcctttgtg cgctctataa tgcagtctct tgataacttt ttgcactgta    6660
ggtccgttaa ggttagaaga aggctacttt ggtgtctatt ttctcttcca taaaaaaagc   6720
ctgactccac ttcccgcgtt tactgattac tagcgaagct gcgggtgcat ttttcaaga    6780 taaaggcatc cccgattata ttctataccg atgtggattg cgcatacttt gtgaacagaa   6840
agtgatagcg ttgatgattc ttcattggtc agaaaattat gaacggtttc ttctattttg   6900
tctctatata ctacgtatag gaaatgttta cattttcgta ttgttttcga ttcactctat   6960
gaatagttct tactacaatt ttttgtcta aagagtaata ctagagataa acataaaaaa    7020
```

<210> SEQ ID NO 85
<211> LENGTH: 7925
<212> TYPE: DNA
<213> ORGANISM: Artificial Sequence
<220> FEATURE:
<223> OTHER INFORMATION: Synthetic Nucleic Acid

<400> SEQUENCE: 85

```
tgtagaggtc gagtttagat gcaagttcaa ggagcgaaag gtggatgggt aggttatata    7080
gggatatagc acagagatat atagcaaaga gatactttg agcaat                    7126 gtttgtggaa gcggtattcg caatttaatt aaagctggtg acaattaatc atcggctcgt      60
ataatgtgtg gaattgaatc gatataagga ggttaatcat gtgaccgtcg ccggcaggat    120
cactgacgcg gtacgcatag gaaatggact tgaccagcga gatctagccc ccgtcgggtg    180
gtacgcacac gaacaggccg tggcgcgact gaaggccagt tcgacgcgg tccccgccgg     240 gcgtcgcgtg cggctggcga agaagacgtc caaccttttc cgcgggcgtt ccggcgaggc    300
agtcgggctc gacgtgtcgg ggctgcacgg cgtcatcgcc gtcgaccccg ttgagggcac    360
cgctgacgtc cagggcatgt gcacgtacga ggacctggtg gacgtcctgc tgccctacgg    420
tctggcgccc accgtcgttc gcagctgaa gaccatcact ctcggcggtg cggtgaccgg     480
catgggggtg gaatccacct ccttccgcaa cggcctgccg cacgaagccg tcctggaaat    540
ggatgtgctc accggtaccg gagacatcct cacctgttcg ccgacccaga acaccgacct    600
ctaccgcggc ttccccaact cctacggttc cctgggatac agcgtgcggc tgaaggtgcg    660
gtgcgaacgg gtggaaccct acgtcgacct gcggcatgta cgcttcgatg acgttcagtc    720
gctcaccgac gccctcgaca acatcgtcgt ggacaaggag tacgagggtg aacgggtcga    780
ctatctcgac ggtgtggtct tcagcctgga ggagagctac ctcgtcctgg acgggcgac     840 cagcgaggcc ggccccgtta gcgactacac ccgcgagcgc agttactacc gttctctgca    900
gcatccgtcg ggggtcctgc gcgacaagtt gaccatccgc gactacctct ggcggtggga    960
cgtcgactgg ttctggtgca accgggcctt cggtacccag aaccccacca tccgtactct    1020
gtggccgcgg gatctcctgc ggtcgagctt ctactggaag atcatcggct gggaccgacg    1080
cttcgacatc gcggaccgga tcgaggcaca aacgggcgc cccgcacgcg agcgcgtcgt     1140
ccaggacatc gaggtcaccc ccgacaacct gccggagttc ctcacgtggt tcttcaccca    1200
ctgcgagatc gagccggtgt ggctgtgccc cattcgactg gccgacgact cgggcgagcg    1260
gacaccgtgg cccctgtacc cgctgtcacc cggcgacacc tgggtcaacg tgggattctg    1320
gagctcggtg cccgccgacc tgatggggaa ggacgccccg accggagcct tcaaccggga    1380
ggtggagaga gtcgtctcgg acctcggcgg acacaagtcg ttgtactccg aggcattcta    1440
ttctgaggaa cagttcgccg ccctctacgg cggtgaacgt cccgcacaac tcaaggcggt    1500
cttcgacccg gatgaccggt tccccgggtt gtacgagaag accgtgggcg gcgtctgacg    1560
acacgcacga cgacgcacac cgagcacgat gacgcacgac aagcacgatg acgcatgatg    1620
accaagagga gagagatgag caggggattc acgccgctga cggtgggaca gatcgtggac    1680
aaggtcatca caccgccggc accgttccgg gtgaccgctt tcgacggatc caccgcgggg    1740
ccggcagacg cggaactggc actggagatc acatcgccgg acgccctggc ctatatcgtg    1800
accgcgccgg cgacctcgg actggcacgc gcctacatca ccggaagcct ccgcgtcacc    1860
ggtgacgagc ccgccaccc gtacctcgtc tttgaccacc tccagcacct ttacgaccag    1920
atccgacgcc cctcggcgaa ggacctgctg gatatcgccc gctcgctgaa ggccatgggg    1980
```

```
gcgatcaagg tgcagccggc accggagcag gagaccctcc cgggctggaa gagggccata    2040 ctcgagggc tgtcccggca ctctccggaa cgggacaagg aggtcgtgag ccgccactac    2100
gacgtgggca atgacttcta cgagctcttc ctcggcgatt ccatggccta cacctgtgcc    2160
tactatcccg agtttgacgg tgagaaccag gtcaccggtc ccaccggcgg gtggcggtac    2220
gacgactggg agaaagggcc gaccgccaac gggccgttga cccaggcgca ggacaacaag    2280
catcgcctgg tcttcgacaa gctgcgactc aacccgggtg accggttgtt ggacgtcggc    2340
tgcgggtggg gcggtatggt gcggtacgcc gcccgccacg gcgtgaaggc catcggtgtc    2400
acgctgtccc gagagcagta cgagtggggt aaggcgaaga tcgaggagga gggtctgcag    2460
gacctcgccg aggtccggtg tatggactac cgtgacgtgc cggagtccga cttcgacgcg    2520
gtcagtgcca tcggcatcct cgagcacatc ggcgtgccca actacgagga ctacttcacc    2580
cgcctgttcg ccaagctgcg cccgggcggt cggatgctga accactgcat cacccgtccg    2640
cacaaccgga gacgaagac cggccagttc atcgaccgct acatcttccc cgacggtgag    2700
ctgaccggct cgggccggat catcacgatc atgcaggaca ccggattcga cgtcgtccac    2760
gaggagaatc tgcgaccgca ctaccagcgc acgttgcatg actggtgtga actgttggcc    2820
accaactggg accaggccgt ccatctcgtg ggcgaggaga cggctcgtct gttcggcctg    2880
tacatgcggg gtcggaatg gggtttcgaa cacaacgtga tccagctcca ccaggttctc    2940
ggcgtgaagc cggacgcggc aggcagttcc ggggtgccgg tccgccagtg gtggaggtcc    3000
tgacggtaac gtcgggacga tgagacggat caccagaggc gctgcggtgg cggtgctgtg    3060
cacaccgttg ctgctcggag cctgcaccat cggcgacgcg gaccgggggg acgagaccac    3120
ggaccctgtc gtggacactg aagcaccgcc cgataaaccg gtgccggact ctgcggcgga    3180
atccggcgct gaagacggac ctgattctga ggtgccggac gaccccgacc agcctgatgc    3240
tgagccggtg gagactgatc ccgacgcccc gggggcccgg ggactggcga tcggtgactg    3300
cgtcgccgac atggaccagc tcgacggcac cggcgacatc gacgtcgtcg actgcgccgg    3360
cccccatgcc ggcgaggtgt acgcacaggc ggatatcgca ggtaagaacc tgttccccgg    3420
caacgagccg ttggggcagg aggcgggagc gatctgcggg ggtgactcct tcaccggcta    3480
tgtcggcatc ggattccccg agtcctcgct ggacgtcgtc acgatgatgc cgtccaagga    3540
gagctgggcg caggaggacc ggacggtgac ctgtgtggtc accgacccga acctcgagca    3600
gatcgccggc acgctcgagc agagctggcg ttagcctcaa aatatatttt ccctctatct    3660
tctcgttgcg cttaatttga ctaattctca ttagcgaggc gcgcctttcc ataggctccg    3720
cccccctgac gagcatcaca aaaatcgacg ctcaagtcag aggtggcgaa acccgacagg    3780
actataaaga taccaggcgt ttccccctgg aagctccctc gtgcgctctc ctgttccgac    3840
cctgccgctt accggatacc tgtccgcctt ctcccttcg ggaagcgtgg cgctttctca    3900
tagctcacgc tgtaggtatc tcagttcggt gtaggtcgtt cgctccaagc tgggctgtgt    3960
gcacgaaccc cccgttcagc ccgaccgctg cgccttatcc ggtaactatc gtcttgagtc    4020
caacccggta agacacgact tatcgccact ggcagcagcc actggtaaca ggattagcag    4080
agcgaggtat gtaggcggtg ctacagagtt cttgaagtgg tggcctaact acggctacac    4140
tagaagaaca gtatttggta tctgcgctct gctgaagcca gttaccttcg gaaaaagagt    4200
tggtagctct tgatccggca aacaaaccac cgctggtagc ggtggttttt ttgtttgcaa    4260
gcagcagatt acgcgcagaa aaaaaggatc tcaagaagat cctttgatct tttctacggg    4320
```

```
gtctgacgct cagtggaacg aaaactcacg ttaagggatt ttggtcatga gattatcaaa    4380
aaggatcttc acctagatcc tttaaatta aaaatgaagt tttaaatcaa tctaaagtat     4440
atatgagtaa acttggtctg acagttacca atgcttaatc agtgaggcac ctatctcagc    4500
gatctgtcta tttcgttcat ccatagttgc ctgactcccc gtcgtgtaga taactacgat    4560
acgggagggc ttaccatctg gccccagtgc tgcaatgata ccgcgagacc cacgctcacc    4620
ggctccagat ttatcagcaa taaaccagcc agccggaagg gccgagcgca gaagtggtcc    4680
tgcaacttta tccgcctcca tccagtctat taattgttgc cgggaagcta gagtaagtag    4740
ttcgccagtt aatagtttgc gcaacgttgt tgccattgct acaggcatcg tggtgtcacg    4800
ctcgtcgttt ggtatggctt cattcagctc cggttcccaa cgatcaaggc gagttacatg    4860 atccccatg ttgtgcaaaa aagcggttag ctccttcggt cctccgatcg ttgtcagaag     4920
taagttggcc gcagtgttat cactcatggt tatggcagca ctgcataatt ctcttactgt    4980
catgccatcc gtaagatgct tttctgtgac tggtgagtac tcaaccaagt cattctgaga    5040
atagtgtatg cggcgaccga gttgctcttg cccggcgtca atacgggata taccgcgcc     5100 acatagcaga actttaaaag tgctcatcat tggaaaacgt tcttcggggc gaaaactctc    5160
aaggatctta ccgctgttga tccagttc gatgtaaccc actcgtgcac ccaactgatc      5220
ttcagcatct tttactttca ccagcgtttc tgggtgagca aaaacaggaa ggcaaaatgc    5280
cgcaaaaaag gaataagggc gacacggaaa atgttgaata ctcatactct tcctttttca    5340
atattattga agcatttatc agggttattg tctcatgagc ggatacatat ttgaatgtat    5400
ttagaaaaat aaacagcgat cgcgcggccg cgggtaataa ctgatataat taaattgaag    5460
ctctaatttg tgagtttagt atacatgcat ttacttataa tacagttttt tagttttgct    5520
ggccgcatct tctcaaatat gcttcccagc ctgcttttct gtaacgttca ccctctacct    5580
tagcatccct tccctttgca aatagtcctc ttccaacaat aataatgtca gatcctgtag    5640
agaccacatc atccacggtt ctatactgtt gacccaatgc gtctcccttg tcatctaaac    5700
ccacaccggg tgtcataatc aaccaatcgt aaccttcatc tcttccaccc atgtctcttt    5760
gagcaataaa gccgataaca aaatctttgt cgctcttcgc aatgtcaaca gtaccccttag   5820 tatattctcc agtagctagg gagcccttgc atgacaattc tgctaacatc aaaaggcctc    5880
taggttcctt tgttacttct tccgccgcct gcttcaaacc gctaacaata cctgggccca    5940
ccacaccgtg tgcattcgta atgtctgccc attctgctat tctgtataca cccgcagagt    6000
actgcaattt gactgtatta ccaatgtcag caaattttct gtcttcgaag agtaaaaaat    6060
tgtacttggc ggataatgcc tttagcggct taactgtgcc ctccatggaa aaatcagtca    6120
agatatccac atgtgttttt agtaaacaaa ttttgggacc taatgcttca actaactcca    6180
gtaattcctt ggtggtacga acatccaatg aagcacacaa gtttgtttgc tttcgtgca    6240 tgatattaaa tagcttggca gcaacaggac taggatgagt agcagcacgt tccttatatg    6300
tagctttcga catgatttat cttcgtttcc tgcaggtttt tgttctgtgc agttgggtta    6360
agaatactgg gcaatttcat gtttcttcaa caccacatat gcgtatatat accaatctaa    6420
gtctgtgctc cttccttcgt tcttccttct gctcggagat taccgaatca aagctagctt    6480
atcgatgata agctgtcaaa gatgagaatt aattccacgg actatagact atactagata    6540
ctccgtctac tgtacgatac acttccgctc aggtccttgt cctttaacga ggccttacca    6600
ctcttttgtt actctattga tccagctcag caaaggcagt gtgatctaag attctatctt    6660
cgcgatgtag taaaactagc tagaccgaga aagagactag aaatgcaaaa ggcacttcta    6720
```

```
caatggctgc catcattatt atccgatgtg acgctgcagc ttctcaatga tattcgaata    6780
cgctttgagg agatacagcc taatatccga caaactgttt tacagattta cgatcgtact    6840
tgttacccat cattgaattt tgaacatccg aacctgggag ttttccctga aacagatagt    6900
atatttgaac ctgtataata atatatagtc tagcgcttta cggaagacaa tgtatgtatt    6960
tcggttcctg gagaaactat tgcatctatt gcataggtaa tcttgcacgt cgcatccccg    7020
gttcattttc tgcgtttcca tcttgcactt caatagcata tctttgttaa cgaagcatct    7080
gtgcttcatt ttgtagaaca aaatgcaac gcgagagcgc taatttttca aacaaagaat    7140
ctgagctgca tttttacaga acagaaatgc aacgcgaaag cgctatttta ccaacgaaga    7200
atctgtgctt cattttttgta aaacaaaaat gcaacgcgac gagagcgcta attttttcaaa   7260 caaagaatct gagctgcatt tttacagaac agaaatgcaa cgcgagagcg ctatttttacc   7320 aacaaagaat ctatacttct tttttgttct acaaaaatgc atcccgagag cgctattttt    7380
ctaacaaagc atcttagatt acttttttttc tcctttgtgc gctctataat gcagtctctt   7440 gataacttttt tgcactgtag gtccgttaag gttagaagaa ggctactttg gtgtctatttt   7500 tctcttccat aaaaaaagcc tgactccact tcccgcgttt actgattact agcgaagctg    7560
cgggtgcatt ttttcaagat aaaggcatcc ccgattatat tctataccga tgtggattgc    7620
gcatactttg tgaacagaaa gtgatagcgt tgatgattct tcattggtca gaaaattatg    7680
aacggtttct tctattttgt ctctatatac tacgtatagg aaatgtttac attttcgtat    7740
tgttttcgat tcactctatg aatagttctt actacaattt ttttgtctaa agagtaaatac   7800 tagagataaa cataaaaaat gtagaggtcg agtttagatg caagttcaag gagcgaaagg    7860
tggatgggta ggttatatag ggatatagca cagagatata tagcaaagag atactttga    7920 gcaat                                                                  7925
```

<210> SEQ ID NO 86
<211> LENGTH: 7141
<212> TYPE: DNA
<213> ORGANISM: Artificial Sequence
<220> FEATURE:
<223> OTHER INFORMATION: Synthetic Nucleic Acid

<400> SEQUENCE: 86

```
gtttgtggaa gcggtattcg caatttaatt aaagctggtg acaattaatc atcggctcgt     60
ataatgtgtg gaattgaatc gatataagga ggttaatcat atgcgggagg gtggacgccc    120
cttccgtgcg catcgcactc tgcccgtcac cgggatcgac gctcaccgcg ccggcgtcga    180
acggcttctc gcgtcctacc gcgcgattcc cacggacgcc accgtgcgac tcgcgaagaa    240
gacgtccaac ctgttccggg gcggggccca gaccagcgca cccggcctcg acgtctccgg    300
gctcggcgga gtcatctcgg tcgacgagca ggaccggacc gcggatgtcg ccggaatgtg    360
cacgtacgaa gacctggtgg acgccaccct cccgtacggg ctggcgccgc tggtggttcc    420
gcaactcaag accatcacac tcggcggcgc ggtcaccggc ctcggcatcg agtcgacgtc    480
gttccgcaac gggctccccc acgaatcggt cctcgagatc gacgtcctga ccggaagcgg    540
cgacatcgtc accgcgagac cggaaggcga gaactccgac ctgttctggg ggttccccaa    600
ctcctacgga accctcggct actccacccg actgcgcatc cagctcgaac ccgtcaaacg    660
gtatgtggca ctgcgccatc tgcgtttcga ctccctggac gagctgcagt cggcaatgga    720
tcgcatcgtc accgagcgcg tccacgacgg catccccgtc gactatctgg acggcgtcgt    780
```

| | |
|---|---|
| gttcaccgcg tccgagagtt acctgacact gggccatcag accgacgagg gcggccccgt | 840 |
| cagcgactac accgggcaga acatcttcta ccggtccatc cagcacagtt ccgtgaacca | 900 |
| ccccaaaacg acaaactca ccatccgaga ctacctgtgg cgctgggaca ccgactggtt | 960 |
| ctggtgctcg cgcgccttcg gcgcccagaa ccccaccatc cgccggctgt ggccgaagaa | 1020 |
| cctcctccgc agcagcttct actggaagct catcgccctc gaccacaagt acgacatcgg | 1080 |
| cgaccgactc gagaagcgca agggcaaccc gccacgcgaa cgcgtcgtgc aggacgtcga | 1140 |
| agtgcccatc gagcgcaccg cggacttcgt ccgctggttc ctcgacgaaa tcccgatcga | 1200 |
| accgctgtgg ctgtgcccgt tgcggttgcg ggaacctgcc ccgccggcg cgtcctcgca | 1260 |
| acgcccctgg cccctgtacc ccctcgaacc gaaacgcacg tacgtgaaca tcggattctg | 1320 |
| gtcatcggtg cccatcgttc cgggccgacc cgaggggggcc gcgaatcggc tgatcgaaga | 1380 |
| caaggtcagt gacttcgacg acacaagtc cctctactcc gattcgtact attcacgcga | 1440 |
| agatttcgaa cgcctctact acggcggcga tcgatacacg gaactgaaaa aacgctacga | 1500 |
| cccgaaatca cgattactgg accttttctc caaggcggtg caacgtcgat gacaactctg | 1560 |
| aaagcttcac gctcccagga ccacaagctg accatcgcag agattctcga aactctgtcc | 1620 |
| gacggcatgc tcccctgcg gttctccgcc tacgacggca gcgccgccgg cccggaggac | 1680 |
| gcccctacg gtctccacct caagacgacc cgaggcacca cctacctggc gaccgccccc | 1740 |
| ggcgacctcg gcatgcccg ggcctacgtg tccggcgacc tcgaggcccg cggcgtccac | 1800 |
| cccggcgacc cgtacgagat cctccgcgtg atgggcgacg aactgcactt ccgccgtccg | 1860 |
| tccgcgctca cgctcgccgc catcacgcgc tcgctcggct gggatctgct cgcccccatc | 1920 |
| gcccctcccc cgcaggagca tctcccgcgg tggcgtcgag tcgcggaagg gttgcggcac | 1980 |
| tccaagtccc gcgacgccga ggtcatccac caccactacg acgtctcgaa caccttctac | 2040 |
| gagtatgtcc tcggcccgtc catgacgtac acgtgcgcct gctacgagaa cgccgagcag | 2100 |
| accctcgaag aggcacagga caacaagtac cgcctcgtct tcgagaagct cggcctccag | 2160 |
| cccggcgacc gactgctcga catcggttgc ggctggggat cgatggtccg gtacgccgcc | 2220 |
| cgccgcggcg tcaaggtcat cggcgccacc ctgtcccgag agcaggccga atgggcacag | 2280 |
| aaggccatcg ccgaagaagg actgtccgac ctcgccgagg tccggttctc cgactaccgt | 2340 |
| gacgtccccg agaccggatt cgacgccatc tcctcgatcg gcctgaccga gcacatcggc | 2400 |
| gtcggcaact accccgccta cttcggactg ctgcagagca agctccgcga gggcggccgg | 2460 |
| ctgctgaacc actgcatcac ccggcccgac aaccagagtc aggcacgcgc gggcggcttc | 2520 |
| atcgaccggt acgtcttccc cgacggcgaa ctcaccggct ccggacgcat catcaccgag | 2580 |
| atccagaact cggactcga ggtgcggcac gaggagaatc tgcgcgagca ctacgcactc | 2640 |
| accctcgccg gctggtgcca gaacctcgtc gacaactggg acgcctgcgt cgccgaggtc | 2700 |
| ggcgaaggca ccgcacgtgt gtggggtctc tacatggccg ggtcgcgact gggcttcgaa | 2760 |
| cgcaacgtcg ttcagctgca ccaggtcctc gccgtcaagc tcggacccaa gggcgaggcg | 2820 |
| catgtgccgc tgcgtccgtg gtggaagtag cctcaaaata tatttttccct ctatcttctc | 2880 |
| gttgcgctta atttgactaa ttctcattag cgaggcgcgc cttttccatag gctccgcccc | 2940 |
| cctgacgagc atcacaaaaa tcgacgctca agtcagaggt ggcgaaaccc gacaggacta | 3000 |
| taaagatacc aggcgtttcc ccctggaagc tccctcgtgc gctctcctgt tccgaccctg | 3060 |
| ccgcttaccg gatacctgtc cgcctttctc ccttcgggaa gcgtggcgct ttctcatagc | 3120 |
| tcacgctgta ggtatctcag ttcggtgtag gtcgttcgct ccaagctggg ctgtgtgcac | 3180 |

```
gaaccccccg ttcagcccga ccgctgcgcc ttatccggta actatcgtct tgagtccaac    3240
ccggtaagac acgacttatc gccactggca gcagccactg gtaacaggat tagcagagcg    3300
aggtatgtag gcggtgctac agagttcttg aagtggtggc ctaactacgg ctacactaga    3360
agaacagtat ttggtatctg cgctctgctg aagccagtta ccttcggaaa aagagttggt    3420
agctcttgat ccggcaaaca aaccaccgct ggtagcggtg gtttttttgt ttgcaagcag    3480
cagattacgc gcagaaaaaa aggatctcaa gaagatcctt tgatcttttc tacgggtct    3540 gacgctcagt ggaacgaaaa ctcacgttaa gggattttgg tcatgagatt atcaaaaagg    3600
atcttcacct agatcctttt aaattaaaaa tgaagtttta atcaatcta aagtatatat    3660 gagtaaactt ggtctgacag ttaccaatgc ttaatcagtg aggcacctat ctcagcgatc    3720
tgtctatttc gttcatccat agttgcctga ctccccgtcg tgtagataac tacgatacgg    3780
gagggcttac catctggccc cagtgctgca atgataccgc gagacccacg ctcaccggct    3840
ccagatttat cagcaataaa ccagccagcc ggaagggccg agcgcagaag tggtcctgca    3900
actttatccg cctccatcca gtctattaat tgttgccggg aagctagagt aagtagttcg    3960
ccagttaata gtttgcgcaa cgttgttgcc attgctacag gcatcgtggt gtcacgctcg    4020
tcgtttggta tggcttcatt cagctccggt tcccaacgat caaggcgagt tacatgatcc    4080
cccatgttgt gcaaaaaagc ggttagctcc ttcggtcctc cgatcgttgt cagaagtaag    4140
ttggccgcag tgttatcact catggttatg gcagcactgc ataattctct tactgtcatg    4200
ccatccgtaa gatgcttttc tgtgactggt gagtactcaa ccaagtcatt ctgagaatag    4260
tgtatgcggc gaccgagttg ctcttgcccg gcgtcaatac gggataatac cgcgccacat    4320
agcagaactt taaaagtgct catcattgga aaacgttctt cggggcgaaa actctcaagg    4380
atcttaccgc tgttgagatc cagttcgatg taacccactc gtgcacccaa ctgatcttca    4440
gcatctttta ctttcaccag cgtttctggg tgagcaaaaa caggaaggca aaatgccgca    4500
aaaaagggaa taagggcgac acggaaatgt tgaatactca tactcttcct ttttcaatat    4560
tattgaagca tttatcaggg ttattgtctc atgagcggat acatatttga atgtatttag    4620
aaaaataaac agcgatcgcg cggccgcggg taataactga tataattaaa ttgaagctct    4680
aatttgtgag tttagtatac atgcatttac ttataataca gttttttagt tttgctggcc    4740
gcatcttctc aaatatgctt cccagcctgc ttttctgtaa cgttcaccct ctaccttagc    4800
atcccttccc tttgcaaata gtcctcttcc aacaataata atgtcagatc ctgtagagac    4860
cacatcatcc acggttctat actgttgacc caatgcgtct cccttgtcat ctaaacccac    4920
accgggtgtc ataatcaacc aatcgtaacc ttcatctctt ccacccatgt ctctttgagc    4980
aataaagccg ataacaaaat ctttgtcgct cttcgcaatg tcaacagtac ccttagtata    5040
ttctccagta gctagggagc ccttgcatga caattctgct aacatcaaaa ggcctctagg    5100
ttcctttgtt acttcttccg ccgcctgctt caaaccgcta acaatacctg gcccaccac    5160 accgtgtgca ttcgtaatgt ctgcccattc tgctattctg tatacacccg cagagtactg    5220
caatttgact gtattaccaa tgtcagcaaa ttttctgtct tcgaagagta aaaaattgta    5280
cttggcggat aatgccttta gcggcttaac tgtgccctcc atggaaaaat cagtcaagat    5340
atccacatgt gttttagta aacaaatttt gggacctaat gcttcaacta actccagtaa    5400
ttccttggtg gtacgaacat ccaatgaagc acacaagttt gtttgctttt cgtgcatgat    5460
attaaatagc ttggcagcaa caggactagg atgagtagca gcacgttcct tatatgtagc    5520
```

```
tttcgacatg atttatcttc gtttcctgca ggttttttgtt ctgtgcagtt gggttaagaa    5580
tactgggcaa tttcatgttt cttcaacacc acatatgcgt atatatacca atctaagtct    5640
gtgctccttc cttcgttctt ccttctgctc ggagattacc gaatcaaagc tagcttatcg    5700
atgataagct gtcaaagatg agaattaatt ccacggacta tagactatac tagatactcc    5760
gtctactgta cgatacactt ccgctcaggt ccttgtcctt taacgaggcc ttaccactct    5820
tttgttactc tattgatcca gctcagcaaa ggcagtgtga tctaagattc tatcttcgcg    5880
atgtagtaaa actagctaga ccgagaaaga gactagaaat gcaaaggca cttctacaat     5940 ggctgccatc attattatcc gatgtgacgc tgcagcttct caatgatatt cgaatacgct    6000
ttgaggagat acagcctaat atccgacaaa ctgttttaca gatttacgat cgtacttgtt    6060
acccatcatt gaattttgaa catccgaacc tgggagtttt ccctgaaaca gatagtatat    6120
ttgaacctgt ataataatat atagtctagc gctttacgga agacaatgta tgtatttcgg    6180
ttcctggaga aactattgca tctattgcat aggtaatctt gcacgtcgca tccccggttc    6240
attttctgcg tttccatctt gcacttcaat agcatatctt tgttaacgaa gcatctgtgc    6300
ttcattttgt agaacaaaaa tgcaacgcga gagcgctaat ttttcaaaca aagaatctga    6360
gctgcatttt tacagaacag aaatgcaacg cgaaagcgct attttaccaa cgaagaatct    6420
gtgcttcatt tttgtaaaac aaaaatgcaa cgcgacgaga gcgctaattt ttcaaacaaa    6480
gaatctgagc tgcattttta cagaacgaaa atgcaacgcg agagcgctat tttaccaaca    6540
aagaatctat acttcttttt tgttctacaa aaatgcatcc gagagcgct atttttctaa     6600 caaagcatct tagattactt ttttttctcct ttgtgcgctc tataatgcag tctcttgata   6660 acttttttgca ctgtaggtcc gttaaggtta gaagaaggct actttggtgt ctattttctc   6720
ttccataaaa aaagcctgac tccacttccc gcgtttactg attactagcg aagctgcggg    6780 tgcattttt caagataaag gcatccccga ttatattcta taccgatgtg gattgcgcat     6840
actttgtgaa cagaaagtga tagcgttgat gattcttcat tggtcagaaa attatgaacg    6900
gtttcttcta ttttgtctct atatactacg tataggaaat gtttacattt tcgtattgtt    6960
ttcgattcac tctatgaata gttcttacta cattttttttt gtctaaagag taatactaga   7020
gataaacata aaaaatgtag aggtcgagtt tagatgcaag ttcaaggagc gaaaggtgga    7080
tgggtaggtt atatagggat atagcacaga gatatatagc aaagagatac ttttgagcaa    7140
t                                                                    7141
```

<210> SEQ ID NO 87
<211> LENGTH: 7588
<212> TYPE: DNA
<213> ORGANISM: Artificial Sequence
<220> FEATURE:
<223> OTHER INFORMATION: Synthetic Nucleic Acid

<400> SEQUENCE: 87

```
gtttgtggaa gcggtattcg caatttaatt aaagctggtg acaattaatc atcggctcgt      60
ataatgtgtg gaattgaatc gatataagga ggttaatcat gtgaactgtc agtcttccgc     120
gtccaacctc gccaaccaca tcaacgcggt gtacagctg cgccgcgcct atgcgcggct      180
gtccgccgac aagccggtgc gcctggcgaa gaccacctcc aacctcttcc gcttccgcag    240
ccgggacgat gccgcgcgtc tcgacgtcag cgctttcacc tcggtgatca gcatcgacac    300
ggaggcgcgg gtcgcggagg tgggcggcat gaccacctac gaggacctgg tcgccgccac    360
cctgcggcat ggcctgatgc cgccggtggt tccgcaactg cgcacgatca ccctgggcgg    420
```

-continued

```
tgcggtcacc gggctgggga tcgaatcctc gtccttccgc aacgggctcc cgcacgagtc    480
agtggaagag atggagatcc tcaccggcag cggccaggtg gtggtggccc ggcgcgacaa    540
cgagcaccgc gacctgttct acggtttccc caactcgtac ggcaccctcg gttacgcgct    600
gcggctccgc atccagctcg aaccggtccg cccctacgtc cacctgcggc acctgcggtt    660
caccgatgcc gcagcggcca tggccgcgct ggagcagatc tgcgcggacc gcacccacga    720
cggggagacc gtcgacttcg tcgacggcgt cgtgttcgcc cgcaacgagc tgtacctgac    780
cttggggacg ttcaccgacc gggctccgtg gaccagcgac tacaccggaa ccgacatcta    840
ctaccggtcg atccccgct acgcgggccc cggccccggc gactacctca ccacgcacga    900
ctacctgtgg cggtgggaca ccgactggtt ctggtgctcc cgcgccttcg gactgcagca    960
tcccgtggtg cgccgcctgt ggccgcgttc cttgaaacgc tccgacgtct accgcaagct   1020
cgtcgcctgg gaccggcgca ctgacgcgag ccgcctgctc gactactacc gcgggcgccc   1080
gcccaaggaa ccggtgatcc aggacatcga ggttgaggtg gggcgggctg ccgagttcct   1140
cgacttcttc cacaccgaga tcggcatgtc cccggtgtgg ctgtgcccgc tgcggctgcg   1200
agaagacaca gccgacgata cggaaccggt ctggccgctc tacccctca aaccccgccg   1260 cctctacgtc aacttcgggt tttggggcct cgttccgatc cgtcccggtg gaggcaggac   1320
ataccacaac cggctgatcg aaaaagaagt gacccggttg gcggggcaca agtcgctcta   1380
ctcggacgcc ttctacgacg aggacgagtt ctgggagctc tacaacgggg agatctaccg   1440
caagctcaaa gctgcctacg accccgacgt cgactgctc gacctgtaca ccaagtgcgt   1500
cggcggcggg tgagaaagga tgagggatgc gactggcgga ggtattcgaa cgtgtcgtcg   1560
gacccgatgc gcccgtccac ttccgggcct acgacggcag cactgcggga gatccacgca   1620
gtgaagtcgc tatcgtggtt cgccacccgg cagccgtcaa ctacatcgtc caagcgccgg   1680
gagcactcgg tttgacccgc gcctacgtgg cgggataccct cgacgtcgaa ggggacatgt   1740
acaccgcgct gcgggcaatg gccgacgtgg tgttccagga ccggccgcgg ctgtcccccg   1800
gggaactgct gcggatcatc cgcgggatcg ggtgggtgaa gttcgtcaac cggcttccac   1860
cgccgccgca ggaggtgcgc cagtcccgcc tcgccgccct gggctggcgc cactccaagc   1920
agcgcgacgc cgaagccatc cagcaccact cgacgtctc caacgccttc tacgccctgg   1980
tcttgggcga gtcgatgacc tacacctgcg cggtctaccc gaccgagcag gccacgctgg   2040
agcaggcaca gttcttcaag cacgagctga tcgcccgcaa gctcggtctt gcccctggga   2100
tacgactgct ggatgtgggg tgcggctggg gcggcatggt catccacgcg gcccgggagc   2160
acggggtcaa agccctgggg gtgaccctgt ccaaagagca ggctgagtgg gcgcagaagc   2220
ggatcgccca cgagggcctg gcgacctggc agaagtccg gcacatggac taccgggacc   2280
tgcccgacgg cgagtacgac gcgatcagct cgatcgggtt gaccgagcac gtcggcaaaa   2340
agaacgtgcc cgcctacttc gcgtcgctgt accgcaagct cgtcccggga ggccgcctgc   2400
tcaaccactg catcacccgg ccccgcaacg acctgccgcc cttcaaacgc ggcggggtga   2460
tcaaccgcta cgtcttcccc gatggggagc tggaagggcc cggctggctg caggcggcga   2520
tgaacgacgc cgggttcgaa atccgccacc aggagaacct gcgggagcac tacgcacgga   2580
ccctgcggga ctggctggcc aacctggacc gcaactggga tgccgcggtg cgggaagtgg   2640
gggagggcac ggcccgagtg tggcggctct acatggccgg gtgcgtgctc ggcttcgaac   2700
gcaacgtggt gcaactgcac cagatcctcg gggtgaagct cgacgggacc gaggcgcgga   2760
```

```
tgccgctgcg ccccgacttc gaaccgccgc tgccttaacc gcggtgcaca gccgggggat   2820
atcagtcgcg gaaccgggca tgatgagccc atggctgcga ccgatgacga ccggcaccac   2880
accaccgtcg ccctcgacct catcgacgcg tatgtgcgcg ccgaccgcag aatgatcggt   2940
gaacgttccg cggggatcag cgcggaggcg ggggagcgga tcgtctccac cctgaaagtg   3000
tgcgcggcct tccttgcccg ccgggtccag gagaccgggg tgccgtggcg cgcagcggac   3060
tcccgggaag cggtcgcccg caccgtcgcc gacctgctgg aacccgaggt ggaattcgcg   3120
gtcgtctccg cctgggaggc gtacgcgatc ggggagcacg aggccgcctg gtccgggcg   3180 cacgcgatc cgctggtctt cgtccacatg ctggccgcgt tctccgctgc tatcggcaca   3240
gcggtctacg gccgtgagga gctgctgccc acgctgcgca gggtgacagc acgataacct   3300
caaaatatat tttccctcta tcttctcgtt gcgcttaatt tgactaattc tcattagcga   3360
ggcgcgcctt tccataggct ccgcccccct gacgagcatc acaaaaatcg acgctcaagt   3420
cagaggtggc gaaacccgac aggactataa agataccagg cgtttccccc tggaagctcc   3480
ctcgtgcgct ctcctgttcc gaccctgccg cttaccggat acctgtccgc ctttctccct   3540
tcgggaagcg tggcgctttc tcatagctca cgctgtaggt atctcagttc ggtgtaggtc   3600
gttcgctcca agctgggctg tgtgcacgaa ccccccgttc agcccgaccg ctgcgcctta   3660
tccggtaact atcgtcttga gtccaacccg gtaagacacg acttatcgcc actggcagca   3720
gccactggta acaggattag cagagcgagg tatgtaggcg gtgctacaga gttcttgaag   3780
tggtggccta actacggcta cactagaaga acagtatttg gtatctgcgc tctgctgaag   3840
ccagttacct tcggaaaaag agttggtagc tcttgatccg gcaaacaaac caccgctggt   3900
agcggtggtt ttttttgttg caagcagcag attacgcgca gaaaaaaagg atctcaagaa   3960
gatcctttga tcttttctac ggggtctgac gctcagtgga acgaaaactc acgttaaggg   4020
attttggtca tgagattatc aaaaaggatc ttcacctaga tccttttaaa ttaaaaatga   4080
agttttaaat caatctaaag tatatatgag taaacttggt ctgacagtta ccaatgctta   4140
atcagtgagg cacctatctc agcgatctgt ctatttcgtt catccatagt tgcctgactc   4200
cccgtcgtgt agataactac gatacgggag ggcttaccat ctggccccag tgctgcaatg   4260
ataccgcgag acccacgctc accggctcca gatttatcag caataaacca gccagccgga   4320
agggccgagc gcagaagtgg tcctgcaact ttatccgcct ccatccagtc tattaattgt   4380
tgccgggaag ctagagtaag tagttcgcca gttaatagtt tgcgcaacgt tgttgccatt   4440
gctacaggca tcgtggtgtc acgctcgtcg tttggtatgg cttcattcag ctccggttcc   4500
caacgatcaa ggcgagttac atgatccccc atgttgtgca aaaaagcggt tagctccttc   4560
ggtcctccga tcgttgtcag aagtaagttg gccgcagtgt tatcactcat ggttatggca   4620
gcactgcata attctcttac tgtcatgcca tccgtaagat gcttttctgt gactggtgag   4680
tactcaacca agtcattctg agaatagtgt atgcggcgac cgagttgctc ttgcccggcg   4740
tcaatacggg ataataccgc gccacatagc agaactttaa aagtgctcat cattggaaaa   4800
cgttcttcgg ggcgaaaact ctcaaggatc ttaccgctgt tgagatccag ttcgatgtaa   4860
cccactcgtg cacccaactg atcttcagca tcttttactt tcaccagcgt ttctgggtga   4920
gcaaaaacag gaaggcaaaa tgccgcaaaa aagggaataa gggcgacacg gaaatgttga   4980
atactcatac tcttcctttt tcaatattat tgaagcattt atcagggtta ttgtctcatg   5040
agcggataca tatttgaatg tatttagaaa aataaacagc gatcgcgcgg ccgcgggtaa   5100
taactgatat aattaaattg aagctctaat ttgtgagttt agtatacatg catttactta   5160
```

```
taatacagtt ttttagtttt gctggccgca tcttctcaaa tatgcttccc agcctgcttt      5220
tctgtaacgt tcaccctcta ccttagcatc ccttcccttt gcaaatagtc ctcttccaac      5280
aataataatg tcagatcctg tagagaccac atcatccacg gttctatact gttgacccaa      5340
tgcgtctccc ttgtcatcta aacccacacc gggtgtcata atcaaccaat cgtaaccttc      5400
atctcttcca cccatgtctc tttgagcaat aaagccgata acaaaatctt tgtcgctctt      5460
cgcaatgtca acagtaccct tagtatattc tccagtagct agggagccct tgcatgacaa      5520
ttctgctaac atcaaaaggc ctctaggttc ctttgttact tcttccgccg cctgcttcaa      5580
accgctaaca atacctgggc ccaccacacc gtgtgcattc gtaatgtctg cccattctgc      5640
tattctgtat acacccgcag agtactgcaa tttgactgta ttaccaatgt cagcaaattt      5700
tctgtcttcg aagagtaaaa aattgtactt ggcggataat gcctttagcg cttaactgt       5760 gccctccatg gaaaaatcag tcaagatatc cacatgtgtt tttagtaaac aaattttggg      5820
acctaatgct tcaactaact ccagtaattc cttggtggta cgaacatcca atgaagcaca      5880
caagtttgtt tgcttttcgt gcatgatatt aaatagcttg gcagcaacag gactaggatg      5940
agtagcagca cgttccttat atgtagcttt cgacatgatt tatcttcgtt tcctgcaggt      6000
ttttgttctg tgcagttggg ttaagaatac tgggcaattt catgtttctt caacaccaca      6060
tatgcgtata tataccaatc taagtctgtg ctccttcctt cgttcttcct tctgctcgga      6120
gattaccgaa tcaaagctag cttatcgatg ataagctgtc aaagatgaga attaattcca      6180
cggactatag actatactag atactccgtc tactgtacga tacacttccg ctcaggtcct      6240
tgtcctttaa cgaggcctta ccactctttt gttactctat tgatccagct cagcaaaggc      6300
agtgtgatct aagattctat cttcgcgatg tagtaaaact agctagaccg agaaagagac      6360
tagaaatgca aaaggcactt ctacaatggc tgccatcatt attatccgat gtgacgctgc      6420
agcttctcaa tgatattcga atacgctttg aggagataca gcctaatatc cgacaaactg      6480
ttttacagat ttacgatcgt acttgttacc catcattgaa ttttgaacat ccgaacctgg      6540
gagttttccc tgaaacagat agtatatttg aacctgtata ataatatata gtctagcgct      6600
ttacggaaga caatgtatgt atttcggttc ctggagaaac tattgcatct attgcatagg      6660
taatcttgca cgtcgcatcc ccggttcatt ttctgcgttt ccatcttgca cttcaatagc      6720
atatctttgt taacgaagca tctgtgcttc attttgtaga acaaaaatgc aacgcgagag      6780
cgctaatttt tcaaacaaag aatctgagct gcattttac agaacagaaa tgcaacgcga      6840
aagcgctatt ttaccaacga agaatctgtg cttcattttt gtaaacaaa atgcaacgc       6900 gacgagagcg ctaatttttc aaacaaagaa tctgagctgc attttacag aacagaaatg      6960 caacgcgaga gcgctatttt accaacaaag aatctatact tctttttgt tctacaaaaa       7020 tgcatcccga gagcgctatt tttctaacaa agcatcttag attactttt ttctcctttg       7080 tgcgctctat aatgcagtct cttgataact ttttgcactg taggtccgtt aaggttagaa      7140
gaaggctact ttggtgtcta ttttctcttc cataaaaaaa gcctgactcc acttcccgcg      7200
tttactgatt actagcgaag ctgcgggtgc atttttcaa gataaaggca tccccgatta       7260
tattctatac cgatgtggat tgcgcatact tgtgaacag aaagtgatag cgttgatgat       7320
tcttcattgg tcagaaaatt atgaacggtt tcttctattt tgtctctata tactacgtat      7380
aggaaatgtt tacattttcg tattgttttc gattcactct atgaatagtt cttactacaa      7440
tttttttgtc taaagagtaa tactagagat aaacataaaa aatgtagagg tcgagtttag      7500
```

-continued

| | |
|---|---|
| atgcaagttc aaggagcgaa aggtggatgg gtaggttata tagggatata gcacagagat | 7560 |
| atatagcaaa gagatacttt tgagcaat | 7588 |

<210> SEQ ID NO 88
<211> LENGTH: 7074
<212> TYPE: DNA
<213> ORGANISM: Artificial Sequence
<220> FEATURE:
<223> OTHER INFORMATION: Synthetic Nucleic Acid

<400> SEQUENCE: 88

| | |
|---|---|
| gtttgtggaa gcggtattcg caatttaatt aaagctggtg acaattaatc atcggctcgt | 60 |
| ataatgtgtg gaattgaatc gatataagga ggttaatcat atgtcacagc tggcggtcac | 120 |
| agaccaccac gagcgagcgg tcgaggcgct gcgcaggtcg tatgcggcga tcccgccggg | 180 |
| cacaccggtc cgcttggcca agcagacctc caacctgttc cgcttccgcg agccgacggc | 240 |
| cgcgcccggc ctggacgtgt ccggcttcaa ccgggtgctg gcggtggacc cggatgcgcg | 300 |
| caccgccgac gtgcagggca tgaccaccta cgaggacctg gtcgacgcca ccctgccgca | 360 |
| cgggctgatg ccgctggtgg tgccccagct caagacgatc acgctgggcg gggcggtgac | 420 |
| cggcctgggc atcgagtcca cctccttccg caacggcctg ccgcacgagt cggtgctgga | 480 |
| gatgcagatc atcaccggcg ccggcgaagt ggtcaccgcc accccggacg gggagcactc | 540 |
| cgacctgttc tggggcttcc ccaactccta cgggacgctg gggtacgccc tgaagctgaa | 600 |
| gatcgaactg gagccggtca agccgtacgt ccggctgcgg cacctgcgct cgacgacgc | 660 |
| cggcgagtgc gccgccaagc tcgccgagct gagcgaaagc cgcgagcacg agggcgatga | 720 |
| ggtgcacttt ttggacggca ccttcttcgg gccgcgcgag atgtacctga cgctcggcac | 780 |
| gttcaccgac accgccccct atgtgtcgga ctacaccggg cagcacatct actaccggtc | 840 |
| gatccagcag cggtcgatcg acttttttgac catccgcgac tacctgtggc gctgggacac | 900 |
| cgactggttc tggtgctcgc gcgccctggg cgtgcagaac ccgctgatcc ggcgggtgtg | 960 |
| gccgaagagc gccaagcggt cggatgtgta ccgcaagctg gtggcctacg aaaagcgcta | 1020 |
| ccagttcaag gcgcgcatcg accggtggac gggcaagccg ccgcgcgagg acgtcatcca | 1080 |
| ggacatcgag gtgccggcag aacgcctgcc ggagttcctg gagttcttcc acgacaagat | 1140 |
| cgggatgagc ccggtgtggc tgtgcccgct gcgggcgcgc accgctggcc gctgtaccc | 1200 |
| gctcaagccc ggcgtcacct acgtcaacgc cggcttctgg gggacggtgc gctgcagcc | 1260 |
| ggggcagatg cccgagtacc acaaccggct gatcgaacgg aaggtcgccc aactggacgg | 1320 |
| ccacaagtct ctgtactcga cggcgttcta ctcgcgtgag gagttctggc ggcactacga | 1380 |
| cggggaaacc taccggcgtc tgaaggacac ctacgacccc gacgcgcgcc tgctcgacct | 1440 |
| ctacgacaag tgcgtgcggg gacgctgacc ggggcggcgg cgatgaagac ccgcggggcg | 1500 |
| ggacggacag gagggaagcg atgacgctgg ccaaggtctt cgaggagctg gtcgggcgg | 1560 |
| acgcccctgt ggagctcacc gcctacgacg gatcgagagc cggacgcctg ggcagtgatc | 1620 |
| tgcgggtcca cgtgaagtcg ccgtacgcgg tgtcctacct ggtgcactcg ccgagcgcgc | 1680 |
| tcgggctggc ccgcgcgtac gtggccgggc acctggacgc ctacgcgac atgtacacgc | 1740 |
| tgctgcggga gatgacgcag ctgaccgagg cgctgacgcc caaggcccgg ctgcggctgc | 1800 |
| tggccggtgt cctgcaggat ccgctgctgc gcgcggcgcg cagccgccgt ctgccgcccc | 1860 |
| cgccgcagga ggtgcggacc ggccgcacct cctggttccg gcacaccaag cggcgggacg | 1920 |
| ccaaggccat ctcccaccac tacgacgtgt ccaacaccct ctatgagtgg gtgctgggcc | 1980 |

```
cgtcgatgac ctacacctgc gcctgtttcc ccaccgagga cgccaccttg gaggaggcgc    2040
agttccacaa gcacgacctg gtcgccaaga agctcgggct gcggccgggc atgcggctgc    2100
tggacgtggg ctgcggctgg ggcggcatgg tgatgcacgc cgccaagcac tacggggtgc    2160
gggcgctggg cgtcacgctg tccaagcagc aggccgagtg ggcgcagaag gccatcgccg    2220
aggcgggcct gagcgacctg gccgaggtcc gccaccagga ctaccgggac gtcaccgagg    2280
gcgacttcga cgccatcagc tcgatcggcc tcaccgagca catcggcaag gccaacctgc    2340
cgtcctactt cggcttcctg tacggcaagc tcaagcccgg cgggcggctg ctcaaccact    2400
gcatcacccg gcccgacaac acccagccgg ccatgaagaa ggacgggttc atcaaccggt    2460
acgtcttccc cgacggggag ctggaggggc ccggctacct gcagacccag atgaacgacg    2520
ccggttttga gatccgccac caggagaacc tgcgcgagca ctacgcccgc accctggccg    2580
gatggtgccg caacctcgat gagcactggg acgaggcggt ggccgaggtc ggcgagggca    2640
ccgcgcgggt gtggcggctg tacatggccg gcagccggcc cggtttcgag ctcaactgga    2700
tccagctgca ccagatcctg ggcgtcaagc tcggcgagcg cggcgagtcc cgcatgccgt    2760
tgcggcccga ctggggcgtg tgacctcaaa atatattttc cctctatctt ctcgttgcgc    2820
ttaatttgac taattctcat tagcgaggcg cgccttttcca taggctccgc ccccctgacg    2880
agcatcacaa aaatcgacgc tcaagtcaga ggtggcgaaa cccgacagga ctataaagat    2940
accaggcgtt ccccctggaa gctccctcg tgcgctctcc tgttccgacc ctgccgctta    3000
ccggatacct gtccgccttt ctcccttcgg aagcgtggc gctttctcat agctcacgct    3060
gtaggtatct cagttcggtg taggtcgttc gctccaagct gggctgtgtg cacgaacccc    3120
ccgttcagcc cgaccgctgc gccttatccg gtaactatcg tcttgagtcc aacccggtaa    3180
gacacgactt atcgccactg gcagcagcca ctggtaacag gattagcaga gcgaggtatg    3240
taggcggtgc tacagagttc ttgaagtggt ggcctaacta cggctacact agaagaacag    3300
tatttggtat ctgcgctctg ctgaagccag ttaccttcgg aaaaagagtt ggtagctctt    3360
gatccggcaa acaaaccacc gctggtagcg gtggtttttt tgtttgcaag cagcagatta    3420
cgcgcagaaa aaaaggatct caagaagatc ctttgatctt ttctacgggg tctgacgctc    3480
agtggaacga aaactcacgt taagggattt tggtcatgag attatcaaaa aggatcttca    3540
cctagatcct tttaaattaa aaatgaagtt ttaaatcaat ctaaagtata tatgagtaaa    3600
cttggtctga cagttaccaa tgcttaatca gtgaggcacc tatctcagcg atctgtctat    3660
ttcgttcatc catagttgcc tgactccccg tcgtgtagat aactacgata cgggagggct    3720
taccatctgg ccccagtgct gcaatgatac cgcgagaccc acgctcaccg gctccagatt    3780
tatcagcaat aaaccagcca gccggaaggg ccgagcgcag aagtggtcct gcaactttat    3840
ccgcctccat ccagtctatt aattgttgcc gggaagctag agtaagtagt tcgccagtta    3900
atagtttgcg caacgttgtt gccattgcta caggcatcgt ggtgtcacgc tcgtcgtttg    3960
gtatggcttc attcagctcc ggttcccaac gatcaaggcg agttacatga tcccccatgt    4020
tgtgcaaaaa agcggttagc tccttcggtc ctccgatcgt tgtcagaagt aagttggccg    4080
cagtgttatc actcatggtt atggcagcac tgcataattc tcttactgtc atgccatccg    4140
taagatgctt ttctgtgact ggtgagtact caaccaagtc attctgagaa tagtgtatgc    4200
ggcgaccgag ttgctcttgc ccggcgtcaa tacgggataa taccgcgcca catagcagaa    4260
ctttaaaagt gctcatcatt ggaaaacgtt cttcggggcg aaaactctca aggatcttac    4320
```

```
cgctgttgag atccagttcg atgtaaccca ctcgtgcacc caactgatct tcagcatctt    4380
ttactttcac cagcgtttct gggtgagcaa aaacaggaag gcaaaatgcc gcaaaaaagg    4440
gaataagggc gacacggaaa tgttgaatac tcatactctt cctttttcaa tattattgaa    4500
gcatttatca gggttattgt ctcatgagcg gatacatatt tgaatgtatt tagaaaaata    4560
aacagcgatc gcgcggccgc gggtaataac tgatataatt aaattgaagc tctaatttgt    4620
gagtttagta tacatgcatt tacttataat acagttttt agttttgctg gccgcatctt     4680
ctcaaatatg cttcccagcc tgcttttctg taacgttcac cctctacctt agcatccctt    4740
cccttttgcaa atagtcctct tccaacaata ataatgtcag atcctgtaga gaccacatca   4800
tccacggttc tatactgttg acccaatgcg tctcccttgt catctaaacc cacaccgggt    4860
gtcataatca accaatcgta accttcatct cttccaccca tgtctctttg agcaataaag    4920
ccgataacaa aatctttgtc gctcttcgca atgtcaacag tacccttagt atattctcca    4980
gtagctaggg agcccttgca tgacaattct gctaacatca aaaggcctct aggttccttt    5040
gttacttctt ccgccgcctg cttcaaaccg ctaacaatac ctgggcccac cacaccgtgt    5100
gcattcgtaa tgtctgccca ttctgctatt ctgtatacac ccgcagagta ctgcaatttg    5160
actgtattac caatgtcagc aaattttctg tcttcgaaga gtaaaaaatt gtacttggcg    5220
gataatgcct ttagcggctt aactgtgccc tccatggaaa aatcagtcaa gatatccaca   5280
tgtgttttta gtaaacaaat tttgggacct aatgcttcaa ctaactccag taattccttg    5340
gtggtacgaa catccaatga agcacacaag tttgtttgct tttcgtgcat gatattaaat    5400
agcttggcag caacaggact aggatgagta gcagcacgtt ccttatatgt agctttcgac    5460
atgatttatc ttcgtttcct gcaggttttt gttctgtgca gttgggttaa gaatactggg    5520
caatttcatg tttcttcaac accacatatg cgtatatata ccaatctaag tctgtgctcc    5580
ttccttcgtt cttccttctg ctcggagatt accgaatcaa agctagctta tcgatgataa    5640
gctgtcaaag atgagaatta attccacgga ctatagacta tactagatac tccgtctact    5700
gtacgataca cttccgctca ggtccttgtc cttaacgag gccttaccac tctttttgtta    5760
ctctattgat ccagctcagc aaaggcagtg tgatctaaga ttctatcttc gcgatgtagt    5820
aaaactagct agaccgagaa agagactaga atgcaaaag gcacttctac aatggctgcc    5880
atcattatta tccgatgtga cgctgcagct tctcaatgat attcgaatac gctttgagga    5940
gatacagcct aatatccgac aaactgtttt acagatttac gatcgtactt gttacccatc    6000
attgaatttt gaacatccga acctgggagt tttccctgaa acagatagta tatttgaacc    6060
tgtataataa tatatagtct agcgctttac ggaagacaat gtatgtattt cggttcctgg    6120
agaaactatt gcatctattg cataggtaat cttgcacgtc gcatccccgg ttcattttct    6180
gcgtttccat cttgcacttc aatagcatat ctttgttaac gaagcatctg tgcttcattt    6240
tgtagaacaa aaatgcaacg cgagagcgct aattttcaa acaaagaatc tgagctgcat    6300
ttttacagaa cagaaatgca acgcgaaagc gctatttac caacgaagaa tctgtgcttc    6360
attttttgtaa aacaaaaatg caacgcgacg agagcgctaa ttttttcaaac aaagaatctg   6420
agctgcattt ttacagaaca gaaatgcaac gcgagagcgc tattttacca acaaagaatc    6480
tatacttctt ttttgttcta caaaaatgca tcccgagagc gctattttc taacaaagca    6540
tcttagatta cttttttttct cctttgtgcg ctctataatg cagtctcttg ataacttttt    6600
gcactgtagg tccgttaagg ttagaagaag gctactttgg tgtctatttt ctcttccata    6660
aaaaaagcct gactccactt cccgcgttta ctgattacta gcgaagctgc gggtgcattt    6720
```

```
tttcaagata aaggcatccc cgattatatt ctataccgat gtggattgcg catactttgt    6780
gaacagaaag tgatagcgtt gatgattctt cattggtcag aaaattatga acggtttctt    6840
ctattttgtc tctatatact acgtatagga aatgtttaca ttttcgtatt gttttcgatt    6900
cactctatga atagttctta ctacaatttt tttgtctaaa gagtaatact agagataaac    6960
ataaaaaatg tagaggtcga gtttagatgc aagttcaagg agcgaaaggt ggatgggtag    7020
gttatatagg gatatagcac agagatatat agcaaagaga tacttttgag caat          7074
```

<210> SEQ ID NO 89
<211> LENGTH: 7331
<212> TYPE: DNA
<213> ORGANISM: Artificial Sequence
<220> FEATURE:
<223> OTHER INFORMATION: Synthetic Nucleic Acid

<400> SEQUENCE: 89

```
gtttgtggaa gcggtattcg caatttaatt aaagctggtg acaattaatc atcggctcgt      60
ataatgtgtg gaattgaatc gatataagga ggttaatcat atgagcggat tagttgaccc     120
ggatagtact ttttaaaga ccatcggaaa actgagcaac agcttgtcca ttggtcgtgg      180
agtagatcaa aaagaggtaa tccccaaagg ctggaacgcc cattgggagg caattacaaa    240
gcttaagaga agctttgacg cgattcctgc tggggagcgg gtgcgtttag ctaagaaaac    300
ctccaacctg ttccgtggac gctccgatgc aggtcacggc ctagatgtgg cagcgcttgg    360
gggagtgatt gccattgatc cggtcaatgc caccgccgat gtacagggca tgtgcacgta    420
tgaagacctg gtagatgcca ctttaagtta tggtctgatg ccgttggttg tgcctcaact    480
gaaaaccatc acgcttggtg gcgcagtgac cggaatgggc gtggaatcca catccttccg    540
caacggtttg ccacacgaat cagtgctgga gatggatatt tttaccggca ctggtgagat    600
cgtgacttgc tcgcccacag aaaatgtcga cctttacaga ggttttccca actcttatgg    660
ttcgctggga tacgcggtgc ggctaaaaat tgagctggaa ccagtgcaag attacgtcca    720
gctgcgccac gtgcgcttca cgatttaga gtctttgacc aaagcgattg aggaagtcgc    780
gtcttctctg gagtttgata accaacccgt cgattacctt gacggcgtgg tgttttcacc    840
cacggaagcc tacttagttc ttggcacgca aacctcacaa cctggcccca ccagcgatta    900
caccagggat ttaagctact accgctccct gcaacaccca gagggcatca cctatgaccg    960
cctgacaatc cgcgattaca tctggcgctg ggacaccgac tggttctggt gttcacgcgc   1020
attcggcacc caaaaccccg tggtgcgcaa actctggccc agggatctgc tgcgctcgag   1080
tttctattgg aagatcatcg gctgggatcg aaaatactcc atcgctgatc gcctggaaga   1140
gcgcaaaggc cgcccggcta gggaacgggt ggtccaagac gtggaagtta cgattgataa   1200
actgccagaa ttttttgaaat ggttctttga aagcagcgac atcgagccgc tgtggctgtg   1260
cccgatcaag cttcgggagg taccaggtag ttcggttggt gctggagaaa ttttgagctc   1320
cgctgaagca atcgactccg gtgctgctga acacccttgg ccgctgtatc ccttgaagaa   1380
ggacgtgctg tgggtcaaca tcggattctg gtcctcagtg ccggttgatc tgatgggctc   1440
cgatgcacca gagggagcat taacagagga aatcgaacgc gtcatggcag agctaggcgg   1500
acataaatcg ctgtactccg aagcgttcta caccaggaa gactttgaaa aactttatgg   1560
cggaaccatc ccggcgctgc taaaaaagca gtgggatccc cacagccgat tcccggttt   1620 gtatgaaaag acagtaaaag gcgcctagga tcgctcactg taggtagagg cttgtggtca   1680
```

```
ctacttgtgg ccacatttta aaaaaatgca caagaagaga aagcaaagca ttatgagtaa    1740
cgccgtagcg caggacctca tgaccatcgc cgacatcgtc gaggccacga ccactgcacc    1800
catcccattc cacatcactg ccttcgatgg aagcttcact ggccctgaag atgctccta    1860
ccagctgttt gttgccaaca cggatgcagt atcctacatc gcaacagcgc caggagattt    1920
gggtttggca cgtgcctacc tcatgggaga cctcatcgtg gaaggtgagc atcccggcca    1980
tccttatggg atctttgatg cgttgaagga gttctaccgc tgcttcaaac gcccagatgc    2040
atccaccacc ttgcagatca tgtggactct gcggaaaatg aatgccttaa aattccagga    2100
aattccacca atggaacaag cccctgcatg gcgtaaagca ctgatcaacg ggctagcatc    2160
caggcactcg aaatcccgcg acaagaaagc cattagctac cactacgacg tgggcaatga    2220
gttctactcc ctgtttttag atgattccat gacctatacc tgcgcgtatt atccaacgcc    2280
agaatcaagt ttggaagaag cccaagaaaa caaataccgc ctcatctttg aaaaactgcg    2340
tctgaaagaa ggcgatcgcc tcctagacgt gggatgcggt tggggaggca tggtccgcta    2400
cgccgccaaa cacggtgtga aagccatcgg agttacgctg tctgaacagc aatatgagtg    2460
gggtcaagca gagatcaaac gccaaggttt ggaagacctc gcggaaattc gcttcatgga    2520
ttaccgcgat gttccagaaa ctggattcga tgcgatctca gcaatcggca tcattgaaca    2580
catcggtgtg aacaactatc ccgactactt gaattgctc agcagcaaac tcaaaacagg    2640
cggactgatg ctcaaccaca gcatcaccta cccagacaac cgcccccgcc acgcaggtgc    2700
atttattgat cgctacattt tccccgacgg tgaactcact ggctctggca ccctgatcaa    2760
gcacatgcag acaacggtt tcgaagtgct gcacgaagaa aacctccgct ttgattacca    2820
acgcaccctg cacgcgtggt gcgaaaacct caagaaaat tgggaggaag cagttgaact    2880
cgccggtgaa cccactgcac gactctttgg cctgtacatg gcaggttcgg aatggggatt    2940
tgcccacaac atcgtccagc tgcaccaagt actgggtgtg aaactcgatg agcagggaag    3000
tcgcggagaa gttcctgaaa gaatgtggtg gactatctaa cctcaaaata tattttccct    3060
ctatcttctc gttgcgctta atttgactaa ttctcattag cgaggcgcgc ctttccatag    3120
gctccgcccc cctgacgagc atcacaaaaa tcgacgctca agtcagaggt ggcgaaaccc    3180
gacaggacta taaagatacc aggcgtttcc ccctggaagc tccctcgtgc gctctcctgt    3240
tccgaccctg ccgcttaccg gatacctgtc cgcctttctc ccttcgggaa gcgtggcgct    3300
ttctcatagc tcacgctgta ggtatctcag ttcggtgtag gtcgttcgct ccaagctggg    3360
ctgtgtgcac gaaccccccg ttcagcccga ccgctgcgcc ttatccggta actatcgtct    3420
tgagtccaac ccggtaagac acgacttatc gccactggca gcagccactg gtaacaggat    3480
tagcagagcg aggtatgtag gcggtgctac agagttcttg aagtggtggc ctaactacgg    3540
ctacactaga agaacagtat ttggtatctg cgctctgctg aagccagtta ccttcggaaa    3600
aagagttggt agctcttgat ccggcaaaca aaccaccgct ggtagcggtg ttttttgtt    3660
ttgcaagcag cagattacgc gcagaaaaaa aggatctcaa gaagatcctt tgatcttttc    3720
tacggggtct gacgctcagt ggaacgaaaa ctcacgttaa gggattttgg tcatgagatt    3780
atcaaaaagg atcttcacct agatcctttt aaattaaaaa tgaagtttta atcaatcta    3840
aagtatatat gagtaaactt ggtctgacag ttaccaatgc ttaatcagtg aggcacctat    3900
ctcagcgatc tgtctatttc gttcatccat agttgcctga ctccccgtcg tgtagataac    3960
tacgatacgg agggcttac catctggccc cagtgctgca atgataccgc gagacccacg    4020
ctcaccggct ccagatttat cagcaataaa ccagccagcc ggaagggccg agcgcagaag    4080
```

```
tggtcctgca actttatccg cctccatcca gtctattaat tgttgccggg aagctagagt    4140
aagtagttcg ccagttaata gtttgcgcaa cgttgttgcc attgctacag gcatcgtggt    4200
gtcacgctcg tcgtttggta tggcttcatt cagctccggt tcccaacgat caaggcgagt    4260
tacatgatcc cccatgttgt gcaaaaaagc ggttagctcc ttcggtcctc cgatcgttgt    4320
cagaagtaag ttggccgcag tgttatcact catggttatg gcagcactgc ataattctct    4380
tactgtcatg ccatccgtaa gatgcttttc tgtgactggt gagtactcaa ccaagtcatt    4440
ctgagaatag tgtatgcggc gaccgagttg ctcttgcccg gcgtcaatac gggataatac    4500
cgcgccacat agcagaactt taaaagtgct catcattgga aaacgttctt cggggcgaaa    4560
actctcaagg atcttaccgc tgttgagatc cagttcgatg taacccactc gtgcacccaa    4620
ctgatcttca gcatctttta ctttcaccag cgtttctggg tgagcaaaaa caggaaggca    4680
aaatgccgca aaaaagggaa taagggcgac acggaaatgt tgaatactca tactcttcct    4740
ttttcaatat tattgaagca tttatcaggg ttattgtctc atgagcggat acatatttga    4800
atgtatttag aaaaataaac agcgatcgcg cggccgcggg taataactga tataattaaa    4860
ttgaagctct aatttgtgag tttagtatac atgcatttac ttataataca gttttttagt    4920
tttgctggcc gcatcttctc aaatatgctt cccagcctgc ttttctgtaa cgttcaccct    4980
ctaccttagc atcccttccc tttgcaaata gtcctcttcc aacaataata atgtcagatc    5040
ctgtagagac cacatcatcc acggttctat actgttgacc caatgcgtct cccttgtcat    5100
ctaaacccac accgggtgtc ataatcaacc aatcgtaacc ttcatctctt ccacccatgt    5160
ctctttgagc aataaagccg ataacaaaat ctttgtcgct cttcgcaatg tcaacagtac    5220
ccttagtata ttctccagta gctagggagc ccttgcatga caattctgct aacatcaaaa    5280
ggcctctagg ttcctttgtt acttcttccg ccgcctgctt caaaccgcta acaataccctg   5340 ggcccaccac accgtgtgca ttcgtaatgt ctgcccattc tgctattctg tatacacccg    5400
cagagtactg caatttgact gtattaccaa tgtcagcaaa ttttctgtct tcgaagagta    5460
aaaaattgta cttggcggat aatgcccttta gcggcttaac tgtgccctcc atggaaaaat    5520
cagtcaagat atccacatgt gttttagta aacaaatttt gggacctaat gcttcaacta    5580
actccagtaa ttccttggtg gtacgaacat ccaatgaagc acacaagttt gtttgctttt    5640
cgtgcatgat attaaatagc ttggcagcaa caggactagg atgagtagca gcacgttcct    5700
tatatgtagc tttcgacatg atttatcttc gtttcctgca ggttttttgtt ctgtgcagtt    5760 gggttaagaa tactgggcaa tttcatgttt cttcaacacc acatatgcgt atatatacca    5820
atctaagtct gtgctccttc cttcgttctt ccttctgctc ggagattacc gaatcaaagc    5880
tagcttatcg atgataagct gtcaaagatg agaattaatt ccacggacta tagactatac    5940
tagatactcc gtctactgta cgatacactt ccgctcaggt ccttgtcctt taacgaggcc    6000
ttaccactct tttgttactc tattgatcca gctcagcaaa ggcagtgtga tctaagattc    6060
tatcttcgcg atgtagtaaa actagctaga ccgagaaaga gactagaaat gcaaaaggca    6120
cttctacaat ggctgccatc attattatcc gatgtgacgc tgcagcttct caatgatatt    6180
cgaatacgct tgaggagat acagcctaat atccgacaaa ctgttttaca gatttacgat    6240
cgtacttgtt acccatcatt gaattttgaa catccgaacc tgggagtttt ccctgaaaca    6300
gatagtatat ttgaacctgt ataataatat atagtctagc gctttacgga agacaatgta    6360
tgtatttcgg ttcctggaga aactattgca tctattgcat aggtaatctt gcacgtcgca    6420
```

| | |
|---|---|
| tccccggttc attttctgcg tttccatctt gcacttcaat agcatatctt tgttaacgaa | 6480 |
| gcatctgtgc ttcattttgt agaacaaaaa tgcaacgcga gagcgctaat ttttcaaaca | 6540 |
| aagaatctga gctgcatttt tacagaacag aaatgcaacg cgaaagcgct attttaccaa | 6600 |
| cgaagaatct gtgcttcatt tttgtaaaac aaaaatgcaa cgcgacgaga gcgctaattt | 6660 |
| ttcaaacaaa gaatctgagc tgcattttta cagaacagaa atgcaacgcg agagcgctat | 6720 |
| tttaccaaca aagaatctat acttctttt tgttctacaa aaatgcatcc cgagagcgct | 6780 |
| attttctaa caaagcatct tagattactt ttttctcct ttgtgcgctc tataatgcag | 6840 |
| tctcttgata acttttgca ctgtaggtcc gttaaggtta gaagaaggct actttggtgt | 6900 |
| ctattttctc ttccataaaa aaagcctgac tccacttccc gcgtttactg attactagcg | 6960 |
| aagctgcggg tgcattttt caagataaag gcatccccga ttatattcta taccgatgtg | 7020 |
| gattgcgcat actttgtgaa cagaaagtga tagcgttgat gattcttcat tggtcagaaa | 7080 |
| attatgaacg gtttcttcta ttttgtctct atatactacg tataggaaat gtttacattt | 7140 |
| tcgtattgtt ttcgattcac tctatgaata gttcttacta caatttttt gtctaaagag | 7200 |
| taatactaga gataaacata aaaatgtag aggtcgagtt tagatgcaag ttcaaggagc | 7260 |
| gaaaggtgga tgggtaggtt atatagggat atagcacaga gatatatagc aaagagatac | 7320 |
| ttttgagcaa t | 7331 |

<210> SEQ ID NO 90
<211> LENGTH: 7126
<212> TYPE: DNA
<213> ORGANISM: Artificial Sequence
<220> FEATURE:
<223> OTHER INFORMATION: Synthetic Nucleic Acid

<400> SEQUENCE: 90

| | |
|---|---|
| gtttgtggaa gcggtattcg caatttaatt aaagctggtg acaattaatc atcggctcgt | 60 |
| ataatgtgtg gaattgaatc gatataagga ggttaatcat gtgtccgctc ctgcgaccga | 120 |
| tgcacgaacc gcccacgccg acggcgtgga gcgattgctc gagagttatc gggcggtgcc | 180 |
| ggcggccgca tcggtgcggc tcgccaagcg cacctcgaac ctcttccggt cccgagcggc | 240 |
| gacggatgcc cctggcctcg acacctccgg cctgacccac gtcatcgcgg tcgaccccgg | 300 |
| ggcgcgcacg gccgacgtcg ccggcatgtg cacctacgac gacctcgtcg ccgcgacact | 360 |
| gccgcatggg ctcgcgccac tcgtggtgcc gcaactgaag accatcaccc tcggggcgc | 420 |
| cgtaacggga ctcggcatcg agtcgacgtc gttccgcaac ggtctgccgc acgagtcggt | 480 |
| gctcgagatc gacgtgctca ccggcgcagg cgagatcatc acggcgtcgc cgatcgagca | 540 |
| cgcagagctg ttccgcgcct tccccaactc gtacggcacc ctcggctacg ccgtgcgcct | 600 |
| gcgcatcgag ctcgagccgg tcgagccgtt cgtcgcactc acgcaccttc ggttccatgc | 660 |
| gctcaccgac ctcatcgagg caatggagcg catcatcgag accggtcgac tcgacggggt | 720 |
| tgccgtcgat tccctcgacg gcgtggtgtt cagcgctgaa gagagctacc tgtgcgtcgg | 780 |
| cacgcagacc gcggcatccg gcccggtcag cgactacacc cgccagcaga tcttctatcg | 840 |
| ctccatccag catgacgacg gtgcgaagca cgaccggctc accatgcacg actacctgtg | 900 |
| gcgctgggac gccgactggt tctggtgctc gcaggcgttc ggcgcgcagc atccgctgat | 960 |
| tcgccggttc tggccgcggc gataccggcg cagccgctcg tactcgacgc tcatgcgcct | 1020 |
| cgaacgcgcga ttcgacctcg gcgatcgcct cgagaagctc aagggccggc cggcgcgcga | 1080 |
| acgcgtgatc caagacgtcg aggtgccgat cgggcgcacc gtcggcttcc tcgaatggtt | 1140 |

```
cctcgcgaac gtgccgatcg agccgatctg gttgtgcccg ctgcgcctgc ggggcgaccg    1200
cggctggcct ctctacccga tccggccgca gcagacctac gtcaacatcg gcttctggtc    1260
gacggttccg gtgggcggct ccagggcga gacgaaccgc tcgatcgagc gcgccgtgag    1320
cgagttcgac ggacacaagt cgctgtactc cgactcgtac tactcgcgcg aggagttcga    1380
ggagctctac ggcggcgagg cgtaccgggc cgtgaagcgg cgatacgacc ccgactctcg    1440
actgctcgac ctctatgcga aggcggtgca acggcgatga ccacgaccaa acgccaggcg    1500
acagcggggc aggctgagac cgcgccgacg acggatgcgg cggccgcacc cgactcgtcg    1560
gcgaagctca ccctcgccga gatcctcgag atcgtcgtcg ccggtcggct gccgctgagg    1620
ttcaccgcct acgacgggag ctcggcgggg ccgcctgacg ccctgttcgg cctcgacctg    1680
aagactccgc gaggaacgac ctatctcgcc accggccgcg gcgatctcgg cctcgcccgc    1740
gcctacatcg cgggcgacct cgagatacag ggggtgcacc ccggagaccc ctacgagctg    1800
ctcaaggcac tcgccgacag cctggtcttc aagctgccac cgccgcgggt gatgacccag    1860
atcatccgtt cgatcggcgt cgaacatctg cggccgatcg cgccgccgcc gcaagaggtg    1920 ccgcccggt ggcgccgcat cgccgagggg ctccgacaca gcaagggccg cgacgccgaa    1980
gcgatccacc accactacga cgtgtcgaac accttctacg aatgggtgct cgggccgtcg    2040
atgacctaca cgtgcgcgtg ctacccgggc ctcgacgcat ccctcgacga ggcgcagcag    2100
aacaagtacc ggctcgtgtt cgagaagctg cggctgaagc cgggcgaccg actgctcgac    2160
gtcggctgcg ggtggggcgg catggtgcgc tacgccgcgc gccacggcgt gcaggcgttg    2220
ggcgtgaccc tgtcgcgaga gcagacggcg tgggcgcagc aggcgatcgc cgtcgagggc    2280
ctcgccgacc tcgccgaggt gcgctacggc gactaccgcg acatcgccga agacggcttc    2340
gatgcggtgt catcgatcgg gctgctcgag cacatcggcg tgcgcaacta cgcttcgtat    2400
ttcggctttc tgcagtcgcg cttgcggccc gggggactct tgctcaacca ctgcatcacc    2460
cggcccgaca atcgctccga ccgtcggcg cgcggcttca tcgaccggta cgtgttcccc    2520 gacgagagc tcaccggctc gggccgcatc atcaccgagg cgcaggatgt cggcttcgaa    2580
gtgctgcacg aagagaacct gcgtcagcat tatgcactga cactgcgcga ttggtgcgcc    2640
aacctcgtcg cgcactggga gaggcggtc gccgaggtcg ggctgccgac cgcgaaggtg    2700
tggggcctct acatggccgg gtcacggctc gcgttcgaga gcggcggcat ccagttgcac    2760
caggtgctgg cggtcagacc agacgatcgc agcgacgccg cccagctgcc gctgcggccg    2820
tggtggacgc catagcctca aaatatattt tccctctatc ttctcgttgc gcttaatttg    2880
actaattctc attagcgagg cgcgcctttc cataggctcc gcccccctga cgagcatcac    2940
aaaaatcgac gctcaagtca gaggtggcga acccgacag gactataaag ataccaggcg    3000 tttcccctg gaagctccct cgtgcgctct cctgttccga ccctgccgct taccggatac    3060
ctgtccgcct ttctcccttc gggaagcgtg gcgctttctc atagctcacg ctgtaggtat    3120
ctcagttcgg tgtaggtcgt tcgctccaag ctgggctgtg tgcacgaacc ccccgttcag    3180
cccgaccgct gcgccttatc cggtaactat cgtcttgagt ccaacccggt aagcacgac     3240 ttatcgccac tggcagcagc cactggtaac aggattagca gagcgaggta tgtaggcggt    3300
gctacagagt tcttgaagtg gtggcctaac tacggctaca ctagaagaac agtatttggt    3360
atctgcgctc tgctgaagcc agttaccttc ggaaaaagag ttggtagctc ttgatccggc    3420
aaacaaacca ccgctggtag cggtggtttt tttgtttgca agcagcagat tacgcgcaga    3480
```

```
aaaaaaggat ctcaagaaga tcctttgatc ttttctacgg ggtctgacgc tcagtggaac   3540
gaaaactcac gttaagggat tttggtcatg agattatcaa aaaggatctt cacctagatc   3600
cttttaaatt aaaaatgaag ttttaaatca atctaaagta tatatgagta aacttggtct   3660
gacagttacc aatgcttaat cagtgaggca cctatctcag cgatctgtct atttcgttca   3720
tccatagttg cctgactccc cgtcgtgtag ataactacga tacgggaggg cttaccatct   3780
ggccccagtg ctgcaatgat accgcgagac ccacgctcac cggctccaga tttatcagca   3840
ataaaccagc cagccggaag ggccgagcgc agaagtggtc ctgcaacttt atccgcctcc   3900
atccagtcta ttaattgttg ccgggaagct agagtaagta gttcgccagt taatagtttg   3960
cgcaacgttg ttgccattgc tacaggcatc gtggtgtcac gctcgtcgtt tggtatggct   4020
tcattcagct ccggttccca acgatcaagg cgagttacat gatcccccat gttgtgcaaa   4080
aaagcggtta gctccttcgg tcctccgatc gttgtcagaa gtaagttggc cgcagtgtta   4140
tcactcatgg ttatggcagc actgcataat tctcttactg tcatgccatc cgtaagatgc   4200
ttttctgtga ctggtgagta ctcaaccaag tcattctgag aatagtgtat gcggcgaccg   4260
agttgctctt gcccggcgtc aatacgggat aataccgcgc cacatagcag aactttaaaa   4320
gtgctcatca ttggaaaacg ttcttcgggg cgaaaactct caaggatctt accgctgttg   4380
agatccagtt cgatgtaacc cactcgtgca cccaactgat cttcagcatc ttttactttc   4440
accagcgttt ctgggtgagc aaaaacagga aggcaaaatg ccgcaaaaaa gggaataagg   4500
gcgacacgga aatgttgaat actcatactc ttcctttttc aatattattg aagcatttat   4560
cagggttatt gtctcatgag cggatacata tttgaatgta tttagaaaaa taaacagcga   4620
tcgcgcggcc gcgggtaata actgatataa ttaaattgaa gctctaatt tgtgagtttag   4680
tatacatgca tttacttata atacagtttt ttagttttgc tggccgcatc ttctcaaata   4740
tgcttcccag cctgcttttc tgtaacgttc accctctacc ttagcatccc ttcccttgc   4800
aaatagtcct cttccaacaa taataatgtc agatcctgta gagaccacat catccacggt   4860
tctatactgt tgacccaatg cgtctccctt gtcatctaaa cccacaccgg gtgtcataat   4920
caaccaatcg taaccttcat ctcttccacc catgtctctt tgagcaataa agccgataac   4980
aaaatctttg tcgctcttcg caatgtcaac agtaccctta gtatattctc cagtagctag   5040
ggagcccttg catgacaatt ctgctaacat caaaaggcct ctaggttcct tgttacttc    5100
ttccgccgcc tgcttcaaac cgctaacaat acctgggccc accacaccgt gtgcattcgt   5160
aatgtctgcc cattctgcta ttctgtatac acccgcagag tactgcaatt tgactgtatt   5220
accaatgtca gcaaattttc tgtcttcgaa gagtaaaaaa ttgtacttgg cggataatgc   5280
ctttagcggc ttaactgtgc cctccatgga aaaatcagtc aagatatcca catgtgtttt   5340
tagtaaacaa attttgggac ctaatgcttc aactaactcc agtaattcct tggtggtacg   5400
aacatccaat gaagcacaca gtttgtttg cttttcgtgc atgatattaa atagcttggc    5460
agcaacagga ctaggatgag tagcagcacg ttccttatat gtagctttcg acatgattta   5520
tcttcgtttc ctgcaggttt ttgttctgtg cagttgggtt aagaatactg gcaatttca    5580
tgtttcttca acaccacata tgcgtatata taccaatcta agtctgtgct ccttccttcg   5640
ttcttccttc tgctcggaga ttaccgaatc aaagctagct tatcgatgat aagctgtcaa   5700
agatgagaat taattccacg gactatagac tatactagat actccgtcta ctgtacgata   5760
cacttccgct caggtccttg tccttttaacg aggccttacc actctttgt tactctattg    5820
atccagctca gcaaaggcag tgtgatctaa gattctatct tcgcgatgta gtaaaactag   5880
```

```
ctagaccgag aaagagacta gaaatgcaaa aggcacttct acaatggctg ccatcattat    5940
tatccgatgt gacgctgcag cttctcaatg atattcgaat acgctttgag gagatacagc    6000
ctaatatccg acaaactgtt ttacagattt acgatcgtac ttgttaccca tcattgaatt    6060
ttgaacatcc gaacctggga gttttccctg aaacagatag tatatttgaa cctgtataat    6120
aatatatagt ctagcgcttt acggaagaca atgtatgtat ttcggttcct ggagaaacta    6180
ttgcatctat tgcataggta atcttgcacg tcgcatcccc ggttcatttt ctgcgtttcc    6240
atcttgcact tcaatagcat atctttgtta acgaagcatc tgtgcttcat tttgtagaac    6300
aaaaatgcaa cgcgagagcg ctaattttcc aaacaaagaa tctgagctgc attttacag    6360 aacagaaatg caacgcgaaa gcgctatttt accaacgaag aatctgtgct tcatttttgt    6420
aaaacaaaaa tgcaacgcga cgagagcgct aattttcaa acaaagaatc tgagctgcat    6480
ttttacagaa cagaaatgca acgcgagagc gctatttac caacaaagaa tctatacttc    6540
ttttttgttc tacaaaaatg catcccgaga gcgcttattt tctaacaaag catcttagat    6600
tacttttttt ctcctttgtg cgctctataa tgcagtctct tgataacttt ttgcactgta    6660
ggtccgttaa ggttagaaga aggctacttt ggtgtctatt ttctcttcca taaaaaaagc    6720
ctgactccac ttcccgcgtt tactgattac tagcgaagct gcgggtgcat tttttcaaga    6780
taaaggcatc cccgattata ttctataccg atgtggattg cgcatacttt gtgaacagaa    6840
agtgatagcg ttgatgattc ttcattggtc agaaaattat gaacggtttc ttctatttg    6900 tctctatata ctacgtatag gaatgtttta catttttcgta ttgttttcga ttcactctat    6960
gaatagttct tactacaatt ttttgtcta aagagtaata ctagagataa acataaaaaa    7020
tgtagaggtc gagtttagat gcaagttcaa ggagcgaaag gtggatgggt aggttatata    7080
gggatatagc acagagatat atagcaaaga gatacttttg agcaat                   7126
```

<210> SEQ ID NO 91
<211> LENGTH: 7505
<212> TYPE: DNA
<213> ORGANISM: Artificial Sequence
<220> FEATURE:
<223> OTHER INFORMATION: Synthetic Nucleic Acid

<400> SEQUENCE: 91

```
gtttgtggaa gcggtattcg caatttaatt aaagctggtg acaattaatc atcggctcgt     60
ataatgtgtg gaattgaatc gatataagga ggttaatcat gtgtctgttg ccgtaaccga    120
cgcacgatcc gcctacgccc acggcgtgca gcggctggtc gcgagttacc gcgccatccc    180
cgccggcgcc accgtccgcc tggccaaacc cacgtccaac ctgttccgcg ccagggcgaa    240
gagcaccgcg gcgggcctcg acacctccgg cctgacacat gtgatcgccg tggaccccga    300
gacgcgcacc gccgaggtcg cggggatgtg cacctacgag gacctggtgg cggcgacgct    360
gccccacggg ctttcaccgc tggtggtccc gcaactcaag acgatcaccc tcggcggcgc    420
cgtcaccggg ctcggcatcg agtcggcgtc gttccgcaac ggccttccgc acgaatcggt    480
cctggagatg gacatcctca ccgggaccgg cgacatcgtg cgcgccgcgc ccgacgagaa    540
tcccgacctt ttccgcacct tcccgaattc ttatggaacg ctgggttact cggttcggct    600
gaagatcgag ctggagccgg tgaagccgtt cgtggcgtta cgccatctcc gcttccactc    660
actgtcgaca ctcatcgcga cgatggaccc catcgtcgac accggggagtc tcgacggtga    720 gcaggtcgac tatctcgacg gagtggtgtt cagcgccgag gagagctacc tgtgcgtcgg    780
```

```
aacacgttcc gcgacaccgg gtcctgtcag cgactacacc ggcgagcaca tcttctaccg    840
gtcgatccag cacgattgcc cgaccgaagg cggacagaag cacgaccggc tgacggcgca    900
cgactacttc tggcgctggg acaccgactg gttctggtgc tcaagggcat tcggcgcgca    960
gaacccgaag gtccgtcggt ggtggccccg acggctccgg cgcagcagct tctactggaa   1020
gctcgtcggc tacgaccagc gtttcggcat cgccgaccgg atcgagaaac accacggccg   1080
gccaccgcgc gaacgcgtcg tccaggacgt cgaggtcccc atcgagcgca ccgtcgaatt   1140
cctgcagtgg ttcctcgaca cgatcccgat agagccgctc tggttgtgcc cgttgcgact   1200
tcgcgatgac aacagctggt cgctgtaccc gctccggccc catcgcacgt atgtcaacgt   1260
gggattctgg tcgtcggtgc ccgtcgggcc ggaggagggt cacaccaaca agctgatcga   1320
acgcaggatc agcgagctgg agggacacaa gtcgctgtac tccgacgcct tctattcggc   1380
cgacgagttc gacgcgctgt acggcggcga gatctaccgg accgtgaaga agacctacga   1440
cccagattct cgtttcctcg acctctatgc gaaggcggtg cgacggcaat gacgactttt   1500
cgggaacata ccgacagttc ggcgtccgac ccggatcgga aactcacttt ggcagaggtg   1560
ttggagatct tcgccgcggg tcgccgtccg ctgaagttca ccgcctatga cggaagtagt   1620
tgcgggcctg aggatgcgac actgggcctc gacctgctga ccccgcgggg cacgacctac   1680
ctggccacgg cgccgggtga tctcggcctg gcgcgggcct acatcgccgg cgatctgcgc   1740
ctcagtggtg tgcatcccgg cgatcccat gacctgctca cggcgctgac ggaacgcctg    1800
gagtacaggc gtccgccggt gcgagtgctg gccaatgttc tgcgctccat cgggatcgag   1860
cacctcaagc ccgtcgcgcc gccaccccag gagcacctgc cgcggtggcg gcggatcgca   1920
gaggggttgc ggcacagcaa gacccgtgac gctgaggcca tccagcacca ctacgacgtc   1980
tcgaacacgt tctactcatg ggtcctgggt ccgtcgatga cctacacctg cgcctgctat   2040
ccacacccgg atgccacgct ggaggaggcg caggagaaca agtaccggct ggtgttcgag   2100
aagcttcgac tcaagcccgg tgaccggctg ctcgacgtcg gttgcggctg ggcggaatg    2160
gtccgctacg ccgcccggca cggggtcaag gtcctggggg tgacgctgtc gaaggagcag   2220
gcgcagtggg cggccgacgc agtcgagcgg gacggcctgg gtgagttggc cgaggtccgc   2280
cacggcgact accgcgacgt gcgcgagtcg cacttcgacg cagtgtcctc gctcgggctc   2340
accgagcaca tcgcgtcgc gaactacccg tcgtacttcc gcttcctgaa gtcgaaactg    2400
cggccgggtg gcctgctgct caaccactgc atcacccgaa acaacaaccg gagtcacgcc   2460
accgcaggcg gattcatcga tcgctatgtc tttcccgacg gggagctgac ggggtcgggg   2520
cgaatcatca ccgaaatgca ggacgtcgga ctcgaggtcg tgcacgagga gaatctgcgt   2580
caccactacg cgctgacgct gcgcgactgg agccgcaacc tggtcgcgca ctgggacgac   2640
gcggtgaccg aggtcggtct gccgactgcc aaggtgtggg gcctctacat cgccgcgtcg   2700
cgagtcgggct tcgagcagaa cgccattcag ctgcaccagg tgctgtcggt caagctcgac   2760
gagcgtggct cggacggcgg actgccgtta cgaccctggt ggaacgccta gccactatgc   2820
tctgcccatg atccggttcc tgctgcgcat cgcggtcttt ctgggctcat cagcgatcgg   2880
gctcctcgtc gccggatggc tggtgcccgg ggtgtcgctg tcggtgtggg gcttcgtcac   2940
ggcagtggtg atcttcaccg tggcgcaggc gatcctgtcc ccgttcttcc tcaagatggc   3000
cagccgctac gcctcggcgt tcctcggcgg gatcggtctg gtgtcgacgt ttgccgcgct   3060
gctgctcgtc tcgctgctgt ccaacggtct gagcatccgc ggcatcggat cctggatcgc   3120
cgcaaccgtg gtggtctggt tggtgaccgc cctggcgacg ctggtgctgc cgatgttggt   3180
```

-continued

```
gctgcgcgag aagaaaaccg cgtcgcgcgt ctgacctcaa aatatatttt ccctctatct    3240
tctcgttgcg cttaatttga ctaattctca ttagcgaggc gcgcctttcc ataggctccg    3300
cccccctgac gagcatcaca aaaatcgacg ctcaagtcag aggtggcgaa acccgacagg    3360
actataaaga taccaggcgt ttccccctgg aagctccctc gtgcgctctc ctgttccgac    3420
cctgccgctt accggatacc tgtccgcctt tctcccttcg ggaagcgtgg cgctttctca    3480
tagctcacgc tgtaggtatc tcagttcggt gtaggtcgtt cgctccaagc tgggctgtgt    3540
gcacgaaccc cccgttcagc ccgaccgctg cgccttatcc ggtaactatc gtcttgagtc    3600
caacccggta agacacgact tatcgccact ggcagcagcc actggtaaca ggattagcag    3660
agcgaggtat gtaggcggtg ctacagagtt cttgaagtgg tggcctaact acggctacac    3720
tagaagaaca gtatttggta tctgcgctct gctgaagcca gttaccttcg gaaaaagagt    3780
tggtagctct tgatccggca aacaaaccac cgctggtagc ggtggttttt ttgtttgcaa    3840
gcagcagatt acgcgcagaa aaaaggatc tcaagaagat cctttgatct tttctacggg    3900
gtctgacgct cagtggaacg aaaactcacg ttaagggatt ttggtcatga gattatcaaa    3960
aaggatcttc acctagatcc ttttaaatta aaaatgaagt tttaaatcaa tctaaagtat    4020
atatgagtaa acttggtctg acagttacca atgcttaatc agtgaggcac ctatctcagc    4080
gatctgtcta tttcgttcat ccatagttgc ctgactcccc gtcgtgtaga taactacgat    4140
acgggagggc ttaccatctg gccccagtgc tgcaatgata ccgcgagacc cacgctcacc    4200
ggctccagat ttatcagcaa taaaccagcc agccggaagg gccgagcgca gaagtggtcc    4260
tgcaacttta tccgcctcca tccagtctat taattgttgc cgggaagcta gagtaagtag    4320
ttcgccagtt aatagtttgc gcaacgttgt tgccattgct acaggcatcg tggtgtcacg    4380
ctcgtcgttt ggtatggctt cattcagctc cggttcccaa cgatcaaggc gagttacatg    4440
atcccccatg ttgtgcaaaa aagcggttag ctccttcggt cctccgatcg ttgtcagaag    4500
taagttggcc gcagtgttat cactcatggt tatggcagca ctgcataatt ctcttactgt    4560
catgccatcc gtaagatgct tttctgtgac tggtgagtac tcaaccaagt cattctgaga    4620
atagtgtatg cggcgaccga gttgctcttg cccggcgtca atacgggata ataccgcgcc    4680
acatagcaga actttaaaag tgctcatcat tggaaaacgt tcttcggggc gaaaactctc    4740
aaggatctta ccgctgttga gatccagttc gatgtaaccc actcgtgcac ccaactgatc    4800
ttcagcatct tttactttca ccagcgtttc tgggtgagca aaaacaggaa ggcaaaatgc    4860
cgcaaaaaag ggaataaggg cgacacggaa atgttgaata ctcatactct ccttttttca    4920
atattattga agcatttatc agggttattg tctcatgagc ggatacatat ttgaatgtat    4980
ttagaaaaat aaacagcgat cgcgcggccg cgggtaataa ctgatataat taaattgaag    5040
ctctaatttg tgagtttagt atacatgcat ttacttataa tacagttttt tagttttgct    5100
ggccgcatct tctcaaatat gcttcccagc ctgcttttct gtaacgttca ccctctacct    5160
tagcatccct tcccttttgca aatagtcctc ttccaacaat aataatgtca gatcctgtag    5220
agaccacatc atccacggtt ctatactgtt gacccaatgc gtctcccttg tcatctaaac    5280
ccacaccggg tgtcataatc aaccaatcgt aaccttcatc tcttccaccc atgtctcttt    5340
gagcaataaa gccgataaca aaatctttgt cgctcttcgc aatgtcaaca gtacccttag    5400
tatattctcc agtagctagg gagcccttgc atgacaattc tgctaacatc aaaaggcctc    5460
taggttcctt tgttacttct tccgccgcct gcttcaaacc gctaacaata cctgggccca    5520
```

| | |
|---|---|
| ccacaccgtg tgcattcgta atgtctgccc attctgctat tctgtataca cccgcagagt | 5580 |
| actgcaattt gactgtatta ccaatgtcag caaattttct gtcttcgaag agtaaaaaat | 5640 |
| tgtacttggc ggataatgcc tttagcggct taactgtgcc ctccatggaa aaatcagtca | 5700 |
| agatatccac atgtgttttt agtaaacaaa ttttgggacc taatgcttca actaactcca | 5760 |
| gtaattcctt ggtggtacga acatccaatg aagcacacaa gtttgtttgc ttttcgtgca | 5820 |
| tgatattaaa tagcttggca gcaacaggac taggatgagt agcagcacgt tccttatatg | 5880 |
| tagctttcga catgatttat cttcgtttcc tgcaggtttt tgttctgtgc agttgggtta | 5940 |
| agaatactgg gcaatttcat gtttcttcaa caccacatat gcgtatatat accaatctaa | 6000 |
| gtctgtgctc cttccttcgt tcttccttct gctcggagat taccgaatca agctagctt | 6060 |
| atcgatgata agctgtcaaa gatgagaatt aattccacgg actatagact atactagata | 6120 |
| ctccgtctac tgtacgatac acttccgctc aggtccttgt cctttaacga ggccttacca | 6180 |
| ctcttttgtt actctattga tccagctcag caaaggcagt gtgatctaag attctatctt | 6240 |
| cgcgatgtag taaaactagc tagaccgaga agagactag aaatgcaaaa ggcacttcta | 6300 |
| caatggctgc catcattatt atccgatgtg acgctgcagc ttctcaatga tattcgaata | 6360 |
| cgctttgagg agatacagcc taatatccga caaactgttt tacagattta cgatcgtact | 6420 |
| tgttacccat cattgaattt tgaacatccg aacctgggag ttttccctga aacagatagt | 6480 |
| atatttgaac ctgtataata atatatagtc tagcgcttta cggaagacaa tgtatgtatt | 6540 |
| tcggttcctg gagaaactat tgcatctatt gcataggtaa tcttgcacgt cgcatccccg | 6600 |
| gttcattttc tgcgtttcca tcttgcactt caatagcata tctttgttaa cgaagcatct | 6660 |
| gtgcttcatt ttgtagaaca aaatgcaac gcgagagcgc taattttca acaaagaat | 6720 |
| ctgagctgca ttttacaga acagaaatgc aacgcgaaag cgctatttta ccaacgaaga | 6780 |
| atctgtgctt catttttgta aaacaaaaat gcaacgcgac gagagcgcta ttttcaaa | 6840 |
| caaagaatct gagctgcatt tttacagaac agaaatgcaa cgcgagagcg ctattttacc | 6900 |
| aacaaagaat ctatacttct tttttgttct acaaaaatgc atcccgagag cgctattttt | 6960 |
| ctaacaaagc atcttagatt actttttttc cctttgtgc gctctataat gcagtctctt | 7020 |
| gataacttt tgcactgtag gtccgttaag gttagaagaa ggctactttg gtgtctattt | 7080 |
| tctcttccat aaaaaaagcc tgactccact tcccgcgttt actgattact agcgaagctg | 7140 |
| cgggtgcatt ttttcaagat aaaggcatcc ccgattatat tctataccga tgtggattgc | 7200 |
| gcatactttg tgaacagaaa gtgatagcgt tgatgattct tcattggtca gaaaattatg | 7260 |
| aacggtttct tctattttgt ctctatatac tacgtatagg aaatgtttac attttcgtat | 7320 |
| tgttttcgat tcactctatg aatagttctt actacaattt ttttgtctaa agagtaaatac | 7380 |
| tagagataaa cataaaaaat gtagaggtcg agtttagatg caagttcaag gagcgaaagg | 7440 |
| tggatgggta ggttatatag ggatatagca cagagatata tagcaaagag atacttttga | 7500 |
| gcaat | 7505 |

<210> SEQ ID NO 92
<211> LENGTH: 7123
<212> TYPE: DNA
<213> ORGANISM: Artificial Sequence
<220> FEATURE:
<223> OTHER INFORMATION: Synthetic Nucleic Acid

<400> SEQUENCE: 92

| | |
|---|---|
| gtttgtggaa gcggtattcg caatttaatt aaagctggtg acaattaatc atcggctcgt | 60 |

-continued

```
ataatgtgtg gaattgaatc gatataagga ggttaatcat atgcacgggc tgttgtcgaa      120
gactagggta tatgtggtgc ctgtccttgg atctgcactc tcggcccaca agtcgggcgt      180
tgaccggctg ctggcaagct atcgatccat tcccgcaacg tccgcggtcc ggctggccaa      240
accgacgtca aacctgttcc gcgcccgcac caaacgtgac gcgcccggct tggacacctc      300
ggggctgacc ggcgtcctga gcgtggatcc cgaaacccgc accgcggacg tcgccggcat      360
gtgcacctac gcggacctgg tggccgcaac gctgccctac ggcctgtcgc cgctggtcgt      420
cccgcagctg aagaccatca ccctcggcgg ggcggtcagc ggcctgggga tcgagtcggc      480
gtcgtttcgc aacgggctgc cgcacgaatc ggtgctggag atggatatcc tcaccggcgc      540
tggcgatttg ctcaccgcat cacgtaccca gcacccggac ctgttccgcg ccttcccgaa      600
ttcctatggg acactggggt attcgacccg gcttcggatc gagctggaac ccgtcgcacc      660
gttcgtcgcg ctgcgccaca tccgcttccg ctcgctgccc gcgctgatcg ccgcggccga      720
acgcatcgtc gacaccggcg ggcagggcgg aaccccggtc gactacctcg acggggtggt      780
cttcagcgcc gacgaaagct acctgtgcgt gggccggcgg accaccaccc ccggcccggt      840
cagcgactac accggcaagg acatctacta ccagtccatc cggcacgacg ccccgggcct      900
ggaggcgacc aaggatgacc ggctgaccat gcacgactac ttctggcgct gggacaccga      960
ttggttctgg tgctcgcgcg cgttcggcgt gcaggacccg cgggtgcgac gcttctggcc     1020
gcgccgttat cggcgcagca gcttctactg gaagctgatt tccctggacc ggcgcttcgg     1080
gatctccgac cgcatcgagg cgcgcaacgg gcggcccccca gcgaacgggt ggtgcaaga      1140 catcgagatt ccaatcgaac ggacctgcga cttcctggag tggttcctgg acaacgtgcc     1200
aatcacgccg atctggttgt gcccgttgcg ccttcgcgac cgcgacggct ggccgttgta     1260
cccgatgcgg ccggatcaca cgtacgtcaa cgtcggcttc tggtcgtcgg tgccgggggg     1320
cgcgaccgag ggcgccgcca accggatgat cgaagaaaag gtgagcgaac tcgacgggca     1380
caagtccctg tactccgatt ccttctactc ccgcgaggac ttcgacgagc tgtacggcgg     1440
cgagacctac aacaccgtca agaaaaccta cgaccccgat tctcgtttac tcgacctcta     1500
cgcaaaggcg gtgcaacggc gatgacgact accaaggaac cccaccgcac gtcgcacggg     1560
aaactgagca tggccgagat cctggaggtc ttcgccgcca ccggccgaca tccgctgaag     1620
ttcaccgcct acgacggcag catcgccggc aacgaggacg ccgaactggg cctggacctt     1680
cgcagccccc gcggcgccac ctatctggcg accgccccg gcgaactcgg cctcgcccgc      1740
gcctacgtgt cgggcgacct gcaggcctac ggcgtccatc ccggcgaccc gtaccaactg     1800
ctcaagacgc tcaccgatcg ggtggaattc aagcggcccc cggtgcgggt gctggccaac     1860
gtcgtgcggt cgctgggggtt cgagcggttg ctgccggtcg cgccgccccc gcaggaggcg     1920
ctgccccggt ggcggcgcat cgccgacggg ctgatgcaca cgaggacccg cgacgccgag     1980
gccatccacc accactacga cgtgtccaac accttctacg aattggtgtt ggggccgtcg     2040
atgacctaca cctgcgcggt gtatcccgat gccgacgcga cactcgaaca ggcgcaggag     2100
aacaagtacc ggctgatctt cgagaagctg cggctgaagg cgggcgaccg gctgctcgac     2160
gtcggctgcg gctggggcgg catggtgcgc tacgcggccc ggcgcggcgt ccgggccacc     2220
ggcgccaccc tgtcggccga acaggcgaag tgggcgcaga aggcgatcgc cgaggaaggc     2280
cttgcggacc tggccgaggt gcgccacacc gactatcggg acgtgggcga ggcggcgttc     2340
gacgccgtgt cctcgatcgg gctgaccgag cacatcggcg tcaagaatta ccccgcctac     2400
```

```
ttcggcttct tgaagtcgaa gctgcgcacc ggcggcctgc tgctcaatca ctgcatcacc    2460
cgccacgaca acacgtcgac gtcgttcgcg ggcggattca ccgatcgcta tgtcttcccg    2520
gacggggagc tgaccggctc gggccgcatc acctgcgacg tccaggactg cggcttcgag    2580
gtgctgcacg cggagaactt ccgccaccac tacgcgatga cgctgcgcga ctggtgccgc    2640
aatctggtcg agaactggga cgccgcggtc agcgaggtcg gcctaccgac cgcgaaggtc    2700
tggggcctgt acatgcggc gtcacgggtt gcgttcgagc agaacaacct tcagctgcat    2760
cacgtgctgg cggccaagac cgacgcgcgg ggcgacgacg acctgccgct gcggccgtgg    2820
tggacggcct gacctcaaaa tatattttcc ctctatcttc tcgttgcgct taatttgact    2880
aattctcatt agcgaggcgc gccttttccat aggctccgcc ccctgacga gcatcacaaa    2940 aatcgacgct caagtcagag gtggcgaaac ccgacaggac tataaagata ccaggcgttt    3000 cccccctggaa gctccctcgt gcgctctcct gttccgaccc tgccgcttac cggatacctg    3060
tccgcctttc tcccttcggg aagcgtggcg ctttctcata gctcacgctg taggtatctc    3120
agttcggtgt aggtcgttcg ctccaagctg ggctgtgtgc acgaaccccc cgttcagccc    3180
gaccgctgcg ccttatccgg taactatcgt cttgagtcca acccggtaag cacgactta    3240 tcgccactgg cagcagccac tggtaacagg attagcagag cgaggtatgt aggcggtgct    3300
acagagttct tgaagtggtg gcctaactac ggctacacta agaacagt atttggtatc    3360 tgcgctctgc tgaagccagt taccttcgga aaagagttg gtagctcttg atccggcaaa    3420
caaaccaccg ctggtagcgg tggtttttt gtttgcaagc agcagattac gcgcagaaaa    3480
aaaggatctc aagaagatcc tttgatcttt tctacggggt ctgacgctca gtggaacgaa    3540
aactcacgtt aagggatttt ggtcatgaga ttatcaaaaa ggatcttcac ctagatcctt    3600
ttaaattaaa aatgaagttt taaatcaatc taaagtatat atgagtaaac ttggtctgac    3660
agttaccaat gcttaatcag tgaggcacct atctcagcga tctgtctatt tcgttcatcc    3720
atagttgcct gactccccgt cgtgtagata actacgatac gggagggctt accatctggc    3780
cccagtgctg caatgatacc gcgagaccca cgctcaccgg ctccagattt atcagcaata    3840
aaccagccag ccggaagggc cgagcgcaga agtggtcctg caactttatc cgcctccatc    3900
cagtctatta attgttgccg ggaagctaga gtaagtagtt cgccagttaa tagtttgcgc    3960
aacgttgttg ccattgctac aggcatcgtg gtgtcacgct cgtcgtttgg tatggcttca    4020
ttcagctccg gttcccaacg atcaaggcga gttacatgat cccccatgtt gtgcaaaaaa    4080
gcggttagct ccttcggtcc tccgatcgtt gtcagaagta agttggccgc agtgttatca    4140
ctcatggtta tggcagcact gcataattct cttactgtca tgccatccgt aagatgcttt    4200
tctgtgactg gtgagtactc aaccaagtca ttctgagaat agtgtatgcg gcgaccgagt    4260
tgctcttgcc cggcgtcaat acgggataat accgcgccac atagcagaac tttaaaagtg    4320
ctcatcattg gaaaacgttc ttcggggcga aaactctcaa ggatcttacc gctgttgaga    4380
tccagttcga tgtaacccac tcgtgcaccc aactgatctt cagcatcttt tactttcacc    4440
agcgtttctg ggtgagcaaa aacaggaagg caaaatgccg caaaaaaggg aataagggcg    4500
acacggaaat gttgaatact catactcttc ctttttcaat attattgaag catttatcag    4560
ggttattgtc tcatgagcgg atacatattt gaatgtattt agaaaaataa acagcgatcg    4620
cgcggccgcg ggtaataact gatataatta aattgaagct ctaatttgtg agtttagtat    4680
acatgcattt acttataata cagttttttta gtttgctgg ccgcatcttc tcaaatatgc    4740
ttcccagcct gcttttctgt aacgttcacc ctctaccttg gcatcccttc cctttgcaaa    4800
```

```
tagtcctctt ccaacaataa taatgtcaga tcctgtagag accacatcat ccacggttct    4860
atactgttga cccaatgcgt ctcccttgtc atctaaaccc acaccgggtg tcataatcaa    4920
ccaatcgtaa ccttcatctc ttccacccat gtctctttga gcaataaagc cgataacaaa    4980
atctttgtcg ctcttcgcaa tgtcaacagt acccttagta tattctccag tagctaggga    5040
gcccttgcat gacaattctg ctaacatcaa aaggcctcta ggttcctttg ttacttcttc    5100
cgccgcctgc ttcaaaccgc taacaatacc tgggcccacc acaccgtgtg cattcgtaat    5160
gtctgcccat tctgctattc tgtatacacc cgcagagtac tgcaatttga ctgtattacc    5220
aatgtcagca aattttctgt cttcgaagag taaaaaattg tacttggcgg ataatgcctt    5280
tagcggctta actgtgccct ccatggaaaa atcagtcaag atatccacat gtgtttttag    5340
taaacaaatt ttgggaccta atgcttcaac taactccagt aattccttgg tggtacgaac    5400
atccaatgaa gcacacaagt ttgtttgctt ttcgtgcatg atattaaata gcttggcagc    5460
aacaggacta ggatgagtag cagcacgttc cttatatgta gctttcgaca tgatttatct    5520
tcgtttcctg caggtttttg ttctgtgcag ttgggttaag aatactgggc aatttcatgt    5580
ttcttcaaca ccacatatgc gtatatatac caatctaagt ctgtgctcct tccttcgttc    5640
ttccttctgc tcggagatta ccgaatcaaa gctagcttat cgatgataag ctgtcaaaga    5700
tgagaattaa ttccacggac tatagactat actagatact ccgtctactg tacgatacac    5760
ttccgctcag gtccttgtcc tttaacgagg ccttaccact cttttgttac tctattgatc    5820
cagctcagca aaggcagtgt gatctaagat tctatcttcg cgatgtagta aaactagcta    5880
gaccgagaaa gagactagaa atgcaaaagg cacttctaca atggctgcca tcattattat    5940
ccgatgtgac gctgcagctt ctcaatgata ttcgaatacg ctttgaggag atacagccta    6000
atatccgaca aactgtttta cagatttacg atcgtacttg ttacccatca ttgaattttg    6060
aacatccgaa cctgggagtt ttccctgaaa cagatagtat atttgaacct gtataataat    6120
atatagtcta gcgctttacg aagacaatg tatgtatttc ggttcctgga gaaactattg    6180
catctattgc ataggtaatc ttgcacgtcg catcccggt tcattttctg cgtttccatc    6240
ttgcacttca atagcatatc tttgttaacg aagcatctgt gcttcatttt gtagaacaaa    6300
aatgcaacgc gagagcgcta attttttcaaa caaagaatct gagctgcatt tttacagaac    6360
agaaatgcaa cgcgaaagcg ctattttacc aacgaagaat ctgtgcttca tttttgtaaa    6420
acaaaaatgc aacgcgacga gagcgctaat ttttcaaaca aagaatctga gctgcatttt    6480
tacagaacag aaatgcaacg cgagagcgct attttaccaa caaagaatct atacttcttt    6540
tttgttctac aaaaatgcat cccgagagcg ctatttttct aacaaagcat cttagattac    6600
tttttttctc ctttgtgcgc tctataatgc agtctcttga taactttttg cactgtaggt    6660
ccgttaaggt tagaagaagg ctactttggt gtctattttc tcttccataa aaaaagcctg    6720
actccacttc ccgcgtttac tgattactag cgaagctgcg ggtgcatttt ttcaagataa    6780
aggcatcccc gattatattc tataccgatg tggattgcgc atactttgtg aacagaaagt    6840
gatagcgttg atgattcttc attggtcaga aaattatgaa cggtttcttc tattttgtct    6900
ctatatacta cgtataggaa atgtttacat tttcgtattg ttttcgattc actctatgaa    6960
tagttcttac tacaattttt ttgtctaaag agtaatacta gagataaaca taaaaaatgt    7020
agaggtcgag tttagatgca agttcaagga gcgaaaggtg gatgggtagg ttatataggg    7080
atatagcaca gagatatata gcaaagagat acttttgagc aat                     7123
```

<210> SEQ ID NO 93
<211> LENGTH: 9807
<212> TYPE: DNA
<213> ORGANISM: Artificial Sequence
<220> FEATURE:
<223> OTHER INFORMATION: Synthetic Nucleic Acid

<400> SEQUENCE: 93

```
ggttatatag ggatatagca cagagatata tagcaaagag atactttga gcaatgtttg      60
tggaagcggt attcgcaatt taattaacgc ttaccttggc cgttagacat catggtaaat    120
ctgcgcagac agccctgtgc agctgaaacg cggttacgta tagcttgcca tatgtctagc    180
catacgtaac cgcaggtaaa aggcatattt ttcgcgtgtc atggctagta ataacaccg     240
gtgtcattta gagtcaggga agacaatga aaaacgaaga aagccaccgg gcggcaaccc    300
gatgactttc gcttatcacc cagcacacac ctgggagaaa tcacggtcat gagtttacag    360
actcatgcgc agaatgcgca cactaaaaca cctacccgcg tcgagcgcga ccgtggtgga    420
ctggacaaca ccccagcatc tgccagtgac cgcgaccttt tacgcgatca tctaggccgc    480
gatgtactcc acggttcagt cacacgagac ttaaaaagg cctatcgacg caacgctgac    540
ggcacgaact cgccgcgtat gtatcgcttc gagactgatg cttaggacg gtgcgagtac    600
gccatgctca ccaccaagca gtacgccgcc gtcctggtcg tagacgttga ccaagtaggt    660
accgcaggcg gtgacccgc agacttaaac ccgtacgtcc gcgacgtggt gcgctcactg    720
attactcata gcgtcgggcc agcctgggtg ggtattaacc caactaacgg caaagcccag    780
ttcatatggc ttattgaccc tgtctacgct gaccgtaacg gtaaatctgc gcagatgaag    840
cttcttgcag caaccacgcg tgtgctgggt gagcttttag accatgaccc gcactttcc    900
caccgcttta gccgcaaccc gttctacaca ggcaaagccc ctaccgctta tcgttggtat    960
aggcagcaca accgggtgat gcgccttgga gacttgataa agcaggtaag ggatatggca   1020
ggacacgacc agttcaaccc cacccacgc cagcaattca gctctggccg cgaacttatc   1080
aacgcggtca agacccgccg tgaagaagcc caagcattca aagcactcgc ccaggacgta   1140
gacgcggaaa tcgccggtgg tctcgaccag tatgacccgg aacttatcga cggtgtgcgt   1200
gtgctctgga ttgtccaagg aaccgcagca cgcgacgaaa cagcctttag acatgcgctt   1260
aagactggcc accgcttgcg ccagcaaggc caacgcctga cagacgcagc aatcatcgac   1320
gcctatgagc acgcctacaa cgtcgcacac acccacggcg gtgcaggccg cgacaacgag   1380
atgccaccca tgcgcgaccg ccaaaccatg gcaaggcgcg tgcgcgggta tgtcgcccaa   1440
tccaagagcg agacctacag cggctctaac gcaccaggta aagccaccag cagcgagcgg   1500
aaagccttgg ccacgatggg acgcagaggc ggacaaaaag ccgcacaacg ctggaaaaca   1560
gaccccgagg gcaaatatgc gcaagcacaa aggtcgaagc ttgaaaagac gcaccgtaag   1620
aaaaaggctc aaggacgatc tacgaagtcc cgtattagcc aaatggtgaa cgatcagtat   1680
ttccagacag ggacagttcc cacgtgggct gaaatagggg cagaggtagg agtctctcgc   1740
gccacggttg ctaggcatgt cgcggagcta agaagagcg gtgactatcc ggacgtttaa    1800
ggggtctcat accgtaagca atatacggtt cccctgccgt taggcagtta gataaaacct   1860
cacttgaaga aaaccttgag gggcagggca gcttatatgc ttcaaagcat gacttcctct   1920
gttctcctag acctcgcaac cctccgccat aacctcaccc tgctctgcga ggctggccgg   1980
ctaccgccgg cgtaacagat gagggcaagc ggatggctga tgaaaccaag ccgcggccgg   2040
gaagccgatc tcggcttgaa cgaattgtta ggtggcggta cttgggtcga tatcaaagtg   2100
```

```
catcacttct tcccgtatgc ccaactttgt atagagagcc actgcgggat cgtcaccgta    2160
atctgcttgc acgtagatca cataagcacc aagcgcgttg gcctcatgct tgaggagatt    2220
gatgagcgcg gtggcaatgc cctgcctccg gtgctcgccg gagactgcga gatcatagat    2280
atagatctca ctacgcggct gctcaaactt gggcagaacg taagccgcga gagcgccaac    2340
aaccgcttct tggtcgaagg cagcaagcgc gatgaatgtc ttactacgga gcaagttccc    2400
gaggtaatcg gagtccggct gatgttggga gtaggtggct acgtctccga actcacgacc    2460
gaaaagatca agagcagccc gcatggattt gacttggtca gggccgagcc tacatgtgcg    2520
aatgatgccc atacttgagc cacctaactt tgttttaggg cgactgccct gctgcgtaac    2580
atcgttgctg ctccataaca tcaaacatcg acccacggcg taacgcgctt gctgcttgga    2640
tgcccgaggc atagactgta caaaaaaaca gtcataacaa gccatgaaaa ccgccactgc    2700
gccgttacca ccgctgcgtt cggtcaaggt tctggaccag ttgcgtgagc gcatacgcta    2760
cttgcattac agtttacgaa ccgagtttaa acagctggtg acaattaatc atcggctcgt    2820
ataatgtgtg gaattgaatc gatataagga ggttaatcat gtgtctgtgg ttactactga    2880
cgcacaggct gccatgccg ccggcgtctc gcgtcttctg gccagctacc gggcgatccc    2940
gcccagcgcg acagtgcgcc ttgcgaaacc gacgtccaac ctgttccgcg cccgcgcccg    3000
caccaatgtg aagggtctcg acgtctcggg cctgaccggt gtgatcggtg tcgaccggga    3060
cgcgcgcacc gccgatgtgg cgggcatgtg cacctacgag gacctggtgg cggccacgct    3120
tccgtacggc cttgccccac tggtggtgcc gcagctcaag accatcacgc tcggtggcgc    3180
ggtcaccggt ctgggcatcg agtccacgtc gttccgcaac ggtctgccgc acgaaagtgt    3240
cctggagatg gacatcttga ccggttcggg cgagatcgtc acggcctcac cggatcagca    3300
ctcggatctg ttccatgcgt tccccaattc atatggaacc cttggttatt ccacccggct    3360
gcgcatcgaa ctggagcccg tgcacccgtt tgtggcgttg cgccacctgc gctttcactc    3420
gatcaccgat ctggtcgcgg cgatggaccg gatcatcgag accggcgggc tggacggtga    3480
acccgtcgac tacctcgacg gcgtggtgtt cagcgcgact gagagttacc tgtgtgttgg    3540
cttcaagacg aaaacgccgg ggccggtcag cgattacaca ggtcagcaga tcttctaccg    3600
gtcgatccag catgacggcg acaccggcgc cgagaaacac gaccggctga ccatccacga    3660
ctacctgtgg cgctgggaca ccgactggtt ctggtgctca cgggcattcg cgctcagca    3720
tccggtgatc cgcaggttct ggccgcggcg gctgcgccgc agcagcttct actggaagct    3780
ggtggcctac gaccagcggt acgacatcgc cgaccgtatc gagaagcgca acgggcgccc    3840
gccgcgcgag cgggtggtcc aggacgtcga ggtgcccatc gagcggtgcg cggacttcgt    3900
cgagtggttc ctgcagaatg tgccgatcga gccgatctgg ctgtgccccc tacggttgcg    3960
tgacagcgcc gacggcggtg cctcgtggcc cctgtatccg ctgaaggcgc accacaccta    4020
cgtcaacatc ggtttctggt catcagtgcc ggtgggcccc gaggagggcc acaccaaccg    4080
cctcatcgag aaaaaagtcg cggagctgga cgggcacaaa tctttgtact cggacgctta    4140
ttacacacgt gacgaattcg acgagctgta cggcggtgag gtctacaaca ccgtcaagaa    4200
gacgtacgac ccggattcac gtctgctaga cctgtattcg aaggcggtgc aaagacaatg    4260
accacattca agaacgcgca gacgtccaca gcggaccgca agctcaccct ggccgagatc    4320
ctcgagatct tcgccgcggg taaggagccg ctgaagttca ctgcgtacga cggcagctcg    4380
gccggtcccg aggacgccac gatgggtctg gacctcaaga ccccgcgtgg gaccacctat    4440
```

```
ctggccacgg cacccggcga tctgggcctg gcccgtgcgt atgtctccgg tgacctggag    4500
ccgcacggcg tgcatcccgg cgatccctac ccgctgctgc gcgccctggc cgaacgcatg    4560
gagttcaagc gcccgcctgc gcgtgtgctg gcgaacatcg tgcgctccat cggcatcgag    4620
cacctcaagc cgatcgcacc gccgccgcag gaggcgctgc cccggtggcg ccgcatcatg    4680
gagggcctgc ggcacagcaa gacccgcgac gccgaggcca tccaccacca ctacgacgtg    4740
tcgaacacgt tctacgagtg ggtgctgggc cgtcgatga cctacacgtg cgcgtgctac    4800
cccaccgagg acgcgaccct cgaagaggcc caggacaaca agtaccgcct ggtgttcgag    4860
aagctgcgcc tgaagcccgg tgaccggttg ctcgacgtgg gctgcggctg gggcggcatg    4920
gtccgctacg cggcccgcca cggcgtcaag gcgctcggtg tcacgctcag ccgcgaacag    4980
gcgacgtggg cgcagaaggc catcgcccag gaaggtctca ccgatctggc cgaggtgcgt    5040
cacggtgatt accgcgacgt catcgaatcc gggttcgacg cggtgtcctc gatcgggctg    5100
accgagcaca tcggcgtgca caactacccg gcgtacttca acttcctcaa gtcgaagctg    5160
cgcaccggtg gcctgctgct caaccactgc atcacccgcc cggacaaccg gtcggcgcca    5220
tcggccggcg ggttcatcga caggtacgtg ttccccgacg gggagctcac cggctcgggc    5280
cgcatcatca ccgaggccca ggacgtgggc cttgaggtga tccacgagga gaacctacgc    5340
aatcactatg cgatgacgct gcgcgactgg tgccgcaacc tggtcgagca ctgggacgag    5400
gcggtcgaag aggtcgggct gcccaccgcg aaggtgtggg gcctgtacat ggccggctca    5460
cgtctgggct tcgagaccaa tgtggttcag ctgcaccagg ttctggcggt caagcttgac    5520
gatcagggca aggacggcgg actgccgttg cggcctggt ggtccgccta gcctcaaaat    5580
atattttccc tctatcttct cgttgcgctt aatttgacta attctcatta gcgaggcgcg    5640
cctttccata ggctccgccc ccctgacgag catcacaaaa atcgacgctc aagtcagagg    5700
tggcgaaacc cgacaggact ataaagatac caggcgtttc cccctggaag ctccctcgtg    5760
cgctctcctg ttccgaccct gccgcttacc ggatacctgt ccgcctttct cccttcggga    5820
agcgtggcgc tttctcatag ctcacgctgt aggtatctca gttcggtgta ggtcgttcgc    5880
tccaagctgg gctgtgtgca cgaaccccc gttcagcccg accgctgcgc cttatccggt    5940
aactatcgtc ttgagtccaa cccggtaaga cacgacttat cgccactggc agcagccact    6000
ggtaacagga ttagcagagc gaggtatgta ggcggtgcta cagagttctt gaagtggtgg    6060
cctaactacg gctacactag aagaacagta tttggtatct gcgctctgct gaagccagtt    6120
accttcggaa aaagagttgg tagctcttga tccggcaaac aaaccaccgc tggtagcggt    6180
ggttttttg tttgcaagca gcagattacg cgcagaaaaa aaggatctca agaagatcct    6240
ttgatctttt ctacggggtc tgacgctcag tggaacgaaa actcacgtta agggattttg    6300
gtcatgagat tatcaaaaag gatcttcacc tagatccttt taaattaaaa atgaagtttt    6360
aaatcaatct aaagtatata tgagtaaact tggtctgaca gttaccaatg cttaatcagt    6420
gaggcaccta tctcagcgat ctgtctattt cgttcatcca tagttgcctg actccccgtc    6480
gtgtagataa ctacgatacg ggagggctta ccatctggcc ccagtgctgc aatgataccg    6540
cgagacccac gctcaccggc tccagattta tcagcaataa accagccagc cggaagggcc    6600
gagcgcagaa gtggtcctgc aactttatcc gcctccatcc agtctattaa ttgttgccgg    6660
gaagctagag taagtagttc gccagttaat agtttgcgca acgttgttgc cattgctaca    6720
ggcatcgtgg tgtcacgctc gtcgtttggt atggcttcat tcagctccgg ttcccaacga    6780
tcaaggcgag ttacatgatc cccatgttg tgcaaaaaag cggttagctc cttcggtcct    6840
```

```
ccgatcgttg tcagaagtaa gttggccgca gtgttatcac tcatggttat ggcagcactg    6900
cataattctc ttactgtcat gccatccgta agatgctttt ctgtgactgg tgagtactca    6960
accaagtcat tctgagaata gtgtatgcgg cgaccgagtt gctcttgccc ggcgtcaata    7020
cgggataata ccgcgccaca tagcagaact ttaaaagtgc tcatcattgg aaaacgttct    7080
tcggggcgaa aactctcaag gatcttaccg ctgttgagat ccagttcgat gtaacccact    7140
cgtgcaccca actgatcttc agcatctttt actttcacca gcgtttctgg gtgagcaaaa    7200
acaggaaggc aaaatgccgc aaaaaaggga ataagggcga cacggaaatg ttgaatactc    7260
atactcttcc ttttcaata ttattgaagc atttatcagg gttattgtct catgagcgga    7320
tacatatttg aatgtattta gaaaaataaa cagcgatcgc gcggccgcgg gtaataactg    7380
atataattaa attgaagctc taatttgtga gtttagtata catgcattta cttataatac    7440 agtttttag ttttgctggc cgcatcttct caaatatgct tcccagcctg cttttctgta    7500
acgttcaccc tctaccttag catccttcc ctttgcaaat agtcctcttc caacaataat    7560
aatgtcagat cctgtagaga ccacatcatc cacggttcta tactgttgac ccaatgcgtc    7620
tcccttgtca tctaaaccca caccgggtgt cataatcaac caatcgtaac cttcatctct    7680
tccacccatg tctctttgag caataaagcc gataacaaaa tctttgtcgc tcttcgcaat    7740
gtcaacagta cccttagtat attctccagt agctagggag cccttgcatg acaattctgc    7800
taacatcaaa aggcctctag gttcctttgt tacttcttcc gccgcctgct tcaaaccgct    7860
aacaatacct gggcccacca caccgtgtgc attcgtaatg tctgcccatt ctgctattct    7920
gtatacaccc gcagagtact gcaatttgac tgtattacca atgtcagcaa attttctgtc    7980
ttcgaagagt aaaaaattgt acttggcgga taatgccttt agcggcttaa ctgtgccctc    8040
catggaaaaa tcagtcaaga tatccacatg tgttttagt aaacaaattt tgggacctaa    8100
tgcttcaact aactccagta attccttggt ggtacgaaca tccaatgaag cacacaagtt    8160
tgtttgcttt tcgtgcatga tattaaatag cttggcagca acaggactag gatgagtagc    8220
agcacgttcc ttatatgtag ctttcgacat gatttatctt cgtttcctgc aggttttttgt    8280 tctgtgcagt tgggttaaga atactgggca atttcatgtt tcttcaacac cacatatgcg    8340
tatatatacc aatctaagtc tgtgctcctt ccttcgttct tccttctgct cggagattac    8400
cgaatcaaag ctagcttatc gatgataagc tgtcaaagat gagaattaat tccacggact    8460
atagactata ctagatactc cgtctactgt acgatacact tccgctcagg tccttgtcct    8520
ttaacgaggc cttaccactc ttttgttact ctattgatcc agctcagcaa aggcagtgtg    8580
atctaagatt ctatcttcgc gatgtagtaa aactagctag accgagaaag agactagaaa    8640
tgcaaaaggc acttctacaa tggctgccat cattattatc cgatgtgacg ctgcagcttc    8700
tcaatgatat tcgaatacgc tttgaggaga tacagcctaa tatccgacaa actgttttac    8760
agatttacga tcgtacttgt tacccatcat tgaattttga acatccgaac ctgggagttt    8820
tccctgaaac agatagtata tttgaacctg tataataata tatagtctag cgctttacgg    8880
aagacaatgt atgtatttcg gttcctggag aaactattgc atctattgca taggtaatct    8940
tgcacgtcgc atccccggtt cattttctgc gtttccatct tgcacttcaa tagcatatct    9000
ttgttaacga agcatctgtg cttcatttg tagaacaaaa atgcaacgcg agagcgctaa    9060
tttttcaaac aaagaatctg agctgcattt ttacagaaca gaaatgcaac gcgaaagcgc    9120
tattttacca acgaagaatc tgtgcttcat ttttgtaaaa caaaaatgca acgcgacgag    9180
```

| | |
|---|---|
| agcgctaatt tttcaaacaa agaatctgag ctgcattttt acagaacaga aatgcaacgc | 9240 |
| gagagcgcta ttttaccaac aaagaatcta tacttctttt ttgttctaca aaaatgcatc | 9300 |
| ccgagagcgc tattttcta acaaagcatc ttagattact tttttctcc tttgtgcgct | 9360 |
| ctataatgca gtctcttgat aacttttgc actgtaggtc cgttaaggtt agaagaaggc | 9420 |
| tactttggtg tctattttct cttccataaa aaagcctga ctccacttcc cgcgtttact | 9480 |
| gattactagc gaagctgcgg gtgcattttt tcaagataaa ggcatccccg attatattct | 9540 |
| ataccgatgt ggattgcgca tactttgtga acagaaagtg atagcgttga tgattcttca | 9600 |
| ttggtcagaa aattatgaac ggtttcttct atttttgtctc tatatactac gtataggaaa | 9660 |
| tgtttacatt ttcgtattgt tttcgattca ctctatgaat agttcttact acaattttt | 9720 |
| tgtctaaaga gtaatactag agataaacat aaaaaatgta gaggtcgagt ttagatgcaa | 9780 |
| gttcaaggag cgaaaggtgg atgggta | 9807 |

<210> SEQ ID NO 94
<211> LENGTH: 10293
<212> TYPE: DNA
<213> ORGANISM: Artificial Sequence
<220> FEATURE:
<223> OTHER INFORMATION: Synthetic Nucleic Acid

<400> SEQUENCE: 94

| | |
|---|---|
| gtttgtggaa gcggtattcg caatttaatt aacgcttacc ttggccgtta gacatcatgg | 60 |
| taaatctgcg cagacagccc tgtgcagctg aaacgcggtt acgtatagct tgccatatgt | 120 |
| ctagccatac gtaaccgcag gtaaaaggca tattttcgc gtgtcatggc tagtaaataa | 180 |
| caccggtgtc atttagagtc agggaaagac aatgaaaaac gaagaaagcc accgggcggc | 240 |
| aacccgatga ctttcgctta tcacccagca cacacctggg agaaatcacg gtcatgagtt | 300 |
| tacagactca tgcgcagaat gcgcacacta aaacacctac ccgcgtcgag cgcgaccgtg | 360 |
| gtggactgga caacacccca gcatctgcca gtgaccgcga ccttttacgc gatcatctag | 420 |
| gccgcgatgt actccacggt tcagtcacac gagactttaa aaaggcctat cgacgcaacg | 480 |
| ctgacggcac gaactcgccg cgtatgtatc gcttcgagac tgatgcttta ggacggtgcg | 540 |
| agtacgccat gctcaccacc aagcagtacg ccgccgtcct ggtcgtagac gttgaccaag | 600 |
| taggtaccgc aggcggtgac cccgcagact taaacccgta cgtccgcgac gtggtgcgct | 660 |
| cactgattac tcatagcgtc gggccagcct gggtgggtat taacccaact aacggcaaag | 720 |
| cccagttcat atggcttatt gaccctgtct acgctgaccg taacggtaaa tctgcgcaga | 780 |
| tgaagcttct tgcagcaacc acgcgtgtgc tgggtgagct tttagaccat gacccgcact | 840 |
| tttcccaccg ctttagccgc aacccgttct acacaggcaa agcccctacc gcttatcgtt | 900 |
| ggtataggca gcacaaccgg gtgatgcgcc ttggagactt gataaagcag gtaagggata | 960 |
| tggcaggaca cgaccagttc aaccccaccc cacgccagca attcagctct ggccgcgaac | 1020 |
| ttatcaacgc ggtcaagacc cgccgtgaag aagcccaagc attcaaagca ctcgcccagg | 1080 |
| acgtagacgc ggaaatcgcc ggtggtctcg accagtatga cccggaactt atcgacggtg | 1140 |
| tgcgtgtgct ctggattgtc caaggaaccg cagcacgcga cgaaacagcc tttagacatg | 1200 |
| cgcttaagac tggccaccgc ttgcgccagc aaggccaacg cctgacagac gcagcaatca | 1260 |
| tcgacgccta tgagcacgcc tacaacgtcg cacacaccca cggcggtgca ggccgcgaca | 1320 |
| acagagatgcc acccatgcgc gaccgccaaa ccatggcaag gcgcgtgcgc gggtatgtcg | 1380 |
| cccaatccaa gagcgagacc tacagcggct ctaacgcacc aggtaaagcc accagcagcg | 1440 |

```
agcggaaagc cttggccacg atgggacgca gaggcggaca aaaagccgca caacgctgga   1500
aaacagaccc cgagggcaaa tatgcgcaag cacaaaggtc gaagcttgaa aagacgcacc   1560
gtaagaaaaa ggctcaagga cgatctacga agtcccgtat tagccaaatg gtgaacgatc   1620
agtatttcca gacagggaca gttcccacgt gggctgaaat aggggcagag gtaggagtct   1680
ctcgcgccac ggttgctagg catgtcgcgg agctaaagaa gagcggtgac tatccggacg   1740
tttaaggggt ctcataccgt aagcaatata cggttcccct gccgttaggc agttagataa   1800
aacctcactt gaagaaaacc ttgaggggca gggcagctta tatgcttcaa agcatgactt   1860
cctctgttct cctagacctc gcaaccctcc gccataacct caccctgctc tgcgaggctg   1920
gccggctacc gccggcgtaa cagatgaggg caagcggatg gctgatgaaa ccaagccgcg   1980
gccgggaagc cgatctcggc ttgaacgaat tgttaggtgg cggtacttgg gtcgatatca   2040
aagtgcatca cttcttcccg tatgcccaac tttgtataga gagccactgc gggatcgtca   2100
ccgtaatctg cttgcacgta gatcacataa gcaccaagcg cgttggcctc atgcttgagg   2160
agattgatga gcgcggtggc aatgccctgc ctccggtgct cgccggagac tgcgagatca   2220
tagatataga tctcactacg cggctgctca aacttgggca gaacgtaagc cgcgagagcg   2280
ccaacaaccg cttcttggtc gaaggcagca agcgcgatga atgtcttact acggagcaag   2340
ttcccgaggt aatcggagtc cggctgatgt tgggagtagg tggctacgtc tccgaactca   2400
cgaccgaaaa gatcaagagc agcccgcatg gatttgactt ggtcagggcc gagcctacat   2460
gtgcgaatga tgcccatact tgagccacct aactttgttt tagggcgact gccctgctgc   2520
gtaacatcgt tgctgctcca taacatcaaa catcgaccca cggcgtaacg cgcttgctgc   2580
ttggatgccc gaggcataga ctgtacaaaa aaacagtcat aacaagccat gaaaaccgcc   2640
actgcgccgt taccaccgct gcgttcggtc aaggttctgg accagttgcg tgagcgcata   2700
cgctacttgc attacagttt acgaaccgag tttaaacagc tggtgacaat taatcatcgg   2760
ctcgtataat gtgtggaatt gaatcgatat aaggaggtta atcatgtgaa ctgtcagtct   2820
tccgcgtcca acctcgccaa ccacatcaac gcggtgtacg agctgcgccg cgcctatgcg   2880
cggctgtccg ccgacaagcc ggtgcgcctg gcgaagacca cctccaacct cttccgcttc   2940
cgcagccggg acgatgccgc gcgtctcgac gtcagcgctt tcacctcggt gatcagcatc   3000
gacacggagg cgcgggtcgc ggaggtgggc ggcatgacca cctacgagga cctggtcgcc   3060
gccaccctgc ggcatggcct gatgccgccg gtggttccgc aactgcgcac gatcaccctg   3120
ggcggtgcgg tcaccgggct ggggatcgaa tcctcgtcct tccgcaacgg gctcccgcac   3180
gagtcagtgg aagagatgga gatcctcacc ggcagcggcc aggtggtggt ggcccggcgc   3240
gacaacgagc accgcgacct gttctacggt ttccccaact cgtacggcac cctcggttac   3300
gcgctgcggc tccgcatcca gctcgaaccg gtccgcccct acgtccacct gcggcacctg   3360
cggttcaccg atgccgcagc ggccatggcc gcgctggagc agatctgcgc ggaccgcacc   3420
cacgacgggg agaccgtcga cttcgtcgac ggcgtcgtgt tcgcccgcaa cgagctgtac   3480
ctgaccttgg gacgttcac cgaccgggct ccgtggacca gcgactacac cggaaccgac   3540
atctactacc ggtcgatccc ccgctacgcg ggccccggcc ccggcgacta cctcaccacg   3600
cacgactacc tgtggcggtg ggacaccgac tggttctggt gctcccgcgc cttcggactg   3660
cagcatcccg tggtgcgccg cctgtggccg cgttccttga aacgctccga cgtctaccgc   3720
aagctcgtcg cctgggaccg gcgcactgac gcgagccgcc tgctcgacta ctaccgcggg   3780
```

```
cgcccgccca aggaaccggt gatccaggac atcgaggttg aggtggggcg ggctgccgag    3840
ttcctcgact tcttccacac cgagatcggc atgtccccgg tgtggctgtg cccgctgcgg    3900
ctgcgagaag acacagccga cgatacggaa ccggtctggc cgctctaccc cctcaaaccc    3960
cgccgcctct acgtcaactt cgggttttgg ggcctcgttc cgatccgtcc cggtggaggc    4020
aggacatacc acaaccggct gatcgaaaaa gaagtgaccc ggttgggcgg gcacaagtcg    4080
ctctactcgg acgccttcta cgacgaggac gagttctggg agctctacaa cggggagatc    4140
taccgcaagc tcaaagctgc ctacgacccc gacggtcgac tgctcgacct gtacaccaag    4200
tgcgtcggcg gcgggtgaga aaggatgagg gatgcgactg gcggaggtat tcgaacgtgt    4260
cgtcggaccc gatgcgcccg tccacttccg ggcctacgac ggcagcactg cgggagatcc    4320
acgcagtgaa gtcgctatcg tggttcgcca cccggcagcc gtcaactaca tcgtccaagc    4380
gccgggagca ctcggtttga cccgcgccta cgtggcggga tacctcgacg tcgaagggga    4440
catgtacacc gcgctgcggg caatggccga cgtggtgttc caggaccggc cgcggctgtc    4500
ccccggggaa ctgctgcgga tcatccgcgg gatcgggtgg gtgaagttcg tcaaccggct    4560
tccaccgccg ccgcaggagg tgcgccagtc ccgcctcgcc gccctgggct ggcgccactc    4620
caagcagcgc gacgccgaag ccatccagca ccactacgac gtctccaacg ccttctacgc    4680
cctggtcttg ggcgagtcga tgacctacac ctgcgcggtc tacccgaccg agcaggccac    4740
gctggagcag gcacagttct tcaagcacga gctgatcgcc cgcaagctcg gtcttgcccc    4800
tgggatacga ctgctggatg tggggtgcgg ctggggcggc atggtcatcc acgcggcccg    4860
ggagcacggg gtcaaagccc tgggggtgac cctgtccaaa gagcaggctg agtgggcgca    4920
gaagcggatc gcccacgagg gcctgggcga cctggcagaa gtccggcaca tggactaccg    4980
ggacctgccc gacggcgagt acgacgcgat cagctcgatc gggttgaccg agcacgtcgg    5040
caaaaagaac gtgcccgcct acttcgcgtc gctgtaccgc aagctcgtcc cgggaggccg    5100
cctgctcaac cactgcatca cccggccccg caacgacctg ccgcccttca acgcggcgg    5160 ggtgatcaac cgctacgtct tccccgatgg ggagctggaa gggcccggct ggctgcaggc    5220
ggcgatgaac gacgccgggt tcgaaatccg ccaccaggag aacctgcggg agcactacgc    5280
acggaccctg cgggactggc tggccaacct ggaccgcaac tgggatgccg cggtgcggga    5340
agtgggggag ggcacggccc gagtgtggcg gctctacatg gccgggtgcg tgctcggctt    5400
cgaacgcaac gtggtgcaac tgcaccagat cctcggggtg aagctcgacg ggaccgaggc    5460
gcggatgccc ctgcgccccg acttcgaacc gccgctgcct taaccgcggt gcacagccgg    5520
gggatatcag tcgcggaacc gggcatgatg agcccatggc tgcgaccgat gacgaccggc    5580
accacaccac cgtcgccctc gacctcatcg acgcgtatgt gcgcgccgac cgcagaatga    5640
tcggtgaacg ttccgcgggg atcagcgcgg aggcggggga gcggatcgtc tccaccctga    5700
aagtgtgcgc ggccttcctt gcccgccggg tccaggagac cggggtgccg tggcgcgcag    5760
cggactcccg ggaagcggtc gcccgcaccg tcgccgacct gctggaaccc gaggtggaat    5820
tcgcggtcgt ctccgcctgg gaggcgtacg cgatcgggga gcacgaggcc gcctgggtcc    5880
gggcgcacgg cgatccgctg gtcttccgtcc acatgctggc cgcgttctcc gctgctatcg    5940
gcacagcggt ctacggccgt gaggagctgc tgcccacgct gcgcagggtg acagcacgat    6000
aacctcaaaa tatattttcc ctctatcttc tcgttgcgct taatttgact aattctcatt    6060
agcgaggcgc gcctttccat aggctccgcc ccctgacga gcatcacaaa aatcgacgct    6120
caagtcagag gtggcgaaac ccgacaggac tataaagata ccaggcgttt ccccctggaa    6180
```

```
gctccctcgt gcgctctcct gttccgaccc tgccgcttac cggatacctg tccgcctttc   6240
tcccttcggg aagcgtggcg ctttctcata gctcacgctg taggtatctc agttcggtgt   6300
aggtcgttcg ctccaagctg ggctgtgtgc acgaaccccc cgttcagccc gaccgctgcg   6360
ccttatccgg taactatcgt cttgagtcca acccggtaag acacgactta tcgccactgg   6420
cagcagccac tggtaacagg attagcagag cgaggtatgt aggcggtgct acagagttct   6480
tgaagtggtg gcctaactac ggctacacta gaagaacagt atttggtatc tgcgctctgc   6540
tgaagccagt taccttcgga aaaagagttg gtagctcttg atccggcaaa caaaccaccg   6600
ctggtagcgg tggttttttt gtttgcaagc agcagattac gcgcagaaaa aaggatctc   6660 aagaagatcc tttgatcttt tctacggggt ctgacgctca gtggaacgaa aactcacgtt   6720
aagggatttt ggtcatgaga ttatcaaaaa ggatcttcac ctagatcctt ttaaattaaa   6780
aatgaagttt taaatcaatc taaagtatat atgagtaaac ttggtctgac agttaccaat   6840
gcttaatcag tgaggcacct atctcagcga tctgtctatt tcgttcatcc atagttgcct   6900
gactccccgt cgtgtagata actacgatac gggagggctt accatctggc cccagtgctg   6960
caatgatacc gcgagaccca cgctcaccgg ctccagattt atcagcaata aaccagccag   7020
ccggaagggc cgagcgcaga agtggtcctg caactttatc cgcctccatc cagtctatta   7080
attgttgccg ggaagctaga gtaagtagtt cgccagttaa tagtttgcgc aacgttgttg   7140
ccattgctac aggcatcgtg gtgtcacgct cgtcgtttgg tatggcttca ttcagctccg   7200
gttcccaacg atcaaggcga gttacatgat cccccatgtt gtgcaaaaaa gcggttagct   7260
ccttcggtcc tccgatcgtt gtcagaagta agttggccgc agtgttatca ctcatggtta   7320
tggcagcact gcataattct cttactgtca tgccatccgt aagatgcttt tctgtgactg   7380
gtgagtactc aaccaagtca ttctgagaat agtgtatgcg gcgaccgagt tgctcttgcc   7440
cggcgtcaat acgggataat accgcgccac atagcagaac tttaaaagtg ctcatcattg   7500
gaaaacgttc ttcggggcga aaactctcaa ggatcttacc gctgttgaga tccagttcga   7560
tgtaacccac tcgtgcaccc aactgatctt cagcatcttt tactttcacc agcgtttctg   7620
ggtgagcaaa aacaggaagg caaaatgccg caaaaaaggg aataagggcg acacggaaat   7680
gttgaatact catactcttc ctttttcaat attattgaag catttatcag ggttattgtc   7740
tcatgagcgg atacatattt gaatgtattt agaaaaataa acagcgatcg cgcggccgcg   7800
ggtaataact gatataatta aattgaagct ctaatttgtg agtttagtat acatgcattt   7860
acttataata cagttttta gttttgctgg ccgcatcttc tcaaatatgc ttcccagcct   7920
gcttttctgt aacgttcacc ctctacctta gcatcccttc cctttgcaaa tagtcctctt   7980
ccaacaataa taatgtcaga tcctgtagag accacatcat ccacggttct atactgttga   8040
cccaatgcgt ctcccttgtc atctaaaccc acaccgggtg tcataatcaa ccaatcgtaa   8100
ccttcatctc ttccacccat gtctctttga gcaataaagc cgataacaaa tctttgtcg   8160 ctcttcgcaa tgtcaacagt acccttagta tattctccag tagctaggga gcccttgcat   8220
gacaattctg ctaacatcaa aaggcctcta ggttcctttg ttacttcttc cgccgcctgc   8280
ttcaaaccgc taacaatacc tgggcccacc acaccgtgtg cattcgtaat gtctgccat   8340 tctgctattc tgtatacacc cgcagagtac tgcaatttga ctgtattacc aatgtcagca   8400
aattttctgt cttcgaagag taaaaaattg tacttggcgg ataatgcctt tagcggctta   8460
actgtgccct ccatggaaaa atcagtcaag atatccacat gtgtttttag taaacaaatt   8520
```

| | |
|---|---|
| ttgggaccta atgcttcaac taactccagt aattccttgg tggtacgaac atccaatgaa | 8580 |
| gcacacaagt ttgtttgctt ttcgtgcatg atattaaata gcttggcagc aacaggacta | 8640 |
| ggatgagtag cagcacgttc cttatatgta gctttcgaca tgatttatct tcgtttcctg | 8700 |
| caggttttttg ttctgtgcag ttgggttaag aatactgggc aatttcatgt ttcttcaaca | 8760 |
| ccacatatgc gtatatatac caatctaagt ctgtgctcct tccttcgttc ttccttctgc | 8820 |
| tcggagatta ccgaatcaaa gctagcttat cgatgataag ctgtcaaaga tgagaattaa | 8880 |
| ttccacggac tatagactat actagatact ccgtctactg tacgatacac ttccgctcag | 8940 |
| gtccttgtcc tttaacgagg ccttaccact cttttgttac tctattgatc cagctcagca | 9000 |
| aaggcagtgt gatctaagat tctatcttcg cgatgtagta aaactagcta gaccgagaaa | 9060 |
| gagactagaa atgcaaaagg cacttctaca atggctgcca tcattattat ccgatgtgac | 9120 |
| gctgcagctt ctcaatgata ttcgaatacg ctttgaggag atacagccta aatccgaca | 9180 |
| aactgtttta cagatttacg atcgtacttg ttacccatca ttgaattttg aacatccgaa | 9240 |
| cctgggagtt ttccctgaaa cagatagtat atttgaacct gtataataat atatagtcta | 9300 |
| gcgctttacg gaagacaatg tatgtatttc ggttcctgga gaaactattg catctattgc | 9360 |
| ataggtaatc ttgcacgtcg catccccggt tcattttctg cgttccatc ttgcacttca | 9420 |
| atagcatatc tttgttaacg aagcatctgt gcttcatttt gtagaacaaa atgcaacgc | 9480 |
| gagagcgcta atttttcaaa caaagaatct gagctgcatt tttacagaac agaaatgcaa | 9540 |
| cgcgaaagcg ctattttacc aacgaagaat ctgtgcttca tttttgtaaa acaaaaatgc | 9600 |
| aacgcgacga gagcgctaat ttttcaaaca aagaatctga gctgcatttt tacagaacag | 9660 |
| aaatgcaacg cgagagcgct attttaccaa caaagaatct atacttcttt tttgttctac | 9720 |
| aaaaatgcat cccgagagcg ctattttct aacaaagcat cttagattac tttttttctc | 9780 |
| ctttgtgcgc tctataatgc agtctcttga taacttttg cactgtaggt ccgttaaggt | 9840 |
| tagaagaagg ctactttggt gtctatttc tcttccataa aaaagcctg actccacttc | 9900 |
| ccgcgtttac tgattactag cgaagctgcg ggtgcatttt ttcaagataa aggcatcccc | 9960 |
| gattatattc tataccgatg tggattgcgc atacttgtg aacagaaagt gatagcgttg | 10020 |
| atgattcttc attggtcaga aaattatgaa cggtttcttc tattttgtct ctatatacta | 10080 |
| cgtataggaa atgtttacat tttcgtattg ttttcgattc actctatgaa tagttcttac | 10140 |
| tacaattttt ttgtctaaag agtaatacta gagataaaca taaaaaatgt agaggtcgag | 10200 |
| tttagatgca agttcaagga gcgaaaggtg gatgggtagg ttatatagg atatagcaca | 10260 |
| gagatatata gcaaagagat acttttgagc aat | 10293 |

<210> SEQ ID NO 95
<211> LENGTH: 5654
<212> TYPE: DNA
<213> ORGANISM: Artificial Sequence
<220> FEATURE:
<223> OTHER INFORMATION: Synthetic Nucleic Acid

<400> SEQUENCE: 95

| | |
|---|---|
| tgggtaggtt atatagggat atagcacaga gatatatagc aaagagatac ttttgagcaa | 60 |
| tgtttgtgga agcggtattc gcaatttaat taaagctggt gacaattaat catcggctcg | 120 |
| tataatgtgt ggaattgaat cgatataagg aggttaatca tatgacgctg gccaaggtct | 180 |
| tcgaggagct ggtcggggcg gacgcccctg tggagctcac cgcctacgac ggatcgagag | 240 |
| ccggacgcct gggcagtgat ctgcgggtcc acgtgaagtc gccgtacgcg gtgtcctacc | 300 |

```
tggtgcactc gccgagcgcg ctcgggctgg cccgcgcgta cgtggccggg cacctggacg    360
cctacggcga catgtacacg ctgctgcggg agatgacgca gctgaccgag gcgctgacgc    420
ccaaggcccg gctgcggctg ctggccggtg tcctgcagga tccgctgctg cgcgcggcgg    480
ccagccgccg tctgccgccc ccgccgcagg aggtgcggac cggccgcacc tcctggttcc    540
ggcacaccaa gcggcgggac gccaaggcca tctcccacca ctacgacgtg tccaacacct    600
tctatgagtg ggtgctgggc ccgtcgatga cctacacctg cgcctgtttc cccaccgagg    660
acgccacctt ggaggaggcg cagttccaca agcacgacct ggtcgccaag aagctcgggc    720
tgcggccggg catgcggctg ctggacgtgg gctgcggctg gggcggcatg gtgatgcacg    780
ccgccaagca ctacggggtg cgggcgctgg gcgtcacgct gtccaagcag caggccgagt    840
gggcgcagaa ggccatcgcc gaggcgggcc tgagcgacct ggccgaggtc cgccaccagg    900
actaccggga cgtcaccgag ggcgacttcg acgccatcag ctcgatcggc ctcaccgagc    960
acatcggcaa ggccaacctg ccgtcctact tcggcttcct gtacggcaag ctcaagccgg    1020
gcgggcggct gctcaaccac tgcatcaccc ggcccgacaa cacccagccg gccatgaaga    1080
aggacgggtt catcaaccgg tacgtcttcc ccgacgggga gctggagggg cccggctacc    1140
tgcagaccca gatgaacgac gccggttttg agatccgcca ccaggagaac ctgcgcgagc    1200
actacgcccg cacctggccc ggatggtgcc gcaacctcga tgagcactgg gacgaggcgg    1260
tggccgaggt cggcgagggc accgcgcggg tgtggcggct gtacatggcc ggcagccggc    1320
tcggtttcga gctcaactgg atccagctgc accagatcct gggcgtcaag ctcggcgagc    1380
gcggcgagtc ccgcatgccg ttgcggcccg actggggcgt gtgacctcaa aatatatttt    1440
ccctctatct tctcgttgcg cttaatttga ctaattctca ttagcgaggc gcgccttttcc    1500 ataggctccg ccccctgac gagcatcaca aaaatcgacg ctcaagtcag aggtggcgaa    1560
acccgacagg actataaaga taccaggcgt ttccccctgg aagctccctc gtgcgctctc    1620
ctgttccgac cctgccgctt accggatacc tgtccgcctt tctcccttcg ggaagcgtgg    1680
cgctttctca tagctcacgc tgtaggtatc tcagttcggt gtaggtcgtt cgctccaagc    1740
tgggctgtgt gcacgaaccc cccgttcagc ccgaccgctg cgccttatcc ggtaactatc    1800
gtcttgagtc caacccggta agacacgact tatcgccact ggcagcagcc actggtaaca    1860
ggattagcag agcgaggtat gtaggcggtg ctacagagtt cttgaagtgg tggcctaact    1920
acggctacac tagaagaaca gtatttggta tctgcgctct gctgaagcca gttaccttcg    1980
gaaaaagagt tggtagctct tgatccggca acaaaccac cgctggtagc ggtggttttt    2040
ttgtttgcaa gcagcagatt acgcgcagaa aaaaggatc tcaagaagat cctttgatct    2100
tttctacggg gtctgacgct cagtggaacg aaaactcacg ttaagggatt ttggtcatga    2160
gattatcaaa aaggatcttc acctagatcc ttttaaatta aaaatgaagt tttaaatcaa    2220
tctaaagtat atatgagtaa acttggtctg acagttacca atgcttaatc agtgaggcac    2280
ctatctcagc gatctgtcta tttcgttcat ccatagttgc ctgactcccc gtcgtgtaga    2340
taactacgat acgggagggc ttaccatctg gccccagtgc tgcaatgata ccgcgagacc    2400
cacgctcacc ggctccagat ttatcagcaa taaaccagcc agccggaagg gccgagcgca    2460
gaagtggtcc tgcaactttta tccgcctcca tccagtctat taattgttgc cgggaagcta    2520
gagtaagtag ttcgccagtt aatagtttgc gcaacgttgt tgccattgct acaggcatcg    2580
tggtgtcacg ctcgtcgttt ggtatggctt cattcagctc cggttcccaa cgatcaaggc    2640
```

-continued

```
gagttacatg atcccccatg ttgtgcaaaa aagcggttag ctccttcggt cctccgatcg    2700
ttgtcagaag taagttggcc gcagtgttat cactcatggt tatggcagca ctgcataatt    2760
ctcttactgt catgccatcc gtaagatgct tttctgtgac tggtgagtac tcaaccaagt    2820
cattctgaga atagtgtatg cggcgaccga gttgctcttg cccggcgtca atacgggata    2880
ataccgcgcc acatagcaga actttaaaag tgctcatcat tggaaaacgt tcttcggggc    2940
gaaaactctc aaggatctta ccgctgttga gatccagttc gatgtaaccc actcgtgcac    3000
ccaactgatc ttcagcatct tttactttca ccagcgtttc tgggtgagca aaaacaggaa    3060
ggcaaaatgc cgcaaaaaag gaataagggc gacacggaa atgttgaata ctcatactct     3120
tcctttttca atattattga agcatttatc agggttattg tctcatgagc ggatacatat    3180
ttgaatgtat ttagaaaaat aaacagcgat cgcgcggccg cgggtaataa ctgatataat    3240
taaattgaag ctctaatttg tgagtttagt atacatgcat ttacttataa tacagttttt    3300
tagttttgct ggccgcatct tctcaaatat gcttcccagc ctgcttttct gtaacgttca    3360
ccctctacct tagcatccct tccctttgca atagtcctc ttccaacaat aataatgtca     3420
gatcctgtag agaccacatc atccacggtt ctatactgtt gacccaatgc gtctcccttg    3480
tcatctaaac ccacaccggg tgtcataatc aaccaatcgt aaccttcatc tcttccaccc    3540
atgtctcttt gagcaataaa gccgataaca aaatctttgt cgctcttcgc aatgtcaaca    3600
gtacccttag tatattctcc agtagctagg gagcccttgc atgacaattc tgctaacatc    3660
aaaaggcctc taggttcctt tgttacttct tccgccgcct gcttcaaacc gctaacaata    3720
cctgggccca ccacaccgtg tgcattcgta atgtctgccc attctgctat tctgtataca    3780
cccgcagagt actgcaattt gactgtatta ccaatgtcag caaattttct gtcttcgaag    3840
agtaaaaaat tgtacttggc ggataatgcc tttagcggct taactgtgcc ctccatggaa    3900
aaatcagtca agatatccac atgtgttttt agtaaacaaa ttttgggacc taatgcttca    3960
actaactcca gtaattcctt ggtggtacga acatccaatg aagcacacaa gtttgtttgc    4020
ttttcgtgca tgatattaaa tagcttggca gcaacaggac taggatgagt agcagcacgt    4080
tccttatatg tagctttcga catgattat cttcgtttcc tgcaggtttt tgttctgtgc     4140
agttgggtta agaatactgg gcaatttcat gtttcttcaa caccacatat gcgtatatat    4200
accaatctaa gtctgtgctc cttccttcgt tcttccttct gctcggagat taccgaatca    4260
aagctagctt atcgatgata agctgtcaaa gatgagaatt aattccacgg actatagact    4320
atactagata ctccgtctac tgtacgatac acttccgctc aggtccttgt cctttaacga    4380
ggccttacca ctcttttgtt actctattga tccagctcag caaaggcagt gtgatctaag    4440
attctatctt cgcgatgtag taaaactagc tagaccgaga aagagactag aaatgcaaaa    4500
ggcacttcta caatggctgc catcattatt atccgatgtg acgctgcagc ttctcaatga    4560
tattcgaata cgctttgagg agatacagcc taatatccga caaactgttt tacagattta    4620
cgatcgtact tgttacccat cattgaattt tgaacatccg aacctgggag ttttccctga    4680
aacagatagt atatttgaac ctgtataata atatatagtc tagcgcttta cggaagacaa    4740
tgtatgtatt tcggttcctg gagaaactat tgcatctatt gcataggtaa tcttgcacgt    4800
cgcatccccg gttcattttc tgcgtttcca tcttgcactt caatagcata tctttgttaa    4860
cgaagcatct gtgcttcatt ttgtagaaca aaaatgcaac gcgagagcgc taatttttca    4920
aacaaagaat ctgagctgca ttttttacaga acagaaatgc aacgcgaaag cgcttattta    4980
ccaacgaaga atctgtgctt cattttttgta aaacaaaaat gcaacgcgac gagagcgcta    5040
```

```
attttttcaaa caaagaatct gagctgcatt tttacagaac agaaatgcaa cgcgagagcg    5100
ctattttacc aacaaagaat ctatacttct tttttgttct acaaaaatgc atcccgagag    5160
cgctattttt ctaacaaagc atcttagatt acttttttc tcctttgtgc gctctataat     5220
gcagtctctt gataacttt tgcactgtag gtccgttaag gttagaagaa ggctactttg     5280
gtgtctattt tctcttccat aaaaaaagcc tgactccact tcccgcgttt actgattact    5340
agcgaagctg cgggtgcatt ttttcaagat aaaggcatcc ccgattatat tctataccga    5400
tgtggattgc gcatactttg tgaacagaaa gtgatagcgt tgatgattct tcattggtca    5460
gaaaattatg aacggtttct tctattttgt ctctatatac tacgtatagg aaatgtttac    5520
attttcgtat tgttttcgat tcactctatg aatagttctt actacaattt ttttgtctaa    5580 agagtaaatac tagagataaa cataaaaaat gtagaggtcg agtttagatg caagttcaag   5640
gagcgaaagg tgga                                                       5654
```

<210> SEQ ID NO 96
<211> LENGTH: 5759
<212> TYPE: DNA
<213> ORGANISM: Artificial Sequence
<220> FEATURE:
<223> OTHER INFORMATION: Synthetic Nucleic Acid

<400> SEQUENCE: 96

```
tgggtaggtt atatagggat atagcacaga gatatatagc aaagagatac ttttgagcaa      60
tgtttgtgga agcggtattc gcaatttaat taaagctggt gacaattaat catcggctcg     120
tataatgtgt ggaattgaat cgatataagg aggttaatca tatgtcacag ctggcggtca     180
cagaccacca cgagcgagcg gtcgaggcgc tgcgcaggtc gtatgcggcg atcccgccgg     240
gcacaccggt ccgcttggcc aagcagacct ccaacctgtt ccgcttccgc gagccgacgg     300
ccgcgcccgg cctggacgtg tccggcttca accgggtgct ggcggtggac ccggatgcgc     360
gcaccgccga cgtgcagggc atgaccacct acgaggacct ggtcgacgcc accctgccgc     420
acgggctgat gccgctggtg gtgccccagc tcaagacgat cacgctgggc ggggcggtga     480
ccggcctggg catcgagtcc acctccttcc gcaacggcct gccgcacgag tcggtgctgg     540
agatgcagat catcaccggc gccggcgaag tggtcaccgc cacccggac ggggagcact      600 ccgacctgtt ctgggcttc cccaactcct acggacgcgt ggggtacgcc ctgaagctga      660
agatcgaact ggagccggtc aagccgtacg tccggctgcg gcacctgcgc ttcgacgacg     720
ccggcgagtg cgccgccaag ctcgccgagc tgagcgaaag ccgcgagcac gagggcgatg     780
aggtgcactt tttggacggc accttcttcg ggccgcgcga gatgtacctg acgctcggca     840
cgttcaccga caccgccccc tatgtgtcgg actacaccgg gcagcacatc tactaccggt     900
cgatccagca gcggtcgatc gacttttttga ccatccgcga ctacctgtgg cgctgggaca    960
ccgactggtt ctggtgctcg cgcgcccctgg gcgtgcagaa cccgctgatc cggcgggtgt   1020
ggccgaagag cgccaagcgg tcggatgtgt accgcaagct ggtggcctac gaaaagcgct   1080
accagttcaa ggcgcgcatc gaccggtgga cgggcaagcc gccgcgcgag gacgtcatcc   1140
aggacatcga ggtgccggca gaacgcctgc cggattcct ggagttcttc cacgacaaga   1200
tcgggatgag cccggtgtgg ctgtgcccgc tgcgggcgcg ccaccgctgg ccgctgtacc   1260
cgctcaagcc cggcgtcacc tacgtcaacg ccggcttctg ggggacggtg ccgctgcagc   1320
cggggcagat gcccgagtac cacaaccggc tgatcgaacg gaaggtcgcc caactggacg   1380
```

-continued

```
gccacaagtc tctgtactcg acggcgttct actcgcgtga ggagttctgg cggcactacg    1440
acggggaaac ctaccggcgt ctgaaggaca cctacgaccc cgacgcgcgc ctgctcgacc    1500
tctacgacaa gtgcgtgcgg ggacgctgac ctcaaaatat attttccctc tatcttctcg    1560
ttgcgcttaa tttgactaat tctcattagc gaggcgcgcc tttccatagg ctccgccccc    1620
ctgacgagca tcacaaaaat cgacgctcaa gtcagaggtg gcgaaacccg acaggactat    1680
aaagatacca ggcgtttccc cctggaagct ccctcgtgcg ctctcctgtt ccgaccctgc    1740
cgcttaccgg atacctgtcc gcctttctcc cttcgggaag cgtggcgctt tctcatagct    1800
cacgctgtag gtatctcagt tcggtgtagg tcgttcgctc caagctgggc tgtgtgcacg    1860
aaccccccgt tcagcccgac cgctgcgcct tatccggtaa ctatcgtctt gagtccaacc    1920
cggtaagaca cgacttatcg ccactggcag cagccactgg taacaggatt agcagagcga    1980
ggtatgtagg cggtgctaca gagttcttga agtggtggcc taactacggc tacactagaa    2040
gaacagtatt tggtatctgc gctctgctga agccagttac cttcggaaaa agagttggta    2100
gctcttgatc cggcaaacaa accaccgctg gtagcggtgg ttttttttgtt tgcaagcagc    2160
agattacgcg cagaaaaaaa ggatctcaag aagatccttt gatcttttct acggggtctg    2220
acgctcagtg gaacgaaaac tcacgttaag ggattttggt catgagatta tcaaaaagga    2280
tcttcaccta gatcctttta aattaaaaat gaagttttaa atcaatctaa agtatatatg    2340
agtaaacttg gtctgacagt taccaatgct taatcagtga ggcacctatc tcagcgatct    2400
gtctatttcg ttcatccata gttgcctgac tccccgtcgt gtagataact acgatacggg    2460
agggcttacc atctggcccc agtgctgcaa tgataccgcg agacccacgc tcaccggctc    2520
cagatttatc agcaataaac cagccagccg aagggccga gcgcagaagt ggtcctgcaa    2580
ctttatccgc ctccatccag tctattaatt gttgccggga agctagagta agtagttcgc    2640
cagttaatag tttgcgcaac gttgttgcca ttgctacagg catcgtggtg tcacgctcgt    2700
cgtttggtat ggcttcattc agctccggtt cccaacgatc aaggcgagtt acatgatccc    2760
ccatgttgtg caaaaaagcg gttagctcct tcggtcctcc gatcgttgtc agaagtaagt    2820
tggccgcagt gttatcactc atggttatgg cagcactgca taattctctt actgtcatgc    2880
catccgtaag atgcttttct gtgactggtg agtactcaac caagtcattc tgagaatagt    2940
gtatgcggcg accgagttgc tcttgcccgg cgtcaatacg ggataatacc gcgccacata    3000
gcagaacttt aaaagtgctc atcattggaa aacgttcttc ggggcgaaaa ctctcaagga    3060
tcttaccgct gttgagatcc agttcgatgt aacccactcg tgcacccaac tgatcttcag    3120
catcttttac tttcaccagc gtttctgggt gagcaaaaac aggaaggcaa aatgccgcaa    3180
aaaagggaat aagggcgaca cggaaatgtt gaatactcat actcttcctt tttcaatatt    3240
attgaagcat ttatcagggt tattgtctca tgagcggata catatttgaa tgtatttaga    3300
aaaataaaca aataccgcgc ggccgcgggt aataactgat ataattaaat tgaagctcta    3360
atttgtgagt ttagtataca tgcatttact tataatacag ttttttagtt ttgctggccg    3420
catcttctca aatatgcttc ccagcctgct tttctgtaac gttcaccctc taccttagca    3480
tcccttccct ttgcaaatag tcctcttcca acaataataa tgtcagatcc tgtagagacc    3540
acatcatcca cggttctata ctgttgaccc aatgcgtctc ccttgtcatc taaacccaca    3600
ccgggtgtca taatcaacca atcgtaacct tcatctcttc cacccatgtc tctttgagca    3660
ataaagccga taacaaaatc tttgtcgctc ttcgcaatgt caacagtacc cttagtatat    3720
tctccagtag ctagggagcc cttgcatgac aattctgcta acatcaaaag gcctctaggt    3780
```

```
tcctttgtta cttcttccgc cgcctgcttc aaaccgctaa caatacctgg gcccaccaca    3840
ccgtgtgcat tcgtaatgtc tgcccattct gctattctgt atacacccgc agagtactgc    3900
aatttgactg tattaccaat gtcagcaaat tttctgtctt cgaagagtaa aaaattgtac    3960
ttggcggata atgcctttag cggcttaact gtgccctcca tggaaaaatc agtcaagata    4020
tccacatgtg tttttagtaa acaaattttg ggacctaatg cttcaactaa ctccagtaat    4080
tccttggtgg tacgaacatc caatgaagca cacaagtttg tttgcttttc gtgcatgata    4140
ttaaatagct tggcagcaac aggactagga tgagtagcag cacgttcctt atatgtagct    4200
ttcgacatga tttatcttcg tttcctgcag gttttttgttc tgtgcagttg ggttaagaat    4260
actgggcaat tcatgtttc ttcaacacca catatgcgta tatataccaa tctaagtctg    4320
tgctccttcc ttcgttcttc cttctgctcg gagattaccg aatcaaagct agcttatcga    4380
tgataagctg tcaaagatga gaattaattc cacggactat agactatact agatactccg    4440
tctactgtac gatacacttc cgctcaggtc cttgtccttt aacgaggcct taccactctt    4500
ttgttactct attgatccag ctcagcaaag gcagtgtgat ctaagattct atcttcgcga    4560
tgtagtaaaa ctagctagac cgagaaagag actagaaatg caaaaggcac ttctacaatg    4620
gctgccatca ttattatccg atgtgacgct gcagcttctc aatgatattc gaatacgctt    4680
tgaggagata cagcctaata tccgacaaac tgttttacag atttacgatc gtacttgtta    4740
cccatcattg aattttgaac atccgaacct gggagttttc cctgaaacag atagtatatt    4800
tgaacctgta taataatata tagtctagcg ctttacggaa gacaatgtat gtatttcggt    4860
tcctggagaa actattgcat ctattgcata ggtaatcttg cacgtcgcat ccccggttca    4920
ttttctgcgt ttccatcttg cacttcaata gcatatcttt gttaacgaag catctgtgct    4980
tcattttgta gaacaaaaat gcaacgcgag agcgctaatt tttcaaacaa agaatctgag    5040
ctgcattttt acagaacaga aatgcaacgc gaaagcgcta ttttaccaac gaagaatctg    5100
tgcttcattt ttgtaaaaca aaaatgcaac gcgacgagag cgctaatttt tcaaacaaag    5160
aatctgagct gcattttttac agaacagaaa tgcaacgcga gagcgctatt ttaccaacaa    5220
agaatctata cttctttttt gttctacaaa atgcatcccc gagagcgcta tttttctaac    5280
aaagcatctt agattacttt ttttctcctt tgtgcgctct ataatgcagt ctcttgataa    5340 cttttttgcac tgtaggtccg ttaaggttag aagaaggcta ctttggtgtc tattttctct    5400
tccataaaaa aagcctgact ccacttcccg cgtttactga ttactagcga agctgcgggt    5460 gcatttttc aagataaagg catccccgat tatattctat accgatgtgg attgcgcata    5520
ctttgtgaac agaaagtgat agcgttgatg attcttcatt ggtcagaaaa ttatgaacgg    5580
tttcttctat tttgtctcta tatactacgt ataggaaatg tttacatttt cgtattgttt    5640
tcgattcact ctatgaatag ttcttactac aatttttttg tctaaagagt aatactagag    5700
ataaacataa aaaatgtaga ggtcgagttt agatgcaagt tcaaggagcg aaaggtgga    5759
```

<210> SEQ ID NO 97
<211> LENGTH: 2664
<212> TYPE: DNA
<213> ORGANISM: Thermomonospora curvata

<400> SEQUENCE: 97

```
atgtcacagc tggcggtcac agaccaccac gagcgagcgg tcgaggcgct gcgcaggtcg     60
tatgcggcga tcccgccggg cacaccggtc cgcttggcca agcagacctc caacctgttc    120
```

| | |
|---|---|
| cgcttccgcg agccgacggc cgcgcccggc ctggacgtgt ccggcttcaa ccgggtgctg | 180 |
| gcggtggacc cggatgcgcg caccgccgac gtgcagggca tgaccaccta cgaggacctg | 240 |
| gtcgacgcca ccctgccgca cgggctgatg ccgctggtgg tgccccagct caagacgatc | 300 |
| acgctgggcg gggcggtgac cggcctgggc atcgagtcca cctccttccg caacggcctg | 360 |
| ccgcacgagt cggtgctgga gatgcagatc atcaccggcg ccggcgaagt ggtcaccgcc | 420 |
| accccggacg gggagcactc cgacctgttc tggggcttcc ccaactccta cgggacgctg | 480 |
| gggtacgccc tgaagctgaa gatcgaactg gagccggtca agccgtacgt ccggctgcgg | 540 |
| cacctgcgct tcgacgacgc cggcgagtgc gccgccaagc tcgccgagct gagcgaaagc | 600 |
| cgcgagcacg agggcgatga ggtgcactt ttggacggca ccttcttcgg gccgcgcgag | 660 |
| atgtacctga cgctcggcac gttcaccgac accgccccct atgtgtcgga ctacaccggg | 720 |
| cagcacatct actaccggtc gatccagcag cggtcgatcg acttttttgac catccgcgac | 780 |
| tacctgtggc gctgggacac cgactggttc tggtgctcgc gcgccctggg cgtgcagaac | 840 |
| ccgctgatcc ggcgggtgtg gccgaagagc gccaagcggt cggatgtgta ccgcaagctg | 900 |
| gtggcctacg aaaagcgcta ccagttcaag gcgcgcatcg accggtggac gggcaagccg | 960 |
| ccgcgcgagg acgtcatcca ggacatcgag gtgccggcag aacgcctgcc ggagttcctg | 1020 |
| gagttcttcc acgacaagat cgggatgagc ccggtgtggc tgtgcccgct gcgggcgcgc | 1080 |
| caccgctggc cgctgtaccc gctcaagccc ggcgtcacct acgtcaacgc cggcttctgg | 1140 |
| gggacggtgc cgctgcagcc ggggcagatg cccgagtacc acaaccggct gatcgaacgg | 1200 |
| aaggtcgccc aactgacggg ccacaagtct ctgtactcga cggcgttcta ctcgcgtgag | 1260 |
| gagttctggc ggcactacga cggggaaacc taccggcgtc tgaaggacac ctacgacccc | 1320 |
| gacgcgcgcc tgctcgacct ctacgacaag tgcgtgcggg gacgcgctgg tggtgccgag | 1380 |
| ggtggcaatg gcggtggcgc catgacgctg gccaaggtct tcgaggagct ggtcggggcg | 1440 |
| gacgcccctg tggagctcac cgcctacgac ggatcgagag ccggacgcct gggcagtgat | 1500 |
| ctgcgggtcc acgtgaagtc gccgtacgcg gtgtcctacc tggtgcactc gccgagcgcg | 1560 |
| ctcgggctgg cccgcgcgta cgtggccggg cacctggacg cctacggcga catgtacacg | 1620 |
| ctgctgcggg agatgacgca gctgaccgag gcgctgacgc ccaaggcccg gctgcggctg | 1680 |
| ctggccggtg tcctgcagga tccgctgctg cgcgcggcgg ccagccgccg tctgccgccc | 1740 |
| ccgccgcagg aggtgcggac cggccgcacc tcctggttcc ggcacaccaa gcggcgggac | 1800 |
| gccaaggcca tctcccacca ctacgacgtg tccaacacct tctatgagtg ggtgctgggc | 1860 |
| ccgtcgatga cctacacctg cgcctgtttc cccaccgagg acgccacctt ggaggaggcg | 1920 |
| cagttccaca agcacgacct ggtcgccaag aagctcgggc tgcggccggg catgcggctg | 1980 |
| ctggacgtgg gctgcggctg gggcggcatg gtgatgcacg ccgccaagca ctacggggtg | 2040 |
| cgggcgctgg gcgtcacgct gtccaagcag caggccgagt gggcgcagaa ggccatcgcc | 2100 |
| gaggcgggcc tgagcgacct ggccgaggtc cgccaccagg actaccggga cgtcaccgag | 2160 |
| ggcgacttcg acgccatcag ctcgatcggc ctcaccgagc acatcggcaa ggccaacctg | 2220 |
| ccgtcctact tcggcttcct gtacggcaag ctcaagccgg gcgggcggct gctcaaccac | 2280 |
| tgcatcaccc ggcccgacaa cacccagccg gccatgaaga aggacgggtt catcaaccgg | 2340 |
| tacgtcttcc ccgacgggga gctggagggg cccggctacc tgcagaccca gatgaacgac | 2400 |
| gccggttttg agatccgcca ccaggagaac ctgcgcgagc actacgcccg cacccctggcc | 2460 |
| ggatggtgcc gcaacctcga tgagcactgg gacgaggcgg tggccgaggt cggcgagggc | 2520 |

-continued

```
accgcgcggg tgtggcggct gtacatggcc ggcagccggc tcggtttcga gctcaactgg    2580
atccagctgc accagatcct gggcgtcaag ctcggcgagc gcggcgagtc ccgcatgccg    2640
ttgcggcccg actggggcgt gtga                                            2664

<210> SEQ ID NO 98
<211> LENGTH: 2664
<212> TYPE: DNA
<213> ORGANISM: Thermomonospora curvata

<400> SEQUENCE: 98
atgacgctgg ccaaggtctt cgaggagctg gtcggggcgg acgccctgt ggagctcacc      60 gcctacgacg gatcgagagc cggacgcctg ggcagtgatc tgcgggtcca cgtgaagtcg    120
ccgtacgcgg tgtcctacct ggtgcactcg ccgagcgcgc tcgggctggc ccgcgcgtac    180
gtggccgggc acctggacgc ctacggcgac atgtacacgc tgctgcggga gatgacgcag    240
ctgaccgagg cgctgacgcc caaggccggc tgcggctgc tggccggtgt cctgcaggat     300
ccgctgctgc gcgcggcggc cagccgccgt ctgccgcccc cgccgcagga ggtgcggacc    360
ggccgcacct cctggttccg gcacaccaag cggcgggacg ccaaggccat ctcccaccac    420
tacgacgtgt ccaacacctt ctatgagtgg gtgctgggcc cgtcgatgac ctacacctgc    480
gcctgtttcc ccaccgagga cgccaccttg gaggaggcgc agttccacaa gcacgacctg    540
gtcgccaaga agctcgggct gcggccgggc atgcggctgc tggacgtggg ctgcggctgg    600
ggcggcatgg tgatgcacgc cgccaagcac tacggggtgc gggcgctggg cgtcacgctg    660
tccaagcagc aggccgagtg ggcgcagaag gccatcgccg aggcgggcct gagcgacctg    720
gccgaggtcc gccaccagga ctaccggggac gtcaccgagg gcgacttcga cgccatcagc    780
tcgatcggcc tcaccgagca catcggcaag gccaacctgc cgtcctactt cggcttcctg    840
tacggcaagc tcaagccggg cggcgcggctg ctcaaccact gcatcacccg gcccgacaac    900
acccagccgg ccatgaagaa ggacgggttc atcaaccggt acgtcttccc cgacggggag    960 ctggagggc ccggctacct gcagacccag atgaacgacg ccggttttga gatccgccac    1020
caggagaacc tgcgcgagca ctacgcccgc accctggccg gatggtgccg caacctcgat    1080
gagcactggg acgaggcggt ggccgaggtc ggcgagggca ccgcgcgggt gtggcggctg    1140
tacatggccg gcagccggct cggtttcgag ctcaactgga tccagctgca ccagatcctg    1200
ggcgtcaagc tcggcgagcg cggcgagtcc cgcatgccgt tgcggcccga ctggggcgtg    1260
gctggtggtg ccgagggtgg caatggcggt ggcgccatgt cacagctggc ggtcacagac    1320
caccacgagc gagcggtcga ggcgctgcgc aggtcgtatg cggcgatccc gccgggcaca    1380
ccggtccgct tggccaagca gacctccaac ctgttccgct ccgcgagcc gacggccgcg    1440 cccggcctgg acgtgtccgg cttcaaccgg gtgctggcgg tggacccgga tgcgcgcacc    1500
gccgacgtgc agggcatgac cacctacgag gacctggtcg acgccaccct gccgcacggg    1560
ctgatgccgc tggtggtgcc ccagctcaag acgatcacgc tgggcggggc ggtgaccggc    1620
ctgggcatcg agtccacctc cttccgcaac ggcctgccgc acgagtcggt gctggagatg    1680
cagatcatca ccggcgccgg cgaagtggtc accgccaccc cggacgggga gcactccgac    1740
ctgttctggg gcttccccaa ctcctacggg acgctggggt acgccctgaa gctgaagatc    1800
gaactggagc cggtcaagcc gtacgtccgg ctgcggcacc tgcgcttcga cgacgccggc    1860
gagtgcgccg ccaagctcgc cgagctgagc gaaagccgcg agcacgaggg cgatgaggtg    1920
```

```
cacttttgg acggcacctt cttcgggccg cgcgagatgt acctgacgct cggcacgttc    1980
accgacaccg ccccctatgt gtcggactac accgggcagc acatctacta ccggtcgatc    2040
cagcagcggt cgatcgactt tttgaccatc cgcgactacc tgtggcgctg ggacaccgac    2100
tggttctggt gctcgcgcgc cctgggcgtg cagaacccgc tgatccggcg ggtgtggccg    2160
aagagcgcca agcggtcgga tgtgtaccgc aagctggtgg cctacgaaaa gcgctaccag    2220
ttcaaggcgc gcatcgaccg gtggacgggc aagccgccgc gcgaggacgt catccaggac    2280
atcgaggtgc cggcagaacg cctgccggag ttcctggagt tcttccacga caagatcggg    2340
atgagcccgg tgtggctgtg cccgctgcgg gcgcgccacc gctggccgct gtacccgctc    2400
aagcccggcg tcacctacgt caacgccggc ttctggggga cggtgccgct gcagccgggg    2460
cagatgcccg agtaccacaa ccggctgatc gaacggaagg tcgcccaact ggacggccac    2520
aagtctctgt actcgacggc gttctactcg cgtgaggagt tctggcggca ctacgacggg    2580
gaaacctacc ggcgtctgaa ggacacctac gaccccgacg cgcgcctgct cgacctctac    2640
gacaagtgcg tgcggggacg ctga                                          2664
```

HETEROLOGOUS PRODUCTION OF 10-METHYLSTEARIC ACID

CROSS REFERENCE TO RELATED APPLICATIONS

This application is a divisional of U.S. patent application Ser. No. 15/710,734, filed Sep. 20, 2017, now U.S. Pat. No. 10,457,963, which claims priority to U.S. Provisional Patent Application Ser. No. 62/396,870, filed Sep. 20, 2016, each of which are incorporated by reference herein in their entirety.

BACKGROUND

Fatty acids derived from agricultural plant and animal oils find use as industrial lubricants, hydraulic fluids, greases, and other specialty fluids in addition to oleochemical feedstocks for processing. The physical and chemical properties of these fatty acids result in large part from their carbon chain length and number of unsaturated double bonds. Fatty acids are typically 16:0 (sixteen carbons, zero double bonds), 16:1 (sixteen carbons, 1 double bond), 18:0, 18:1, 18:2, or 18:3. Importantly, fatty acids with no double bonds (saturated) have high oxidative stability, but they solidify at low temperature. Double bonds improve low-temperature fluidity, but decrease oxidative stability. This trade-off poses challenges for lubricant and other specialty-fluid formulations because consistent long term performance (high oxidative stability) over a wide range of operating temperatures is desirable. High 18:1 (oleic) fatty acid oils provide low temperature fluidity with relatively good oxidative stability. Accordingly, several commercial products, such as high oleic soybean oil, high oleic sunflower oil, and high oleic algal oil, have been developed with high oleic compositions. Oleic acid is an alkene, however, and subject to oxidative degradation.

SUMMARY

The nucleic acids, cells, and methods described herein are generally useful for the production of branched (methyl) lipids, such as 10-methylstearic acid, and compositions that include such lipids. Saturated branched (methyl)lipids like 10-methylstearic acid have favorable low-temperature fluidity and favorable oxidative stability, which are desirable properties for lubricants and specialty fluids.

Various aspects relate to nucleic acids comprising a recombinant tmsB gene encoding a methyltransferase protein, a recombinant tmsA gene encoding a reductase protein, and/or a recombinant tmsC gene encoding a tmsC protein. The methyltransferase protein, reductase protein, and/or tmsC protein may be proteins expressed by species of *Actinobacteria*, and the recombinant tmsB gene, recombinant tmsA gene, and/or recombinant tmsC gene may be codon-optimized for expression in a different phylum of bacteria (e.g., Proteobacterium) or in eukaryotes (e.g., yeast, such as *Arxula adeninivorans* (also known as *Blastobotrys adeninivorans* or *Trichosporon adeninivorans*), *Saccharomyces cerevisiae*, or *Yarrowia lipolytica*). The recombinant tmsB gene, recombinant tmsA gene, or recombinant tmsC gene may be operably-linked to a promoter capable of driving expression in a phylum of bacteria other than Actinobacteria (e.g., Proteobacterium) or in eukaryotes (e.g., yeast). The nucleic acid may be a plasmid or a chromosome.

Some aspects relate to a cell comprising a nucleic acid as described herein. The cell may comprise a branched (methyl)lipid, such as 10-methylstearic acid, and/or an exomethylene-substituted lipid, such as 10-methylenestearic acid. The cell may be a eukaryotic cell, such as an algae cell, yeast cell, or plant cell.

Some aspects relate to a composition produced by cultivating a cell culture comprising cells as described herein. The oil composition may comprise a branched (methyl)lipid, such as 10-methylstearic acid, and or an exomethylene-substituted lipid, such as 10-methylenestearic acid.

BRIEF DESCRIPTION OF THE DRAWINGS

FIGS. 3A and 3B depict prokaryotic operons encoding enzymes that catalyze the transfer of methyl groups to alkyl chains from sixteen different species of bacteria, labeled A-H (FIG. 3A) and I-P (FIG. 3B). The tmsA and tmsB genes are particularly important for methylating alkyl chains. The tmsC gene may also be important for methylating alkyl chains. The nucleotide sequences of these genes and the amino acid sequences that they encode are shown in SEQ ID NO:1-76.

Figure 7A:
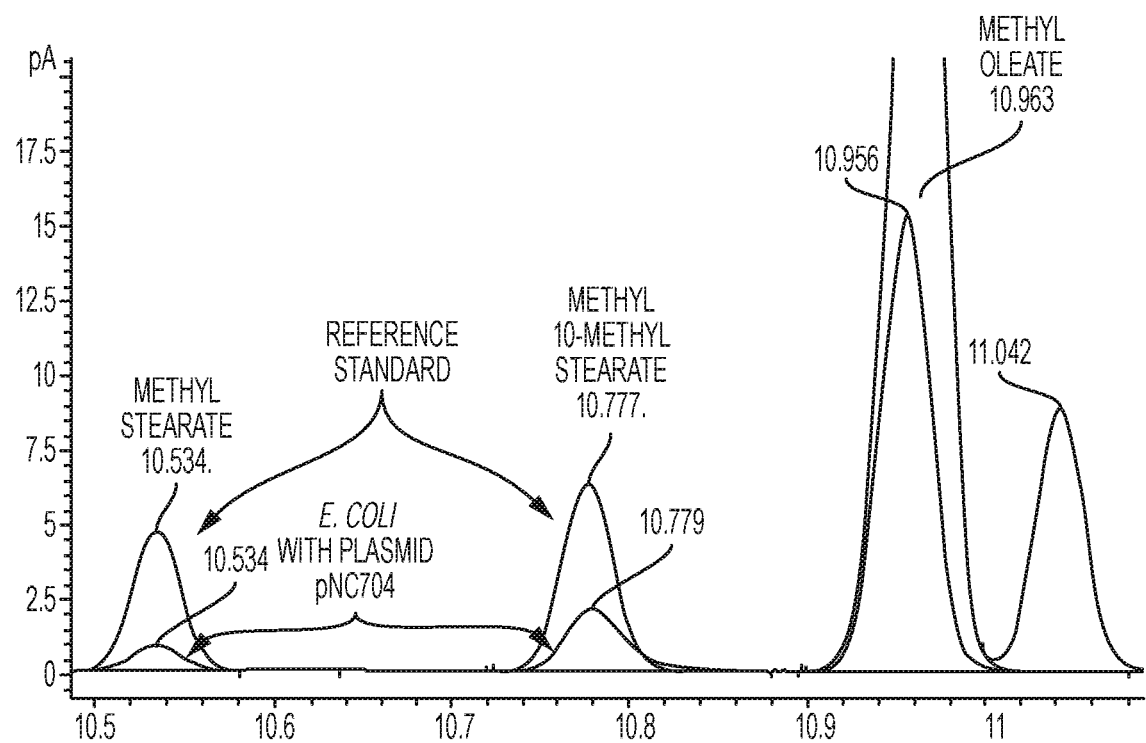
Figure 7B:
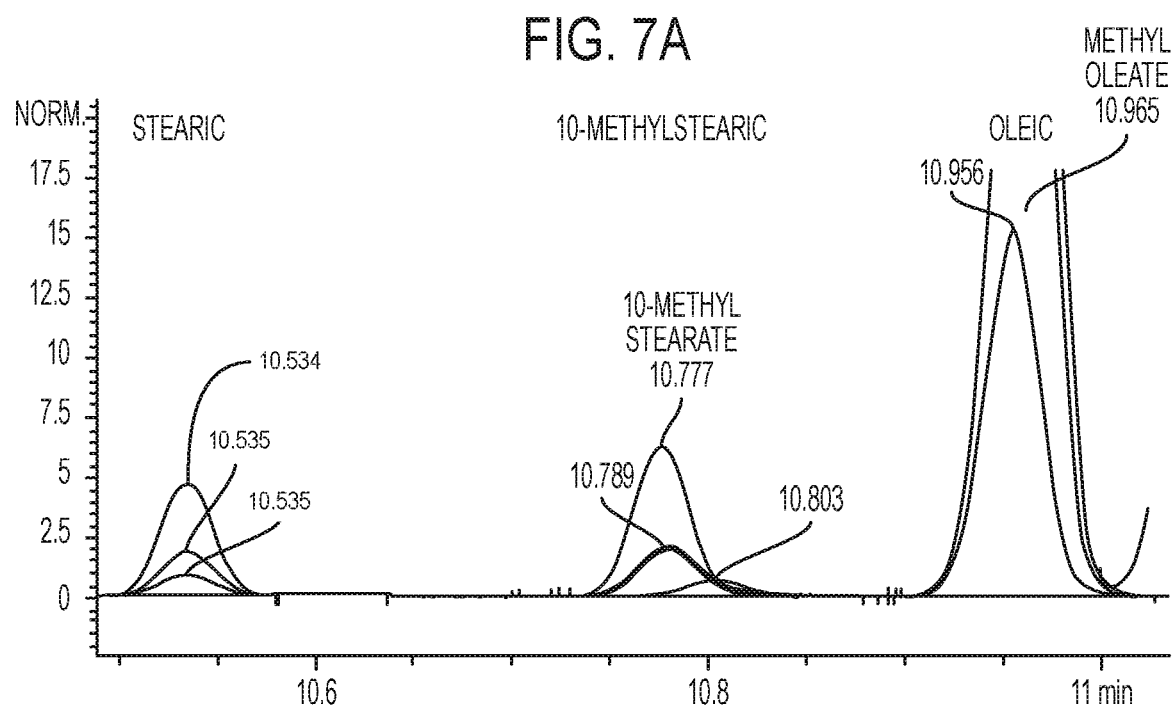

FIGS. 7A and 7B consist of overlaid gas chromatography (GC) traces of various fatty acid standards and lipids extracted from various samples. The standards were stearic acid, 10-methylstearic acid, and oleic acid. Each sample and standard was transesterified into fatty acid methyl esters (FAMEs) prior to analysis. FIG. 7A depicts the GC trace of FAMEs prepared from E. coli that express the tmsA and tmsB genes from Mycobacterium smegmatis as well as the GC traces of each standard. The tmsA/tmsB sample displayed a peak at about 10.777 minutes, corresponding to the 10-methylstearic acid standard. FIG. 7B depicts each trace of FIG. 7A and two additional traces. The first additional trace corresponds to FAMEs prepared from E. coli that express the ufa gene from Mycobacterium tuberculosis. This sample displayed a peak at about 10.777 minutes, corresponding to the 10-methylstearic acid standard. The second additional trace corresponds to FAMEs prepared from E. coli that had been transfected with an empty vector. This control did not display a peak at 10.777 minutes, suggesting that the tmsA and tmsB genes synthesized 10-methylstearic acid in the transformed E. coli.

Figure 8A:
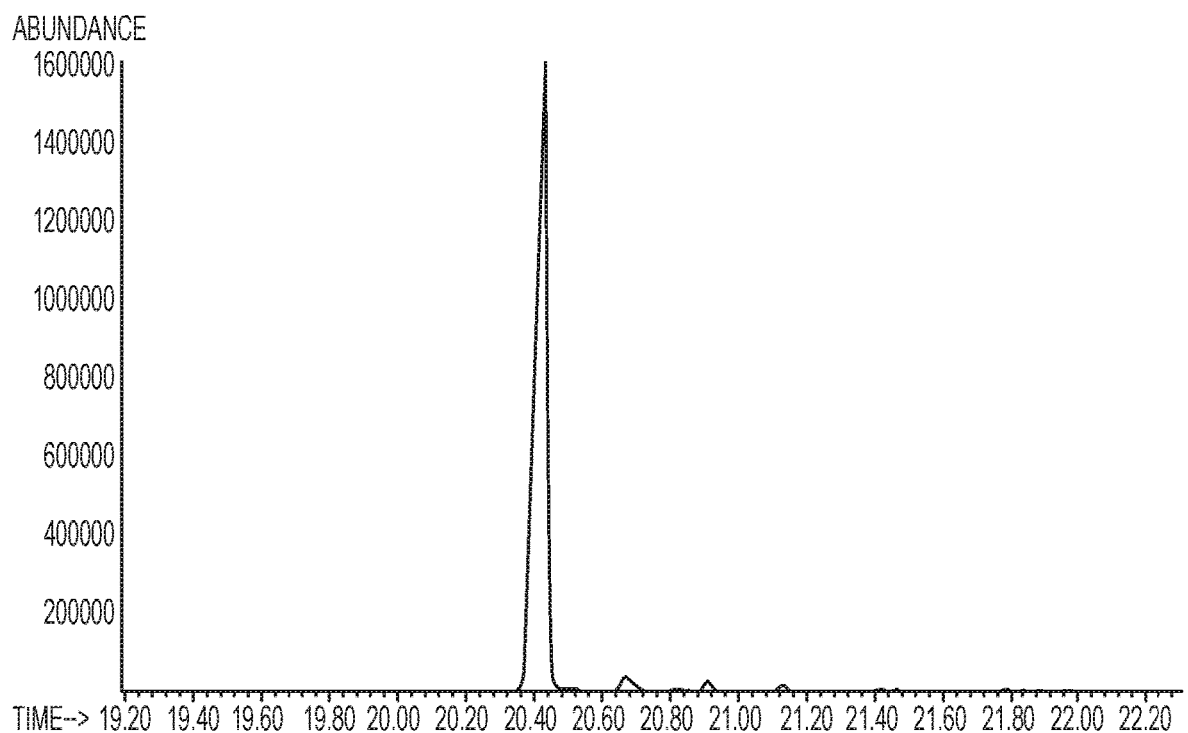
Figure 8B:
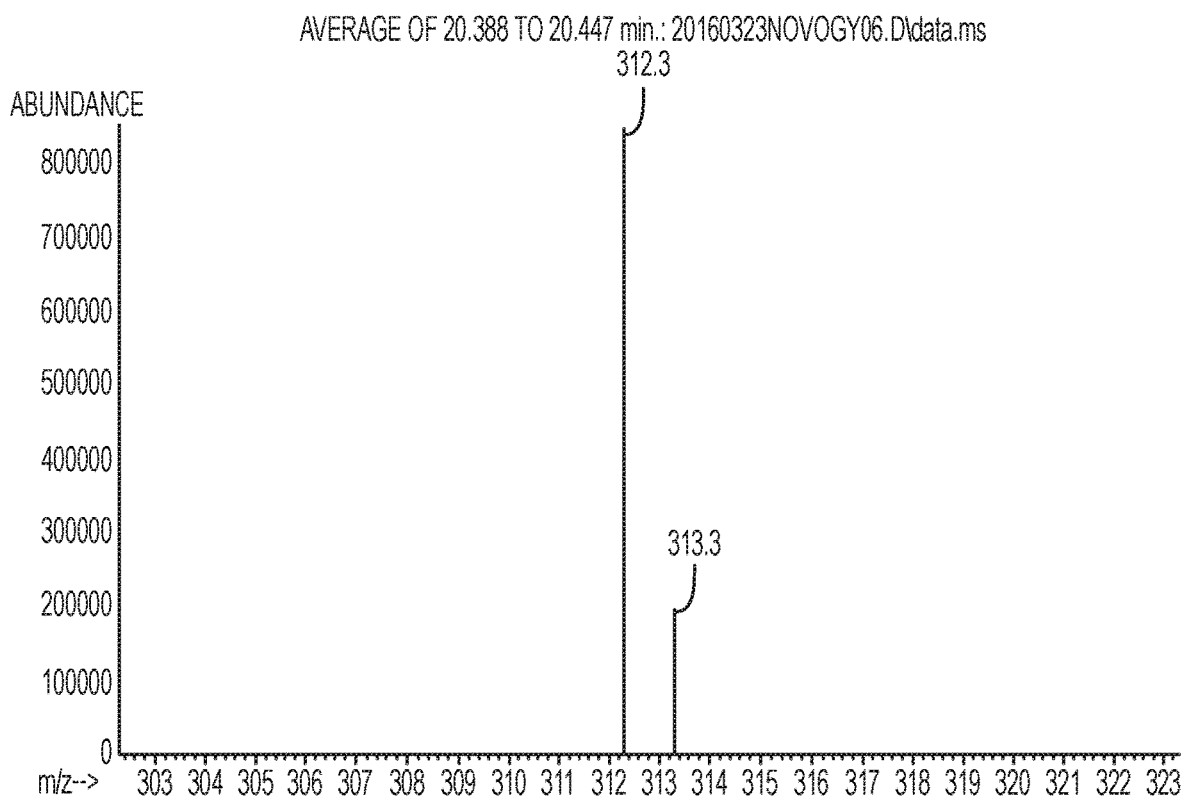
Figure 9A:
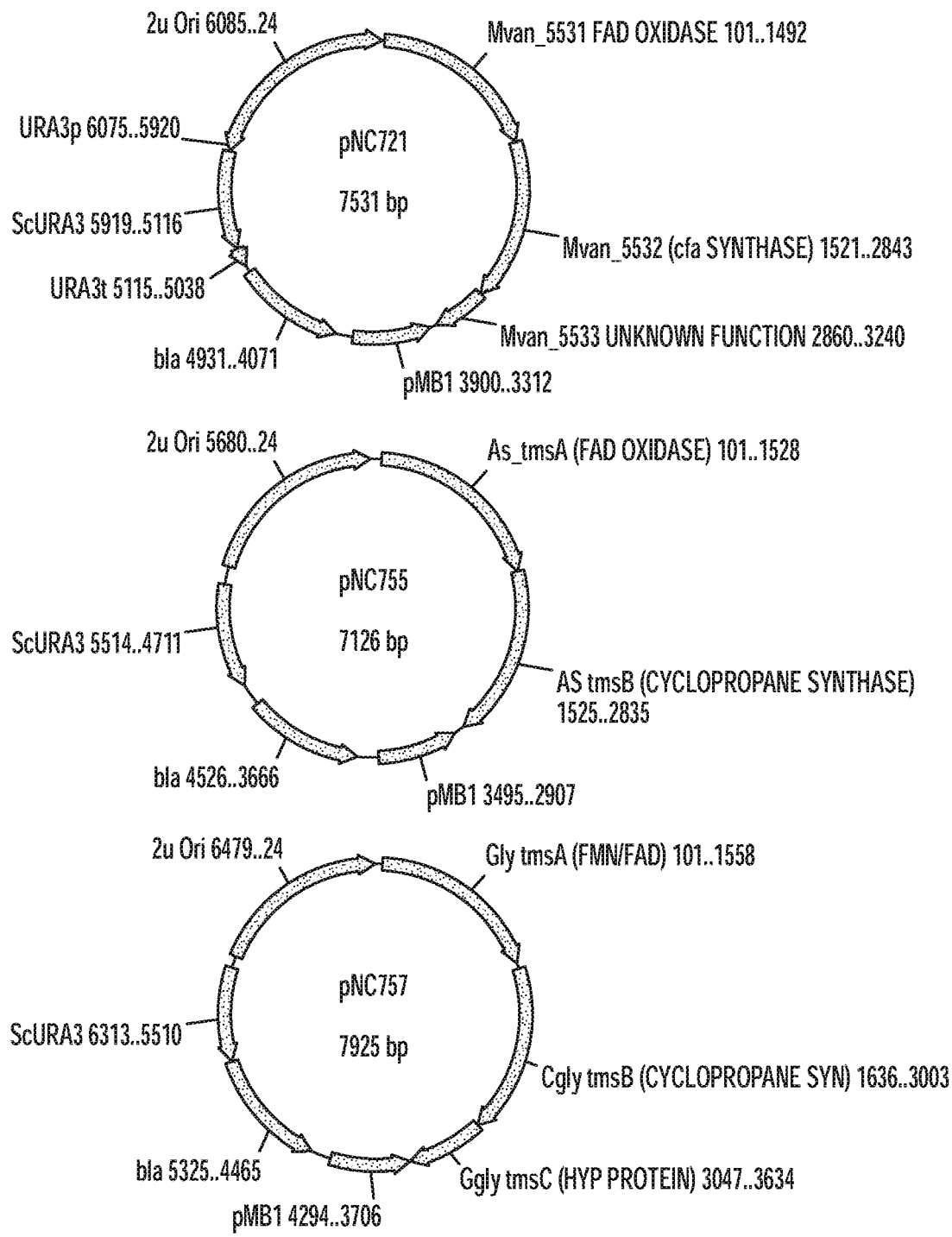
Figure 9B:
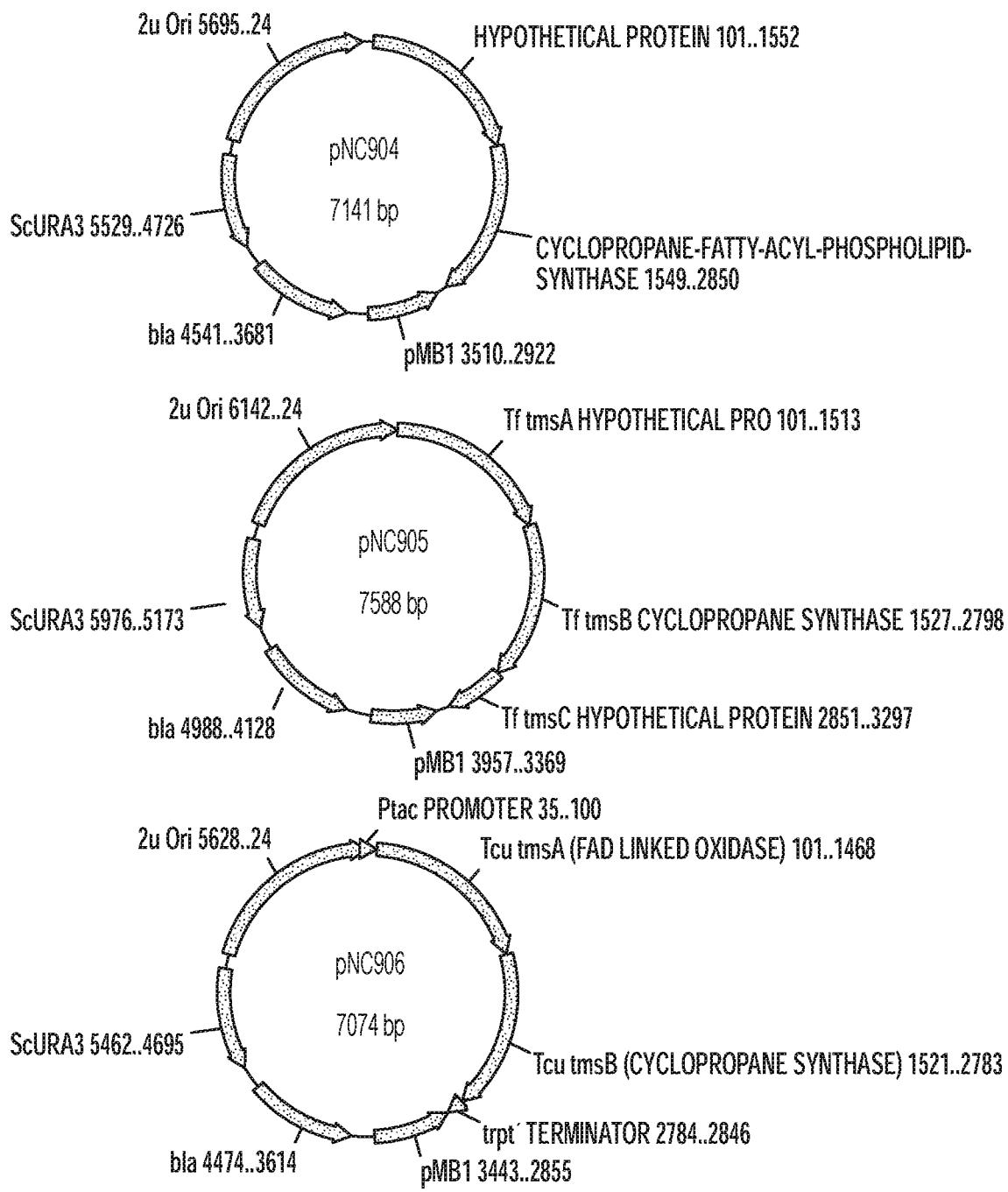
Figure 9C:
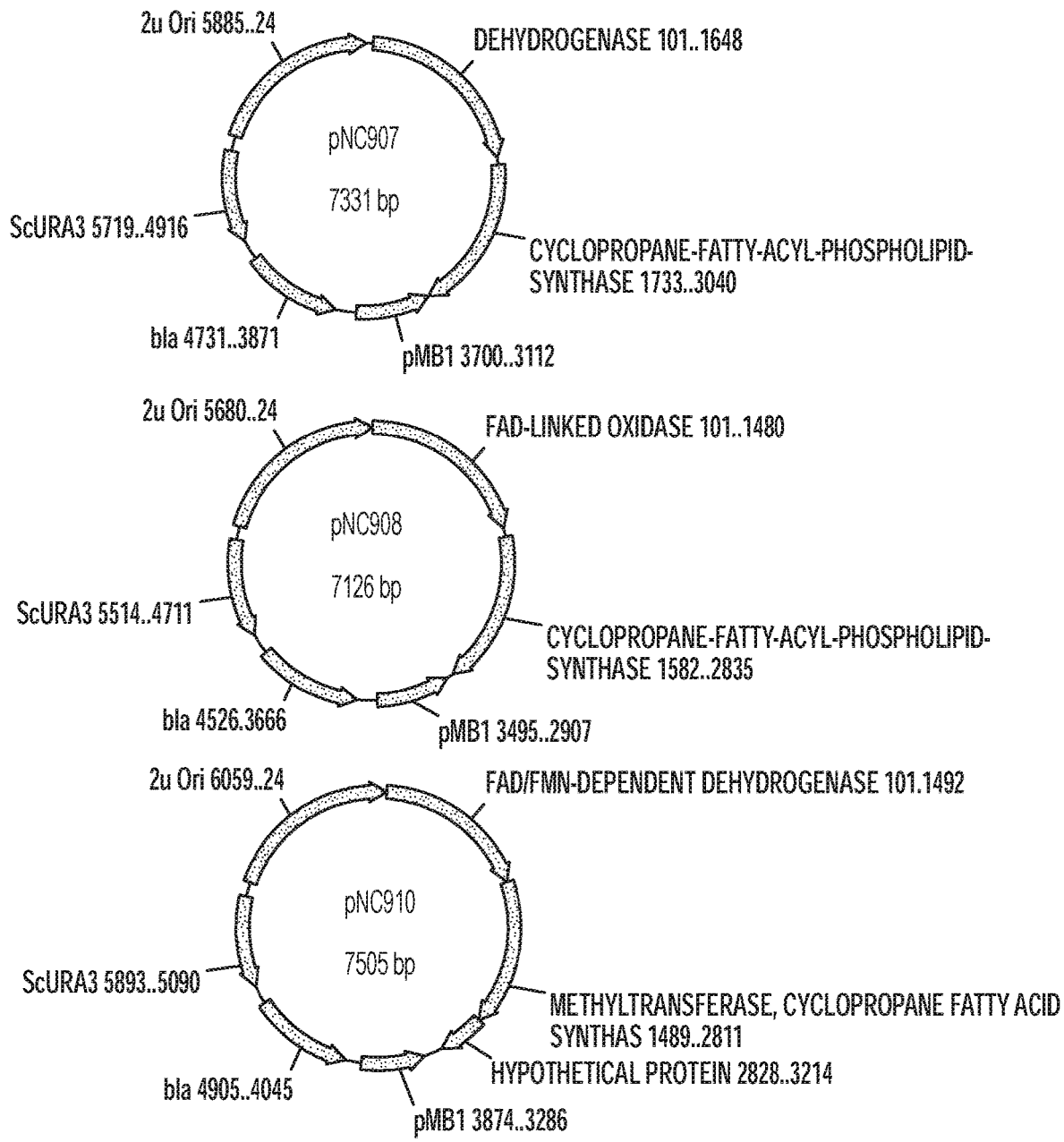
Figure 9D:
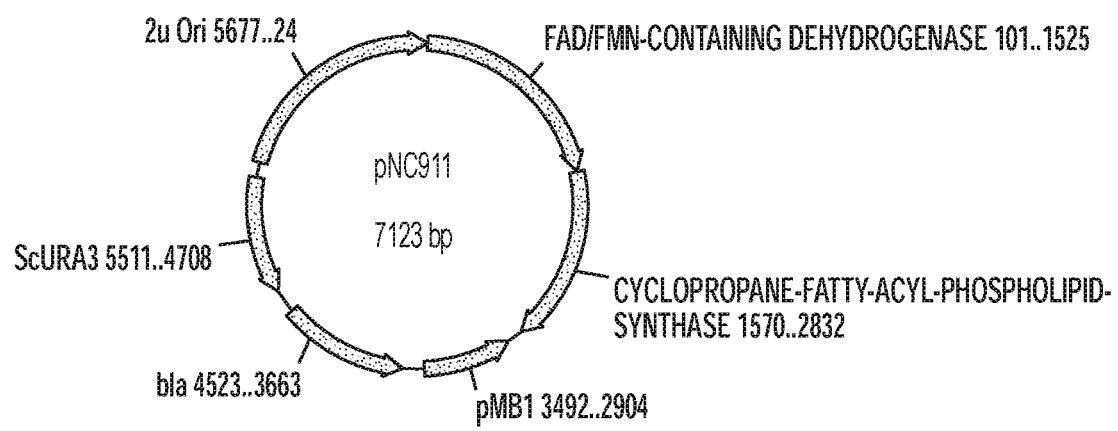

FIGS. 8A and 8B depict GC-MS result. FIG. 8A is a gas chromatography (GC) trace of lipids eluting from a GC column. The lipids were purified from E. coli that had been transfected with pNC704 encoding Mycobacterium smegmatis genes tmsA and tmsB, and the lipids were converted into fatty acid methyl esters. FIG. 8B is a mass spectroscopy spectrum of the lipids eluted during the GC run of panel A from 20.388 to 20.447 minutes. The mass spectrum is gated for the 10-methylstearate fatty acid methyl ester, which has a molecular weight of 312. The spectrum also displays a peak at 313 m/z corresponding to 10-methylstearate methyl esters comprising natural-abundance isotopes (e.g., a single $^{13}C$).

FIGS. 9A-9D depict maps of the following vectors, which can be used to express the tmsA and tmsB genes of the indicated species: pNC721 (Mycobacterium vanbaaleni) (SEQ ID NO:83), pNC755 (Amycolicicoccus subflavus) (SEQ ID NO:84), pNC757 (Corynebacterium glyciniphilum) (SEQ ID NO:85), pNC 904 (Rhodococcus opacus) (SEQ ID NO:86), pNC905 (Thermobifida fusca) (SEQ ID NO:87), pNC906 (Thermomonospora curvata) (SEQ ID NO:88), pNC907 (Corynebacterium glutamicum) (SEQ ID NO:89), pNC908 (Agromycies subbeticus) (SEQ ID NO:90), pNC910 (Mycobacterium gilvum) (SEQ ID NO:91), pNC911 (Mycobacterium sp. indicus) (SEQ ID NO:92).

Figure 10:
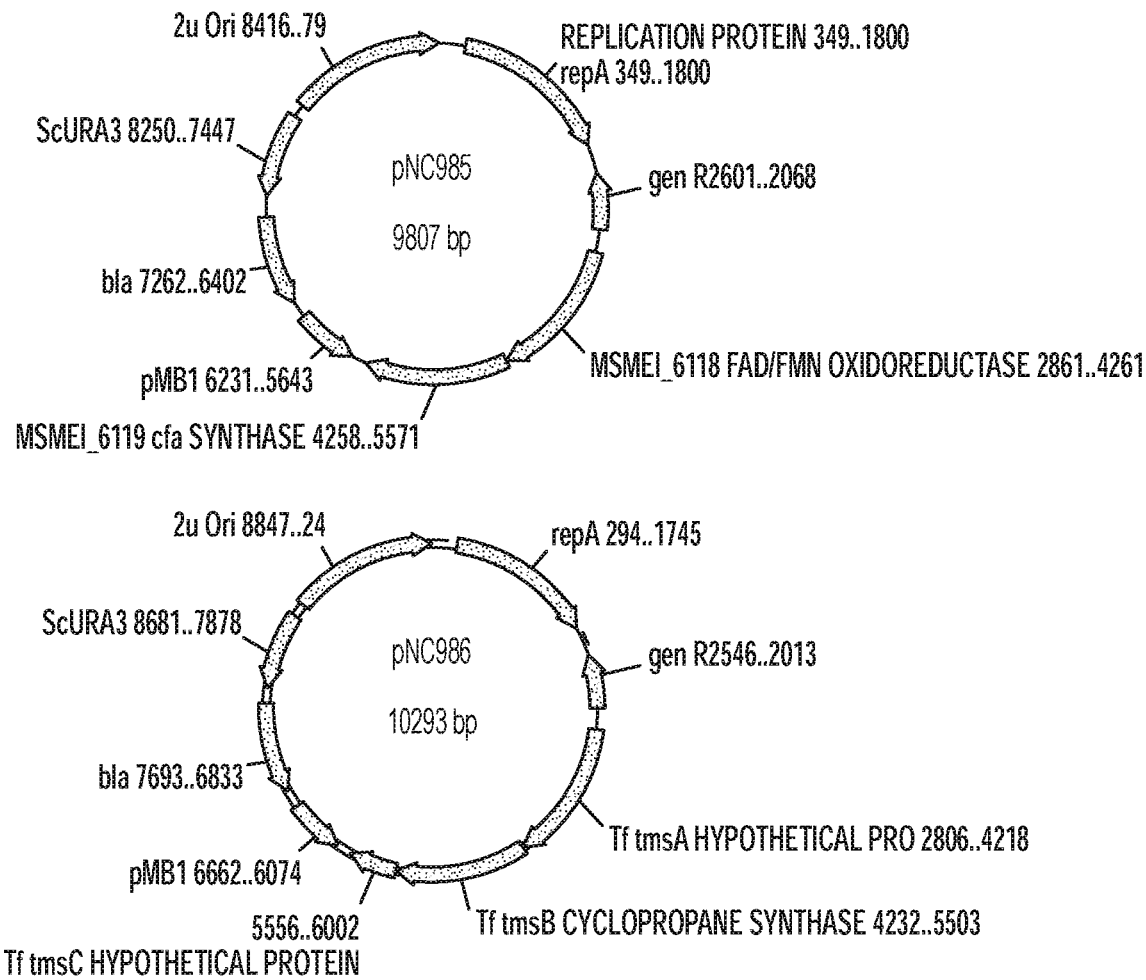

FIG. 10 depicts maps of vectors pNC985 (SEQ ID NO:93), which can be used to express the M. smegmatis tmsAB genes in Rhodococcus bacteria, and pNC986 (SEQ ID NO:94), which can be used to express the T. fusca tmsAB genes in Rhodococcus bacteria.

Figure 11:
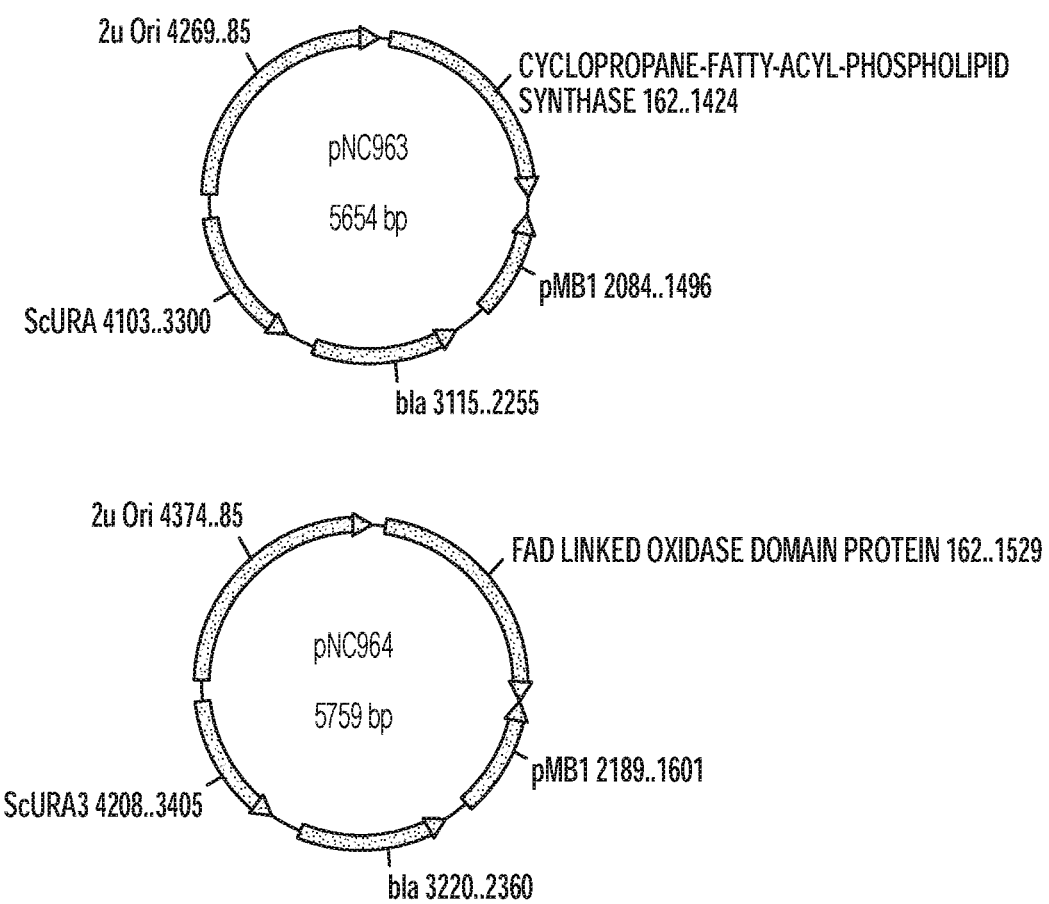

FIG. 11 depicts maps of vectors pNC963 (SEQ ID NO:95), which encodes the T. curvata tmsB gene under control of the constitutive tac promoter, and pNC964 (SEQ ID NO:96), which encodes the T curvata tmsA gene under control of the constitutive tac promoter.

Figure 12:
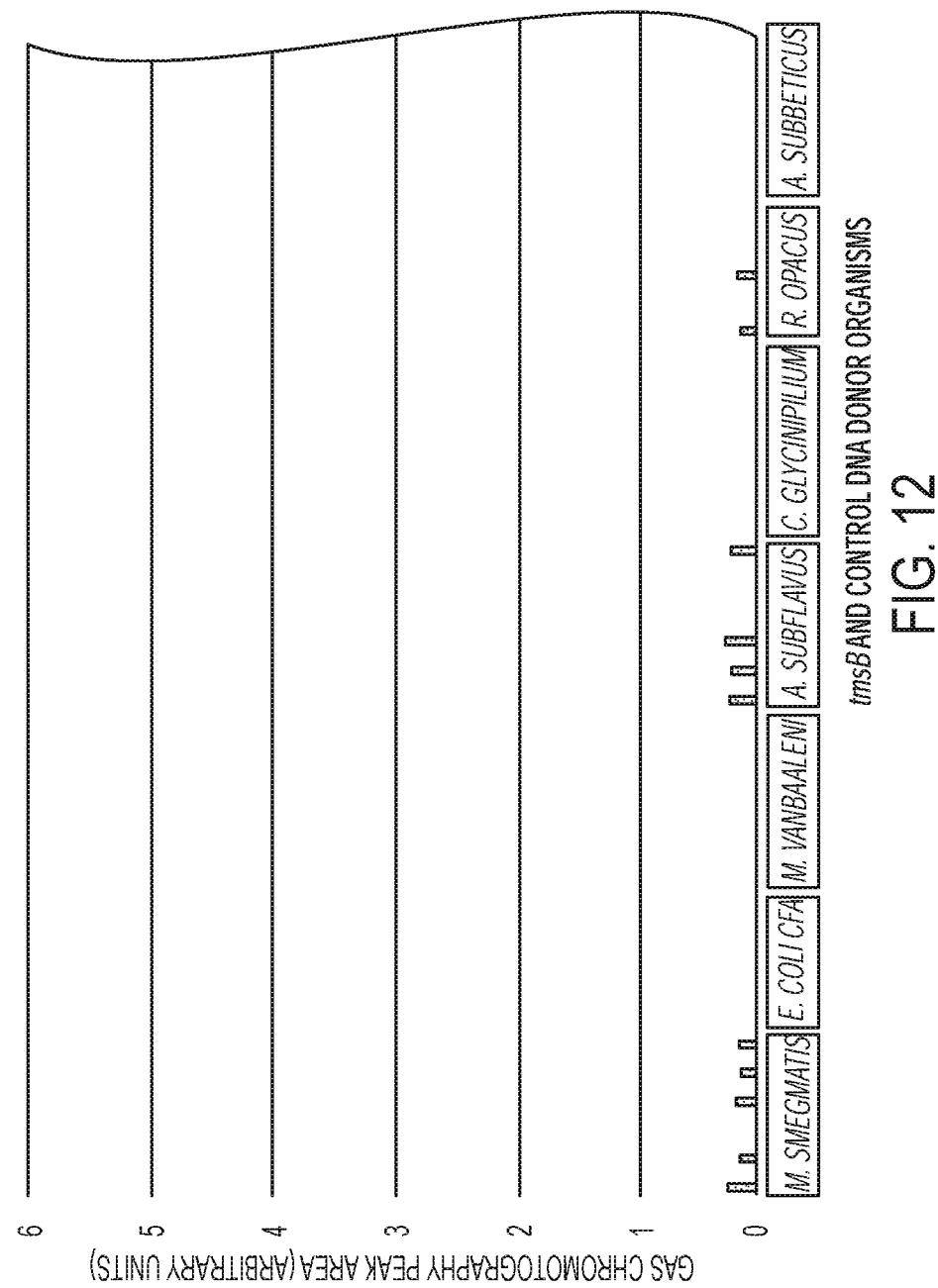

FIG. 12 is a graph showing gas chromatographic detection of 10-methylene stearic acid in Y. lipolytica expressing tmsB genes from various organisms.

Figure 13:
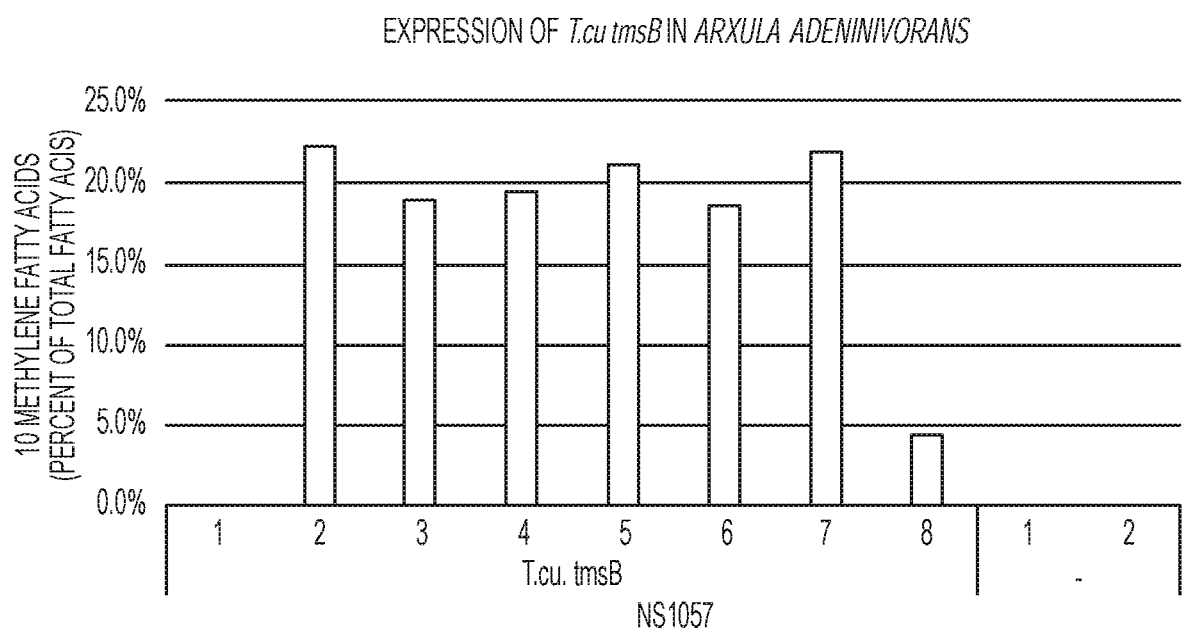

FIG. 13 is a graph showing percentage of 10-methylene fatty acids as compared to total fatty acids in 8 transformants of Arxula adeninivorans containing a plasmid encoding T. curvata tmsB. The two isolates furthest to the right were transformed with empty vector control.

Figure 14:
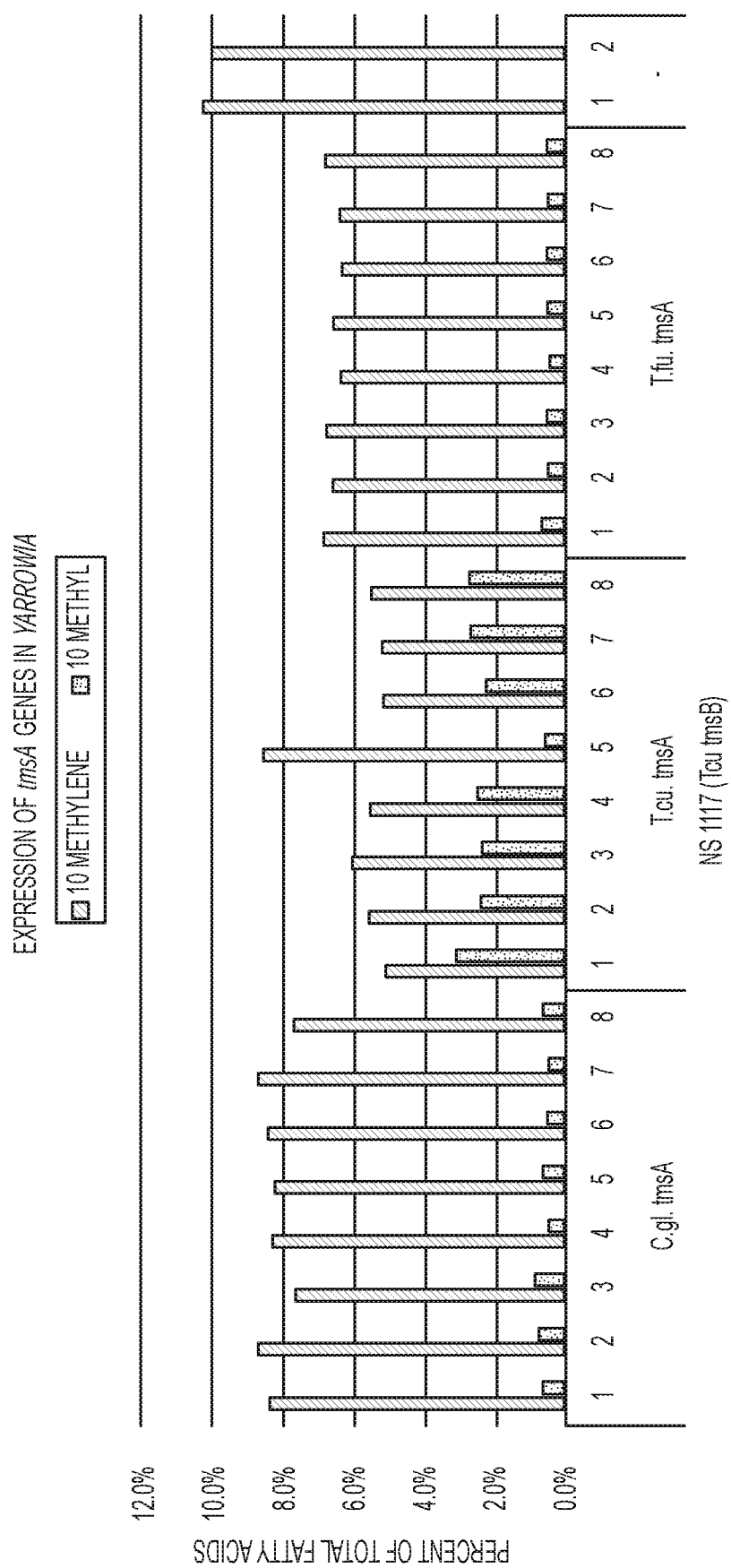

FIG. 14 is a graph showing the percentage by weight of 10-methylene fatty acids and 10-methyl fatty acids in Yarrowia lipolytica containing a stably integrated copy of the T. curvata tmsB gene and transformed with plasmids expressing tmsA from C. glutamicum (C.gl.), T. curvata (T.cu.), or T. fusca (T.fu.), or an empty vector control (the two transformants furthest to the right).

Figure 15:
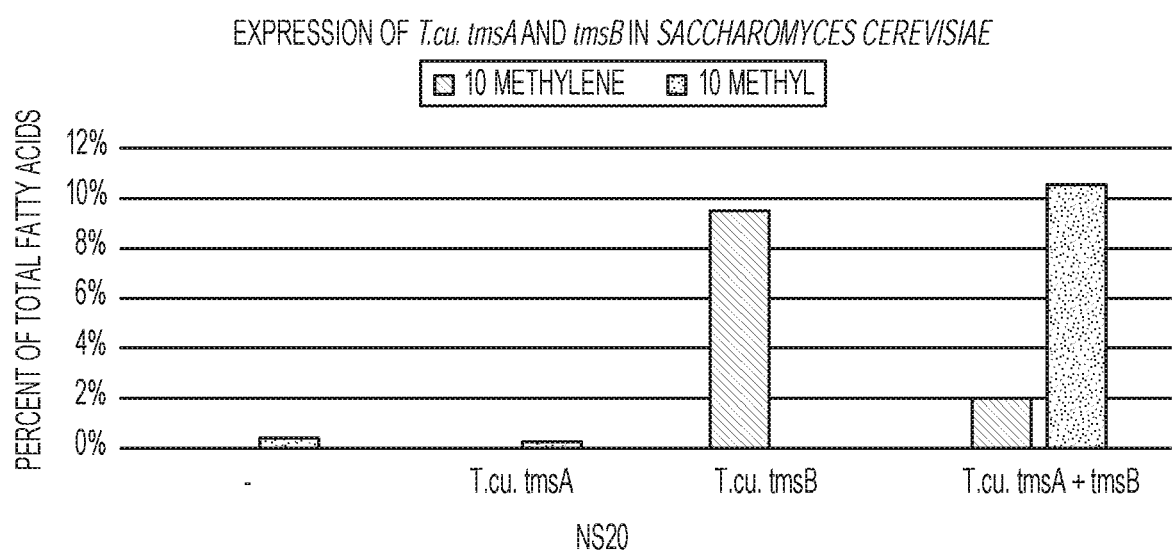

FIG. 15 is a graph showing the percentage by weight of 10-methylene fatty acids and 10-methyl fatty acids as compared to total fatty acids in transformants of S. cerevisiae transformed with empty vector (–) or vectors encoding T. curvata tmsA (T.cu. tmsA), T. curvata tmsB (T.cu. tmsB), or both T. curvata tmsA and tmsB (T.cu. tmsA+tmsB).

Figure 16:
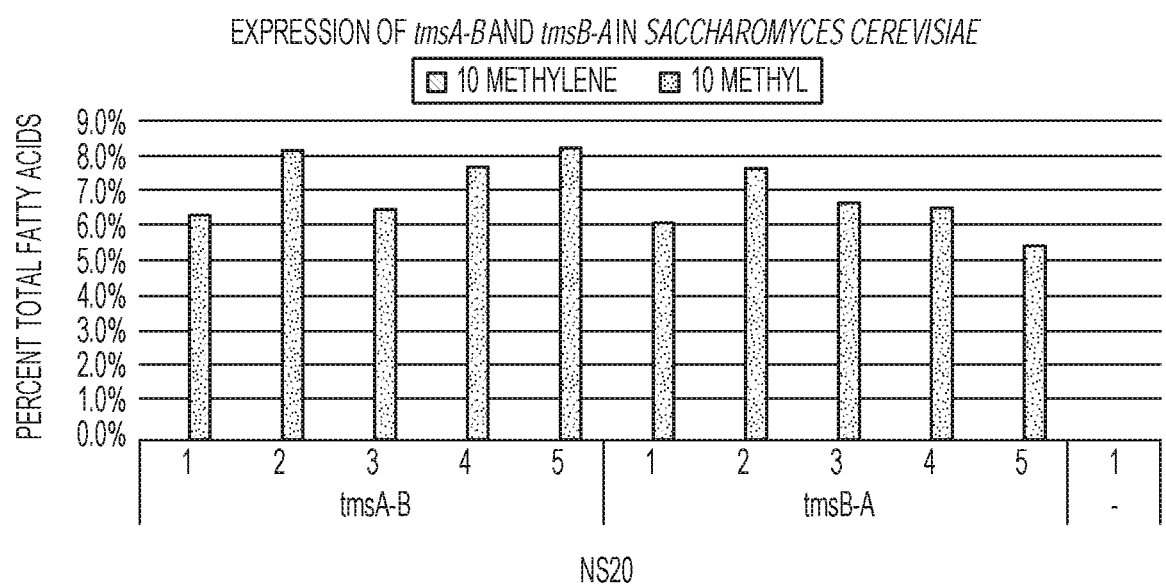

FIG. 16 is a graph showing the percentage by weight of 10-methylene fatty acids and 10-methyl fatty acids as compared to total fatty acids in transformants of S. cerevisiae containing the tmsA-B fusion protein, the tmsB-A fusion protein, or empty vector (–).

Figure 17:
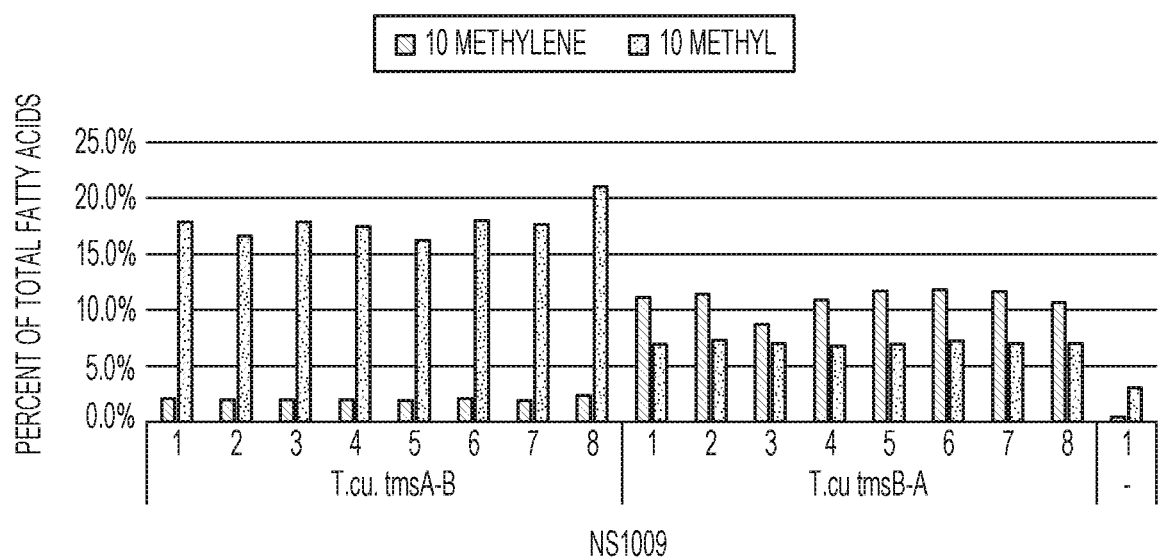

FIG. 17 is a graph showing the percentage by weight of 10-methylene fatty acids and 10-methyl fatty acids as compared to total fatty acids in transformants of Y. lipolytica containing the tmsA-B fusion protein, the tmsB-A fusion protein, or empty vector (–).

Figure 18:
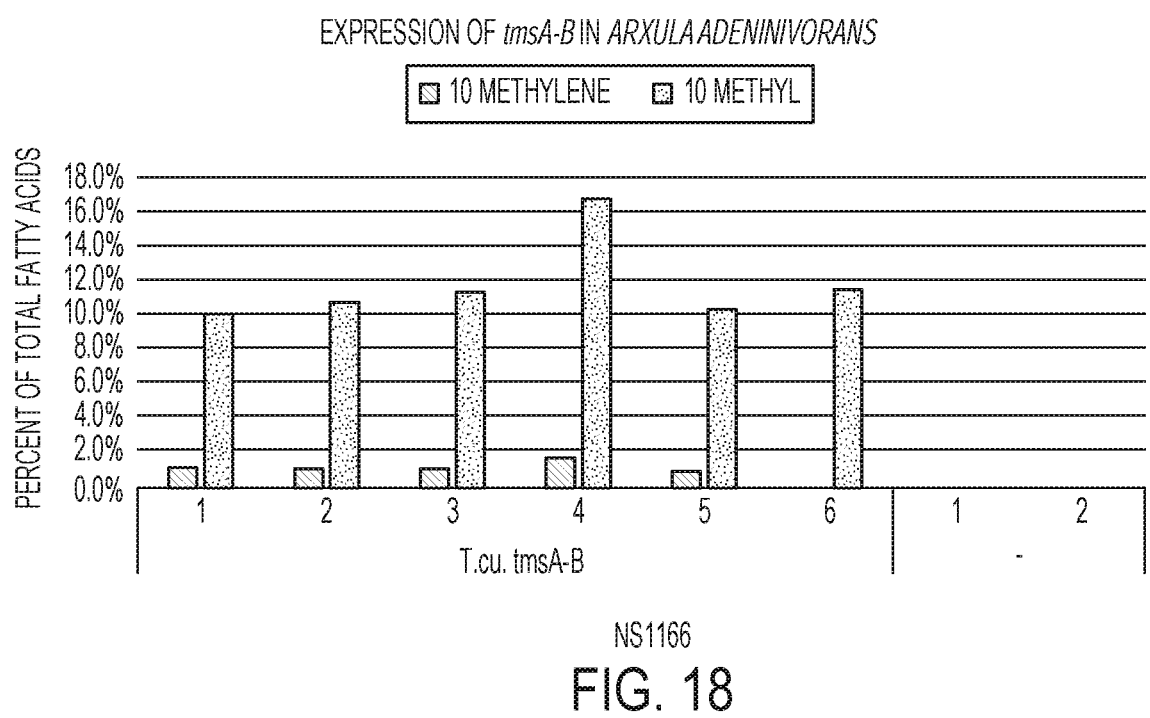

FIG. 18 is a graph showing the percentage by weight of 10-methylene fatty acids and 10-methyl fatty acids as compared to total fatty acids in transformants of A. adeninivorans containing the tmsA-B fusion protein or empty vector (–).

FIGS. 19A-19D show a CLUSTAL OMEGA alignment of TmsB protein sequences encoded by the tmsB genes from Mycobacterium smegmatis (SEQ ID NO:4), Mycobacterium vanbaaleni (SEQ ID NO:54), Amycolicicoccus subflavus (SEQ ID NO:12), Corynebacterium glyciniphilum (SEQ ID NO:20), Corynebacterium glutamicum (SEQ ID NO:16), Rhodococcus opacus (SEQ ID NO:60), Agromyces subbeticus (SEQ ID NO:8), Knoellia aerolata (SEQ ID NO:26), Mycobacterium gilvum (SEQ ID NO:36), Mycobacterium sp. Indicus (SEQ ID NO:42), Thermobifida fusca (SEQ ID NO:70), and Thermomonospora curvata (SEQ ID NO:76), along with the cyclopropane fatty acid synthase (Cfa) enzyme from Escherichia coli.

FIGS. 20A-20E show a CLUSTAL OMEGA alignment of TmsA protein sequences encoded by the tmsA genes from Mycobacterium smegmatis (SEQ ID NO:2), Mycobacterium vanbaaleni (SEQ ID NO:52), Amycolicicoccus subflavus (SEQ ID NO:10), Corynebacterium glyciniphilum (SEQ ID NO:18), Corynebacterium glutamicum (SEQ ID NO:14), Rhodococcus opacus (SEQ ID NO:58), Agromyces subbeticus (SEQ ID NO:6), Knoellia aerolata (SEQ ID NO:24), Mycobacterium gilvum (SEQ ID NO:34), Mycobacterium sp. Indicus (SEQ ID NO:40), Thermobifida fusca (SEQ ID NO:68), and Thermomonospora curvata (SEQ ID NO:74), along with the Glycolate oxidase subunit GlcD enzyme from Escherichia coli.

DETAILED DESCRIPTION

Definitions

The articles "a" and "an" are used herein to refer to one or to more than one (i.e., to at least one) of the grammatical object of the article. By way of example, "an element" means one element or more than one element.

The term "biologically-active portion" refers to an amino acid sequence that is less than a full-length amino acid sequence, but exhibits at least one activity of the full length sequence. For example, a biologically-active portion of a methyltransferase may refer to one or more domains of tmsB having biological activity for converting oleic acid (e.g., a phospholipid comprising an ester of oleate) and methionine (e.g., S-adenosyl methionine) into 10-methylenestearic acid (e.g., a phospholipid comprising an ester of 10-methylenestearate). A biologically-active portion of a reductase may refer to one or more domains of tmsA having biological activity for converting 10-methylenestearic acid (e.g., a phospholipid comprising an ester of 10-methylenestearate) and a reducing agent (e.g., NADH, NADPH, FAD, FADH2, FMNH2) into 10-methylstearic acid (e.g., a phospholipid comprising an ester of 10-methylstearate). Biologically-active portions of a protein include peptides or polypeptides comprising amino acid sequences sufficiently identical to or derived from the amino acid sequence of the protein, e.g., the amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, or 76, which include fewer amino acids than the full length protein, and exhibit at least one activity of the protein, especially methyltransferase or reductase activity. A biologically-active portion of a protein may comprise, comprise at least, or comprise to most, for example, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or more amino acids or any range derivable therein. Typically, biologically-active portions comprise a domain or motif having a catalytic activity, such as catalytic activity for producing 10-methylenestearic acid or 10-methylstearic acid. A biologically-active portion of a protein includes portions of the protein that have the same activity as the full-length peptide and every portion that has more activity than background. For example, a biologically-active portion of an enzyme may have, have at least, or have at most 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, 400% or higher activity relative to the full-length enzyme (or any range derivable therein). A biologically-active portion of a protein may include portions of a protein that lack a domain that targets the protein to a cellular compartment.

The terms "codon optimized" and "codon-optimized for the cell" refer to coding nucleotide sequences (e.g., genes) that have been altered to substitute at least one codon that is relatively rare in a desired host cell with a synonymous codon that is relatively prevalent in the host cell. Codon optimization thereby allows for better utilization of the tRNA of a host cell by matching the codons of a recombinant gene with the tRNA of the host cell. For example, the codon usage of the species of Actinobacteria (prokaryotes) varies from the codon usage of yeast (eukaryotes). The translation efficiency in a yeast host cell of an mRNA encoding a Actinobacteria protein may be increased by substituting the codons of the corresponding Actinobacteria gene with codons that are more prevalent in the particular species of yeast. A codon optimized gene thereby has a nucleotide sequence that varies from a naturally-occurring gene.

The term "constitutive promoter" refers to a promoter that mediates the transcription of an operably linked gene independent of a particular stimulus (e.g., independent of the presence of a reagent such as isopropyl β-D-1-thiogalactopyranoside).

The term "DGAT1" refers to a gene that encodes a type 1 diacylglycerol acyltransferase protein, such as a gene that encodes a yeast DGA2 protein.

The term "DGAT2" refers to a gene that encodes a type 2 diacylglycerol acyltransferase protein, such as a gene that encodes a yeast DGA1 protein.

"Diacylceride," "diacylglycerol," and "diglyceride," are esters comprised of glycerol and two fatty acids.

The terms "diacylglycerol acyltransferase" and "DGA" refer to any protein that catalyzes the formation of triacylglycerides from diacylglycerol. Diacylglycerol acyltransferases include type 1 diacylglycerol acyltransferases (DGA2), type 2 diacylglycerol acyltransferases (DGA1), and type 3 diacylglycerol acyltransferases (DGA3) and all homologs that catalyze the above-mentioned reaction.

The terms "diacylglycerol acyltransferase, type 1" and "type 1 diacylglycerol acyltransferases" refer to DGA2 and DGA2 orthologs.

The terms "diacylglycerol acyltransferase, type 2" and "type 2 diacylglycerol acyltransferases" refer to DGA1 and DGA1 orthologs.

The term "domain" refers to a part of the amino acid sequence of a protein that is able to fold into a stable three-dimensional structure independent of the rest of the protein.

The term "drug" refers to any molecule that inhibits cell growth or proliferation, thereby providing a selective advantage to cells that contain a gene that confers resistance to the drug. Drugs include antibiotics, antimicrobials, toxins, and pesticides.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed. The term "% dry weight," when referring to a specific fatty acid (e.g., oleic acid or 10-methylstearic acid), includes fatty acids that are present as carboxylates, esters, thioesters, and amides. For example, a cell that comprises 10-methylstearic acid as a percentage of total fatty acids by % dry cell weight includes 10-methylstearic acid, 10-methylstearate, the 10-methylstearate portion of a diacylglycerol comprising a 10-methylstearate ester, the 10-methylstearate portion of a triacylglycerol comprising a 10-methylstearate ester, the 10-methylstearate portion of a phospholipid comprising a 10-methylstearate ester, and the 10-methylstearate portion of 10-methylstearate CoA. The term "% dry weight," when referring to a specific type of fatty acid (e.g., C16 fatty acids, C18 fatty acids), includes fatty acids that are present as carboxylates, esters, thioesters, and amides as described above (e.g., for 10 methylstearic acid).

The term "encode" refers to nucleic acids that comprise a coding region, portion of a coding region, or compliments thereof. Both DNA and RNA may encode a gene. Both DNA and RNA may encode a protein.

The term "enzyme" as used herein refers to a protein that can catalyze a chemical reaction.

The term "expression" refers to the amount of a nucleic acid or amino acid sequence (e.g., peptide, polypeptide, or protein) in a cell. The increased expression of a gene refers to the increased transcription of that gene. The increased expression of an amino acid sequence, peptide, polypeptide, or protein refers to the increased translation of a nucleic acid encoding the amino acid sequence, peptide, polypeptide, or protein.

The term "gene," as used herein, may encompass genomic sequences that contain exons, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence. In other embodiments, the genes are synthesized, non-native cDNA wherein the codons have been optimized for expression in *Y. lipolytica* or *A. adeninivorans* based on codon usage. The term can further include nucleic acid molecules comprising upstream, downstream, and/or intron nucleotide sequences.

The term "inducible promoter" refers to a promoter that mediates the transcription of an operably linked gene in response to a particular stimulus.

The term "integrated" refers to a nucleic acid that is maintained in a cell as an insertion into the cell's genome, such as insertion into a chromosome, including insertions into a plastid genome.

"In operable linkage" refers to a functional linkage between two nucleic acid sequences, such a control sequence (typically a promoter) and the linked sequence (typically a sequence that encodes a protein, also called a coding sequence). A promoter is in operable linkage with a gene if it can mediate transcription of the gene.

The term "knockout mutation" or "knockout" refers to a genetic modification that prevents a native gene from being transcribed and translated into a functional protein.

The term "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "phospholipid" refers to esters comprising glycerol, two fatty acids, and a phosphate. The phosphate may be covalently linked to carbon-3 of the glycerol and comprise no further substitution, i.e., the phospholipid may be a phosphatidic acid. The phosphate may be substituted with ethanolamine (e.g., phosphatidylethanolamine), choline (e.g., phosphatidylcholine), serine (e.g., phosphatidylserine), inositol (e.g., phosphatidylinositol), inositol phosphate (e.g., phosphatidylinositol-3-phosphate, phosphatidylinositol-4-phosphate, phosphatidylinositol-5-phosphate), inositol bisphosphate (e.g., phosphatidylinositol-4,5-bisphosphate), or inositol triphosphate (e.g., phosphatidylinositol-3,4,5-bisphosphate).

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

A "promoter" is a nucleic acid control sequence that directs the transcription of a nucleic acid. As used herein, a promoter includes the necessary nucleic acid sequences near the start site of transcription.

The term "protein" refers to molecules that comprise an amino acid sequence, wherein the amino acids are linked by peptide bonds.

"Transformation" refers to the transfer of a nucleic acid into a host organism or into the genome of a host organism, resulting in genetically stable inheritance. Host organisms containing the transformed nucleic acid are referred to as "recombinant," "transgenic," or "transformed" organisms. Thus, nucleic acids of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The terms "triacylglyceride," "triacylglycerol," "triglyceride," and "TAG" are esters comprised of glycerol and three fatty acids.

Microbe Engineering

A. Overview

Genes and gene products may be introduced into microbial host cells. Suitable host cells for expression of the genes and nucleic acid molecules are microbial hosts that can be found broadly within the fungal or bacterial families. Examples of suitable host strains include but are not limited to fungal or yeast species, such as *Arxula, Aspegillus, Aurantiochytrium, Candida, Claviceps, Cryptococcus, Cunninghamella, Hansenula, Kluyveromyces, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Yarrowia*, or bacterial species, such as members of proteobacteria and actinomycetes, as well as the genera *Acinetobacter, Arthrobacter, Brevibacterium, Acidovorax, Bacillus, Clostridia, Streptomyces, Escherichia, Salmonella, Pseudomonas*, and *Cornyebacterium. Yarrowia lipolytica* and *Arxula adeninivorans* are suited for use as a host microorganism because they can accumulate a large percentage of their weight as triacylglycerols.

Microbial expression systems and expression vectors containing regulatory sequences that direct high level expression of foreign proteins are known to those skilled in the art. Any of these could be used to construct chimeric genes to produce any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and an aforementioned starting parent strain as a host can be transformed with the resulting plasmid. This approach can increase the copy number of each of the genes encoding the enzymes and, as a result, the activities of the enzymes can be increased. The plasmid is not particularly limited so long as it renders a desired genetic modification inheritable to the microorganism's progeny.

Vectors or cassettes useful for the transformation of suitable host cells are well known. Typically the vector or cassette contains sequences that direct the transcription and translation of the relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. In certain embodiments both control regions are derived from genes homologous to the transformed host cell, although it is to be understood that such control regions need not be derived from the genes native to the specific species chosen as a production host. Promoters, cDNAs, and 3'UTRs, as well as other elements of the vectors, can be generated through cloning techniques using fragments isolated from native sources (see, e.g., Green & Sambrook, *Molecular Cloning: A Laboratory Manual*, (4th ed., 2012); U.S. Pat. No. 4,683,202 (incorporated by reference)). Alternatively, elements can be generated synthetically using known methods (see, e.g., Gene 164:49-53 (1995)).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has many practical implications for what can be carried out at the molecular genetic level and is useful in the generation of a microbe that can produce a desired product. By its nature homologous recombination is a precise gene targeting event and, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements, such as promoters/UTRs, to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion, and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transforming microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in operable linkage with the coding sequence of interest, the coding sequence can be transformed into the cells such that it becomes operably linked to an endogenous promoter at the point of vector integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, e.g., substantially, transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chen & Orozco, Nucleic Acids Research 16:8411 (1988)).

2. Genes and Codon Optimization

Typically, a gene includes a promoter, a coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA. Resources for codon-optimization of gene sequences are described in Puigbo et al. (Nucleic Acids Research 35:W126-31 (2007)), and principles underlying codon optimization strategies are described in Angov (Biotechnology Jornal 6:650-69 (2011)). Public databases providing statistics for codon usage by different organisms are available, including at www.kazusa.or.jp/codon/ and other publicly available databases and resources.

D. Transformation

Cells can be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of expression of transgenes in oleaginous yeast (e.g., *Yarrowia lipolytica*) can be found in the literature (Bordes et al., J. Microbiological Methods, 70:493 (2007); Chen et al., Applied Microbiology & Biotechnology 48:232 (1997)). Examples of expression of exogenous genes in bacteria such as *E. coli* are well known (Green & Sambrook, *Molecular Cloning: A Laboratory Manual*, (4th ed., 2012)).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

Exemplary Cells, Nucleic Acids, Compositions, and Methods

A. Transformed Cell

In some embodiments, the transformed cell is a prokaryotic cell, such as a bacterial cell. In some embodiments, the cell is a eukaryotic cell, such as a mammalian cell, a yeast cell, a filamentous fungi cell, a protist cell, an algae cell, an avian cell, a plant cell, or an insect cell. In some embodiments, the cell is a yeast. Those with skill in the art will recognize that many forms of filamentous fungi produce yeast-like growth, and the definition of yeast herein encompasses such cells. The cell may cell may be selected from the group consisting of algae, bacteria, molds, fungi, plants, and yeasts. The cell may be a yeast, fungus, or yeast-like algae. The cell may be selected from thraustochytrids (Aurantiochytrium) and achlorophylic unicellular algae (Prototheca).

The cell may be selected from the group consisting of *Arxula, Aspegillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces,* and *Yarrowia*. It is specifically contemplated that one or more of these cell types may be excluded from embodiments of this invention.

The cell may be selected from the group of consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii,* and *Yarrowia lipolytica*. It is specifically contemplated that one or more of these cell types may be excluded from embodiments of this invention.

The cell may be *Saccharomyces cerevisiae, Yarrowia lipolytica*, or *Arxula adeninivorans*.

In certain embodiments, the transformed cell comprises at least 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more lipid as measured by % dry cell weight, or any range derivable therein. In some embodiments, the transformed cell comprises C18 fatty acids at a concentration of at least 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or higher as a percentage of total C16 and C18 fatty acids in the cell, or any range derivable therein.

In some embodiments, the transformed cell comprises oleic acid at a concentration of at least 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, or higher as a percentage of total C16 and C18 fatty acids in the cell, or any range derivable therein. In some embodiments, the transformed cell comprises a linear fatty acid with a chain length of 14-20 carbons with a methyl branch at the Δ9, Δ10, or Δ11 position (e.g., 10-methylstearic acid) at a concentration of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight or higher as a percentage of total fatty acids in the cell, or any range derivable therein. In some embodiments, the fatty acid has a chain length of 14, 15, 16, 17, 18, 19, or 20 carbons, or any range derivable therein.

A cell may be modified to increase its oleate content, which serves as a substrate for 10-methylstearate synthesis. Genetic modifications that increase oleate content are known (see, e.g., PCT Patent Application Publication No. WO16/094520, published Jun. 16, 2016, hereby incorporated by reference in its entirety). For example, a cell may comprise a Δ12 desaturase knockdown or knockout, which favors the accumulation of oleate and disfavors the production of linoleate. A cell may comprise a recombinant Δ9 desaturase gene, which favors the production of oleate and disfavors the accumulation of stearate. The recombinant Δ9 desaturase gene may be, for example, the Δ9 desaturase gene from *Y. lipolytica, Arxula adeninivorans*, or *Puccinia graminis*. A cell may comprise a recombinant elongase 1 gene, which favors the production of oleate and disfavors the accumulation of palmitate and palmitoleate. The recombinant elongase 1 gene may be the elongase 1 gene from *Y. lipolytica*. A cell may comprise a recombinant elongase 2 gene, which favors the production of oleate and disfavors the accumulation of palmitate and palmitoleate. The recombinant elongase 2 gene may be the elongase 2 gene from *R. norvegicus*.

A cell may be modified to increase its triacylglycerol content, thereby increasing its 10-methylstearate content. Genetic modifications that increase triacylglycerol content are known (see, e.g., PCT Patent Application Publication No. WO16/094520, published Jun. 16, 2016, hereby incorporated by reference in its entirety). A cell may comprise a recombinant diacylglycerol acyltransferase gene (e.g., DGAT1, DGAT2, or DGAT3), which favors the production of triacylglycerols and disfavors the accumulation of diacylglycerols. The recombinant diacylglycerol acyltransferase gene may be, for example, DGAT2 (encoding protein DGA1) from *Y. lipolytica*, DGAT1 (encoding protein DGA2) from *C. purpurea*, or DGAT2 (encoding protein DGA1) from *R. toruloides*. The cell may comprise a glycerol-3-phosphate acyltransferase gene (Sct1) knockdown or knockout, which may favor the accumulation of triacylglycerols, depending on the cell type. The cell may comprise a recombinant glycerol-3-phosphate acyltransferase gene (Sct1) such as the Sct1 gene from *A. adeninivorans*, which may favor the accumulation of triacylglycerols. The cell may comprise a triacylglycerol lipase gene (TGL) knockdown or knockout, which may favor the accumulation of triacylglycerols in the cell.

Various aspects of the invention relate to a transformed cell. The transformed cell may comprise a recombinant methyltransferase gene (e.g., a tmsB gene), a recombinant reductase gene (e.g., a tmsA gene), an exomethylene-substituted lipid, and/or a branched (methyl)lipid. A transformed cell may comprise a tmsC gene. A branched (methyl) lipid may be a carboxylic acid (e.g., 10-methylstearic acid, 10-methylpalmitic acid, 12-methyloleic acid, 13-methyloleic acid, 10-methyl-octadec-12-enoic acid), carboxylate (e.g., 10-methylstearate, 10-methylpalmitate, 12-methyloleate, 13-methyloleate, 10-methyl-octadec-12-enoate), ester (e.g., diacylglycerol, triacylglycerol, phospholipid), thioester (e.g., 10-methylstearyl CoA, 10-methylpalmityl CoA, 12-methyloleoyl CoA, 13-methyloleoyl CoA, 10-methyl-octadec-12-enoyl CoA), or amide. An exomethylene-substituted lipid may be a carboxylic acid (e.g., 10-methylenestearic acid, 10-methylenepalmitic acid, 12-methyleneoleic acid, 13-methyleneoleic acid, 10-methylene-octadec-12-enoic acid), carboxylate (e.g., 10-methylenestearate, 10-methylenepalmitate, 12-methyleneoleate, 13-methyleneoleate, 10-methylene-octadec-12-enoate), ester (e.g., diacylglycerol, triacylglycerol, phospholipid), thioester (e.g., 10-methylenestearyl CoA, 10-methylenepalmityl CoA, 12-methyleneoleoyl CoA, 13-methyleneoleoyl CoA, 10-methylene-octadec-12-enoyl CoA), or amide. It is specifically contemplated that one or more of the above lipids may be excluded from embodiments of this invention.

"Fatty acids" generally exist in a cell as a phospholipid or triacylglycerol, although they may also exist as a monoacylglycerol or diacylglycerol, for example, as a metabolic intermediate. Free fatty acids also exist in the cell in equilibrium between a relatively abundant carboxylate anion and a relatively scarce, neutrally-charged acid. A fatty acid may exist in a cell as a thioester, especially as a thioester with coenzyme A (CoA), during biosynthesis or oxidation. A fatty acid may exist in a cell as an amide, for example, when covalently bound to a protein to anchor the protein to a membrane.

A cell may comprise any one of the nucleic acids described herein, infra (see, e.g., Section B, below).

A branched (methyl)lipid may comprise a saturated branched aliphatic chain (e.g., 10-methylstearic acid, 10-methylpalmitic acid) or an unsaturated branched aliphatic chain (e.g., 12-methyloleic acid, 13-methyloleic acid, 10-methyl-octadec-12-enoic acid). The branched (methyl) lipid may comprise a saturated or unsaturated branched aliphatic chain comprising a branching methyl group.

An exomethylene-substituted lipid may comprise a branched aliphatic chain (e.g., 10-methylenestearic acid, 10-methylenepalmitic acid, 12-methyleneoleic acid, 13-methyleneoleic acid, 10-methylene-octadec-12-enoic acid). The aliphatic chain may be branched because the aliphatic chain is substituted with an exomethylene group.

A branched (methyl)lipid may be 10-methylstearate, or an acid (10-methylstearic acid), ester (e.g., diacylglycerol, triacylglycerol, phospholipid), thioester (e.g., 10-methylstearyl CoA), or amide (e.g., 10-methylstearyl amide) thereof. For example, the branched (methyl)lipid may be a diacylglycerol, triacylglycerol, or phospholipid, and the diacylglycerol, triacylglycerol, or phospholipid may comprise an ester of 10-methylstearate.

An exomethylene-substituted lipid may be 10-methylenestearate, or an acid (10-methylenestearic acid), ester (e.g., diacylglycerol, triacylglycerol, phospholipid), thioester (e.g., 10-methylenestearyl CoA), or amide (e.g., 10-methylenestearyl amide) thereof. For example, the exomethylene-substituted lipid may be a diacylglycerol, triacylglycerol, or phospholipid, and the diacylglycerol, triacylglycerol, or phospholipid may comprise an ester of 10-methylenestearate.

In some embodiments, about, at most about, or at least about 1% of the fatty acids of the cell may be 10-methylstearic acid as measured by % dry cell weight. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the fatty acids of the cell may be 10-methylstearic acid as measured by % dry cell weight, or any range derivable therein.

In some embodiments, about, at least about, or at most about 1% of the fatty acids of the cell may be 10-methylenestearic acid as measured by % dry cell weight. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the fatty acids of the cell may be 10-methylenestearic acid as measured by % dry cell weight, or any range derivable therein.

In some embodiments, about, at least about, or at most about 1% by weight of the fatty acids of the cell may be one or more of the branched (methyl)lipids described herein. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids of the cell may be one or more of the branched (methyl)lipids described herein, or any range derivable therein.

In some embodiments, about, at least about, or at most about 1% by weight of the fatty acids of the cell may one or more of the branched (methyl)lipids described herein (e.g., a linear fatty acid with a chain length of 14-20 carbons with a methyl branch at the Δ9, Δ10, or Δ11 position). About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the fatty acids of the cell may one or more of the branched (methyl)lipids described herein (e.g., a linear fatty acid with a chain length of 14-20 carbons with a methyl branch at the Δ9, Δ10, or Δ11 position), or any range derivable therein.

In some embodiments, the cell may comprise about, at least about, or at most about 1% 10-methylstearic acid as measured by % dry cell weight. The cell may comprise about, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% 10-methylstearic acid as measured by % dry cell weight, or any range derivable therein.

In some embodiments, the cell may comprise about, at least about, or at most about 1% 10-methylenestearic acid as measured by % dry cell weight. The cell may comprise about, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% 10-methylenestearic acid as measured by % dry cell weight, or any range derivable therein.

An unmodified cell of the same type (e.g., species) as a cell of the invention may not comprise 10-methylstearate, or an acid (10-methylstearic acid), ester (e.g., diacylglycerol, triacylglycerol, phospholipid), thioester (e.g., 10-methylstearyl CoA), or amide (e.g., 10-methylstearyl amide) thereof (e.g., wherein the unmodified cell does not comprise a recombinant methyltransferase gene or a recombinant reductase gene). An unmodified cell of the same type (e.g., species) as a cell of the invention may not comprise 10-methylenestearate, or an acid (10-methylenestearic acid), ester (e.g., diacylglycerol, triacylglycerol, phospholipid), thioester (e.g., 10-methylenestearyl CoA), or amide (e.g., 10-methylenestearyl amide) thereof (e.g., wherein the unmodified cell does not comprise a recombinant methyltransferase gene or a recombinant reductase gene). In some embodiments, an unmodified cell of the same species as the cell does not comprise a branched (methyl)lipid and/or an exomethylene-substituted lipid. In some embodiments, an unmodified cell of the same species as the cell does not comprise one or more of the branched (methyl)lipids or exomethylene-substituted lipids described herein.

A cell may constitutively express the protein encoded by a recombinant methyltransferase gene. A cell may constitutively express the protein encoded by a recombinant reductase gene. A cell may constitutively express the protein encoded by a recombinant tmsC gene. A cell may constitutively express a methyltransferase protein. A cell may constitutively express a reductase protein. A cell may constitutively express a tmsC protein.

B. Nucleic Acids

Various aspects of the invention relate to a nucleic acid comprising a recombinant methyltransferase gene, a recombinant reductase gene, or both. The nucleic acid may be, for example, a plasmid. In some embodiments, a recombinant methyltransferase gene and/or a recombinant reductase gene is integrated into the genome of a cell, and thus, the nucleic acid may be a chromosome. In some embodiments, the invention relates to a cell comprising a recombinant methyltransferase gene, e.g., wherein the recombinant methyltransferase gene is present in a plasmid or chromosome. In some embodiments, the invention relates to a cell comprising a recombinant reductase gene, e.g., wherein the recombinant reductase gene is present in a plasmid or chromosome. A recombinant methyltransferase gene and a recombinant reductase gene may be present in a cell in the same nucleic acid (e.g., same plasmid or chromosome) or in different nucleic acids (e.g., different plasmids or chromosomes).

A nucleic acid may be inheritable to the progeny of a transformed cell. A gene such as a recombinant methyltransferase gene or recombinant reductase gene may be inheritable because it resides on a plasmid or chromosome. In certain embodiments, a gene may be inheritable because it is integrated into the genome of the transformed cell.

A gene may comprise conservative substitutions, deletions, and/or insertions while still encoding a protein that has activity. For example, codons may be optimized for a particular host cell, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions.

Proteins may comprise conservative substitutions, deletions, and/or insertions while still maintaining activity. Conservative substitution tables are well known in the art (Creighton, *Proteins* (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. Unless otherwise specified, when percent identity between two amino acid sequences is referred to herein, it refers to the percent identity as determined using the Needleman and Wunsch (J. Molecular Biology 48:444-453 (1970)) algorithm which has been incorporated into the GAP program in the GCG software package (available at www.gcg.com), using a Blosum 62 matrix, a gap weight of 10, and a length weight of 4. In some embodiments, the percent identity between two amino acid sequences is determined the Needleman and Wunsch algorithm using a Blosum 62 matrix or a PAM250 matrix, and a gap weight of 16, 14, 12, 10, 8, 6, or 4 and a length weight of 1, 2, 3, 4, 5, or 6. Unless otherwise specified, when percent identity between two nucleotide sequences is referred to herein, it refers to percent identity as determined using the GAP program in the GCG software package (available at www.gcg.com), using a NWSgapdna.CMP matrix and a gap weight of 60 and a length weight of 4. In yet another embodiment, the percent identity between two nucleotide sequences can be determined using a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0 U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, e.g., ClustalW, ClustalX, and Clustal Omega.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5' →3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

Any nucleic acid that is referred to herein as having a certain percent sequence identity to a sequence set forth in a SEQ ID NO, includes nucleic acids that have the certain percent sequence identity to the complement of the sequence set forth in the SEQ ID NO.

i. Nucleic Acids Comprising a Recombinant Methyltransferase Gene

A methyltransferase gene (e.g., a recombinant methyltransferase gene) encodes a methyltransferase protein, which is an enzyme capable of transferring a carbon atom and one or more protons bound thereto from a substrate such as S-adenosyl methionine to a fatty acid such as oleic acid (e.g., wherein the fatty acid is present as a free fatty acid, carboxylate, phospholipid, diacylglycerol, or triacylglycerol). A methyltransferase gene (e.g., a recombinant methyltransferase gene) may comprise any one of the nucleotide sequences set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, and SEQ ID NO:81. A methyltransferase gene (e.g., a recombinant methyltransferase gene) may be a 10-methylstearic B gene (tmsB) as described herein, or a biologically-active portion thereof (i.e., wherein the biologically-active portion thereof comprises methyltransferase activity).

A methyltransferase gene (e.g., a recombinant methyltransferase gene) may be derived from a gram-positive species of *Actinobacteria*, such as *Mycobacteria, Corynebacteria, Nocardia, Streptomyces,* or *Rhodococcus*. A methyltransferase gene (e.g., a recombinant methyltransferase gene) may be selected from the group consisting of *Mycobacterium smegmatis* gene tmsB, *Agromyces subbeticus* gene tmsB, *Amycolicicoccus subflavus* gene tmsB, *Corynebacterium glutamicum* gene tmsB, *Corynebacterium glyciniphilium* gene tmsB, *Knoella aerolata* gene tmsB, *Mycobacterium austroafricanum* gene tmsB, *Mycobacterium gilvum* gene tmsB, *Mycobacterium indicus pranii* gene tmsB, *Mycobacterium phlei* gene tmsB, *Mycobacterium tuberculosis* gene tmsB, *Mycobacterium vanbaalenii* gene tmsB, *Rhodococcus opacus* gene tmsB, *Streptomyces regnsis* gene tmsB, *Thermobifida fusca* gene tmsB, and *Thermomonospora curvata* gene tmsB. It is specifically contemplated that one or more of the above methyltransferase genes may be excluded from embodiments of this invention.

A recombinant methyltransferase gene may be recombinant because it is operably-linked to a promoter other than the naturally-occurring promoter of the methyltransferase gene. Such genes may be useful to drive transcription in a particular species of cell. A recombinant methyltransferase gene may be recombinant because it contains one or more nucleotide substitutions relative to a naturally-occurring methyltransferase gene. Such genes may be useful to increase the translation efficiency of the methyltransferase gene's mRNA transcript in a particular species of cell.

A nucleic acid may comprise a recombinant methyltransferase gene and a promoter, wherein the recombinant methyltransferase gene and promoter are operably-linked. The recombinant methyltransferase gene and promoter may be derived from different species. For example, the recombinant methyltransferase gene may encode the methyltransferase protein of a gram-positive species of Actinobacteria, and the recombinant methyltransferase gene may be operably-linked to a promoter that can drive transcription in another phylum of bacteria (e.g., a Proteobacterium, such as

*E. coli*) or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant methyltransferase gene, and the recombinant methyltransferase gene may be operably-linked to a promoter capable of driving transcription of the recombinant methyltransferase gene in the cell. The cell may be a species of yeast, and the promoter may be a yeast promoter. The cell may be a species of bacteria, and the promoter may be a bacterial promoter (e.g., wherein the bacterial promoter is not a promoter from Actinobacteria). The cell may be a species of algae, and the promoter may be an algae promoter. The cell may be a species of plant, and the promoter may be a plant promoter.

A recombinant methyltransferase gene may be operably-linked to a promoter that cannot drive transcription in the cell from which the recombinant methyltransferase gene originated. For example, the promoter may not be capable of binding an RNA polymerase of the cell from which a recombinant methyltransferase gene originated. In some embodiments, the promoter cannot bind a prokaryotic RNA polymerase and/or initiate transcription mediated by a prokaryotic RNA polymerase. In some embodiments, a recombinant methyltransferase gene is operably-linked to a promoter that cannot drive transcription in the cell from which the protein encoded by the gene originated. For example, the promoter may not be capable of binding an RNA polymerase of a cell that naturally expresses the methyltransferase enzyme encoded by a recombinant methyltransferase gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1α; Glycerol-3-phosphate dehydrogenase; Triosephosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/$P_i$ cotransporter; Pyruvate decarboxylase; Phytase; or Alpha-amylase, e.g., wherein the gene is a yeast gene, such as a gene from *Yarrowia lipolytica* or *Arxula adeninivorans*.

A recombinant methyltransferase gene may comprise a nucleotide sequence with at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity (or any range derivable therein) with 150, 200, 250, 300, 350, 400, 450, 500, 550, 600, 650, 700, 750, 800, 850, 900, 950, 1000, 1050, 1100, 1150, 1200, 1250, or 1300 contiguous base pairs (or any range derivable therein) starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, or 1200 of the nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase may or may not have 100% sequence identity with any one of the nucleotide sequences set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase gene may or may not have 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs of the nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81, and the recombinant methyltransferase gene may encode a methyltransferase protein with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. For example, SEQ ID NO:81 is a gene that is codon-optimized for expression in yeast. SEQ ID NO:81 has about 70% sequence identity (69.86% sequence identity) with SEQ ID NO:3, and the protein encoded by SEQ ID NO:81 has 100% sequence identity with the amino acid sequence set forth in by SEQ ID NO:4. Thus, even though SEQ ID NO:81 and SEQ ID NO:3 have 69.86% sequence identity, the two nucleotide sequences encode the same amino acid sequence.

A recombinant methyltransferase gene may vary from a naturally-occurring methyltransferase gene because the recombinant methyltransferase gene may be codon-optimized for expression in a eukaryotic cell, such as a plant cell, algae cell, or yeast cell. A cell may comprise a recombinant methyltransferase gene, wherein the recombinant methyltransferase gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant methyltransferase gene may vary from a naturally-occurring methyltransferase gene or may be unchanged from a naturally-occurring methyltransferase gene. For example, a recombinant methyltransferase gene may comprise a nucleotide sequence with at least about 65% sequence identity with the naturally-occurring nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, or SEQ ID NO:75 (e.g., at least 70%, 75%, 80%, 85%, 90%, 95%, 96%, 97%, 98%, or 99% sequence identity), and at least 5 codons of the nucleotide sequence of the recombinant methyltransferase gene may vary from the naturally-occurring nucleotide sequence (e.g., at least 10, 15, 20, 25, 30, 35, 40, 45, 50, 60, 70, 80, 90, or 100 codons (or any range deriable therein)).

A methyltransferase gene encodes a methyltransferase protein. A methyltransferase protein may be a protein expressed by a gram-positive species of *Actinobacteria*, such as *Mycobacteria, Corynebacteria, Nocardia, Streptomyces*, or *Rhodococcus*. A recombinant methyltransferase gene may encode a naturally-occurring methyltransferase protein even if the recombinant methyltransferase gene is not a naturally-occurring methyltransferase gene. For example, a recombinant methyltransferase gene may vary from a naturally-occurring methyltransferase gene because the recombinant methyltransferase gene is codon-optimized for expression in a specific cell. The codon-optimized, recombinant methyltransferase gene and the naturally-occurring methyltransferase gene may nevertheless encode the same naturally-occurring methyltransferase protein.

A recombinant methyltransferase gene may encode a methyltransferase protein selected from *Mycobacterium smegmatis* enzyme tmsB, *Agromyces subbeticus* enzyme tmsB, *Amycolicicoccus subflavus* enzyme tmsB, *Corynebacterium glutamicum* enzyme tmsB, *Corynebacterium gliciniphilium* enzyme tmsB, *Knoella aerolata* enzyme tmsB, *Mycobacterium austroafricanum* enzyme tmsB, *Mycobacterium gilvum* enzyme tmsB, *Mycobacterium indicus pranii* enzyme tmsB, *Mycobacterium phlei* enzyme tmsB, *Mycobacterium tuberculosis* enzyme tmsB, *Mycobacterium vanbaalenii* enzyme tmsB, *Rhodococcus opacus* enzyme tmsB, *Streptomyces regnsis* enzyme tmsB, *Thermobifida fusca* enzyme tmsB, and *Thermomonospora curvata* enzyme tmsB. It is specifically contemplated that one or more of the above methyltransferase proteins may be excluded from embodiments of this invention. A recombinant methyltransferase gene may encode a methyltransferase protein, and the methyltransferase protein may be substantially identical to any one of the foregoing enzymes, but the recombinant methyltransferase gene may vary from the naturally-occurring gene that encodes the enzyme. The recombinant methyltransferase gene may vary from the naturally-occurring gene because the recombinant methyltransferase gene may be codon-optimized for expression in a specific phylum, class, order, family, genus, species, or strain of cell.

The sequences of naturally-occurring methyltransferase proteins are set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. A recombinant methyltransferase gene may or may not encode a protein comprising 100% sequence identity with the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. For example, a recombinant methyltransferase gene may encode a protein having 100% sequence identity with a biologically-active portion of an amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76.

A recombinant methyltransferase gene may encode a methyltransferase protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity (or any range derivable therein) with the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76, or a biologically-active portion thereof. A recombinant methyltransferase gene may encode a methyltransferase protein having at least about 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, or 400% methyltransferase activity (or any range deriable therein) relative to a protein comprising the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. A recombinant methyltransferase gene may encode a protein having at least 70%, 75%, 80%, 85%, 90%, 91%, 92%, 93%, 94%, 95%, 96%, 97%, 98%, 99%, 99.9%, or 100% sequence identity with 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous amino acids starting at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 of SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76.

Substrates for the methyltransferase protein may include any fatty acid from 14 to 20 carbons long with an unsaturated double bond in the Δ9, Δ10, or Δ11 position. The methyltransferase protein may be capable of catalyzing the formation of a methylene substitution at the Δ9, Δ10, or Δ11 position of such a substrate.

In some embodiments, the recombinant methyltransferase gene encodes a methyltransferase protein that includes an S-adenosylmethionine-dependent methyltransferase domain. In some embodiments the S-adenosylmethionine-dependent methyltransferase domain has, has at least, or has at most 70%, 75%, 80%, 85%, 90%, 91%, 92%, 93%, 94%, 95%, 96%, 97%, 98%, 99%, 99.9%, or 100% sequence identity to amino acids 192-291 of *T. curvata* TmsB (SEQ ID NO:76) or to a corresponding portion of TmsB from *Mycobacterium smegmatis*, *Mycobacterium vanbaaleni*, *Amycolicicoccus subflavus*, *Corynebacterium glyciniphilum*, *Corynebacterium glutamicum*, *Rhodococcus opacus*, *Agromyces subbeticus*, *Knoellia aerolata*, *Mycobacterium gilvum*, *Mycobacterium* sp. *Indicus*, or *Thermobifida fusca*, according to the alignment set forth in FIGS. 19A-D.

In some embodiments, the recombinant methyltransferase gene encodes a methyltransferase protein that has specific amino acids unchanged from the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. The unchanged amino acids can include 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids selected from D23, G24, A59, H128, F147, Y148, L180, L193, M203, G236, A241, R313, R318, E320, L359, L400, V196, G197, C198, G199, W200, G201, G202, T219, L220, Q246, D247, Y248, and D262 of *T. curvata* TmsB (SEQ ID NO:76) or corresponding amino acids in TmsB from *Mycobacterium smegmatis*, *Mycobacterium vanbaaleni*, *Amycolicicoccus subflavus*, *Corynebacterium glyciniphilum*, *Corynebacterium glutamicum*, *Rhodococcus opacus*, *Agromyces subbeticus*, *Knoellia aerolata*, *Mycobacterium gilvum*, *Mycobacterium* sp. *Indicus*, or *Thermobifida fusca*, according to the alignment set forth in FIGS. 19A-D.

ii. Nucleic Acids Comprising a Recombinant Reductase Gene

A reductase gene (e.g., a recombinant reductase gene) encodes a reductase protein, which is an enzyme capable of reducing, often in an NADPH-dependent manner, a double bond of a fatty acid (e.g., wherein the fatty acid is present as a free fatty acid, carboxylate, phospholipid, diacylglycerol, or triacylglycerol). A reductase gene (e.g., a recombinant reductase gene) may comprise any one of the nucleotide sequences set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, and SEQ ID NO:80. A reductase gene (e.g., a recombinant reductase gene) may be a 10-methylstearic A gene (tmsA) as described herein, or a biologically-active portion thereof (i.e., wherein the biologically-active portion thereof comprises reductase activity).

A reductase gene (e.g., a recombinant reductase gene) may be derived from a gram-positive species of *Actinobacteria*, such as *Mycobacteria*, *Corynebacteria*, *Nocardia*, *Streptomyces*, or *Rhodococcus*. A reductase gene (e.g., a recombinant reductase gene) may be selected from the group consisting of *Mycobacterium smegmatis* gene tmsA, *Agromyces subbeticus* gene tmsA, *Amycolicicoccus subflavus* gene tmsA, *Corynebacterium glutamicum* gene tmsA, *Corynebacterium glyciniphilium* gene tmsA, *Knoella aerolata* gene tmsA, *Mycobacterium austroafricanum* gene tmsA, *Mycobacterium gilvum* gene tmsA, *Mycobacterium indicus pranii* gene tmsA, *Mycobacterium phlei* gene tmsA, *Mycobacterium tuberculosis* gene tmsA, *Mycobacterium vanbaalenii* gene tmsA, *Rhodococcus opacus* gene tmsA, *Streptomyces regnsis* gene tmsA, *Thermobifida fusca* gene tmsA, and *Thermomonospora curvata* gene tmsA. It is specifically contemplated that one or more of the above reductase genes may be excluded from embodiments of this invention.

A recombinant reductase gene may be recombinant because it is operably-linked to a promoter other than the naturally-occurring promoter of the reductase gene. Such genes may be useful to drive transcription in a particular species of cell. A recombinant reductase gene may be recombinant because it contains one or more nucleotide substitutions relative to a naturally-occurring reductase gene. Such genes may be useful to increase the translation efficiency of the reductase gene's mRNA transcript in a particular species of cell.

A nucleic acid may comprise a recombinant reductase gene and a promoter, wherein the recombinant reductase gene and promoter are operably-linked. The recombinant reductase gene and promoter may be derived from different species. For example, the recombinant reductase gene may encode the reductase protein of a gram-positive species of *Actinobacteria*, and the recombinant reductase gene may be operably-linked to a promoter that can drive transcription in another phylum of bacteria (e.g., a Proteobacterium, such as *E. coli*) or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant reductase gene, and the recombinant reductase gene may be operably-linked to a promoter capable of driving transcription of the recombinant reductase gene in the cell. The cell may be a species of yeast, and the promoter may be a yeast promoter. The cell may be a species of bacteria, and the promoter may be a bacterial promoter (e.g., wherein the bacterial promoter is not a promoter from Actinobacteria). The cell may be a species of algae, and the promoter may be an algae promoter. The cell may be a species of plant, and the promoter may be a plant promoter.

A recombinant reductase gene may be operably-linked to a promoter that cannot drive transcription in the cell from which the recombinant reductase gene originated. For example, the promoter may not be capable of binding an RNA polymerase of the cell from which a recombinant reductase gene originated. In some embodiments, the promoter cannot bind a prokaryotic RNA polymerase and/or initiate transcription mediated by a prokaryotic RNA polymerase. In some embodiments, a recombinant reductase gene is operably-linked to a promoter that cannot drive transcription in the cell from which the protein encoded by the gene originated. For example, the promoter may not be capable of binding an RNA polymerase of a cell that naturally expresses the reductase enzyme encoded by a recombinant reductase gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1α; Glycerol-3-phosphate dehydrogenase; Triosephosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/$P_i$ cotransporter; Pyruvate decarboxylase; Phytase; or Alpha-amylase, e.g., wherein the gene is a yeast gene, such as a gene from *Yarrowia lipolytica* or *Arxula adeninivorans*.

A recombinant reductase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase gene may comprise a nucleotide sequence with, with at least, with at most 65%, 70%, 75%, 80%, 85%, 90%, 95%, 96%, 97%, 98%, or 99% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, or 1200 of the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase may or may not have 100% sequence identity with any one of the nucleotide sequences set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase gene may or may not have 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs of the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80, and the recombinant reductase gene may encode a reductase protein with at least about 95%, 96%, 97%, 98%, 99%, or 100% sequence identity with the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. For example, SEQ ID NO:80 is a gene that is codon-optimized for expression in yeast. SEQ ID NO:80 has about 70% sequence identity (70.09% sequence identity) with SEQ ID NO:1, and the protein encoded by SEQ ID NO:80 has at least about 99% sequence identity with the amino acid sequence set forth in SEQ ID NO:2. The protein encoded by SEQ ID NO:1 has 100% sequence identity with the amino acid sequence set forth in SEQ ID NO:2.

A recombinant reductase gene may vary from a naturally-occurring reductase gene because the recombinant reductase gene may be codon-optimized for expression in a eukaryotic cell, such as a plant cell, algae cell, or yeast cell. A cell may comprise a recombinant reductase gene, wherein the recombinant reductase gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant reductase gene may vary from a naturally-occurring reductase gene or may be unchanged from a naturally-occurring reductase gene. For example, a recombinant reductase gene may comprise a nucleotide sequence with at least 65% sequence identity with the naturally-occurring nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, or SEQ ID NO:73 (e.g., at least 70%, 75%, 80%, 85%, 90%, 95%, 96%, 97%, 98%, or 99% sequence identity), and at least 5 codons of the nucleotide sequence of the recombinant reductase gene may vary from the naturally-occurring nucleotide sequence (e.g., at least 10, 15, 20, 25, 30, 35, 40, 45, 50, 60, 70, 80, 90, or 100 codons).

A reductase gene encodes a reductase protein. A reductase protein may be a protein expressed by a gram-positive species of *Actinobacteria*, such as *Mycobacteria*, *Corynebacteria*, *Nocardia*, *Streptomyces*, or *Rhodococcus*. A recombinant reductase gene may encode a naturally-occurring reductase protein even if the recombinant reductase gene is not a naturally-occurring reductase gene. For example, a recombinant reductase gene may vary from a naturally-occurring reductase gene because the recombinant reductase gene is codon-optimized for expression in a specific cell. The codon-optimized, recombinant reductase gene and the naturally-occurring reductase gene may nevertheless encode the same naturally-occurring reductase protein.

A recombinant reductase gene may encode a reductase protein selected from *Mycobacterium smegmatis* enzyme tmsA, *Agromyces subbeticus* enzyme tmsA, *Amycolicicoccus subflavus* enzyme tmsA, *Corynebacterium glutamicum* enzyme tmsA, *Corynebacterium glyciniphilium* enzyme tmsA, *Knoella aerolata* enzyme tmsA, *Mycobacterium austroafricanum* enzyme tmsA, *Mycobacterium gilvum* enzyme tmsA, *Mycobacterium indicus pranii* enzyme tmsA, *Mycobacterium phlei* enzyme tmsA, *Mycobacterium tuberculosis* enzyme tmsA, *Mycobacterium vanbaalenii* enzyme tmsA, *Rhodococcus opacus* enzyme tmsA, *Streptomyces regnsis* enzyme tmsA, *Thermobifida fusca* enzyme tmsA, and *Thermomonospora curvata* enzyme tmsA. It is specifically contemplated that one or more of the above reductase proteins may be excluded from embodiments of this invention. A recombinant reductase gene may encode a reductase protein, and the reductase protein may be substantially identical to any one of the foregoing enzymes, but the recombinant reductase gene may vary from the naturally-occurring gene that encodes the enzyme. The recombinant reductase gene may vary from the naturally-occurring gene because the recombinant reductase gene may be codon-optimized for expression in a specific phylum, class, order, family, genus, species, or strain of cell.

The sequences of naturally-occurring reductase proteins are set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. A recombinant reductase gene may or may not encode a protein comprising 100% sequence identity with the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. For example, a recombinant reductase gene may encode a protein having 100% sequence identity with a biologically-active portion of an amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74.

A recombinant reductase gene may encode a reductase protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74, or a biologically-active portion thereof. A recombinant reductase gene may encode a reductase protein having about, at least about, or at most about 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, or 400% reductase activity relative to a protein comprising the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. A recombinant reductase gene may encode a protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous amino acids starting at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 of the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74.

Substrates for the reductase protein may include any fatty acid from 14 to 20 carbons long with a methylene substitution in the Δ9, Δ10, or Δ11 position. The fatty acid substrate may be 14, 15, 16, 17, 18, 19, or 20 carbons long, or any range derivable therein. The reductase protein may be capable of catalyzing the reduction of a methylene-substituted fatty acid substrate to a (methyl)lipid. The reductase protein, together with a methyltransferase protein, may be capable of catalyzing the production of a methylated branch from any fatty acid from 14 to 20 carbons long with an unsaturated double bond in the Δ9, Δ10, or Δ11 position.

In some embodiments, the recombinant reductase gene encodes a reductase protein that includes a Flavin adenine dinucleotide (FAD) binding domain. In some embodiments, the FAD binding domain has at least 80%, 85%, 90%, 91%, 92%, 93%, 94%, 95%, 96%, 97%, 98%, 99%, 99.9%, or 100% sequence identity to amino acids 9-141 of *T. curvata* TmsA (SEQ ID NO:74) or to a corresponding portion of TmsA from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 20A-E.

In some embodiments, the recombinant reductase gene encodes a reductase protein that includes a FAD/FMN-containing dehydrogenase domain. In some embodiments, the FAD/FMN-containing dehydrogenase domain has, has at least, or has at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to amino acids 22-444 of *T. curvata* TmsA (SEQ ID NO:74) or to a corresponding portion of TmsA from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 20A-E.

In some embodiments, the recombinant reductase gene encodes a reductase protein that has specific amino acids unchanged from the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. The unchanged amino acids can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, or amino acids selected from R31, A33, S37, N38, L39, F40, R43, D52, V59, D63, G73, M74, T76, Y77, D79, L80, V81, L85, P91, V93, V94, Q96, L97, T99, I100, T101, A105, G108, G110, E112, 5113, 5115, F116, R117, N118, P121, H122, E123, V125, E127, G133, P154, N155, Y157, Y162, L166, E171, V173, V177, H181, V208, G213, F216, Y222, L223, 5236, D237, Y238, T239, Y245, 5247, D254, T257, Y261, W263, R264, W265, D266, D268, W269, C272, A275, G277, Q279, R284, W287, R293, 5294, G318, E232, V325, P328, E330, F339, F343, W353, C355, P356, W363, L365, Y366, P367, N376, F379, W380, V383, P384, N395, E399, G407, H408, K409, S410, L411, Y412, 5413, Y417, F422, Y426, G428, R443, L447, and V452 of *T. curvata* TmsA (SEQ ID NO:74) or corresponding amino acids in TmsA from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 20A-E.

iii. Nucleic acids comprising a recombinant tmsC gene.

A nucleic acid may comprise a 10-methylstearic C gene (tmsC), as described herein. A tmsC gene (e.g., a recombinant tmsC gene) may comprise any one of the nucleotide sequences set forth in SEQ ID NO:21, SEQ ID NO:31, SEQ ID NO:37, SEQ ID NO:55, SEQ ID NO:65, and SEQ ID NO:71. A tmsC gene (e.g., a recombinant tmsC gene) may be derived from a gram-positive species of *Actinobacteria*, such as *Mycobacteria, Corynebacteria, Nocardia, Streptomyces*, or *Rhodococcus*. A tmsC gene (e.g., a recombinant tmsC gene) may be selected from the group consisting of *Corynebacterium glyciniphilium* gene tmsC, *Mycobacterium austroafricanum* gene tmsC, *Mycobacterium gilvum* gene tmsC, *Mycobacterium vanbaalenii* gene tmsC, *Streptomyces regnsis* gene tmsC, and *Thermobifida fusca* gene tmsC.

A recombinant tmsC gene may be recombinant because it is operably-linked to a promoter other than the naturally-occurring promoter of the tmsC gene. Such genes may be useful to drive transcription in a particular species of cell. A recombinant tmsC gene may be recombinant because it contains one or more nucleotide substitutions relative to a naturally-occurring tmsC gene. Such genes may be useful to increase the translation efficiency of the tmsC gene's mRNA transcript in a particular species of cell.

A nucleic acid may comprise a recombinant tmsC gene and a promoter, wherein the recombinant tmsC gene and promoter are operably-linked. The recombinant tmsC gene and promoter may be derived from different species. For example, the recombinant tmsC gene may encode the tmsC protein of a gram-positive species of Actinobacteria, and the recombinant tmsC gene may be operably-linked to a promoter that can drive transcription in another phylum of bacteria (e.g., a Proteobacterium, such as *E. coli*) or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant tmsC gene, and the recombinant tmsC gene may be operably-linked to a promoter capable of driving transcription of the recombinant tmsC gene in the cell. The cell may be a species of yeast, and the promoter may be a yeast promoter. The cell may be a species of bacteria, and the promoter may be a bacterial promoter (e.g., wherein the bacterial promoter is not a promoter from Actinobacteria). The cell may be a species of algae, and the promoter may be an algae promoter. The cell may be a species of plant, and the promoter may be a plant promoter.

A recombinant tmsC gene may be operably-linked to a promoter that cannot drive transcription in the cell from which the recombinant tmsC gene originated. For example, the promoter may not be capable of binding an RNA polymerase of the cell from which a recombinant tmsC gene originated. In some embodiments, the promoter cannot bind a prokaryotic RNA polymerase and/or initiate transcription mediated by a prokaryotic RNA polymerase. In some embodiments, a recombinant tmsC gene is operably-linked to a promoter that cannot drive transcription in the cell from which the protein encoded by the gene originated. For example, the promoter may not be capable of binding an RNA polymerase of a cell that naturally expresses the tmsC enzyme encoded by a recombinant tmsC gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1α; Glycerol-3-phosphate dehydrogenase; Triose-phosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/$P_i$ cotransporter; Pyruvate decarboxylase; Phytase; or Alpha-amylase, e.g., wherein the gene is a yeast gene, such as a gene from *Yarrowia lipolytica* or *Arxula adeninivorans*.

A recombinant tmsC gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:21, SEQ ID NO:31, SEQ ID NO:37, SEQ ID NO:55, SEQ ID NO:65, or SEQ ID NO:71. A recombinant tmsC may or may not have 100% sequence identity with any one of the nucleotide sequences set forth in SEQ ID NO:21, SEQ ID NO:31, SEQ ID NO:37, SEQ ID NO:55, SEQ ID NO:65, and SEQ ID NO:71. A recombinant tmsC gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:21, SEQ ID NO:31, SEQ ID NO:37, SEQ ID NO:55, SEQ ID NO:65, and SEQ ID NO:71, and the recombinant tmsC gene may encode a tmsC protein with at least about 95%, 96%, 97%, 98%, 99%, or 100% sequence identity with the amino acid sequence set forth in SEQ ID NO:22, SEQ ID NO:32, SEQ ID NO:38, SEQ ID NO:56, SEQ ID NO:66, and SEQ ID NO:72.

A recombinant tmsC gene may vary from a naturally-occurring tmsC gene because the recombinant tmsC gene may be codon-optimized for expression in a eukaryotic cell, such as a plant cell, algae cell, or yeast cell. A cell may comprise a recombinant tmsC gene, wherein the recombinant tmsC gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant tmsC gene may vary from a naturally-occurring tmsC gene or may remain unchanged from a naturally-occurring tmsC gene. For example, a recombinant tmsC gene may comprise a nucleotide sequence with at least about 65% sequence identity with the naturally-occurring nucleotide sequence set forth in SEQ ID NO:21, SEQ ID NO:31, SEQ ID NO:37, SEQ ID NO:55, SEQ ID NO:65, or SEQ ID NO:71 (e.g., at least about 70%, 75%, 80%, 85%, 90%, 95%, 96%, 97%, 98%, or 99% sequence identity), and at least 5 codons of the nucleotide sequence of the recombinant tmsC gene may vary from the naturally-occurring nucleotide sequence (e.g., at least about 10, 15, 20, 25, 30, 35, 40, 45, 50, 60, 70, 80, 90, or 100 codons).

A tmsC gene encodes a tmsC protein. A tmsC protein may be a protein expressed by a gram-positive species of *Actinobacteria*, such as *Mycobacteria, Corynebacteria, Nocardia, Streptomyces*, or *Rhodococcus*. A recombinant tmsC gene may encode a naturally-occurring tmsC protein even if the recombinant tmsC gene is not a naturally-occurring tmsC gene. For example, a recombinant tmsC gene may vary from a naturally-occurring tmsC gene because the recombinant tmsC gene is codon-optimized for expression in a specific cell. The codon-optimized, recombinant tmsC gene and the naturally-occurring tmsC gene may nevertheless encode the same naturally-occurring tmsC protein.

A recombinant tmsC gene may encode a tmsC protein selected from *Corynebacterium glyciniphilium* enzyme tmsC, *Mycobacterium austroafricanum* enzyme tmsC, *Mycobacterium gilvum* enzyme tmsC, *Mycobacterium vanbaalenii* enzyme tmsC, *Streptomyces regnsis* enzyme tmsC, and *Thermobifida fusca* enzyme tmsC. A recombinant tmsC gene may encode a tmsC protein, and the tmsC protein may be substantially identical to any one of the foregoing enzymes, but the recombinant tmsC gene may vary from the naturally-occurring gene that encodes the enzyme. The recombinant tmsC gene may vary from the naturally-occurring gene because the recombinant tmsC gene may be codon-optimized for expression in a specific phylum, class, order, family, genus, species, or strain of cell.

The sequences of naturally-occurring tmsC proteins are set forth in SEQ ID NO:22, SEQ ID NO:32, SEQ ID NO:38, SEQ ID NO:56, SEQ ID NO:66, and SEQ ID NO:72. A recombinant tmsC gene may or may not encode a protein comprising 100% sequence identity with the amino acid sequence set forth in SEQ ID NO:22, SEQ ID NO:32, SEQ ID NO:38, SEQ ID NO:56, SEQ ID NO:66, and SEQ ID NO:72. For example, a recombinant tmsC gene may encode a protein having 100% sequence identity with a biologically-active portion of an amino acid sequence set forth in SEQ ID NO:22, SEQ ID NO:32, SEQ ID NO:38, SEQ ID NO:38, SEQ ID NO:56, SEQ ID NO:66, and SEQ ID NO:72. A recombinant tmsC gene may encode a tmsC protein having at least about 95%, 96%, 97%, 98%, or 99% sequence identity with the amino acid sequence set forth in SEQ ID NO:22, SEQ ID NO:32, SEQ ID NO:38, SEQ ID NO:56, SEQ ID NO:66, or SEQ ID NO:72, or a biologically-active portion thereof.

iv. Nucleic Acids Comprising a Recombinant Methyltransferase Gene and a Recombinant Reductase Gene A nucleic acid may comprise both a recombinant methyltransferase gene and a recombinant reductase gene. The recombinant methyltransferase gene and the recombinant reductase gene may encode proteins from the same species or from different species. A nucleic acid may comprise a recombinant methyltransferase gene, a recombinant reductase gene, and/or a tmsC gene. A recombinant methyltransferase gene, recombinant reductase gene, and a tmsC gene may encode proteins from 1, 2, or 3 different species (i.e., the genes may each be from the same species, two genes may be from the same species, or all three genes may be from different species).

A nucleic acid may comprise the nucleotide sequence set forth in SEQ ID NO:77, SEQ ID NO:78, or SEQ ID NO:79. A nucleic acid may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:77, SEQ ID NO:78, SEQ ID NO:79, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, or SEQ ID NO:92.

In some embodiments, the nucleic acid encodes a fusion protein that includes both a methyltransferase and a reductase or fragments thereof. In the context of the present invention, "fusion protein" means a single protein molecule containing two or more distinct proteins or fragments thereof, covalently linked via peptide bond in a single peptide chain. In some embodiments, the fusion protein comprises enzymatically active domains from both a methyltransferase protein and a reductase protein. The nucleic acid may further encode a linker peptide between the methyltransferase and the reductase. In some embodiments, the linker peptide comprises the amino acid sequence AGGAEGGNGGGA. The linker may comprise about or at least about 2, 3, 4, 5, 6, 7, 8, 9, 10, 15, 20, 25, or 30 amino acids, or any range derivable therein. The nucleic acid may comprise any of the methyltransferase and reductase genes described herein, and the fusion protein encoded by the nucleic acid can comprise any of the methyltransferase and reductase proteins described herein, including biologically active fragments thereof. In some embodiments, the fusion protein is a tmsA-B protein, in which the TmsA protein is closer to the N-terminus than the TmsB protein. An example of such a tmsA-B protein is encoded by the nucleic acid sequence of SEQ ID NO:97. In some embodiments, the fusion protein is a tmsB-A protein, in which the tmsB protein is closer to the N-terminus than the tmsA protein. An example of such a tmsB-A protein is encoded by the nucleic acid sequence of SEQ ID NO:98. In some embodiments, the fusion protein has at least about 80%, 85%, 90%, 91%, 92%, 93%, 94%, 95%, 96%, 97%, 98%, 99%, or 99.9% identity to the amino acid sequence of a fusion protein encoded by SEQ ID NO:97 or SEQ ID NO:98.

C. Compositions

Various aspects of the invention relate to compositions produced by the cells described herein. The composition may be an oil composition comprised of about or at least about 75%, 80%, 85%, 90%, 95%, or 99% lipids. The composition may comprise branched (methyl)lipids and/or exomethylene-substituted lipids. The branched (methyl) lipid may be a carboxylic acid (e.g., 10-methylstearic acid, 10-methylpalmitic acid, 12-methyloleic acid, 13-methyloleic acid, 10-methyl-octadec-12-enoic acid), carboxylate (e.g., 10-methylstearate, 10-methylpalmitate, 12-methyloleate, 13-methyloleate, 10-methyl-octadec-12-enoate), ester (e.g., diacylglycerol, triacylglycerol, phospholipid), thioester (e.g., 10-methylstearyl CoA, 10-methylpalmityl CoA, 12-methyloleoyl CoA, 13-methyloleoyl CoA, 10-methyl-octadec-12-enoyl CoA), or amide. The exomethylene-substituted lipid may be a carboxylic acid (e.g., 10-methylenestearic acid, 10-methylenepalmitic acid, 12-methyleneoleic acid, 13-methyleneoleic acid, 10-methylene-octadec-12-enoic acid), carboxylate (e.g., 10-methylene stearate, 10-methylenepalmitate, 12-methyleneoleate, 13-methyleneoleate, 10-methylene-octadec-12-enoate), ester (e.g., diacylglycerol, triacylglycerol, phospholipid), thioester (e.g., 10-methylenestearyl CoA, 10-methylenepalmityl CoA, 12-methyleneoleoyl CoA, 13-methyleneoleoyl CoA, 10-methylene-octadec-12-enoyl CoA), or amide.

10-methyl lipids, 10-methylene lipids, or both. It is specifically contemplated that one or more of the above lipids may be excluded from certain embodiments.

In some aspects, the composition is produced by cultivating a culture comprising any of the cells described herein and recovering the oil composition from the cell culture. The cells in the culture may contain any of the recombinant methyltransferase genes described herein and/or any of the recombinant reductase genes described herein. The culture medium and conditions can be chosen based on the species of the cell to be cultured and can be optimized to provide for maximal production of the desired lipid profile.

Various methods are known for recovering an oil composition from a culture of cells. For example, lipids, lipid derivatives, and hydrocarbons can be extracted with a hydrophobic solvent such as hexane. Lipids and lipid derivatives can also be extracted using liquefaction, oil liquefaction, and supercritical $CO_2$ extraction. The recovery process may include harvesting cultured cells, such as by filtration or centrifugation, lysing cells to create a lysate, and extracting the lipid/hydrocarbon components using a hydrophobic solvent.

In addition to accumulating within cells, the lipids described herein may be secreted by the cells. In that case, a process for recovering the lipid may not require creating a lysate from the cells, but collecting the secreted lipid from the culture medium. Thus, the compositions described herein may be made by culturing a cell that secretes one of the lipids described herein, such as a a linear fatty acid with a chain length of 14-20 carbons with a methyl branch at the Δ9, Δ10 or Δ11 position.

In some embodiments, the oil composition comprises about, at least about, or at most about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of a branched (methyl)lipid, such as a 10-methyl fatty acid, or any range derivable therein. In some embodiments, 10-methyl fatty acids comprise about, at least about, or at most about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids in the composition, or any range derivable therein.

D. Methods of Producing a Branched (Methyl)Lipid

Various aspects of the invention relate to a method of producing a branched (methyl)lipid. The method may comprise incubating a cell or plurality of cells as described herein, supra, with media. The media may optionally be supplemented with an unbranched, unsaturated fatty acid, such as oleic acid, that serves as a substrate for methylation. The media may optionally be supplemented with methionine or s-adenosyl methionine, which may similarly serve as a substrate. Thus, the method may comprise contacting a cell or plurality of cells with oleic acid, methionine, or both. The method may comprise incubating a cell or plurality of cells as described herein, supra, in a bioreactor. The method may comprise recovering lipids from the cells and/or from the culture medium, such as by extraction with an organic solvent.

The method may comprise degumming the cell or plurality of cells, e.g., to remove proteins. The method may comprise transesterification or esterification of the lipids of the cells. An alcohol such as methanol or ethanol may be used for transesterification or esterification, e.g., thereby producing a fatty acid methyl ester or fatty acid ethyl ester.

EXEMPLIFICATION

The present description is further illustrated by the following examples, which should not be construed as limiting in any way.

Example 1: Identification of 10-Methylstearic Genes tmsA, tmsB, and tmsC

Two different genes have been identified as responsible for 10-methylstearate production in *M. tuberculosis* (see Meena, L. S., and P. E. Kolattukudy, BIOTECHNOLOGY & APPLIED BIOCHEMISTRY 60(4):412 (2013) and Meena, L. S., et al. BIOLOGICAL CHEMISTRY 394(7):871 (2013)). Curiously, neither gene is conserved throughout each Actinobacteria species that produces 10-methylstearate. While it is possible that different species of *Actinobacteria* each independently evolved genes that synthesize 10-methylstearate, such convergent evolution is rare. A simpler explanation is that a single common gene or set of genes is responsible for 10-methylstearate production in Actinobacteria.

Figure 1:
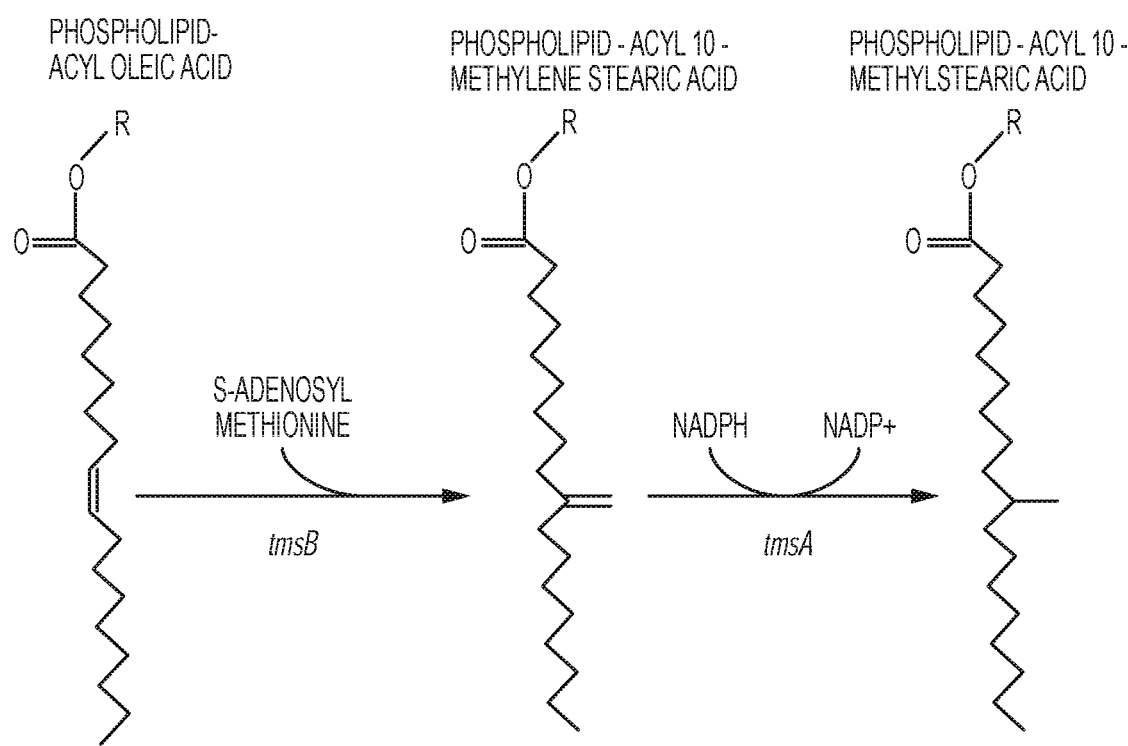
FIG. 1 depicts one possible mechanism for the conversion of oleic acid to 10-methylstearic acid. An oleic acid substrate may be present as an acyl chain of a glycerolipid or phospholipid. A methionine substrate, which donates the methyl group, may be present as S-adenosyl methionine. The oleic acid and methionine substrates may be converted to 10-methylenestearic acid (e.g., present as an acyl chain of a glycerolipid or phospholipid) and homocysteine (e.g., present as S-adenosyl homocysteine). This reaction may be catalyzed by a tmsB protein as described herein, infra. 10-methylenestearic acid (e.g., present as an acyl chain of a glycerolipid or phospholipid) may be reduced to 10-methylstearic acid. The reduction may be catalyzed by a tmsA protein as describe herein, infra, for example, using NADPH as a reducing agent. The language of the specification and claims, however, is not limited to any particular reaction mechanism.
Figure 2:
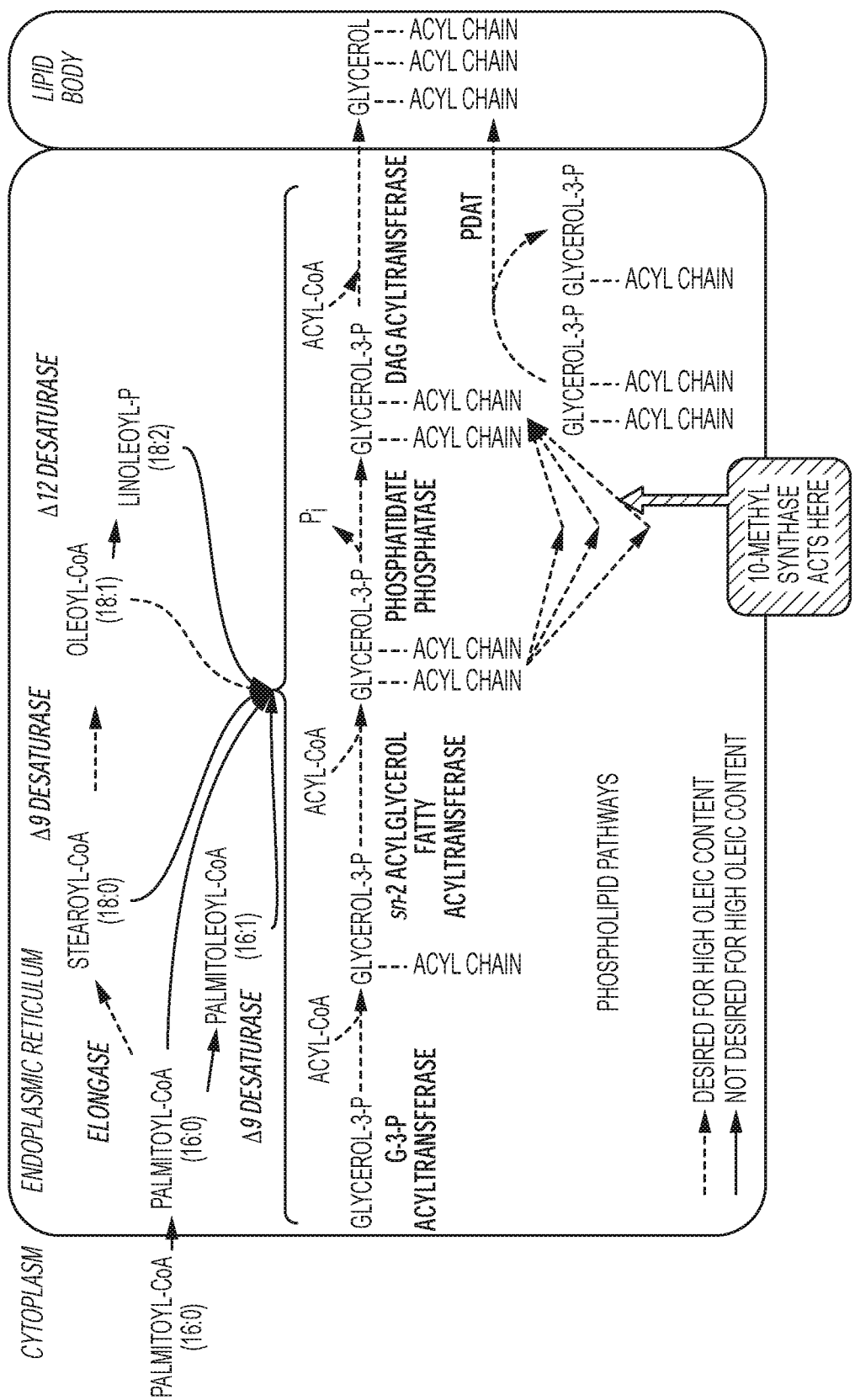
FIG. 2 depicts one possible mechanism for the conversion of oleic acid to 10-methylstearic acid. Oleic acid, present as a carboxylic acid in the cytosol, may be added to monoacylglycerol-3-phosphate to form a diacylglycerol-3-phosphate comprising an oleate acyl group. "10-methyl synthase" may convert diacylglycerol-3-phosphate comprising an oleate acyl group to diacylglycerol-3-phosphate comprising a 10-methylsterate acyl group. The diacyl-3-phosphate may subsequently be converted to a triacylglycerol, converted into another phospholipid, such as phosphatidylcholine, or converted back into a monoacylglycerol-3-phosphate (e.g., thereby releasing free 10-methylstearate into the cytosol). The language of the specification and claims, however, is not limited to any particular reaction mechanism.
Figure 3A:
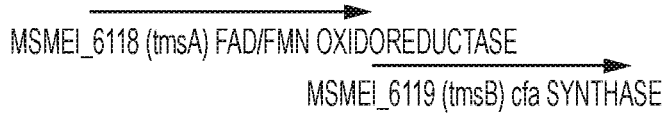
Figure 3A:
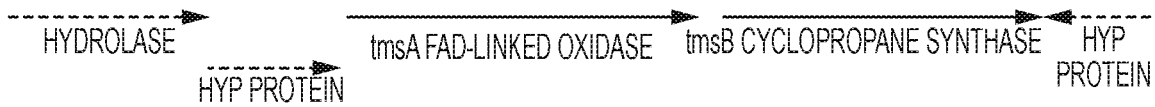
Figure 3A:
Figure 3A:
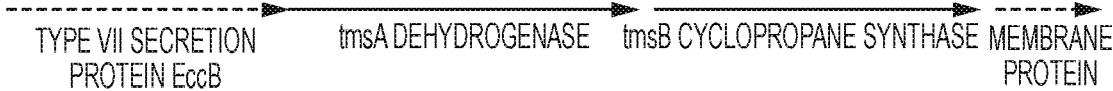
Figure 3A:
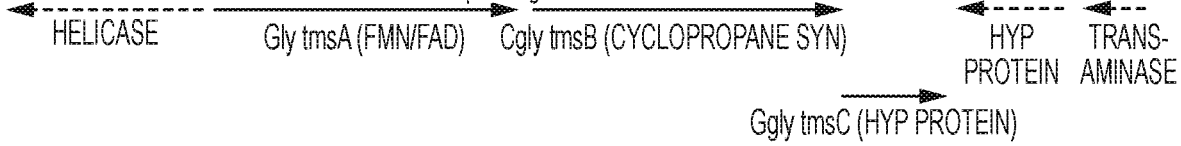
Figure 3A:
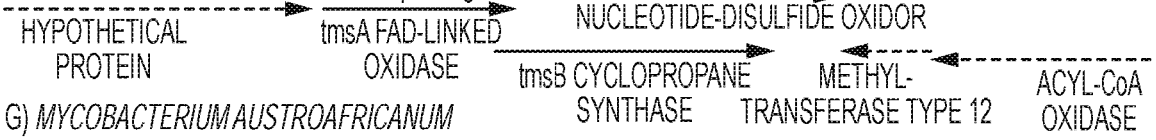
Figure 3A:
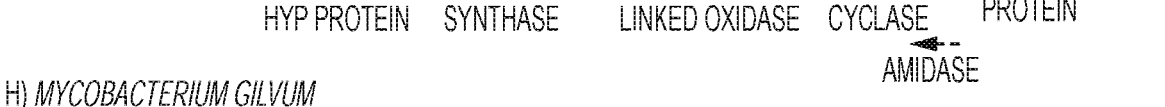
Figure 3A:

To identify genes that may be responsible for 10-methylstearate production in Actinobacteria, genes with sequence homology to those that encode enzymes that catalyze lipid synthesis reactions were aligned from various species of 10-methylstearate-producing Actinobacteria. Two unique genes were identified and named 10-methystearic A (tmsA) and 10-methylstearic B (tmsB), which each occur in the same operon within each 10-methystearate producing species of *Actinobacteria* (FIGS. 3A and 3B). A third gene named 10-methylstearic C (tmsC) was identified as occurring in the same operon as tmsA and tmsB for some of the 10-methylstearate-producing species.

The 10-methylstearate B gene has sequence homology with cyclopropane synthases, which suggests that the 10-methylstearate B gene may be capable of transferring a methyl group to a fatty acid. The 10-methylstearic A gene has sequence homology with oxidoreductases, which suggests that it may be capable of reducing the exomethylene group of a branched fatty acid.

Figure 4:
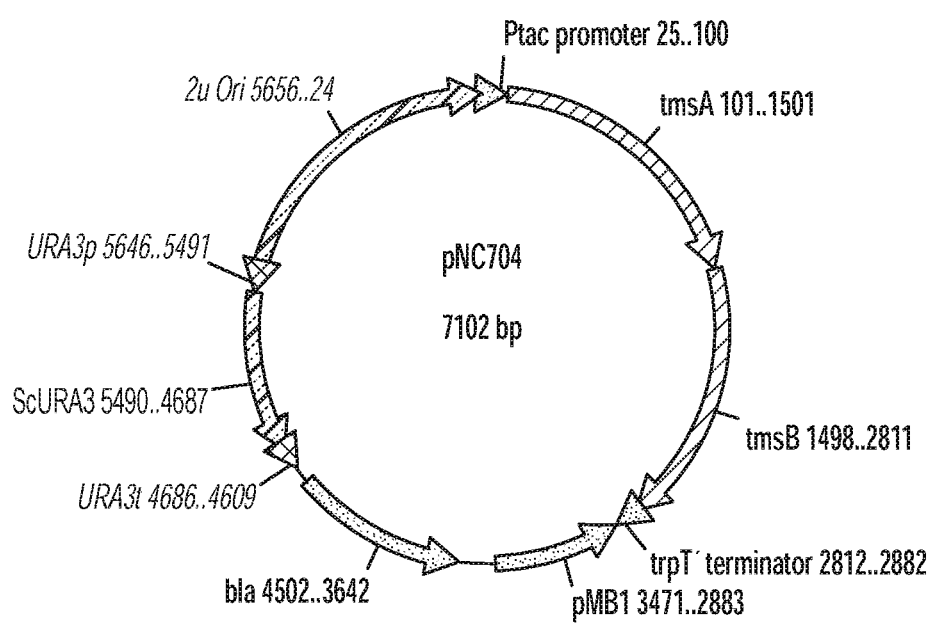
FIG. 4 is a map of plasmid pNC704, which may be used to express *Mycobacterium smegmatis* genes tmsA (SEQ ID NO:1) and tmsB (SEQ ID NO:3) in *E. coli*. The nucleotide sequence of plasmid pNC738 is set forth in SEQ ID NO:77.
Figure 5:
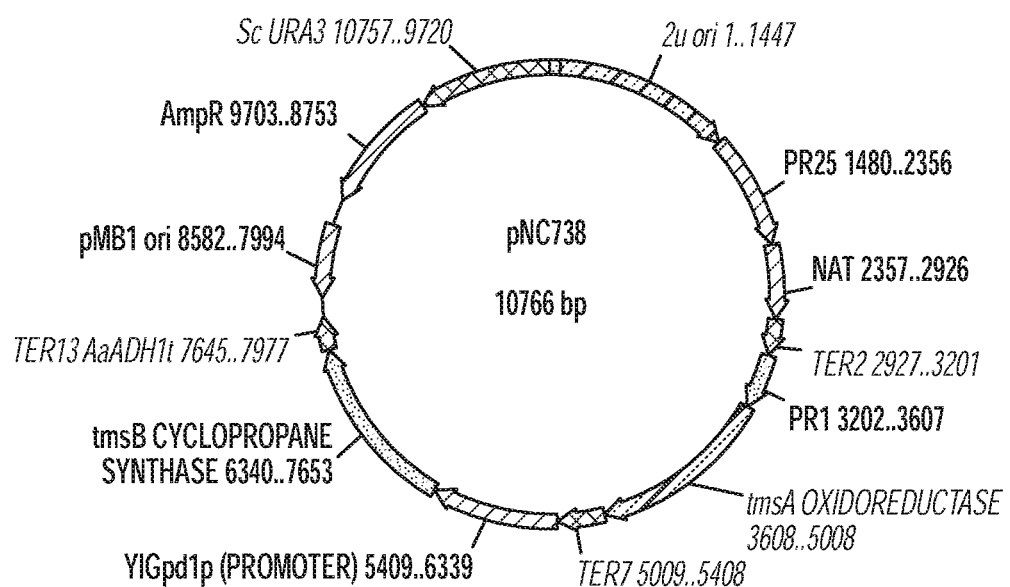
FIG. 5 is a map of plasmid pNC738, which may be used to express codon-optimized versions of *Mycobacterium smegmatis* genes tmsA (SEQ ID NO:80) and tmsB (SEQ ID NO:81) in yeast, such as *Arxula adeninivorans*, *Saccharomyces cerevisiae*, and *Yarrowia lipolytica*. The nucleotide sequence of plasmid pNC738 is set forth in SEQ ID NO:78.
Figure 6:
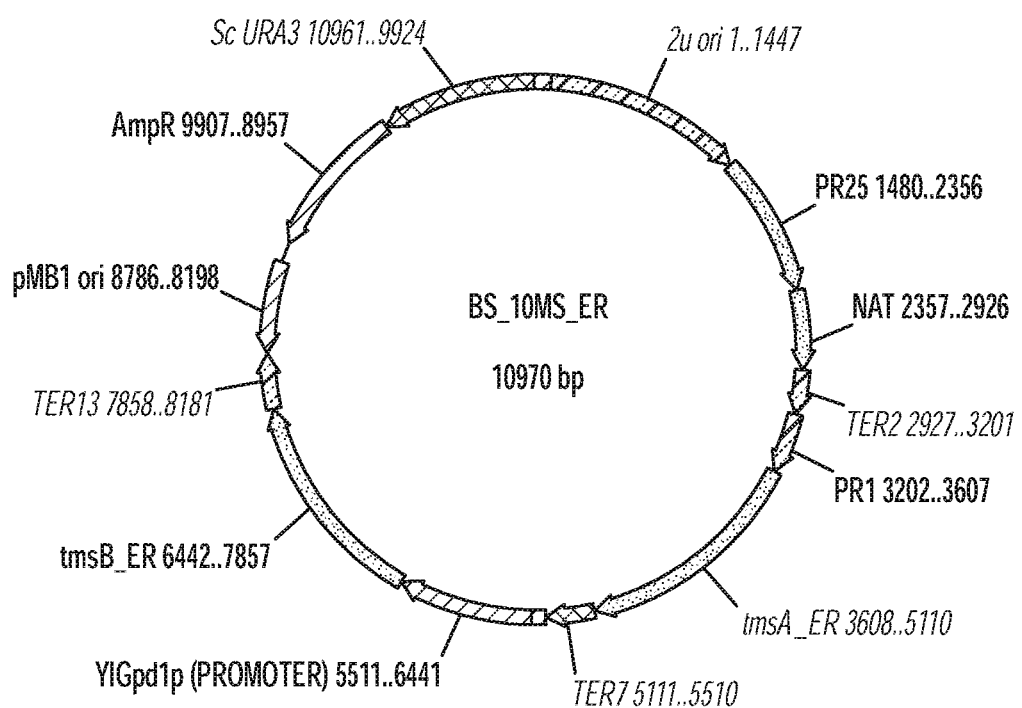
FIG. 6 is a map of plasmid BS-10MS_ER, which may be used to express codon-optimized versions of *Mycobacte-* rium smegmatis genes tmsA (SEQ ID NO:80) and tmsB (SEQ ID NO:81) in yeast, such as Arxula adeninivorans, Saccharomyces cerevisiae, and Yarrowia lipolytica. The nucleotide sequence of plasmid BS-10MS_ER is set forth in SEQ ID NO:79.

The 10-methylstearate A and 10-methylstearate B genes from *M. smegmatis* were cloned into a plasmid (named pNC704) for expression in *E. coli* (FIG. 4). The pNC704 plasmid harboring *M. smegmatis* tmsA and tmsB was used to transform *E. coli*. The transformed cells were grown for 20 hours at 37° C. in LB media supplemented with 100 μg/mL oleic acid. *E. coli* was transformed with an empty vector pNC53 (SEQ ID NO:81) and grown in parallel as a control. Each of two *E. coli* colonies transformed with pNC704 produced 10-methylstearate at a concentration of 2.0% and 2.1% of the total fatty acids in the cell (Table 1). The control did not produce 10-methylstearate

TABLE 1

Fatty acid concentration as a percentage of total cellular fatty acids. "10-MS" corresponds to 10-methylstearate

| | Fatty acid composition | | | | |
|---|---|---|---|---|---|
| | % 10-MS | % 16:1 | % 16:0 | % 18:0 | % 18:1 |
| E. coli TOP10 + pNC53 | 0.0 | 4.0 | 56.8 | 1.4 | 30.6 |
| E. coli TOP10 + pNC704 isolate 1 | 2.1 | 4.2 | 55.0 | 0.8 | 30.9 |
| E. coli TOP10 + pNC704 isolate 2 | 2.0 | 3.9 | 55.5 | 0.8 | 30.8 |

Cellular lipids were transesterified to produce fatty acid methyl esters (FAMEs) in a solution of HCl in methanol. Stearic acid, 10-methylstearic acid, and oleic acid were transesterified into FAMEs as standards. Each sample/standard was extracted into isooctane and analyzed by various gas chromatography methods (FIGS. 7 and 8). FAMEs were first analyzed by capillary gas chromatography using a flame-ionization detector (GC-FID). The FAMEs produced from E. coli displayed a GC peak corresponding to the 10-methylstearic acid FAME standard, which suggests that the M. smegmatis tmsA and tmsB genes express proteins that are capable of synthesizing 10-methylstearic acid (FIG. 7A).

FAMEs were also produced from E. coli that was transformed with the empty vector pNC53 and analyzed by GC-FID as above. This sample did not display a GC peak corresponding to the 10-methylstearic acid FAME, further suggesting that the M. smegmatis tmsA and tmsB genes express proteins that are capable of synthesizing 10-methylstearic acid (FIG. 7B).

The FAMEs produced from the tmsA/tmsB sample were analyzed using a GC-MS configured in single-ion monitoring mode (SIM), which monitored m/z at 312.3 and 313.3 amu. The mass spectrum displayed a peak at 312.3 amu, corresponding to the molecular weight of a 10-methylstearate methyl ester (FIG. 8B). Additionally, the ratio of the peak at 312.3 amu to 313.3 amu suggests that the ion observed at 312.3 amu contains 20.6 carbons, which corresponds to the actual number of carbons (20) in the 10-methylstearate methyl ester.

Example 2: Production of 10-Methyl Fatty Acid in E. coli Using tmsB and tmsA Genes from Different Donor Organisms Methods:

Donor bacteria genomic DNA was obtained from Deutsche Sammlung von Mikroorganismen and Zellkulturen (DSMZ), Germany. Plasmids were constructed with standard molecular biology techniques using the "yeast gap repair" method (Shanks, et al., Appl. Microbiol. Biotechnol., 48:232 (1997)). The empty E. coli expression vector pNC53 (SEQ ID NO:82) was restriction digested with enzyme PmeI (New England Biolabs, MA), creating a double strand break between the tac promoter and trpT' terminator sequences on this vector. tmsAB gene operons were PCR amplified from genomic DNA with primer flanking sequence such that the tmsB ATG start site integrated into the end of the tac promoter via homologous recombination. E. coli transcription and translation was driven by the tac promoter. The stop codon of the tmsA gene similarly integrated into the beginning of the trpT' terminator region. E. coli translation of the operon-embedded tmsA gene relied on native translation signals from the donor organism DNA. Where necessary, the first codon of tmsB was altered from GTG or TTG to ATG; otherwise the native codon sequence was kept in the E. coli expression vectors.

Vectors were checked by DNA sequencing and restriction digest for correct construction. The vectors created for this example are illustrated in FIG. 9. Vectors transformed into E. coli Top10 (Invitrogen) were then used for fermentation studies. Cells were inoculated in 50 mL LB medium supplemented with 100 mg/L ampicillin and 100 mg/L oleic acid from a stock solution of 100 mg/mL oleic acid in ethanol. Cultures were incubated at 37° C. and 200 rpm in baffled shake flasks for 41 hours. At the end of cultivation, cells were harvested by centrifugation at 4000 rpm for 15 minutes in an Eppendorf 5810 R clinical centrifuge, washed once with and equal volume of deionized water, resuspended in 0.1 mL deionized water, and frozen at −80° C. Cells were then lyophilized to dryness and used to perform an acid-catalyzed transesterification with a solution of 0.5 N HCl in methanol (20×1 mL ampule, Sigma) at 85° C. for 90 minutes. After the transesterification was completed, the lipid-soluble components of the reaction mixture were separated from the water-soluble components using a two-phase liquid extraction by adding water and isooctane and subsequently analyzed with a capillary gas chromatograph (GC) equipped with a robotic injector, flame ionization detector (Agilent Technologies 7890B GC system and 7396 Autosampler) and HP-INNOWAX capillary column (30 m×0.25 mm×0.15 micrometers, Agilent). A 10-methylstearic acid reference standard was obtained from Larodan AB, Sweden.

Results:

Conversion of oleic acid to 10-methylstearic acid was observed for 4 of the 11 vectors tested. Highest percent conversion occurred with tmsAB genes from Thermobifida fusca (22%) and Thermomonospora curvata (38%), as indicated in Table 2 below.

TABLE 2

| E. coli vector | Sequence | Donor organism | % oleic acid conversion to 10-methylstearic acid |
|---|---|---|---|
| pNC704 | SEQ ID NO: 77 | Mycobacterium smegmatis | 4.9% ± 0.6% |
| pNC721 | SEQ ID NO: 83 | Mycobacterium vanbaaleni | 0 |
| pNC755 | SEQ ID NO: 84 | Amycolicicoccus subflavus | 0 |
| pNC757 | SEQ ID NO: 85 | Corynebacterium glyciniphilum | 0 |
| pNC904 | SEQ ID NO: 86 | Rhodococcus opacus | 1.2% ± 0.2% |
| pNC905 | SEQ ID NO: 87 | Thermobifida fusca | 22.0% ± 0.3% |
| pNC906 | SEQ ID NO: 88 | Thermomonospora curvata | 38.3% ± 0.5% |
| pNC907 | SEQ ID NO: 89 | Corynebacterium glutamicum | 0 |
| pNC908 | SEQ ID NO: 90 | Agromyces subbeticus | 0 |
| pNC910 | SEQ ID NO: 91 | Mycobacterium gilvum | 0 |
| pNC911 | SEQ ID NO: 92 | Mycobacterium sp. indicus | 0 |

Example 3: tmsB and tmsA Expression in Rhocococcus opacus PD630

The oleaginous bacteria Rhocococcus opacus can produce 10-methyl fatty acids natively at low levels (0.2% of total fatty acids (Wältermann et al., Microbiology, 72:5027 (2006)), and additionally possesses native homologs of the tmsB and tmsA gens, although they have not been identified as such in the literature. In this Example, the inventors tested whether overexpression of the tmsB and tmsA genes in *R. opacus* can increase 10-methyl branched fatty acid content.

Methods:

*Rhodococcus opacus* PD630 was obtained from the German Collection of Microorganisms and Cell Cultures (DSMZ) from stock DSM 44193. The culture was revived by dilution with 4 mL LB media and incubated at 30° C. for 3 days in a drum roller. Once visible growth occurred, 10 µL broth was struck to single colonies on an LB plate and incubated an additional 3 days at 30° C. One colony was isolated and designated strain NS1104.

All *R. opacus* growth was performed at 30° C. Routine culturing was performed in LB medium supplemented with appropriate antibiotics. Genetic transformation was performed in Nutrient Broth medium as modified by Kalscheuer et al. (Appl. Microbiol. and Biotechnol., 52:508 (1999)), which contained 5 g/L peptone, 2 g/L yeast extract, 1 g/L beef extract, 5 g/L NaCl, 8.5 g/L glycine, and 10 g/L sucrose. Lipid production was performed in defined medium containing the following components and adjusted to pH 7.6 with NaOH and filter sterilized before use.

| R. opacus fermentation medium | |
| --- | --- |
| Component | g/L |
| Glucose | 40 |
| $(NH_4)_2SO_4$ | 1.4 |
| $MgSO_4 \cdot 7H_2O$ | 1 |
| $CaCl_2 \cdot 6H_2O$ | 0.02 |
| $KH_2PO_4$ | 0.4 |
| MOPS acid | 5 |
| Trace element solution | 1 mL |

| Trace element solution | g/L stock solution |
| --- | --- |
| $FeSO_4 \cdot 7H_2O$ | 0.5 |
| $CuSO_4 \cdot 5H_2O$ | 0.005 |
| $ZnSO_4 \cdot 7H_2O$ | 0.4 |
| $MnCl_2 \cdot 2H_2O$ | 0.02 |
| $Na_2MoO_4 \cdot 2H_2O$ | 0.02 |
| $CoCl_2 \cdot 6H_2O$ | 0.05 |
| EDTA | 0.25 |
| $H_3BO_3$ | 0.015 |
| $NiCl_2 \cdot 6H_2O$ | 0.01 |

Plasmids were constructed with standard molecular biology techniques using the "yeast gap repair" method (Shanks et al., Applied and Environmental Biology 72:5207-36 (2006)). A synthetic DNA sequence containing the *Rhodococcus* repA origin of replication and gentamicin resistance marker (Lessard, BMC Microbiol., 4:15 (2004)) was used to create a *R. opacus-E. coli-S. cerevisiae* shuttle vector from two plasmids containing the tmsAB genes from *Mycobacterium smegmatis* and *Thermobifida fusca* under control of the tac promoter. Briefly, the repA and gen$^R$ synthetic DNA was constructed with approximately 50 bp flanking homology regions to the tmsAB destination plasmids. Destination plasmids were restriction digested with PacI, and the flanking homology regions repaired the gap, enabling genetic selection via the ura3 gene in *S. cerevisiae*. DNA was isolated from *S. cerevisiae* by phenol/chloroform extraction and ethanol precipitation and used to transform *E. coli*. Correct plasmid constructions were isolated by mini-prep (Qiagen, USA) and screened by restriction digest. Plasmids pNC985 (SEQ ID NO:93), containing *M. smegmatis* tmsAB, and pNC986 (SEQ ID NO:94) (FIG. 10), containing T. *fusca* tmsAB were isolated and used to transform *R. opacus*.

*R. opacus* was transformed following the protocol described by Kalscheuer et al. (Kalscheuer 1999). Cells were grown overnight in modified nutrient broth, then transferred to 50 mL modified nutrient broth medium at a starting optical density of 0.13. Cells were harvested at OD 0.36, washed twice in 50 mL ice cold water, and resuspended in 1.7 mL ice cold water. Cells were then subdivided to 350 µL volumes and 2 µL plasmid DNA at 400-600 ng/µL concentration. Cells plus DNA were incubated at 39° C. for 5 minutes immediately prior to cooling on ice and electrotransformation. Electric pulses were delivered using 2 mm gap cuvettes with a 2 kV pulse (600Ω, 25 µF, 12 ms time constant). Cells were then diluted with 600 µL SOC medium and incubated overnight at 30° C. 200 µL overnight cell broth was then plated on LB agar containing 10 µg/mL gentamicin and incubated an additional 4 days at 30° C. for colony formation. Gentamicin resistant colonies were picked for further analysis, no resistant colonies were seen on control plates without added plasmid DNA.

Fermentation was performed at 30° C. for 4 days in 250 mL shake flasks (25 mL working volume with defined medium, 10 µg/mL gentamicin added as appropriate) at 200 rpm. Inoculum was prepared from 48 hour grown cultures in LB+10 µg/mL gentamicin. Inoculation amount was 1:25 v/v of the final volume. At the end of fermentation cells were harvested and resuspended in 1 mL distilled water and frozen at −80° C. After freezing, cells were lyophilized to dryness and then whole cells were transesterified in situ with methanolic HCl at 80° C. before extraction into isooctane and quantification by gas chromatography with flame ionization detection.

Results:

*R. opacus* was transformed with two vectors, pNC985 expressing the *M. smegmatis* tmsAB genes, and pNC986 expressing the *T. fusca* tmsAB genes. As shown in Table 3 below, one isolate of the pNC986 transformation, strain NS1155, produced 10-methylstearic acid at 7.2% by weight of total fatty acids, as compared to the control strain NS1104 at 3.6% by weight of total fatty acids.

TABLE 3

Weight percent 10-methylstearic acid measured in *R. opacus* strains transformed with tmsAB expression vectors.

| Description | 10-methylstearic acid (% of total FA) |
| --- | --- |
| R. opacus PD630 (NS1104) | 3.6 |
| R. opacus + pNC985 #1 (Msm tmsAB) | 3.9 |
| R. opacus + pNC985 #2 | 3.3 |
| R. opacus + pNC985 #3 | 3.3 |
| R. opacus + pNC986 #1 (Tfu tmsAB) | 7.2 |
| R. opacus + pNC986 #2 | 3.0 |
| R. opacus + pNC986 #3 | 3.1 |

Example 4: Acyl Chain Substrate Range for tmsB and tmsA

The inventors performed the following experiments to determine the acyl-chain substrate range of the tmsB and tmsA enzymes from *Thermomonospora curvata*, particularly the fatty acid chain length and double bond position.

Methods:

Unsaturated fatty acids were purchased from Nu-Check Prep, Inc., Elysian Minn. Fatty acids were dissolved in DMSO at a concentration of 100 mg/mL, with the exceptions of palmitoleic acid, oleic acid, and vaccenic acid, which were dissolved in ethanol at a concentration of 100 mg/mL. A 10-methyl stearic acid reference standard was obtained from Larodan AB, Sweden.

E. coli strains NS1161 and NS1162 were used in this experiment; strain NS1161 was constructed by transforming the control (empty) vector plasmid into E. coli CGSC 9407 (aka JW1653-1 Keio collection) which holds a kan$^R$ disruption of the native E. coli cyclopropane fatty acid synthase (cfa) gene. Strain NS1162 was constructed by transforming plasmid pNC906 (SEQ ID NO:88) (FIG. 9B), containing the T. curvata tmsB and tmsA genes under control of the constitutive tac promoter, into E. coli CGSC 9407.

E. coli strains were grown in LB media supplemented with 100 mg/L ampicillin and 100 mg/L of fatty acid. Cultures were inoculated with a 1:1000 dilution of overnight pre-culture and grown in 14 mL plastic culture tubes with a 5 mL working volume at 37° C. in a rotary drum roller for 24 hours. At the end of cultivation cells were harvested by centrifugation at 4000 rpm for 15 minutes in an Eppendorf 5810 R clinical centrifuge, washed once with and equal volume of deionized water, resuspended in 0.1 mL deionized water, and frozen at −80° C. Cells were then lyophilized to dryness and used to perform a HCl-methanol catalyzed transesterification reaction to produce fatty acid methyl esters (FAME). These samples were dissolved in isooctane and injected into a gas chromatography system (Agilent Technologies) equipped with a flame ionization detector.

Results:

When fed exogenous free fatty acids, E. coli can incorporate them into its phospholipids and other lipid structures. Strains NS1161 and NS1162 were cultured with 18 different unsaturated fatty acids and in a control medium with no fatty acid supplementation, and FAME profiles for the two strains were compared. To identify new unsaturated fatty acids, a GC peak corresponding to the supplemented fatty acid was identified via the strain NS1161 FAME profile as compared to the un-supplemented reference culture. and then the strain NS1162 FAME profile was checked for the same GC peak, and a new peak at a characteristic retention time shift (0.24 to 0.08 minutes forward, with the relative shift decreasing as overall retention time increases) corresponding to a methylated fatty acid. A 10-methyl stearic acid reference standard (Larodan AB, Sweden) was used as a control to assign retention time to 10-methylstearic acid.

As observed in Table 4 below, methylation occurred on fatty acids with 14, 15, 16, 17, 18, 19 and 20 carbons, and on 49, MO, and 411 double bond positions. The highest percent conversion to methylated fatty acids occurred at 16 and 18 carbon fatty acids at the 49 and 411 positions.

TABLE 4

| Fatty acid | Name | Unsaturated FA Retention time (min) | Methyl-branched FA retention time (min) | % conversion to methyl branched FA |
|---|---|---|---|---|
| 12:1Δ11 | 11-Dodecenoic acid | 4.627 | — | 0.0% |
| 13:1Δ12 | 12-Tridecenoic acid | 5.765 | — | 0.0% |
| 14:1Δ9 | Myristoleic acid | 6.785 | 6.546 | 3.4% |
| 15:1Δ10 | 10-Pentadecenoic acid | 7.926 | 7.715 | 1.7% |
| 16:1Δ9 | Palmitoleic acid | 8.907 | 8.772 | 30.4% |
| 17:1Δ10 | 10-Heptadecenoic acid | 9.999 | 9.859 | 11.1% |
| 18:1Δ6 | Petroselinic acid | 10.943 | — | 0.0% |
| 18:1Δ9 | Oleic acid | 10.978 | 10.862 | 33.7% |
| 18:1Δ11 | Vaccenic acid | 11.065 | 10.917 | 21.8% |
| 18:1Δ9, 12-OH | Ricinoleic acid | 12.737 | — | 0.0% |
| 18:1Δ9, 12 | Linoleic acid | 11.656 | — | 0.0% |
| 19:1Δ7 | 7-Nondecenoic acid | 11.941 | — | 0.0% |
| 19:1Δ10 | 10-Nondecenoic acid | 12.01 | 11.888 | 6.1% |
| 20:1Δ5 | 5-Eicosenoic acid | 12.652 | — | 0.0% |
| 20:1Δ8 | 8-Eicosenoic acid | 12.713 | — | 0.0% |
| 20:1Δ11 | 11-Eicosenoic acid | 12.743 | 12.666 | 2.2% |
| 22:1Δ13 | Erucic acid | 13.406 | — | 0.0% |
| 24:1Δ15 | Nervonic acid | 13.86 | — | 0.0% |

Example 5: tmsA Co-Factor Usage

The inventors performed the following experiments to determine which redox co-factor the tmsA enzyme (10-methylene reductase) uses to produce fully saturated 10-methyl fatty acids from the intermediate 10-methylene fatty acids.

Methods:

E. coli strains NS1161, NS1163, and NS1164 were used in this experiment; strain NS1161 was constructed by transforming the control (empty) vector plasmid pNC53 into E. coli CGSC 9407 (aka JW1653-1 Keio collection) which holds a kan$^R$ disruption of the native E. coli cyclopropane fatty acid synthase (cfa) gene. Strain NS1163 was constructed by transforming plasmid pNC963 (SEQ ID NO:95) (FIG. 11), containing the T. curvata tmsB gene under control of the constitutive tac promoter, into E. coli CGSC 9407. Strain NS1164 was constructed by transforming plasmid pNC964 (SEQ ID NO:96) (FIG. 11), containing the T. curvata tmsA gene under control of the constitutive tac promoter, into E. coli CGSC 9407.

Strain NS1163 was grown in 1 L LB media supplemented with 100 mg/L ampicillin for 24 hours at 37° C. (2×500 mL in 2 L baffled flasks). After cultivation, cells were harvested by centrifugation at 4000 rpm for 15 minutes in an Eppendorf 5810 R clinical centrifuge and washed twice in 100 mL PBS buffer. After concentration to 40 mL PBS buffer, cells were heat inactivated at 85° C. for 30 min. Inactivated cells were then dispensed into 1 mL aliquots and disrupted with 0.3 grams of 0.1 mm glass beads using a MP fastprep-24 on "E. coli" setting (MP biomedicals, LLC). Whole cell lysed suspension was collected by micro-centrifugation at 2000×g for 30 seconds to remove beads and then 0.7 mL of suspension per tube was transferred to new tubes and frozen at −80° C. until further use.

On the day of assay, strains NS1161 and NS1164 were grown via inoculation from overnight cultures (1:1000 dilution) in 50 mL LB medium supplemented with 100 mg/L ampicillin in 37° C. and 200 rpm in baffled shake flasks. After 4 hours of cultivation, cells were harvested at 5° C., washed 1× in ice cold PBS and then resuspended in 750 µL PBS in 1 mL plastic screw tubes. 0.3 grams of 0.1 mm glass beads were added and cells were lysed with a MP fastprep-24 on the "E. coli" setting. The cell suspension was then micro-centrifuged for 5 min at 12,000×g, and the supernatant transferred to a fresh tube and held on ice until assay.

Assay reaction: 700 µL of NS1163 whole lysate, 200 µL of 37.2 mg/mL NADPH solution (assay concentration 10 mM), 33.2 mg/mL NADH solution (assay concentration 10 mM), or PBS buffer, and 100 µL of cell free extract or PBS buffer. Assay tubes were sealed and rotated on a drum roller at 37° C. for 16 hours. To end the assay, tubes were frozen at −80° C., then lyophilized to dryness followed by in situ extraction and transesterification with methanolic HCL. Fatty acid profiles were determined by GC with flame ionization detection, and the 10-methyl fatty acid peak area was compared to the total fatty acid peak area to determine assay activity.

Results:

Strain NS1163, which accumulates 10-methylene intermediate fatty acids via expression of the *Thermomonospora curvata* tmsB gene, was grown, harvested, inactivated, and lysed for use as a substrate for the tmsA (10-methylene reductase) assay. To this substrate cell-free extract *E. coli* strain NS1164 expressing the *T. curvata* tmsA gene or *E. coli* strain NS1161 containing an empty expression vector were added, along with NADPH or NADH. As observed Table 5 below, only the presence of *T. curvata* tmsA and NADPH resulted in synthesis of 10-methyl fatty acids in this assay.

TABLE 5

| E. coli (Δcfa background) cell free extract | co-factor | relative 10Me16 + 10Me18 peak area | SD |
|---|---|---|---|
| Tcu tmsA | NADPH | 0.059 | 0.003 |
| Tcu tmsA | NADH | ND | |
| Tcu tmsA | none | ND | |
| empty vector | NADPH | ND | |
| empty vector | NADH | ND | |
| empty vector | none | ND | |
| none | NADPH | ND | |
| none | NADH | ND | |
| none | none | ND | |

ND = Not detected by this assay

Example 6: Expression of tmsB Genes in Yeast *Yarrowia lipolytica* and *Arxula adeninivorans*

Sequences encoding the native bacterial codon tmsB sequences from *Mycobacterium smegmatis*, *Mycobacterium vanbaaleni*, *Amycolicicoccus subflavus*, *Corynebacterium gliniphilum*, *Rhodococcus opacus*, *Agromyces subbeticus*, *Knoellia aerolata*, *Mycobacterium gilvum*, *Mycobacterium* sp. *Indicus*, *Thermobifida fusca*, and *Thermomonospora curvata* were cloned into a standard *Yarrowia* expression vector driven by the *Y. lipolytica* TEF1 promoter and containing an ARS68 *Y. lipolytica* replication origin, a nourseothricin antibiotic resistance gene for selection, and the 2µ origin and URA3 gene for high copy maintenance in *Saccharomyces cerevisiae*. Cloning was performed using the yeast-gap repair method (Shanks 2006) with selection on uracil dropout media. *Y. lipolytica* was transformed following a standard lithium acetate heat-shock protocol with selection on YPD medium supplemented with 500 µg/mL nourseothricin. Colonies were selected and transferred to a 96 well plate containing 300 µL nitrogen-limited lipid production media per well and incubated at 30° C. with shaking at 900 rpm for 96 hours. The medium contained 100 g/L glucose, 0.5 g/L urea, 1.5 g/L yeast extract, 0.85 g/L casamino acids, 1.7 g/L YNB base without amino acids, and 5.1 g/L potassium hydrogen phthalate at pH 5.5. After fermentation, cells were centrifuged, washed with distilled water, and frozen at −80° C. prior to lyophilization to dryness. Dried cells were transesterified in situ with 0.5 N HCl in methanol at 85° C. for 90 minutes to produce fatty acid methyl esters (FAME) suitable for gas chromatography analysis. These samples were dissolved in isooctane and injected into a gas chromatography system (Agilent Technologies) equipped with a flame ionization detector. Total C16 and C18 branched fatty acids were identified and quantified based on known standards and the 10 methylene and 10 methyl fatty acids identified in *E. coli* tms expression experiments. 10-methyl and 10-methylene fatty acid identities were verified by mass spec in an independent experiment. FIG. 12 shows that *Y. lipolytica* transformed with tmsB from *T. fusca* and *T. curvata* produced the highest amounts of 10-methylene stearic acid.

To test tmsB activity in *Arxula adeninivorans*, the top performing tmsB gene from *Yarrowia*, *T. curvata* tmsB (SEQ ID NO:75) was cloned into a constitutive expression vector under the *Arxula* ADH1 promoter, resulting in plasmid pNC1065. Individual transformant colonies were isolated and grown in a standard industrial media (with a high C:N ratio to promote lipid accumulation) for 4 days at 40° C. Cell pellets were isolated, washed once with water, and lyophilized. Total C16 and C18 fatty acids were transesterified as for *Yarrowia* strains and were analyzed by GC. FIG. 13 shows that *A. adeninivorans* transformed with tmsB from *T. curvata* produce 10-methylene fatty acids.

Example 7: tmsA and tmsB Coexpression in *Yarrowia Lipolytica* and *Saccharomyces cerevisiae*

The inventors discovered that simultaneous expression of tmsA and tmsB genes can produce branched 10-methyl and 10-methylene fatty acids, respectively, in *Saccharomyces* and *Yarrowia* yeast strains. For expression in *Yarrowia*, plasmids constitutively expressing the native bacterial sequences for tmsA from *T. curvata* (pNC984), *T. fusca* (pNC983) and *C. glutamicum* (pNC991) were each transformed into strain NS1117 containing a stably integrated copy of the *T. curvata* tmsB gene (isolated from Example 6 above). Individual transformants were isolated and grown for 4 days at 30° C. in shake flask medium. Fatty acids were isolated and analyzed by GC as in Example 6. As shown in FIG. 14, all tmsA genes analyzed produce at detectable levels of 10 methyl fatty acids in *Yarrowia*, compared to the parental strain. The *T. curvata* tmsA gene produced more 10-methyl fatty acids than the other tmsA genes analyzed.

For expression in *Saccharomyces*, plasmids with demonstrated gene activity in *Yarrowia*, pNC984 (*T. curvata* tmsA with a NAT marker) and pNC1025 (*T. curvata* tmsB with a HYG marker) were transformed individually and together into *S. cerevisiae* strain NS20, and transformants were selected on media containing the appropriate antibiotic(s). Individual transformation isolates were grown for 2 days in YPD medium at 30° C. Cell pellets were processed, and total fatty acids were analyzed as for *Yarrowia*. As shown in FIG.

15, the strain transformed with only tmsB produced only 10-methylene fatty acids, and the strain transformed with both tmsA and tmsB produced a relatively high percentage of 10-methyl fatty acids.

Example 8: Expression of a tmsA-B fusion protein in E. coli, Saccharomyces ceverisiae, Yarrowia lipolytica and Arxula adeninivorans The inventors discovered that expressing the tmsA and tmsB enzymes in a single polypeptide improves conversion of 10-methylene fatty acids to 10-methyl fatty acids. Single proteins containing both tmsA and tmsB activity were created by fusing the genes for Thermomonospora curvata tmsA and tmsB in frame, separated by a flexible linker domain. The Thermomonospora curvata tmsA and tmsB enzymes were chosen because they produced the most 10-methyl branched fatty acids in yeast. A short 12 amino acid linker with the sequence AGGAEGGNGGA which occurs naturally in the Yarrowia FAS2 gene was chosen to connect the two enzymes. Two fusion enzymes were tested for activity in bacteria and yeast, tmsA-B (NG540; encoded by SEQ ID NO:97) and tmsB-A (NG541; encoded by SEQ ID NO:98).

For E. coli expression, plasmids pNC1069 and pNC1070 containing the T. curvata tmsA-B and tmsB-A genes with the tac promoter and trpT' terminator were each transformed into E. coli CGSC 9407. Individual transformed strains were grown and total fatty acids were assayed as in Example 2 above. As shown in Table 6 below, both the tmsA-B and tmsB-A genes resulted in production of methylated stearic acid in E. coli.

TABLE 6

Methylation of oleic and vaccenic acid was calculated as the percent of C18:1 fatty acids converted into 10- and 12-methyl fatty acids.

| Vector | % C18:1 methylated |
| --- | --- |
| None | 0 |
| T. curvata tmsA-B | 19.4 |
| T. curvata tmsB-A | 26.25 |

For Saccharomyces cerevisiae and Yarrowia lipolytica expression, NG540 (SEQ ID NO:97) and NG541 (SEQ ID NO:98) were individually cloned into standard Yarrowia expression vectors containing a yeast 2 u origin of replication for high copy retention in Saccharomyces, resulting in the respective vectors pNC1067 and pNC1068.

Plasmids pNC1067 and pNC1068 were transformed into Saccharomyces strain NS20 by a standard protocol and individual transformed strains were selected for assay of branched fatty acid production. Strains were grown for 2 days at 30° C. in 25 ml YPD medium. Cell pellets were lyophilized and total fatty acids were analyzed by basic transesterification and GC analysis as in Example 2. FIG. 16 shows that expression of both tmsA-B and tmsB-A in S. cerevisiae led to production of 10 methyl fatty acids.

Plasmids pNC1067 and pNC1068 were transformed into Yarrowia lipolytica by a standard heat shock protocol. Individual resulting transformant strains were chosen for analysis of 10-methylene and 10-methyl fatty acid production. Strains were grown and analyzed by GC as in Example 7. FIG. 17 shows that expression of both tmsA-B and tmsB-A in E lipolytica led to production of 10 methyl fatty acids, although tmsA-B was more efficient at converting 10-methylene fatty acids to 10-methyl fatty acids.

For expression in Arxula adeninivorans, NG540 was cloned into a standard expression vector containing the constitutive Arxula ADH1 promoter resulting in pNC1151. pNC1151 was transformed into Arxula strain NS1166 and individual transformants were selected to assay of 10-methyl fatty acid production. Arxula strains were grown and analyzed by GC as in Example 7.

These experiments showed that 10-methyl C16 and C18 fatty acids were detected in E. coli. (Table 6), Saccharomyces cerevisiae (FIG. 16), Yarrowia lipolytica (FIG. 17), and Arxula adeninivorans (FIG. 18), indicating that the fusion enzymes contain both tmsA and tmsB activities. The low production of 10-methylene intermediates (undetectable in E. coli and Saccharomyces, at low levels in Yarrowia and Arxula) indicate that the fusion protein efficiently converts unsaturated fatty acids into 10 methyl fatty acids.

Example 9: tmsB Sequence Analysis

TmsB protein sequences coded by the tmsB genes from Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium sp. Indicus, Thermobifida fusca, and Thermomonospora curvata were aligned with the cyclopropane fatty acid synthase (Cfa) enzyme from Escherichia coli with the CLUSTAL OMEGA software program (European Molecular Biology Laboratory, EMBL). FIGS. 19A-D show the alignment of these protein sequences. E. coli Cfa shares homology to the TmsB enzyme and carries out a similar reaction to TmsB, with methylation of a fatty acid phospholipid double bond, but produces a cyclopropane moiety rather than a methylene moiety.

Certain amino acids of the E. coli Cfa enzyme are thought to bind the active site bicarbonate ion. Iwig et al., J. Am. Chem. Soc. 127:11612-13(2005). These amino acids are C139, E239, H266, I268, and Y317 of the E. coli enzyme, which are conserved in the consensus tmsB protein sequence (C160, E266, H293, I295, and Y348 on the T. curvata TmsB sequence SEQ ID NO:76).

Additionally, there are sixteen amino acid residues that are conserved for all twelve TmsB protein sequences, but not in the E. coli Cfa sequence. These amino acids may be specific for 10-methylene addition to fatty acid phospholipids rather than the cyclopropane addition performed by the E. coli Cfa protein. These conserved amino acids, numbered with the T. curvata TmsB sequence, are D23, G24, A59, H128, F147, Y148, L180, L193, M203, G236, A241, R313, R318, E320, L359, L400 of SEQ ID NO:76.

A BLASTp conserved domains analysis (National Center for Biotechnology Information, NCBI) identifies a S-adenosylmethionine-dependent methyltransferase domain from amino acids 192-291 of T. curvata TmsB. S-adenosylmethionine binding site amino acid residues are identified as V196, G197, C198, G199, W200, G201, G202, T219, L220, Q246, D247, Y248, and D262.

Table 7 shows the percent sequence identity of the indicated protein relative to T. curvata tmsB:

TABLE 7

| Species | % Identity |
| --- | --- |
| Thermomonospora curvata tmsB | 100 |
| Mycobacterium smegmatis tmsB | 60 |
| Mycobacterium vanbaaleni tmsB | 59 |

TABLE 7-continued

| Species | % Identity |
| --- | --- |
| Amycolicicoccus subflavus tmsB | 55 |
| Corynebacterium glyciniphilum tmsB | 47 |
| Corynebacterium glutamicum tmsB | 50 |
| Rhodococcus opacus tmsB | 59 |
| Agromyces subbeticus tmsB | 57 |
| Knoellia aerolata tmsB | 47 |
| Mycobacterium gilvum tmsB | 58 |
| Mycobacterium sp. Indicus tmsB | 58 |
| Thermobifida fusca tmsB | 67 |
| Escherichia coli Cfa | 34 |

As shown in Table 7, there is a great deal of variation among the tmsB protein sequences from the different species. Nevertheless, despite the sequence variation, several of the proteins are shown herein to have the same ability to catalyze the production of a methylene-substituted lipid.

Example 10: tmsA Sequence Analysis

TmsA protein sequences coded by the tmsA genes from Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium sp. Indicus, Thermobifida fusca, and Thermomonospora curvata were aligned with the Glycolate oxidase subunit GlcD enzyme from Escherichia coli with the CLUSTAL OMEGA software program (European Molecular Biology Laboratory, EMBL). The E. coli GlcD enzyme does not appear to perform a similar enzymatic reaction as TmsA, but it is the most closely homologous protein to TmsA in the E. coli genome.

FIGS. 20A-E show the alignment of the TmsA proteins. There are 114 amino acid residues that are conserved for all twelve TmsA protein sequences, but not in the E. coli GlcD sequence. These amino acids are (numbered according to the T. curvata sequence (SEQ ID NO:74)): R31, A33, S37, N38, L39, F40, R43, D52, V59, D63, G73, M74, T76, Y77, D79, L80, V81, L85, P91, V93, V94, Q96, L97, T99, I100, T101, A105, G108, G110, E112, S113, S115, F116, R117, N118, P121, H122, E123, V125, E127, G133, P154, N155, Y157, Y162, L166, E171, V173, V177, H181, V208, G213, F216, Y222, L223, S236, D237, Y238, T239, Y245, S247, D254, T257, Y261, W263, R264, W265, D266, D268, W269, C272, A275, G277, Q279, R284, W287, R293, S294, G318, E232, V325, P328, E330, F339, F343, W353, C355, P356, W363, L365, Y366, P367, N376, F379, W380, V383, P384, N395, E399, G407, H408, K409, S410, L411, Y412, S413, Y417, F422, Y426, G428, R443, L447, and V452.

A BLASTp conserved domains analysis (National Center for Biotechnology Information, NCBI) identifies a Flavin adenine dinucleotide (FAD) binding domain from amino acids 9-141 of T. curvata TmsA (SEQ ID NO:74), as well as a FAD/FMN-containing dehydrogenase domain from amino acids 22-444. Table 8 shows the percent sequence identity of the indicated protein relative to T. curvata tmsA:

TABLE 8

| Species | % Identity |
| --- | --- |
| Thermomonospora curvata tmsA | 100 |
| Mycobacterium smegmatis tmsA | 61 |
| Mycobacterium vanbaaleni tmsA | 61 |
| Amycolicicoccus subflavus tmsA | 60 |
| Corynebacterium glyciniphilum tmsA | 55 |
| Corynebacterium glutamicum tmsA | 53 |
| Rhodococcus opacus tmsA | 61 |
| Agromyces subbeticus tmsA | 59 |
| Knoellia aerolata tmsA | 60 |
| Mycobacterium gilvum tmsA | 59 |
| Mycobacterium sp. Indicus tmsA | 58 |
| Thermobifida fusca tmsA | 64 |
| Escherichia coli GlcD | 28 |

As shown in Table 8, there is a great deal of variation among the tmsA protein sequences from the different species. Nevertheless, despite the sequence variation, several of the proteins are shown herein to have the same ability to catalyze the production of a methyl-substituted lipid.

INCORPORATION BY REFERENCE

Each of the patents, published patent applications, and non-patent references cited herein is hereby incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of producing a branched (methyl)lipid or an exomethylene-substituted lipid comprising contacting a yeast cell with oleic acid, methionine, or both oleic acid and methionine,
   wherein the branched (methyl)lipid or the exomethylene-substituted lipid is a carboxylic acid, carboxylate, ester, thioester, or amide,
   wherein (a) the branched (methyl)lipid comprises (i) a saturated branched aliphatic chain comprising a branching methyl group or (ii) an unsaturated branched aliphatic chain comprising a branching methyl group, or (b) the exomethylene-substituted lipid comprises a branched aliphatic chain wherein the branched aliphatic chain is substituted with an exomethylene group,
   wherein the yeast cell comprises a methyltransferase gene encoding a *Thermomonospora curvata* tmsB enzyme, and
   wherein the yeast cell produces the branched (methyl) lipid or the exomethylene-substituted lipid.

2. The method of claim 1, wherein the branched (methyl) lipid or the exomethylene-substituted lipid comprises a linear lipid with a chain length of 14-20 carbons and a methyl branch at the Δ9 position, the Δ10 position, or the Δ11 position.

3. The method of claim 2, wherein the branched (methyl) lipid or the exomethylene-substituted lipid is a diacylglycerol, a triacylglycerol, or a phospholipid, and wherein the diacylglycerol, triacylglycerol, or phospholipid comprises an ester of 10-methylstearate or an ester of 10-methylenestearate.

4. The method of claim 1, wherein at least 1% by weight of fatty acids of the yeast cell are one or more linear fatty acids with a chain length of 14-20 carbons and a methyl branch at the Δ9 position, the Δ10 position, or the Δ11 position.

5. The method of claim 1, wherein the yeast cell comprises at least 1% lipid as measured by % dry cell weight.

6. The method of claim 1, wherein the yeast cell further comprises a recombinant reductase gene.

7. The method of claim 6, wherein the recombinant reductase gene encodes tmsA from *Thermomonospora curvata*.

8. The method of claim 6, wherein the yeast cell encodes a fusion protein comprising (A) a reductase protein encoded by the recombinant reductase gene and (B) the tmsB enzyme.

9. The method of claim 1, wherein the methyltransferase gene is codon-optimized for the yeast cell, or wherein the yeast cell further comprises a reductase gene and the reductase gene is codon-optimized for the yeast cell.

10. The method of claim 1, wherein the yeast cell is *Arxula*, *Saccharomyces*, or *Yarrowia*.

11. The method of claim 10, wherein the yeast cell is *Arxula adeninivorans*, *Saccharomyces cerevisiae*, or *Yarrowia lipolytica*.

12. The method of claim 1, wherein the yeast cell comprises a methyltransferase protein encoded by the methyltransferase gene, wherein the methyltransferase protein comprises an amino acid sequence with at least 95% sequence identity with the amino acid sequence of SEQ ID NO:76.

13. The method of claim 12, wherein the yeast cell comprises a methyltransferase protein encoded by the methyltransferase gene, wherein the methyltransferase protein comprises the amino acid sequence of SEQ ID NO:76.

14. The method of claim 1, wherein the methyltransferase gene comprises a nucleotide sequence with at least 95% sequence identity with the nucleotide sequence of SEQ ID NO:75.

15. The method of claim 14, wherein the methyltransferase gene comprises the nucleotide sequence of SEQ ID NO:75.

* * * * *